(12) United States Patent
Li et al.

(10) Patent No.: US 7,491,724 B2
(45) Date of Patent: Feb. 17, 2009

(54) SUBSTITUTED CYCLIC HYDROXAMATES AS INHIBITORS OF MATRIX METALLOPROTEINASES

(75) Inventors: Yun-Long Li, Wilmington, DE (US); Jincong Zhuo, Boothwyn, PA (US); David Burns, Philadelphia, PA (US); Wenqing Yao, Kennett Square, PA (US); Ravi Kumar Jalluri, Avondale, PA (US)

(73) Assignee: Incyte Corporation, Wilmington, DE (US)

( * ) Notice: Subject to any disclaimer, the term of this patent is extended or adjusted under 35 U.S.C. 154(b) by 337 days.

(21) Appl. No.: 10/965,215

(22) Filed: Oct. 15, 2004

(65) Prior Publication Data

US 2005/0113344 A1 May 26, 2005

Related U.S. Application Data

(60) Provisional application No. 60/586,646, filed on Jul. 12, 2004, provisional application No. 60/515,352, filed on Oct. 28, 2003, provisional application No. 60/512,016, filed on Oct. 17, 2003.

(51) Int. Cl.
*A61K 31/497* (2006.01)
*C07D 403/00* (2006.01)

(52) U.S. Cl. .............................. 514/252.13; 514/255.01; 514/317; 514/318; 514/326; 544/359; 544/386; 546/268.1; 546/268.4

(58) Field of Classification Search ................. 544/357, 544/360, 386, 359; 546/268.1, 268.4; 514/252.13, 514/255.01, 317, 318, 326, 330
See application file for complete search history.

(56) References Cited

U.S. PATENT DOCUMENTS

| 5,872,152 | A | 2/1999 | Brown et al. |
| 5,892,112 | A | 4/1999 | Levy et al. |
| 5,968,795 | A | 10/1999 | Dixon et al. |
| 6,268,379 | B1 | 7/2001 | Xue et al. |
| 6,436,960 | B1 * | 8/2002 | Shin et al. ............ 514/326 |
| 6,500,847 | B2 | 12/2002 | Van Zandt et al. |
| 6,858,626 | B2 * | 2/2005 | Xue et al. ............ 514/312 |
| 2004/0247606 | A1 | 12/2004 | Friedman et al. |
| 2004/0259896 | A1 | 12/2004 | Yao et al. |
| 2005/0250789 | A1 | 11/2005 | Burns et al. |
| 2007/0117809 | A1 | 5/2007 | Fridman |
| 2007/0280943 | A1 | 12/2007 | Friedman et al. |

FOREIGN PATENT DOCUMENTS

WO WO 99/65867 * 12/1999
WO WO 01/70673 A2 9/2001
WO WO 02/055491 A2 7/2002

OTHER PUBLICATIONS

Xue et al., 1999, CAS: 49888.*
Wolfsberg et al., *J. Cell Bio.* vol. 131, pp. 275-278 Oct. 25, 1995.
Hooper, 1994, *FEBS Lett*, vol. 354, pp. 1-6.
Stocker et al., 1995, *Curr Opin Struct Biol*, vol. 5, pp. 383-390.
Bode et al., 1996, *Adv Exp Med Biol*, vol. 389, pp. 1-11.
Moscatelli et al., 1988, *Biochim Biophys Acta*, vol. 948, pp. 67-85.
Parks, 2002, *J Clin Invest.*, vol. 110, pp. 613-614.
Winyard et al., 1991, *FEBS Letts*, vol. 279, pp. 91-94.
Seals et al., 2003, *Genes and Development*, vol. 17, pp. 7-30.
Black, 2002, *Int J Biochem Cell Biol*, vol. 34, pp. 1-5.
Herren et al., 1997, *FASEB J.*, vol. 11, pp. 173-180.
Bohm et al., 1999, *Arthritis Rheum*, vol. 42, pp. 1946-1950.
Horiuchi et al., 2003, *Mol Cell Biol*, vol. 23, pp. 5614-5624.
Novak et al., 2001, *Curr Opin Immunol*, vol. 13, pp. 721-726.
Mayer et al., 2002, *Inflamm Res*, vol. 51, pp. 85-90.
Yardem et al., 2001, *Nature Reviews*, vol. 2, pp. 127-137.
Slamon et al., 1987, *Science*, vol. 235, pp. 177-182.
Rio et al, 2000, *J Biol Chem*, vol. 275, pp. 10379-10387.
Codony-Servat et al., 1999, *Cancer Res*, vol. 59, pp. 1196-1201.
Moss et al., 2002, *Essays Biochem*, vol. 38, pp. 141-153.
Tang, 2001, *Int J Biochem Cell Biol*, vol. 33, pp. 33-44.
Kaushal et al., 2000, *J Clin Invest*, vol. 105, pp. 1335-1337.
Levin et al., *Syn. Comm.* 1982, vol. 12, p. 989.
Wang et al., *J. Org. Chem.* 1992, vol. 57, p. 6101.
Moss et al., 2001, *Drug Discov Today*, vol. 6, pp. 417-426.
"Comprehensive Organic Synthesis" (B. M. Trost, I. Fleming, Eds. Pergamon, 1991, vol. 8, Part 1.2, P25, Part 3.1, p. 729.

(Continued)

*Primary Examiner*—Rei-tsang Shiao
(74) *Attorney, Agent, or Firm*—Fish & Richardson P.C.

(57) ABSTRACT

The present invention provides compounds of the formula I:

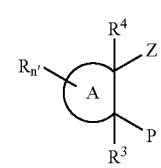

its enantiomers, diastereomers, racemic mixtures thereof, prodrugs, crystalline forms, non-crystalline forms, amorphous forms thereof, solvates thereof, metabolites thereof, and pharmaceutically acceptable salts, wherein the ring A substituent groups are fully defined in the following disclosure. The compounds of formula I are inhibitors of metalloproteases such as matrix metalloproteases and sheddases, and are useful in treating diseases such as rheumatoid arthritis, psoriasis, neoplastic diseases, allergies and all those diseases wherein inhibition of MMPs is desirable.

10 Claims, No Drawings

OTHER PUBLICATIONS

Gais et al. *J. Org. Chem.* 1989, vol. 54, p. 5115.

Joucla et al., *Chem. Commun.* 1985, p. 1566.

Xue et al., *J. Org. Chem.* 2002, vol. 67, p. 865.

Jacobsen, *Acc. Chem. Res.* 2000, vol. 33, p. 421.

Combs et al., *Journal of Combinatorial Chemistry* 2002, vol. 4, p. 179.

Louie, *Tetrahedron Lett.* 1995, vol. 36, p. 3609.

Mishani et. al. *Tetrahedron Lett.* 1996, vol. 37, p. 319.

Dankwardt et al, *Tetrahedron Lett.* 1995, vol. 36, p. 4923.

Bursavich et al., *Org. Lett.* 2001, vol. 3, p. 2625.

Burns, D. M. et al., "Conversion of an MMP-potent scaffold to an MMP-selective HER-2 sheddase inhibitor via scaffold hybridization and subtle $P'_1$ permutations," *Bioorg. Med. Chem. Lett.*, 2008, 18, 560-564.

Fridman, J.S. et al., "Selective Inhibition of ADAM Metalloproteases as a Novel Approach for Modulating ErbB pathways in Cancer", *Clin. Canc. Res.*, 2007, 13(6), 1892-1901.

Liu, P.C.C. et al., "Indentification of ADAM 10 AS A Major Source of HER-2 Ectodomain Sheddase Activity in HER2 Overexpressing Breast Cancer Cells", *Cancer Biol. Ther.*, 2006, 5:6, 657-664.

Liu, X. et al., "Selective Inhibition of ADAM Metalloproteases blocks HER-2 Extracellular Domain (ECD) Cleavage and Potentiates the Anti-Tumor Effects of Trastuzumab", *Cancer Biol. Ther.*, 2006, 5:6, 648-655.

Muller, A.J. and Scherle, P.A., "Targeting the Mechanisms of Tumoral Immune Tolerance with Small-molecule Inhibitors" *Nature Rev. Cancer*, 2006, 6, 613-626.

Yao, W. et al., "Discovery of Potent, Selective, and Orally Active Human Epidermal Growth Factor Receptor-2 Sheddase Inhibitor of the Treatment of Cancer," *J. Med. Chem.* 2007, 50, 603-606.

Yao, W., et al., "Design and identification of selective HER-2 sheddase inhibitors via P1'manipulation and unconventional P2'perturbations to induce a molecular metamorphosis", *Bioorg. Med. Chem. Lett.*, 2008, 18, 159-163.

Zhou, Bin-Bing S. et al., "Targeting ADAM-mediated Ligand Cleavage to Inhibit HER3 and EGFR Pathways in Non-small Cell Lung Cancer", *Cancer Cell*, 2006, 10, 39-50.

Zhuo, J., et al., "Asymmetric Synthesis of Conformationally Constrained trans-2,3-Piperidine-Dicarboxylic Acid Derivatives", *SYNLETT*, 2007, No. 3, 460-464.

USPTO file of U.S. Appl. No. 10/831,265 (Publ. No. US2004/0259896). Office Action mailed Jan. 29, 2007 (Restriction Requirement), Examiners Ebenezer O. Sackey and James O. Wilson.

USPTO file of U.S. Appl. No. 10/831,265 (Publ. No. US2004/0259896). Applicants' Reply filed Feb. 26, 2007 by Applicants' Agent, Christine A. Goodard.

USPTO file of U.S. Appl. No. 10/831,265 (Publ. No. US2004/0259896). Office Action mailed May 17, 2007 (Non-Final Action), Examiners Ebenezer O. Sackey and James O. Wilson.

USPTO file of U.S. Appl. No. 10/831,265 (Publ. No. US2004/0259896). Applicant's Amendment filed Aug. 8, 2007 by Applicant's Agent, Christine A. Goodard.

USPTO file of U.S. Appl. No. 10/831,265 (Publ. No. US2004/0259896). Office Action mailed Oct. 19, 2007 (Ex Parte Quayle Action), Examiners Ebenezer O. Sackey and James O. Wilson.

USPTO file to U.S. Appl. No. 10/831,265 (Publ. No. US2004/0259896). Request for Continued Examination filed Dec. 18, 2007 filed by Applicant's Agent, Christine A. Goodard.

USPTO file of U.S. Appl. No. 10/831,265 (Publ. No. US2004/0259896). Notice of Allowance mailed Mar. 5, 2008, Examiners Ebenezer O. Sackey and James O. Wilson.

\* cited by examiner

SUBSTITUTED CYCLIC HYDROXAMATES AS INHIBITORS OF MATRIX METALLOPROTEINASES

FIELD OF THE INVENTION

The present invention relates to compounds which are useful in treating diseases, pathologic conditions and disorders associated with unwanted metalloprotease activity. The instant invention is also directed to matrix metalloprotease (MMPS) inhibitors and their use as medicinal agents. The present invention further relates to novel compounds and medical methods of treatment of many diseases, and other disorders especially those wherein inhibition of metalloprotease activity would be of benefit. More particularly, the present invention relates to cyclic hydroxamate derivatives and their use as MMP's inhibitors especially sheddase inhibitors and metalloprotease-disintegrins (ADAMs) inhibitors.

BACKGROUND OF THE INVENTION

Most tissues exist in a highly regulated dynamic equilibrium wherein new tissue is formed and existing tissue is degraded and eliminated. The degradation of the extracellular matrix (ECM), including connective tissue and basement membranes, is effected by the metalloproteinases which are released from connective tissue and invading inflammatory cells. Excessive unregulated activity of these enzymes can result in undesirable tissue destruction and their activity is regulated at the transcription level, by controlled activation of the latent proenzyme and, after translation, by intracellular specific inhibitory factors such as TIMP ("Tissue Inhibitors of MetalloProteinase") or by more general proteinase inhibitors such as α2-macroglobulins.

Several structurally related metalloproteases (MPs) are known to play an important role in the breakdown of structural proteins. These metalloproteases typically act on the intercellular matrix, and thus are involved in tissue breakdown and remodeling. Such proteins have been referred to as metalloproteases or MPs. There are several different families of MPs, classified by sequence homology. Several families of known MPs, as well as examples thereof, are disclosed in the art.

These MPs include Matrix-Metallo Proteases [MMPs], zinc metalloproteases, many of the membrane-bound metalloproteases, TNF converting enzymes, angiotensin-converting enzymes (ACEs), disintegrins, including ADAMs (See Wolfsberg et al, 131 J. Cell Bio. 275-78 Oct., 25 1995), and the enkephalinases. Examples of MPs include human skin fibroblast collagenase, human skin fibroblast gelatinase, human sputum collagenase, aggrecanase and gelatinase, and human stromelysin. Collagenase, stromelysin, aggrecanase and related enzymes are thought to be important in mediating the symptomatology of a number of diseases.

Zinc proteases are subdivided according to the primary structure of their catalytic sites and include gluzincin, metzincin, inuzincin, carboxypeptidase, and DD carboxypeptidase subgroups (Hooper N M, 1994, FEBS Lett, 354:1-6). The metzincin subgroup is further divided into serralysins, astacins, matrixins, and adamalysins (Stocker W and Bode W, 1995, Curr Opin Struct Biol, 5:383-390).

The matrixins include the matrix metalloproteases, or MMPs. MMPs constitute a family of structurally similar zinc-containing metalloproteases, which are involved in the remodeling and degradation of extracellular matrix proteins, both as part of normal physiological processes and in pathological conditions. For a review see Bode, W et al., 1996, Adv Exp Med Biol, 389:1-11. Connective tissue, extracellular matrix constituents and basement membranes are the biological materials that provide rigidity, differentiation, attachment sites and, in some cases, elasticity to biological systems. Connective tissue components include, for example, collagen, elastin, proteoglycans, fibronectin and laminin that form the scaffold for all human tissues. Under normal conditions, connective tissue turnover and/or repair processes are controlled and in equilibrium. The loss of this balance, for whatever reason, leads to a number of disease states. Inhibition of the enzymes responsible for loss of equilibrium provides a control mechanism for this tissue decomposition and, therefore, a treatment for these diseases. The uncontrolled breakdown of connective tissue by metalloproteases is a feature of many pathological conditions.

Besides a role in the regulation of extracellular matrix, there is also evidence to suggest that MMPs mediate the migration of inflammatory cells into tissues (Moscatelli D and Rifkin D B, 1988, Biochim Biophys Acta, 948: 67-85). Several reports have demonstrated that various MMPs can activate a variety of important non-matrix proteins, including cytokines, chemokines, integrins, and antimicrobial peptides (see Parks W C, 2002, J Clin Invest, 110:613-4). Many of the human MMPs are over-expressed in human tumors and are associated with peritumor tissue degradation and metastasis formation. Another important function of certain MMPs is to activate various enzymes, including other MMPs, by cleaving the pro-domains from their protease domains. Thus some MMPs act to regulate the activities of other MMPs, so that over-production of one MMP may lead to excessive proteolysis of extracellular matrix by another. It has also been reported that MMPs can cleave and thereby inactivate the endogenous inhibitors of other proteinases such as elastase (Winyard P G et al., 1991, FEBS Letts, 279: 91-94). Inhibitors of MMPs could thus influence the activity of other destructive proteinases by modifying the level of their endogenous inhibitors. In addition, increasing or maintaining the levels of an endogenous or administered serine protease inhibitor supports the treatment and prevention of diseases such as emphysema, pulmonary diseases, inflammatory diseases and diseases of aging (such as loss of skin or organ stretch and resiliency.) Thus, MMPs should not be viewed solely as proteinases of ECM catabolism, but rather as extracellular processing enzymes involved in regulating cell-cell and cell-ECM signaling events.

The adamalysins include the reprolysins, snake venom metalloproteases and the ADAMs. The ADAMs (a disintegrin and metalloprotease domain) are an important family of metalloproteases. They are a family of type I transmembrane glycoproteins that are important in diverse biologic processes, such as cell adhesion and the proteolytic shedding of cell surface receptors. ADAM family members have been identified from mammalian and non-mammalian sources, including *Xenopus, Drosophila*, and *Caenorhabditis elegans*. Members of the family have a modular design, characterized by the presence of metalloprotease and integrin receptor-binding activities, and a cytoplasmic domain that in many family members specifies binding sites for various signal-transducing proteins. The ADAMs family has been implicated in the control of membrane fusion, cytokine, growth factor and growth factor receptor shedding, and cell migration, as well as processes such as muscle development, fertilization, neurogenesis, and cell fate determination. Loss of regulation can lead to disease and pathology. Pathologies such as infertility, inflammation and cancer have been shown to involve ADAMs family members. For a review, see Wolfsberg T G and White J M, 1998, ADAM metalloproteinases. In Handbook of Proteolytic Enzymes (Barrett A J, Rawlings N D and Woessner J F eds), p.1310-1313, Academic Press, London as well as Seals D F and Courtneidge S A, 2003, Genes and Development, 17:7-30.

Some specific examples of important ADAM metalloproteases include the TNFα-converting enzyme, TACE or ADAM17, that is currently an important target for anti-inflammatory drugs (Moss M L et al., 2001, Drug Discov Today, 6:417-426 and Black R A; 2002, Int J Biochem Cell Biol, 34:1-5). Other members of the family are also likely to be good therapeutic targets. ADAM8 has been reported to be expressed almost exclusively in cells of the immune system, particularly B-cells, monocytes, eosinophils and granulocytes. ADAM8 therefore represents a therapeutic target for human immunologically-based diseases. ADAM15 is found in human aortic smooth muscle and cultured umbilical vein endothelial cells. While ADAM15 is not expressed in normal blood vessels, it has been detected in developing atherosclerotic lesions (Herren B et al., 1997, FASEB J, 11:173-180), and has also been shown to be up-regulated in osteoarthritic versus normal human cartilage (Bohm B B et al., 1999, Arthritis Rheum, 42:1946-1950). Thus ADAM15 may play a role in atherosclerosis and cartilage degenerative diseases. In addition, ADAM15 knockout mice have reduced neovascularization and smaller tumors compared to wildtype controls, suggesting that ADAM 15 may also be important in cancer (Horiuchi, K et al., 2003, Mol Cell Biol, 23:5614-5624.) The lymphocyte-specific expression of the ADAM28 suggests that it may have an important immunological function.

Excessive production of IgE is believed to be a major mediator of allergic responses. CD23, the low affinity receptor for IgE, is subject to ADAM-type metalloprotease-dependent proteolytic release of soluble extracellular fragments, which have been shown to cause upregulation of IgE production and induction of inflammatory cytokines (see Novak N et al, 2001, Curr Opin Immunol, 13:721-726 and Mayer R J et al., 2002, Inflamm Res, 51:85-90). Increased levels of soluble CD23 have been observed in allergic asthma, in chronic B-lymphocytic leukemia and in rheumatoid arthritis. Inhibition of the enzyme(s) responsible for CD23 processing may offer a therapeutic approach for the treatment of various immune-based diseases. ADAM metalloproteases also appear to be responsible for the release or shedding of soluble receptors (for example, CD30 and receptors for TNF), adhesion molecules (for example, L-selectin, ICAM-1, fibronectin), growth factors and cytokines (for example Fas ligand, TGF-α, EGF, HB-EGF, SCF IL-6, IL-1, TSH and M-CSF), and growth factor receptors (for example EGFR family members, such as Her-2 and Her-4, which have been implicated in the pathogenesis of different types of cancer) (Yarden Y and Sliwkowski M X, 2001, Nature Reviews 2:127-137). For example, Her-2 is over-expressed in 25-30% of human breast cancers and is associated with an increased risk of relapse and death (Slamon D J et al, 1987, Science, 235:177-182). ADAM17 has recently been shown to be critical for the regulated shedding of Her-4 (Rio C et al, 2000, J Biol Chem, 275:10379-10387). The protease responsible for Her-2 cleavage, known as Her-2 sheddase, is an unknown MMP that may also be a member of the ADAM family (Codony-Servat J et al, 1999, Cancer Res 59:1196-1201). Modulation of this activity might therefore have an important role in the modulation of human disease. For a review of the sheddase activity of ADAMs see Moss M L and Lambert N H, 2002, Essays Biochem, 38:141-153.

ADAM-TS (also shown as "ADAMTS") proteases have been identified as members of the ADAM family. These proteins are novel in that they contain unique thrombospondin (TS) type I motifs in addition to some of the structurally conserved domains of other ADAM family members. The ADAM-TSs are also distinguished from the ADAMs by their lack of cysteine-rich, EGF-like, transmembrane, and cytoplasmic domains. ADAM-TS proteins have also been shown to be associated with a number of pathological or human disease states. For example, ADAMTS-1 is a tumor-selective gene expressed in colon tumor cells and is also an inflammation-associated protein. A human ortholog of ADAMTS-1, known as METH-1, and the related protein METH-2 have been recently shown to have antiangiogenic activity, and these or other ADAM-TS family members may play important roles in regulating vascular development. ADAMTS-2 has been implicated in the normal development of the skin. This enzyme was long known as procollagen N-proteinase, a proteinase that proteolytically removes amino peptides in the processing of type I and type II procollagens to collagens, and it was shown to be deficient in the skin of individuals with the inherited connective tissue disorder type VIIC Ehlers-Danros syndrome. ADAMTS-4 and ADAMTS-11, are known as aggrecanase-1 and -2 because of their ability to cleave specific sites in aggrecan, a proteoglycan that maintains the mechanical properties of cartilage. Progressive degradation and depletion of aggrecan has been implicated in degenerative joint diseases such as osteoarthritis and inflammatory joint diseases such as rheumatoid arthritis. For a review of the ADAM-TS metalloproteases see Tang B L, 2001, Int J Biochem Cell Biol, 33:33-44 and Kaushal G P and S V Shah, 2000, J Clin Invest 105:1335-1337.

The metalloproteases are one of the older classes of proteinases and are found in bacteria, fungi as well as in higher organisms. Many enzymes contain the sequence HEXXH, which provides two histidine ligands for the zinc, whereas the third ligand is either a glutamic acid (thermolysin, neprilysin, alanyl aminopeptidase) or a histidine (astacin). Other families exhibit a distinct mode of binding of the Zn atom. Metalloproteases have therefore been isolated from a number of prokaryotic and eukaryotic sources. Acidic metalloproteases have been isolated from broad-banded copperhead and rattlesnake venoms. Neutral metalloproteases, specifically those having optimal activity at neutral pH have, for example, been isolated from *Aspergillus sojae*. Alkaline metalloproteases, for example, have been isolated from *Pseudomonas aeruginosa* and the insect pathogen *Xenorhabdus* luminescens. Inhibition of microbial metalloproteases may lead to growth inhibition and represent an antibiotic strategy. Inhibition of metalloproteases associated with snake venom or insect toxicity may also lead to new therapeutic strategies.

Potential therapeutic indications of MP inhibitors have been discussed in the literature. See for example, U.S. Pat. No. 6,500,847 (Bayer Corporation), U.S. Pat. No. 6,268,379 (DuPont Pharmaceuticals Company), U.S. Pat. No. 5,968,795 (Bayer Corporation), U.S. Pat. No. 5,892,112 (Glycomed Incorporated and The University of Florida), and U.S. Pat. No. 5,872,152 (British Biotech Pharmaceuticals Limited).

Matrix metalloprotease inhibitors are useful in treating diseases caused, at least in part, by breakdown of structural proteins. Although a variety of MMP inhibitors have been prepared in the relevant field, there is a continuing need for potent matrix metalloprotease inhibitors useful in treating diseases caused, at least in part, by breakdown of structural proteins. Applicants have found that, surprisingly, the compounds of the present invention are potent metalloprotease inhibitors.

OBJECTS OF THE INVENTION

With the foregoing in mind, it is an object of the present invention to provide a novel class of substituted carbocyclic or substituted heterocyclic compounds of the formulae I and IA, possessing therapeutic utility as metalloprotease inhibitors.

It is another object of the invention to provide a smaller class (relative to formula I) of novel substituted carbocyclic or substituted heterocyclic compounds of the formulae II and IIA, possessing therapeutic utility as metalloprotease inhibitors.

It is a further object of the invention to identify and claim a smaller class (relative to formuale I and II) of novel, substituted, cyclic hydroxamate derivatives of the formulae III, IIIA, IV, and IVA possessing therapeutic utility as metalloprotease inhibitors.

It is an additional object of the invention to identify and claim a smaller class (relative to formuale I and II) of novel, substituted, cyclic hydroxamate derivatives of the formula V, VA, VI, and VIA possessing therapeutic utility as metalloprotease inhibitors.

It is a further object of the invention to provide compounds of the formulae I, IA, II, IIA, III, IIIA, IV, IVA, V VA, VI, and VIA possessing one or more therapeutic utilities as a matrix metalloprotease (MMP) inhibitor, a sheddase inhibitor, and an ADAM inhibitor.

Another object of the invention to provide pharmaceutically useful compositions comprising such metalloprotease inhibitors, or more specifically MMP inhibitor, sheddase inhibitor, and/or ADAM inhibitor, of the formulae I, IA, II, IIA, III, IIIA, IV, IVA, V VA, VI, and VIA in therapeutically effective quantities in conjunction with one or more pharmaceutically acceptable carriers and/or excipients.

Yet another object of the invention is to provide a method of treatment for metalloprotease-related maladies or conditions and disease states that are characterized by unwanted metalloprotease activity.

It is another object to use the compounds of the invention in methodolgies for treating allergic conditions.

It is an object of the invention to provide Her-2 sheddase inhibiting compounds and also a further embodiment of utilizing compositions comprising such Her-2 sheddase inhibitors to treat neoplastic diseases.

It is a further object of the invention to provide compounds that are inhibitors of ADAM 10, ADAM15, ADAM28, ADAM33 embodied as anti-cancer agents.

It is a further object of the invention to provide compounds that are inhibitors of ADAM17/TACE (a.k.a. TNF alpha convertase) embodied as anti-inflammatory agents, and further embodied in methodologies for treating inflammatory disease states.

Further still, an object of the invention is to provide compounds that are inhibitors of matrix metalloprotease 12 (a.k.a. MMP 12) embodied as anti-inflammatory agents, and further embodied in methodologies for treating inflammatory disease states.

Additionally, the invention provides novel selective, small molecule inhibitors of matrix metalloproteinases which can be used to modulate the progression of the underlying diseases and to treat diseases associated with excessive MMP-induced tissue damage.

Other objects and embodiments of the present invention will be discussed below. However, there are additional embodiments of the invention, not specifically enumerated or described in the following specification, but which nevertheless fall within the spirit and scope of the subject matter of the present disclosure and of the appended claims. These additional embodiments will be readily appreciated by one skilled in the art without resort to undue experimentation.

SUMMARY OF THE INVENTION

The present invention provides, in its broadest embodiment, compounds having the formula IA:

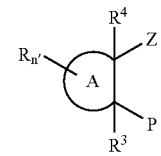

IA its enantiomers, diastereomers, enantiomerically enriched mixtures, racemic mixtures thereof, prodrugs, crystalline forms, non-crystalline forms, amorphous forms thereof, solvates thereof, metabolites thereof, and pharmaceutically acceptable salts, wherein:

ring A is a 3-13 membered carbocycle or heterocycle comprising carbon atoms, 0-3 carbonyl groups, 0-4 double bonds, and from 0-4 ring heteroatoms selected from the group consisting of O, N, NR, and $S(O)_p$, provided that ring A contains other than a S—S, O—O, or S—O bond;

n' is an integer from 1-3;

Z is selected from the group consisting of —$COR^5$, —$CO_2H$, —$CH_2CO_2H$, —$CO_2R^6$, —CONHOH, —CONHOR$^5$, —CON($R^6$)OH, —CONHOR$^6$, —NHR$^a$, —N(OH)C(O)R$^5$, —N(OH)CHO, —SH, —$CH_2SH$, —S(O)(=NH)R$^a$, —$SN_2H_2R^a$, —$PO(OR^g)_2$, —PO(OH)NHR$^a$,

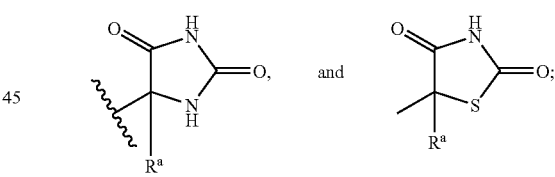

$R^g$ is independently selected from the group consisiting of H, $CH_2OCOR^a$,

P is —D-E-G-Q-L-T-X-Y, wherein

D is absent or is selected from the group consisting of O, $NR^{a1}$, C(O), C(O)O, OC(O), C(O)$NR^{a1}$, $NR^{a1}$C(O), OC(O)O, OC(O)$NR^{a1}$, $NR^{a1}$C(O)O, $NR^{a1}$C(O)$NR^{a1}$, $S(O)_p$, $S(O)_pNR^{a1}$, $NR^{a1}S(O)_p$, and $NR^{a1}SO_2NR^{a1}$;

E is absent or is selected from the group consisting of $C_{1-10}$alkylene, $C_{2-10}$ alkenylene, and $C_{2-10}$ alkynylene;

G is absent or is selected from the group consisting of O, $NR^{a1}$, $S(O)_p$, and C(O);

Q is absent or is selected from the group consisting of a $C_{3-13}$ carbocycle substituted with 0-5 $R^b$, and a 5-14 membered heterocycle comprising carbon atoms and 1-4 heteroatoms selected from the group consisting of N, O, and $S(O)_p$, and said heterocycle being substituted with 0-5 $R^b$;

L is absent or is selected from the group consisting of O, $NR^{a1}$, C(O), C(O)O, OC(O), C(O)$NR^{a1}$, $NR^{a1}$C(O), OC(O)O, OC(O)NR$^{a1}$, NR$^{a1}$C(O)O, NR$^{a1}$C(O)NR$^{a1}$, S(O)$_p$, S(O)$_p$NR$^{a1}$, NR$^{a1}$S(O)$_p$, and NR$^{a1}$SO$_2$NR$^{a1}$;

T is absent or is selected from the group consisting of C$_{1-10}$ alkylene, C$_{2-10}$ alkenylene, and C$_{2-10}$ alkynylene;

X is absent or is selected from the group consisting of O, NR$^{a1}$, S(O)$_p$, and C(O);

Y is selected from the group consisting of H, a C$_{3-13}$ carbocycle substituted with 0-5 R$^c$ and a 5-14 membered heterocycle comprising carbon atoms and 1-4 heteroatoms selected from the group consisting of N, O, and S(O)$_p$, and said heterocycle being substituted with 0-5 R$^c$; provided that D, E, G, Q, L, T, X and Y do not combine to form a N—N, N—O, O—N, O—O, S(O)$_p$—O, O—S(O)$_p$ or S(O)$_p$—S(O)$_p$ group;

R, at each occurrence, is independently selected from (C$_{1-10}$ alkylene substituted with 1-3 R$^{b1}$)-M, (C$_{2-10}$ alkenylene substituted with 1-3 R$^{b1}$)-M, (C$_{2-10}$ alkynylene substituted with 1-3 R$^{b1}$)-M, OH, Cl, F, Br, I, —CN, NO$_2$, CF$_3$, CF$_2$CF$_3$, CH$_2$F, CHF$_2$, CF$_2$CH$_3$, C(CH$_3$)$_2$F, OCF$_3$, OCHF$_2$, OCF$_2$CF$_3$, O(CR$^d$R$^{d1}$)$_r$-M, NR$^a$(CR$^d$R$^{d1}$)$_r$-M, OC(O)(CR$^d$R$^{d1}$)-M, NR$^a$C(O)(CR$^d$R$^{d1}$)$_r$-M, OC(O)O(CR$^d$R$^{d1}$)$_r$-M, OC(O)NR$^a$(CR$^d$R$^{d1}$)$_r$-M, NR$^a$C(O)O(CR$^d$R$^{d1}$)$_r$-M, NR$^a$C(O)NR$^{a1}$(CR$^d$R$^{d1}$)$_r$-M, S(O)$_p$(CR$^d$R$^{d1}$)$_r$-M, S(O)$_2$NR$^a$(CR$^d$R$^{d1}$)$_r$-M, NR$^a$S(O)$_2$(CR$^d$R$^{d1}$)$_r$-M, and NR$^a$S(O)$_2$NR$^{a1}$(CR$^d$R$^{d1}$)$_r$-M, (CR$^d$R$^{d1}$)$_r$P(O)(OR$^a$)$_2$, (CR$^d$R$^{d1}$)$_r$P(O)(OR$^a$)(NR$^d$R$^{d1}$), (CR$^d$R$^{d1}$)$_r$P(O)(N$^a$R$^{a1}$)$_2$, (CR$^d$R$^{d1}$)$_r$OP(O)(OR$^a$)$_2$, (CR$^d$R$^{d1}$)$_r$OP(O)(OR$^a$)(NR$^a$R$^{a1}$), (CR$^d$R$^{d1}$)$_r$OP(O)(NR$^a$R$^{a1}$)$_2$, (CR$^d$R$^{d1}$)$_r$NR$^a$P(O)(OR$^a$)$_2$, (CR$^d$R$^{d1}$)$_r$NR$^a$P(O)(OR$^a$)(NR$^a$R$^{a1}$), (CR$^d$R$^{d1}$)$_r$NR$^a$P(O)(NR$^a$R$^{a1}$)$_2$; C(=NR$^a$)NR$^{a1}$R$^{a2}$; C(=CR$^d$R$^{d1}$)NR$^{a1}$R$^{a2}$; a C$_{3-13}$ carbocycle substituted with 0-5 R$^d$, and a 5-14 membered heterocycle comprising carbon atoms and 1-4 heteroatoms selected from the group consisting of N, O, S(O)$_p$ and said heterocycle being substituted with 0-5 R$^d$; alternatively, two R, together with a carbon atom on A, form the group C$_A$=CR$^d$R$^{d1}$, where the atom C$_A$ is said atom on A;

M is selected from the group consisting of H, C$_{2-10}$ alkenylene substituted with 0-3 R$^{b1}$, C$_{2-10}$ alkynylene substituted with 0-3 R$^{b1}$, OR$^a$, Cl, F, Br, I, —CN, NO$_2$, NR$^a$R$^{a1}$, C(O)R$^a$, C(O)OR$^a$, C(O)NR$^a$R$^{a1}$, R$^a$NC(O)NR$^a$R$^{a1}$, OC(O)NR$^a$R$^{a1}$, NR$^a$C(O)OR$^a$, NR$^a$C(O)R$^a$, S(O)$_2$NR$^a$R$^{a1}$, NR$^a$S(O)$_2$R$^{a2}$, NR$^a$S(O)$_2$NR$^a$R$^{a1}$, OS(O)$_2$NR$^a$R$^{a1}$, S(O)R$_1$, CF$_3$, CF$_2$CF$_3$, CH$_2$F, CHF$_2$, CF$_2$CH$_3$, C(CH$_3$)$_2$F, OCF$_3$, OCF$_2$CF$_3$, OCHF$_2$, a C$_{3-13}$ carbocycle substituted with 0-5 R$^d$, and a 5-14 membered heterocycle comprising carbon atoms and 1-4 heteroatoms selected from the group consisting of N, O, S(O)$_p$ and said heterocycle being substituted with 0-5 R$^d$;

alternatively, R, at each occurrence, is independently selected from a C$_{1-10}$ alkylene-M$^1$, C$_{2-10}$ alkenylene-M$^1$, C$_{2-10}$ alkynylene-M$^1$, (CR$^d$R$^{d1}$)$_r$O(CR$^d$R$^{d1}$)$_r$-M$^1$, (CR$^d$R$^{d1}$)$_r$NR$^a$(CR$^d$R$^{d1}$)$_r$-M$^1$, (CR$^d$R$^{d1}$)$_r$C(O)(CR$^d$R$^{d1}$)$_r$-M$^1$, (CR$^d$R$^{d1}$)$_r$C(O)O(CR$^d$R$^{d1}$)$_r$-M$^1$, (CR$^d$R$^{d1}$)$_r$OC(O)(CR$^d$R$^{d1}$)$_r$-M$^1$, (CR$^d$R$^{d1}$)$_r$C(O)NR$^a$(CR$^d$R$^{d1}$)$_r$-M$^1$, (CR$^d$R$^{d1}$)$_r$NR$^a$C(O)(CR$^d$R$^{d1}$)$_r$-M$^1$, (CR$^d$R$^{d1}$)$_r$OC(O)O(CR$^d$R$^{d1}$)$_r$-M$^1$, (CR$^d$R$^{d1}$)$_r$OC(O)NR$^a$(CR$^d$R$^{d1}$)$_r$-M$^1$, (CR$^d$R$^{d1}$)$_r$NR$^a$C(O)O(CR$^d$R$^{d1}$)$_r$-M$^1$, (CR$^d$R$^{d1}$)$_r$NR$^a$C(O)NR$^{a1}$(CR$^d$R$^{d1}$)$_r$-M$^1$, (CR$^d$R$^{d1}$)$_r$S(O)$_p$(CR$^d$R$^{d1}$)$_r$-M$^1$, (CR$^d$R$^{d1}$)$_r$S(O)$_2$NR$^a$(CR$^d$R$^{d1}$)$_r$-M$^1$, (CR$^d$R$^{d1}$)$_r$NR$^a$S(O)$_2$(CR$^d$R$^{d1}$)$_r$-M$^1$, and (CR$^d$R$^{d1}$)$_r$NR$^a$S(O)$_2$NR$^{a1}$(CR$^d$R$^{d1}$)$_r$-M$^1$;

M$^1$ is selected from the group consisting of OR$^a$, Cl, F, Br, I, —CN, NO$_2$, NR$^a$R$^{a1}$, C(O)R$^a$, C(O)OR$^a$, C(O)NR$^a$R$^{a1}$, R$^a$NC(O)NR$^a$R$^{a1}$, OC(O)NR$^a$R a, R$^a$NC(O)OR$^a$, S(O)$_2$NR$^a$R$^{a1}$, NR$^a$S(O)$_2$R$^{a2}$, NR$^a$S(O)$_2$NR$^a$R$^{a1}$, OS(O)$_2$NR$^a$R$^{a1}$, S(O)$_p$R$^{a2}$, CF$_3$, CF$_2$CF$_3$, CH$_2$F, CHF$_2$, CF$_2$CH$_3$, C(CH$_3$)$_2$F, OCF$_3$, OCF$_2$CF$_3$ and a 5-14 membered non-aromatic heterocycle comprising carbon atoms and 1-4 heteroatoms selected from the group consisting of N, O, S(O)$_p$ and said heterocycle being substituted with 0-5 R$^d$; a C$_3$-C$_{13}$ carbocycle, C$_4$-C$_{14}$ heterocycle and wherein said C$_3$-C$_{13}$ carbocycle and C$_4$-C$_{14}$ heterocycle are substituted with 1-3 R$^h$, and CF$_3$, CF$_2$CF$_3$, CH$_2$F, CHF$_2$, CF$_2$CH$_3$, C(CH$_3$)$_2$F, OCF$_3$, OCHF$_2$, OCF$_2$CF$_3$ and OCH$_2$CF$_3$;

alternatively, when two R groups are attached to adjacent ring A atoms, together with the atoms to which they are attached they may form a 3-8 membered saturated, partially saturated or unsaturated ring comprised of carbon atoms and 0-3 heteroatoms selected from the group consisting of N, NR$^a$, O, and S(O)$_p$, wherein said ring may be benzene-fused and/or substituted with R$^d$;

alternatively, when two R groups are attached to the same ring A carbon, together with the carbon to which they are attached they may form a 3-8 membered saturated, partially saturated or unsaturated spiro-ring comprised of carbon atoms and 0-3 heteroatoms selected from the group consisting of N, NR$^a$, O, and S(O)$_p$, wherein said spiro-ring may be benzene-fused and/or substituted with R$^d$;

provided that either two or more R or M, M$^1$ and the atom to which they are attached do not combine to form a N—N, N—O, O—N, O—O, N-halogen, O-halogen, S-halogen, S(O)$_p$—O, O—S(O)$_p$, S(O)$_p$—S(O)$_p$ group, or C(O)F, C(O)Cl, C(O)Br, or C(O)I reactive group;

R$^a$, R$^{a1}$, and R$^{a2}$ at each occurrence are independently selected from the group consisting of H, C$_1$-C$_8$ alkyl, C$_2$-C$_8$ alkenyl, C$_2$-C$_8$ alkynyl, wherein said alkyl, alkenyl and alkynyl groups are optionally substituted with O(primary, secondary, or tertiary)C$_1$-C$_8$, OH, Cl, F, Br, I, =O, —CN, NO$_2$, alkylamino, dialkylamino, alkarylamino, arylamino, alkylcarbonyl, aralkylcarbonyl, arylcarbonyl, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamidoalkyl, N-alkylsufonamidodialkyl, alkylamidosulfonate, dialkylamidosulfonate, alkylsulfinyl, alkylsulfonyl, CF$_3$, CF$_2$CF$_3$, CH$_2$F, CHF$_2$, CF$_2$CH$_3$, C(CH$_3$)$_2$F, OCF$_3$, OCF$_2$CF$_3$ and OCH$_2$CF$_3$; C$_3$-C$_{10}$ carbocycle, heterocycles, C$_3$-C$_{10}$ carbocyclylalkyl, heterocyclylalkyl and wherein said C$_3$-C$_{10}$ carbocycle, heterocycles, C$_3$-C$_{10}$ carbocyclylalkyl, and heterocyclylalkyl may be optionally substituted with one or more substituents selected from the group consisting of C$_1$-C$_8$ alkyl, O(primary, secondary, or tertiary)C$_1$-C$_8$, OH, Cl, F, Br, I, =O, —CN, NO$_2$, alkylamino, dialkylamino, alkarylamino, arylamino, alkylcarbonyl, aralkylcarbonyl, arylcarbonyl, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamido-alkyl, N-alkylsufonamidodialkyl, alkylamidosulfonate, dialkylamidosulfonate, alkylsulfinyl, alkylsulfonyl, CF$_3$, CF$_2$CF$_3$, CH$_2$F, CHF$_2$, CF$_2$CH$_3$, C(CH$_3$)$_2$F, OCF$_3$, OCF$_2$CF$_3$ and OCH$_2$CF$_3$;

alternatively, R$^a$ and R$^{a1}$ taken together with the nitrogen to which they are attached form a 4 to 8 membered ring containing from 0-1 additional heteroatoms selected from the group consisting of N, O, and S, wherein said ring may be substituted with R$^d$;

R$^b$ at each occurrence is independently selected from the group consisting of C$_{1-6}$ alkyl optionally substituted with R$^{c1}$, O(primary, secondary, or tertiary)C$_1$-C$_8$, OH, Cl, F, Br, I, =O, —CN, NO$_2$, NR$^a$R$^{a1}$, C(O)R$^a$, C(O)OR$^a$, C(O)

$NR^aR^{a1}$, $R^aNC(O)NR^aR^a$, $OC(O)NR^aR^{a1}$, $R^aNC(O)$ $OR^{a1}$, $S(O)_2 NR^aR^{a1}$, $NR^aS(O)_2R^{a2}NR^aS(O)_2 NR^aR^{a1}$, $OS(O)_2 NR^aR^{a1}S(O)_p R^{a2}$, $CF_3$, $CF_2CF_3$, $CH_2F$, $CHF_2$, $CF_2CH_3$, $C(CH_3)_2F$, $OCF_3$, $OCHF_2$, $OCF_2CF_3$ and $OCH_2CF_3$; $C_{3-10}$ carbocyclic residue, and a 5-14 membered heterocyclic system containing from 1-4 heteroatoms selected from the group consisting of N, O, and S, $C_3$-$C_{10}$ carbocyclyl($C_{1-8}$)alkyl, and 5-14 heterocyclyl-($C_{1-8}$)alkyl and said $C_{3-10}$ carbocyclic residue, heterocyclic system, $C_3$-$C_{10}$ carbocyclyl($C_{1-8}$)alkyl, and 5-14 heterocyclyl($C_{1-8}$)alkyl are optionally substituted with $R^{c1}$;

$R^{b1}$ at each occurrence is independently selected from the group consisting of $OR^a$, F, =O, —CN, $NO_2$, $NR^aR^{a1}$ and $S(O)_pR^a$, $R^c$ at each occurrence is independently selected from the group consisting of $C_{1-6}$ alkyl optionally substituted with $R^{c1}$, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^a$, $OC(O)$ $NR^aR^{a1}$, $R^aNC(O)OR^{a1}$, $S(O)_2 NR^aR^{a1}$, $NR^aS(O)_2R^{a2}$, $NR^aS(O)_2 NR^aR^{a1}$, $OS(O)_2 NR^aR^{a1}$, $S(O)_pR^{a2}$, $CF_3$, $CF_2CF_3$, $CH_2F$, $CHF_2$, $CF_2CH_3$, $C(CH_3)_2F$, $OCF_3$, $OCHF_2$, $OCF_2CF_3$ and $OCH_2CF_3$; a $C_{3-10}$ carbocyclic residue, and a 5-14 membered heterocyclic system containing from 1-4 heteroatoms selected from the group consisting of N, O, and S, $C_3$-$C_{10}$ carbocyclyl($C_{1-8}$)alkyl, and 5-14 heterocyclyl($C_{1-8}$)alkyl; said $C_{3-10}$ carbocyclic residue, heterocyclic system $C_3$-$C_{10}$ carbocyclyl($C_{1-8}$)alkyl, and 5-14 heterocyclyl($C_{1-8}$)alkyl are optionally substituted with $R^{c1}$.

$R^{c1}$ at each occurrence is independently selected from the group consisting of $C_{1-6}$ alkyl, $OR^a$, Cl, F, Br, I, =O, —CN, $NO_2$, $NR^aR^{a1}$, $C(O)R^a$, $C(O)OR^a$, $C(O)NR^aR^{a1}$, $OC(O)NR^aR^{a1}$, $R^aNC(O)OR^a$, $S(O)_2NR^aR^{a1}$, $NR^aS(O)_2 R^{a2}$, $NR^aS(O)_2NR^aR^{a1}$, $S(O)_pR^a$, $CF_3$, and $CF_2CF_3$, $CH_2F$, and $CHF_2$;

$R^d$ at each occurrence is independently selected from the group consisting of H, $C_{1-6}$ alkyl optionally substituted with $R^{c1}$, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^a$, $OC(O)NR^aR^{a1}$, $R^aNC(O)OR^{a1}$, $S(O)_2 NR^aR^{a1}$, $NR^aS(O)_2 R^a$, $NR^aS(O)_2 NR^aR^{a1}$, $OS(O)_2 NR^aR^{a1}$, $S(O)_pR^{a2}$, $CF_3$, $CF_2CF_3$, $CH_2F$, $CHF_2$, $CF_2CH_3$, $C(CH_3)_2F$, $OCF_3$, $OCHF_2$, $OCF_2CF_3$ and $OCH_2CF_3$; $C_{3-10}$ carbocyclic residue, and a 5-14 membered heterocyclic system containing from 1-4 heteroatoms selected from the group consisting of N, O, and S, $C_3$-$C_{10}$ carbocyclyl($C_{1-8}$)alkyl, and 5-14 heterocyclyl($C_{1-8}$)alkyl; said $C_{3-10}$ carbocyclic residue, heterocyclic system $C_3$-$C_{10}$ carbocyclyl($C_{1-8}$)alkyl, and 5-14 heterocyclyl($C_{1-8}$)alkyl optionally substituted with $R^{c1}$.

$R^{d1}$ at each occurrence is independently selected from the group consisting of H, $C_{1-6}$ alkyl optionally substituted with $R^{c1}$, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^a$, $OC(O)NR^aR^{a1}$, $R^aNC(O)OR^{a1}$, $S(O)_2 NR^aR^{a1}$, $NR^aS(O)_2 R^{a2}$, $NR^aS(O)_2 NR^aR^{a1}$, $OS(O)_2 NR^aR^{a1}$, $S(O)_pR^{a2}$, $CF_3$, $CF_2CF_3$, $CH_2F$, $CHF_2$, $CF_2CH_3$, $C(CH_3)_2F$, $OCF_3$, $OCHF_2$, $OCF_2CF_3$ and $OCH_2CF_3$; $C_{3-10}$ carbocyclic residue, and a 5-14 membered heterocyclic system containing from 1-4 heteroatoms selected from the group consisting of N, O, and S, $C_3$-$C_{10}$ carbocyclyl($C_{1-8}$)alkyl, and 5-14 heterocyclyl($C_{1-8}$)alkyl; said $C_{3-10}$ carbocyclic residue, heterocyclic system $C_3$-$C_{10}$ carbocyclyl($C_{1-8}$)alkyl, and 5-14 heterocyclyl($C_{1-8}$)alkyl optionally substituted with $R^{c1}$.

alternatively, $R^d$ and $R^{d1}$ taken together with the atom to which they are attached form a 4 to 8 membered ring containing from 0-1 heteroatoms selected from the group consisting of N, O, and S, wherein said ring may be substituted with $R^d$;

$R^h$ at each occurrence is independently selected from the group consisting of $OR^j$, $NR^jR^a$, $COR^j$, $C(O)OR^j$, $C(O)NR^jR^a$, $NR^aC(O)NR^jR^{a1}$, $OC(O)NR^jR^a$, $S(O)_pNR^jR^{a1}$, $NR^aS(O)_pR^j$, $NR^aS(O)_pNR^jR^a$, $C_{1-6}$ alkyl substituted with $R^c$.

$R^j$ at each occurrence is independently selected from the group consisting of $CF_3$, $CH_2F$, $CHF_2$, $CF_2CF_3$, $C_1$-$C_8$ alkyl substituted with O(primary, secondary, or tertiary) $C_1$-$C_8$, OH, Cl, F, Br, I, =O, —CN, $NO_2$, alkylamino, dialkylamino, alkarylamino, arylamino, alkylcarbonyl, aralkylcarbonyl, arylcarbonyl, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamidoalkyl, N-alkylsufonamidodialkyl, alkylamidosulfonate, dialkylamidosulfonate, alkylsulfinyl, alkylsulfonyl, $CF_3$, $CF_2CF_3$, $CH_2F$, $CHF_2$, $CF_2CH_3$, $C(CH_3)_2F$, $OCF_3$, $OCHF_2$, $OCF_2CF_3$ and $OCH_2CF_3$; $C_2$-$C_8$ alkenyl, $C_2$-$C_8$ alkynyl, wherein said alkenyl and alkynyl groups are optionally substituted with $C_1$-$C_8$ alkyl, O(primary, secondary, or tertiary)$C_1$-$C_8$, OH, Cl, F, Br, I, =O, —CN, $NO_2$, alkylamino, dialkylamino, alkarylamino, arylamino, alkylcarbonyl, aralkylcarbonyl, arylcarbonyl, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamidoalkyl, N-alkylsufonamidodialkyl, alkylamidosulfonate, dialkylamidosulfonate, alkylsulfinyl, alkylsulfonyl, $CF_3$, $CF_2CF_3$, $CH_2F$, $CHF_2$, $CF_2CH_3$, $C(CH_3)_2F$, $OCF_3$, $OCHF_2$, $OCF_2CF_3$ and $OCH_2CF_3$; $C_3$-$C_{10}$ carbocycle, heterocycles, $C_3$-$C_{10}$ carbocyclylalkyl, heterocyclylalkyl and wherein said $C_3$-$C_{10}$ carbocycle, heterocycles, $C_3$-$C_{10}$ carbocyclylalkyl, and heterocyclylalkyl may be optionally substituted with one or more substituents selected from the group consisting of O(primary, secondary, or tertiary)$C_1$-$C_8$, OH, Cl, F, Br, I, =O, —CN, $NO_2$, alkylamino, dialkylamino, alkarylamino, arylamino, alkylcarbonyl, aralkylcarbonyl, arylcarbonyl, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamidoalkyl, N-alkylsufonamidodialkyl, alkylamidosulfonate, dialkylamidosulfonate, alkylsulfinyl, alkylsulfonyl, $CF_3$, $CF_2CF_3$, $CH_2F$, $CHF_2$, $CF_2CH_3$, $C(CH_3)_2F$, $OCF_3$, $OCF_2CF_3$ and $OCH_2CF_3$, with the proviso that said $C_3$-$C_{10}$ carbocycle can not be a phenyl group and $C_3$-$C_{10}$ carbocyclylalkyl can not be a benzyl group;

$R^3$ is H or $C_{1-6}$ alkyl $OR^a$, $NR^aR^{a1}$, and $S(O)_pR^a$, $R^4$ is selected from the group consisting of H, $C_{1-6}$ alkyl, $OR^a$, $NR^aR^{a1}$, and $S(O)_pR^a$, $R^5$ at each occurrence is selected from the group consisting of $C_{1-10}$ alkyl substituted with 0-2 $R^b$, and $C_{1-8}$ alkyl substituted with 0-2 $R^e$;

$R^e$ at each occurrence is selected from the group consisting of phenyl substituted with 0-2 $R^b$ and biphenyl substituted with 0-2 $R^b$;

$R^6$ at each occurrence is selected from the group consisting of phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$-$C_5$ alkyl)-1,3-dioxacyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$alkyl-$NR^7R^{7a}$, —$CH(R^8)OC(O)R^9$, and —$CH(R^8)OC(O)OR^9$;

alternatively, $R^4$ and $R^6$ can be taken together to form a 5-10 membered ring optionally substituted with $R^c$;

$R^7$ is selected from the group consisting of H, $C_{10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from the group consisting of H, $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from the group consisting of H and $C_{1-4}$ linear alkyl;

$R^9$ is selected from the group consisting of H, $C_{1-8}$ alkyl substituted with 1-2 $R^f$, $C_{3-8}$ cycloalkyl substituted with 1-2 $R^f$, and phenyl substituted with 0-2 $R^b$;

$R^f$ at each occurrence is selected from the group consisting of H, $C_{1-4}$ alkyl, $C_{3-8}$ cycloalkyl, $C_{1-5}$ alkoxy, and phenyl substituted with 0-2 $R^b$;

p at each occurrence is 0, 1, and 2; and r at each occurrence is 0, or an integer from 1 to 10.

As defined above, Formula IA is intended to be the union of Formulae I-VI and more specific embodiments as described below. Specifically, Formulae I-VI and other embodiments explicitly provide for 1, 2, and 3 substituents to be present on ring A. Accordingly, Formula IA provides for ring A to be substituted by 1, 2, or 3 R groups.

In another embodiment of the invention, compounds of formula I are provided. As with compounds of formula IA, these compounds also possess utility as metalloprotease inhibitors, and preferably as matrix metalloprotease inhibitors, sheddase inhibitors, and inhibitors of ADAM metalloproteases. Compounds of formula IA, like those of formula I, are either substituted carbocyclic or substituted heterocyclic compounds having the following general structure:

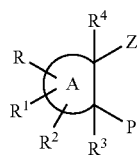
I

The variables in Formula I have the same meaning as those defined above for Formula IA. Specifically, R, $R^1$, and $R^2$ are defined identically.

In another embodiment of the invention compounds of the formula IIA and II are provided. This group of compounds, like those of formula I, also possess utility as metalloprotease inhibitors, and preferably as matrix metalloprotease inhibitors, sheddase inhibitors, and inhibitors of ADAM metalloproteases. Compounds of formula IIA and II, like those of formula I, are either substituted carbocyclic or substituted heterocyclic compounds. Compounds of formula IIA have the following general structure:

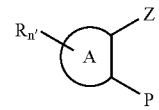
IIA wherein ring A is a 4-10 membered non-aromatic carbocycle or heterocycle comprising carbon atoms, 0-1 carbonyl groups and from 0-2 ring heteroatoms selected from the group consisting of O, N, NR, provided that ring A contains other than a O—O bond. Variable n' is 1 or 2. A subset of compounds of Formula IIA conform to Formula II, which has the following structure:

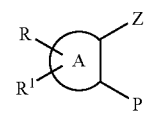
II

The A-ring substituent groups R, $R^1$, P, and Z are described in full detail below with regard to the description of the preferred embodiments; for the sake of summary suffice it to say that each of the substituent groups is defined as a more preferred subset of the corresponding substituent group as defined for the formula I compounds.

In a further preferred embodiment the invention provides for cyclic hydroxamate compounds and/or derivatives possessing potent metalloprotease inhibitory activity, these compounds having the structural formula IIIA or IVA:

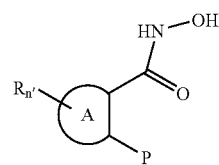
IIIA

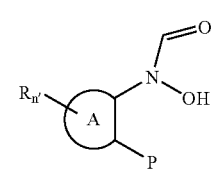
IVA wherein ring A is a 5-7 membered non-aromatic carbocycle or heterocycle comprising carbon atoms, 0-1 carbonyl groups and from 0-2 ring heteroatoms selected from the group consisting of O, N, NR, provided that ring A contains other than a O—O bond. Variable n' is 1 or 2. Subsets of compounds according to Formulae IIIA and IVA are those of Formulae III and IV, respectively. The structures of these compounds are shown below:

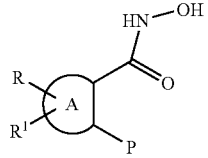

III

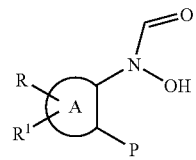

IV

The A-ring substituent groups R, R¹, and P are described in full detail below with regard to the description of the preferred embodiments; for the sake of summary suffice it to say that each of the substituent groups is defined as a more preferred subset of the corresponding substituent group as defined for the formula I compounds.

In another preferred embodiment the invention provides for cyclic hydroxamate compounds and/or derivatives possessing potent metalloprotease inhibitory activity, these compounds having the structural formulas VA and VIA

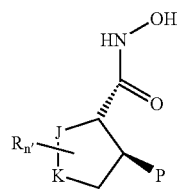

VA

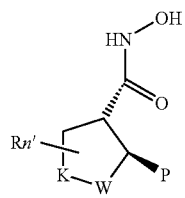

VIA

Variable n' is 1 or 2. A subset of compounds according for Formulae VA and VIA are those of Formulae V and VI, which have the following structures:

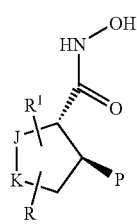

V

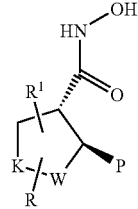

VI

The invention also provides a method for treating a disease associated with unwanted metalloprotease activity in a mammalian subject, the method comprising administering to said mammal in need thereof, an effective amount of a metalloprotease inhibitor compound of formulae I, IA, II, IIA, III, IIIA, IV, IVA, V, VA, VI, or VIA.

The instant invention further provides a method for treating a diseases modulated by metalloproteases in a mammalian subject, wherein the disease is selected from the group consisting of arthritis, cancer, cardiovascular disorders, skin disorders, inflammation and allergic conditions by administering to said mammal in need of such treatment, an effective amount of a metalloprotease inhibitor compound of formulae I, IA, II, IIA, III, IIIA, IV, IVA, V, VA, VI, or VIA.

The present invention also provides a method of inhibiting pathological changes mediated by elevated levels of matrix metalloproteases, such as MMP 12, in mammals comprising administering to said mammal in need thereof a therapeutically effective amount of a matrix metalloprotease inhibiting compound of formulae I, IA, II, IIA, III, IIIA, IV, IVA, V, VA, VI, or VIA.

The invention further relates to a method for treating a disease associated with unwanted sheddase activity, such as Her-2 sheddase, other growth factor sheddase and cytokine sheddases, in a mammalian subject, the method comprising administering to said mammal in need thereof, an effective amount of a sheddase inhibitor compound of formulae I, IA, II, IIA, III, IIIA, IV, IVA, V, VA, VI, or VIA.

The instant invention also provides a method for treating a disease associated with unwanted TNF-α converting enzyme and ADAM 10 activity in a mammalian subject, the method comprising administering to said mammal in need thereof, an effective amount of a TNF-α converting enzyme inhibitor compound of formulae I, IA, II, IIA, III, IIIA, IV, IVA, V, VA, VI, or VIA.

Additionally, the invention also provides a pharmaceutical composition for use in therapy, comprising a compound according to the invention in a therapeutically effective amount, and at least a pharmaceutically-acceptable diluent or carrier, and other optional excipients necessitated by the dosage form and the intended route of administration.

DESCRIPTION OF THE PREFERRED EMBODIMENTS

The instant invention provides new compounds and pharmaceutical compositions of matter for treating pathological conditions which are associated with the rapid unregulated breakdown of extracellular matrix tissue by MMPs including MMP 12 and MMP 13. Some of these conditions include rheumatoid arthritis, osteoarthritis, septic arthritis, corneal, epidermal or gastric ulceration; periodontal disease, proteinuria, coronary thrombosis associated with atherosclerotic plaque rupture and bone disease. The new compounds of the invention are also useful for treating tumor metastasis and angiogenesis which also appears to be dependent on MMP activity. Also, since the cycle of tissue damage and response is associated with a worsening of the disease state, limiting MMP-induced tissue damage due to elevated levels of the proteinases with the specific inhibitors of the instant invention is a generally useful therapeutic approach to many of these debilitating diseases. The compounds of the invention are also inhibitors TNFα converting enzyme and sheddases including Her2 sheddase and HB-EGF sheddase and other growth factor and cytokine sheddase.

The instant invention also provides novel compounds, novel compositions, methods of their use and methods of their manufacture, such compounds generally pharmacologically useful as agents in those disease states alleviated by the inhibition or antagonism of matrix metalloproteases, metalloproteases, ADAMs, ADAM-TS and/or tumor necrosis factor-α (TNF), which pathologically involve aberrant extracellular matrix degradation, shedding of cell surface protein ectodomains, and/or TNF synthesis, such disease states including arthritis, tumor metastasis and diabetes. The aforementioned pharmacologic activities are useful in the treatment of mammals.

More specifically, the instant invention relates to new anticancer, anti-inflammatory and immunomodulatory cyclic hydroxamate bioactive compounds and pharmaceutical compositions thereof that act via antagonism of MMPs, ADAMs, ADAMTS, sheddase such as Her2 sheddase and therefore leading to new therapeutic modalities.

The present invention also relates to compounds that inhibit metalloproteases such as MMP12, ADAMs family metalloproteases including TNF α-convertase, Adam-10 and related sheddases such as Her2 sheddase, heparin-binding EGF sheddase and are therefore useful in the treatment of mammals having disease states alleviated by the inhibition of such metalloprotease activity.

The instant invention also relates to inhibitors of ADAM metalloproteases which are responsible for the release or shedding of soluble receptors (for example, CD30 and receptors for TNF), adhesion molecules (for example, L-selectin, ICAM-1, fibronectin), growth factors and cytokines (for example Fas ligand, TGF-α, EGF, HB-EGF, SCF IL-6, IL-1, TSH and M-CSF), and growth factor receptors (for example EGFR family members, such as Her-2 and Her-4, which have been implicated in the pathogenesis of different types of cancer.)

More in particular, the present invention provides new compounds having the formula IA:

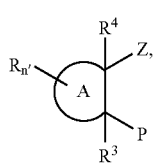

IA its enantiomers, diastereomers, enantiomerically enriched mixtures, racemic mixtures thereof, prodrugs, crystalline forms, non-crystalline forms, amorphous forms thereof, solvates thereof, metabolites thereof, and pharmaceutically acceptable salts, wherein:

ring A is a 3-13 membered carbocycle or heterocycle comprising carbon atoms, 0-3 carbonyl groups, 0-4 double bonds, and from 0-4 ring heteroatoms selected from the group consisting of O, N, NR, and $S(O)_p$, provided that ring A contains other than a S—S, O—O, or S—O bond;

n' is 1, 2, or 3;

Z is selected from the group consisting of —$COR^5$, —$CO_2H$, —$CH_2CO_2H$, —$CO_2R^6$, —CONHOH, —CONHOR$^5$, —CON($R^6$)OH, —CONHOR$^6$, —NHR$^a$, —N(OH)C(O)R$^5$, —N(OH)CHO, —SH, —$CH_2SH$, —S(O)(=NH)R$^a$, —$SN_2H_2R^a$, —PO(OR$^g$)$_2$, —PO(OH)NHR$^a$,

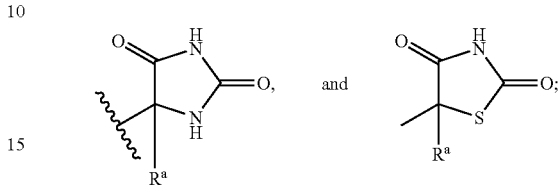

$R^g$ is independently selected from the group consisiting of H, $CH_2OCOR^a$,

P is —D-E-G-Q-L-T-X-Y, wherein

D is absent or is selected from the group consisting of O, $NR^{a1}$, C(O), C(O)O, OC(O), C(O)$NR^{a1}$, $NR^{a1}$C(O), OC(O)O, OC(O)$NR^{a1}$, $NR^{a1}$, C(O)O, $NR^{a1}$C(O)$NR^{a1}$, $S(O)_p$, $S(O)_pNR^{a1}$, $NR^{a1}S(O)_p$, and $NR^{a1}SO_2NR^{a1}$;

E is absent or is selected from the group consisting of $C_{1-10}$alkylene, $C_{2-10}$ alkenylene, and $C_{2-10}$ alkynylene;

G is absent or is selected from the group consisting of O, $NR^{a1}$, $S(O)_p$, and C(O);

Q is absent or is selected from the group consisting of a $C_{3-13}$ carbocycle substituted with 0-5 $R^b$, and a 5-14 membered heterocycle comprising carbon atoms and 1-4 heteroatoms selected from the group consisting of N, O, and $S(O)_p$, and said heterocycle being substituted with 0-5 $R^b$;

L is absent or is selected from the group consisting of O, $NR^{a1}$, C(O), C(O)O, OC(O), C(O)$NR^{a1}$, $NR^{a1}$C(O), OC(O)O, OC(O)$NR^{a1}$, $NR^{a1}$C(O)O, $NR^{a1}$C(O)$NR^{a1}$, $S(O)_p$, $S(O)_pNR^{a1}$, $NR^{a1}S(O)_p$, and $NR^{a1}SO_2NR^{a1}$;

T is absent or is selected from the group consisting of $C_{1-10}$ alkylene, $C_{2-10}$ alkenylene, and $C_{2-10}$ alkynylene;

X is absent or is selected from the group consisting of O, $NR^{a1}$, $S(O)_p$, and C(O);

Y is selected from the group consisting of H, a $C_{3-13}$ carbocycle substituted with 0-5 $R^c$ and a 5-14 membered heterocycle comprising carbon atoms and 1-4 heteroatoms selected from the group consisting of N, O, and $S(O)_p$, and said heterocycle being substituted with 0-5 $R^c$; provided that D, E, G, Q, L, T, X and Y do not combine to form a N—N, N—O, O—N, O—O, $S(O)_p$—O, O—$S(O)_p$ or $S(O)_p$—$S(O)_p$ group;

R, at each occurrence, is independently selected from ($C_{1-10}$ alkylene substituted with 1-3 $R^{b1}$)-M, ($C_{2-10}$ alkenylene substituted with 1-3 $R^{b1}$)-M, ($C_{2-10}$ alkynylene substituted with 1-3 $R^{b1}$)-M, OH, Cl, F, Br, I, —CN, $NO_2$, $CF_3$, $CF_2CF_3$, $CH_2F$, $CHF_2$, $CF_2CH_3$, $C(CH_3)_2F$, $OCF_3$, $OCF_2CF_3$, $OCHF_2$, $O(CR^dR^{d1})_r$-M, $NR^a(CR^dR^{d1})_r$-M, $OC(O)(CR^dR^{d1})_r$-M, $NR^aC(O)(CR^dR^{d1})_r$-M, OC(O)O $(CR^dR^{d1})_r$-M, $OC(O)NR^a(CR^dR^{d1})_r$-M, $NR^aC(O)O$ $(CR^dR^{d1})_r$-M, $NR^aC(O)NR^{a1}(CR^dR^{d1})_r$-M, $S(O)_p$ $(CR^dR^{d1})_r$-M, $S(O)_2NR^a(CR^dR^{d1})_r$-M, $NR^aS(O)_2$ $(CR^dR^{d1})_r$-M, and $NR^aS(O)_2NR^{a1}(CR^dR^{d1})_r$-M, $(CR^dR^{d1})_rP(O)(OR^a)_2$, $(CR^dR^{d1})_rP(O)(OR^a)(NR^aR^{d1})$, $(CR^dR^{d1})_rP(O)(NR^aR^{a1})_2$, $(CR^dR^{d1})_rOP(O)(OR^a)_2$, $(CR^dR^{d1})_rOP(O)(OR^a)(NR^aR^{a1})$, $(CR^dR^{d1})_rOP(O)$ $(NR^aR^{a1})_2$, $(CR^dR^{d1})_rNR^aP(O)(OR^a)_2$, $(CR^dR^{d1})_rNR^aP$ $(O)(OR^a)(NR^aR^{a1})$, $(CR^dR^{d1})_rNR^aP(O)(NR^aR^{a1})_2$; $C(=NR^a)NR^{a1}R^{a2}$; $C(=CR^dR^{d1})NR^{a1}R^{a2}$ a $C_{3-13}$ carbocycle substituted with 0-5 $R^d$, and a 5-14 membered heterocycle comprising carbon atoms and 1-4 heteroatoms selected from the group consisting of N, O, S(O)$_p$ and said heterocycle being substituted with 0-5 $R^d$; alternatively, two R, together with a carbon atom on A, form the group $C_A$=$CR^dR^d$, where the atom $C_A$ is said atom on A;

M is selected from the group consisting of H, $C_{2-10}$ alkenylene substituted with 0-3 $R^{b1}$, $C_{2-0}$ alkynylene substituted with 0-3 $R^{b1}$, $OR^a$, Cl, F, Br, I, —CN, NO$_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $NR^aC(O)OR^a$, $NR^aC(O)R^a$, $S(O)_2NR^aR^{a1}$, $NR^aS(O)_2R^{a2}$, $NR^aS(O)_2NR^aR^{a1}$, $OS(O)_2NR^aR^{a1}$, $S(O)_pR^{a2}$, CF$_3$, CF$_2$CF$_3$, CH$_2$F, CHF$_2$, CF$_2$CH$_3$, C(CH$_3$)$_2$F, OCF$_3$, OCHF$_2$, a $C_{3-13}$ carbocycle substituted with 0-5 $R^d$, and a 5-14 membered heterocycle comprising carbon atoms and 1-4 heteroatoms selected from the group consisting of N, O, S(O)$_p$ and said heterocycle being substituted with 0-5 $R^d$;

alternatively, R, at each occurrence, is independently selected from $C_{1-10}$ alkylene-$M^1$, $C_{2-10}$ alkenylene-$M^1$, $C_{2-10}$ alkynylene-$M^1$, $(CR^dR^{d1})_rO(CR^dR^{d1})_r$-$M^1$, $(CR^dR^{d1})_rNR^a(CR^dR^{d1})_r$-$M^1$, $(CR^dR^{d1})_rC(O)(CR^dR^{d1})_r$-$M^1$, $(CR^dR^{d1})_rC(O)O(CR^dR^{d1})_r$-$M^1$, $(CR^dR^{d1})_rOC(O)(CR^dR^{d1})_r$-$M^1$, $(CR^dR^{d1})_rC(O)NR^a(CR^dR^{d1})_r$-$M^1$, $(CR^dR^{d1})_rNR^aC(O)(CR^dR^{d1})_r$-$M^1$, $(CR^dR^{d1})_rOC(O)O(CR^dR^{d1})_r$-$M^1$, $(CR^dR^{d1})_rOC(O)NR^a(CR^dR^{d1})_r$-$M^1$, $(CR^dR^{d1})_rNR^aC(O)O(CR^dR^{d1})_r$-$M^1$, $(CR^dR^{d1})_rNR^aC(O)NR^{a1}(CR^dR^{d1})_r$-$M^1$, $(CR^dR^{d1})_rS(O)_p(CR^dR^{d1})_r$-$M^1$, $(CR^dR^{d1})_rS(O)_2NR^a(CR^dR^{d1})_r$-$M^1$, $(CR^dR^{d1})_rNR^aS(O)_2(CR^dR^{d1})_r$-$M^1$, and $(CR^dR^{d1})_rNR^aS(O)_2NR^{a1}(CR^dR^{d1})_r$-$M^1$;

$M^1$ is selected from the group consisting of $OR^a$, Cl, F, Br, I, —CN, NO$_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^a$, $S(O)_2NR^aR^{a1}$, $NR^aS(O)_2R^{a2}$, $NR^aS(O)_2NR^aR^{a1}$, $OS(O)_2NR^aR^{a1}$, $S(O)_pR^{a2}$, CF$_3$, CF$_2$CF$_3$, CH$_2$F, CHF$_2$, CF$_2$CH$_3$, C(CH$_3$)$_2$F, OCF$_3$, OCF$_2$CF$_3$, and a 5-14 membered non-aromatic heterocycle comprising carbon atoms and 1-4 heteroatoms selected from the group consisting of N, O, S(O)$_p$ and said heterocycle being substituted with 0-5 $R^d$; a $C_3$-$C_{13}$ carbocycle, $C_4$-$C_{14}$ heterocycle and wherein said $C_3$-$C_{13}$ carbocycle and $C_4$-$C_{14}$ heterocycle are substituted with 1-3 $R^h$, and CF$_3$, CF$_2$CF$_3$, CH$_2$F, CHF$_2$, CF$_2$CH$_3$, C(CH$_3$)$_2$F, OCF$_3$, OCHF$_2$, OCF$_2$CF$_3$ and OCH$_2$CF$_3$;

alternatively, when two R groups are attached to adjacent ring A atoms, together with the atoms to which they are attached they may form a 3-8 membered saturated, partially saturated or unsaturated ring comprised of carbon atoms and 0-3 heteroatoms selected from the group consisting of N, $NR^a$, O, and S(O)$_p$, wherein said ring may be benezene-fused and/or substituted with $R^d$;

alternatively, when two R groups are attached to the same ring A carbon, together with the carbon to which they are attached they may form a 3-8 membered saturated, partially saturated or unsaturated spiro-ring comprised of carbon atoms and 0-3 heteroatoms selected from the group consisting of N, $NR^a$, O, and S(O)$_p$, wherein said spiro-ring may be benezene-fused and/or substituted with $R^d$;

provided that either two or more R or M, $M^1$ and the atom to which they are attached do not combine to form a N—N, N—O, O—N, O—O, N-halogen, O-halogen, S-halogen, S(O)$_p$—O, O— S(O)$_p$, S(O)$_p$—S(O)$_p$ group, or C(O)F, C(O)Cl, C(O)Br, or C(O)I reactive group;

$R^a$, $R^{a1}$, and $R^{a2}$ at each occurrence are independently selected from the group consisting of H, $C_1$-$C_8$ alkyl, $C_2$-$C_8$ alkenyl, $C_2$-$C_8$ alkynyl, wherein said alkyl, alkenyl and alkynyl groups are optionally substituted with O(primary, secondary, or tertiary)$C_1$-$C_8$, OH, Cl, F, Br, I, =O, —CN, NO$_2$, alkylamino, dialkylamino, alkarylamino, arylamino, alkylcarbonyl, aralkylcarbonyl, arylcarbonyl, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamidoalkyl, N-alkylsufonamidodialkyl, alkylamidosulfonate, dialkylamidosulfonate, alkylsulfinyl, alkylsulfonyl, CF$_3$, CF$_2$CF$_3$, CH$_2$F, CHF$_2$, CF$_2$CH$_3$, C(CH$_3$)$_2$F, OCF$_3$, OCF$_2$CF$_3$ and OCH$_2$CF$_3$; $C_3$-$C_{10}$ carbocycle, heterocycles, $C_3$-$C_{10}$ carbocyclylalkyl, heterocyclylalkyl and wherein said $C_3$-$C_{10}$ carbocycle, heterocycles, $C_3$-$C_{10}$ carbocyclylalkyl, and heterocyclylalkyl may be optionally substituted with one or more substituents selected from the group consisting of $C_1$-$C_8$ alkyl, O(primary, secondary, or tertiary)$C_1$-$C_8$, OH, Cl, F, Br, I, =O, —CN, NO$_2$, alkylamino, dialkylamino, alkarylamino, arylamino, alkylcarbonyl, aralkylcarbonyl, arylcarbonyl, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamido-alkyl, N-alkylsufonamidodialkyl, alkylamidosulfonate, dialkylamidosulfonate, alkylsulfinyl, alkylsulfonyl, CF$_3$, CF$_2$CF$_3$, CH$_2$F, CHF$_2$, CF$_2$CH$_3$, C(CH$_3$)$_2$F, OCF$_3$, OCF$_2$CF$_3$ and OCH$_2$CF$_3$;

alternatively, $R^a$ and $R^{a1}$ taken together with the nitrogen to which they are attached form a 4 to 8 membered ring containing from 0-1 additional heteroatoms selected from the group consisting of N, O, and S, wherein said ring may be substituted with $R^d$;

$R^b$ at each occurrence is independently selected from the group consisting of $C_{1-6}$ alkyl optionally substituted with $R^{c1}$, O(primary, secondary, or tertiary)$C_1$-$C_8$, OH, Cl, F, Br, I, =O, —CN, NO$_2$, $NR^aR^{a1}$, $C(O)R^a$, $C(O)OR^a$, $C(O)NR^aR^{a1}$, $R^aNC(O)NR^aR^a$, $OC(O)NR^aR^{a1}$, $R^aNC(O)OR^{a1}$, $S(O)_2NR^aR^{a1}$, $NR^aS(O)_2R^{a2}$, $NR^aS(O)_2NR^aR^{a1}$, $OS(O)_2NR^aR^{a1}$, $S(O)_p R^{a2}$, CF$_3$, CF$_2$CF$_3$, CH$_2$F, CHF$_2$, CF$_2$CH$_3$, C(CH$_3$)$_2$F, OCF$_3$, OCHF$_2$, OCF$_2$CF$_3$ and OCH$_2$CF$_3$; $C_{3-10}$ carbocyclic residue, and a 5-14 membered heterocyclic system containing from 1-4 heteroatoms selected from the group consisting of N, O, and S, $C_3$-$C_{10}$ carbocyclyl($C_{1-8}$)alkyl, and 5-14 heterocyclyl-($C_{1-8}$)alkyl and said $C_{3-10}$ carbocyclic residue, heterocyclic system, $C_3$-$C_{10}$ carbocyclyl($C_{1-8}$)alkyl, and 5-14 heterocyclyl($C_{1-8}$)alkyl are optionally substituted with $R^{c1}$;

$R^{b1}$ at each occurrence is independently selected from the group consisting of $OR^a$, F, =O, —CN, NO$_2$, $NR^aR^{a1}$ and $S(O)_pR^a$, $R^c$ at each occurrence is independently selected from the group consisting of $C_{1-6}$ alkyl optionally substituted with $R^{c1}$, $OR^a$, Cl, F, Br, I, =O, —CN, NO$_2$, $NR^aR^{a1}$, $C(O)R^a$, $C(O)OR^a$, $C(O)NR^aR^{a1}$, $R^aNC(O)NR^aR^a$, $OC(O)NR^aR^{a1}$, $R^aNC(O)OR^{a1}$, $S(O)_2$ $NR^aR^{a1}$, $NR^aS(O)_2$ $R^{a2}$, $NR^aS(O)_2$ $NR^aR^{a1}$, $OS(O)_2$ $NR^aR^{a1}$, $S(O)_p$ $R^{a2}$, CF$_3$, CF$_2$CF$_3$, CH$_2$F, CHF$_2$, CF$_2$CH$_3$, C(CH$_3$)$_2$F, OCF$_3$, OCHF$_2$, OCF$_2$CF$_3$ and OCH$_2$CF$_3$; a $C_{3-10}$ carbocyclic residue, and a 5-14 membered heterocyclic system containing from 1-4 heteroatoms selected from the group consisting of N, O, and S, $C_3$-$C_{10}$ carbocyclyl($C_{1-8}$)alkyl, and 5-14 heterocyclyl($C_{1-8}$)alkyl; said $C_3$-10 carbocyclic residue, heterocyclic system $C_3$-$C_{10}$ carbocyclyl($C_{1-8}$)alkyl, and 5-14 heterocyclyl($C_{1-8}$)alkyl are optionally substituted with $R^{c1}$.

$R^{c1}$ at each occurrence is independently selected from the group consisting of $C_{1-6}$ alkyl, $OR^a$, Cl, F, Br, I, =O, —CN, NO$_2$, $NR^aR^{a1}$, $C(O)R^a$, $C(O)OR^a$, $C(O)NR^aR^{a1}$, $OC(O)NR^aR^{a1}$, $R^aNC(O)OR^a$, $S(O)_2NR^aR^{a1}$, $NR^aS(O)_2$ $R^{a2}$, $NR^aS(O)_2NR^aR^{a1}$, $S(O)_pR^{a2}$, $CF_3$, and $CF_2CF_3$, $CH_2F$, and $CHF_2$;

$R^d$ at each occurrence is independently selected from the group consisting of H, $C_{1-6}$ alkyl optionally substituted with $R^{c1}$, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^a$, $OC(O)NR^aR^{a1}$, $R^aNC(O)OR^{a1}$, $S(O)_2NR^aR^{a1}$, $NR^aS(O)_2$ $R^{a2}$, $NR^aS(O)_2 NR^aR^{a1}$, $OS(O)_2 NR^aR^{a1}$, $S(O)_pR^{a2}$, $CF_3$, $CF_2CF_3$, $CH_2F$, $CHF_2$, $CF_2CH_3$, $C(CH_3)_2F$, $OCF_3$, $OCHF_2$, $OCF_2CF_3$ and $OCH_2CF_3$; $C_{3-10}$ carbocyclic residue, and a 5-14 membered heterocyclic system containing from 1-4 heteroatoms selected from the group consisting of N, O, and S, $C_3$-$C_{10}$ carbocyclyl($C_{1-8}$)alkyl, and 5-14 heterocyclyl($C_{1-8}$)alkyl; said $C_{3-10}$ carbocyclic residue, heterocyclic system $C_3$-$C_{10}$ carbocyclyl($C_{1-8}$)alkyl, and 5-14 heterocyclyl($C_{1-8}$)alkyl optionally substituted with $R^{c1}$.

$R^{d1}$ at each occurrence is independently selected from the group consisting of H, $C_{1-6}$ alkyl optionally substituted with $R^{c1}$, $OR^a$, Cl, F, Br, I, =O, —CN, $NO_2$, $NR^aR^{a1}$, $C(O)R^a$, $C(O)OR^a$, $C(O)NR^aR^{a1}$, $R^aNC(O)NR^aR^a$, $OC(O)NR^aR^{a1}$, $R^aNC(O)OR^{a1}$, $S(O)_2 NR^aR^{a1}$, $NR^aS(O)_2$ $R^{a2}$, $NR^aS(O)_2NR^aR^{a1}$, $OS(O)_2NR^aR^{a1}$, $S(O)_pR^{a2}$, $CF_3$, $CF_2CF_3$, $CH_2F$, $CHF_2$, $CF_2CH_3$, $C(CH_3)_2F$, $OCF_3$, $OCHF_2$, $OCF_2CF_3$ and $OCH_2CF_3$; $C_{3-10}$ carbocyclic residue, and a 5-14 membered heterocyclic system containing from 1-4 heteroatoms selected from the group consisting of N, O, and S, $C_3$-$C_{10}$ carbocyclyl($C_{1-8}$)alkyl, and 5-14 heterocyclyl($C_{1-8}$)alkyl; said $C_{3-10}$ carbocyclic residue, heterocyclic system $C_3$-$C_{10}$ carbocyclyl($C_{1-8}$)alkyl, and 5-14 heterocyclyl($C_{1-8}$)alkyl optionally substituted with $R^{c1}$.

alternatively, $R^d$ and $R^{d1}$ taken together with the atom to which they are attached form a 4 to 8 membered ring containing from 0-1 heteroatoms selected from the group consisting of N, O, and S, wherein said ring may be substituted with $R^d$;

$R^h$ at each occurrence is independently selected from the group consisting of $OR^j$, $NR^jR^a$, $COR^j$, $C(O)OR^j$, $C(O)NR^jR^{a1}$, $NR^aC(O)NR^jR^{a1}$, $OC(O)NR^jR^a$, $S(O)_pNR^jR^{a1}$, $NR^aS(O)_pR^j$, $NR^aS(O)_pNR^jR^a$, $C_{1-6}$ alkyl substituted with $R^c$.

$R^j$ at each occurrence is independently selected from the group consisting of $CF_3$, $CH_2F$, $CHF_2$, $CF_2CF_3$, $C_1$-$C_8$ alkyl substituted with O(primary, secondary, or tertiary)$C_1$-$C_8$, OH, Cl, F, Br, I, =O, —CN, $NO_2$, alkylamino, dialkylamino, alkarylamino, arylamino, alkylcarbonyl, aralkylcarbonyl, arylcarbonyl, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamidoalkyl, N-alkylsufonamidodialkyl, alkylamidosulfonate, dialkylamidosulfonate, alkylsulfinyl, alkylsulfonyl, $CF_3$, $CF_2CF_3$, $CH_2F$, $CHF_2$, $CF_2CH_3$, $C(CH_3)_2F$, $OCF_3$, $OCHF_2$, $OCF_2CF_3$ and $OCH_2CF_3$; $C_2$-$C_8$ alkenyl, $C_2$-$C_8$ alkynyl, wherein said alkenyl and alkynyl groups are optionally substituted with $C_1$-$C_8$ alkyl, O(primary, secondary, or tertiary)$C_1$-$C_8$, OH, Cl, F, Br, I, =O, —CN, $NO_2$, alkylamino, dialkylamino, alkarylamino, arylamino, alkylcarbonyl, aralkylcarbonyl, arylcarbonyl, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsufonamidodialkyl, alkylamidosulfonate, dialkylamidosulfonate, alkylsulfinyl, alkylsulfonyl, $CF_3$, $CF_2CF_3$, $CH_2F$, $CHF_2$, $CF_2CH_3$, $C(CH_3)_2F$, $OCF_3$, $OCHF_2$, $OCF_2CF_3$ and $OCH_2CF_3$; $C_3$-$C_{10}$ carbocycle, heterocycles, $C_3$-$C_{10}$ carbocyclylalkyl, heterocyclylalkyl and wherein said $C_3$-$C_{10}$ carbocycle, heterocycles, $C_3$-$C_{10}$ carbocyclylalkyl, and heterocyclylalkyl may be optionally substituted with one or more substituents selected from the group consisting of O(primary, secondary, or tertiary)$C_1$-$C_8$, OH, Cl, F, Br, I, =O, —CN, $NO_2$, alkylamino, dialkylamino, alkarylamino, arylamino, alkylcarbonyl, aralkylcarbonyl, arylcarbonyl, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamidoalkyl, N-alkylsufonamidodialkyl, alkylamidosulfonate, dialkylamidosulfonate, alkylsulfinyl, alkylsulfonyl, $CF_3$, $CF_2CF_3$, $CH_2F$, $CHF_2$, $CF_2CH_3$, $C(CH_3)_2F$, $OCF_3$, $OCF_2CF_3$ and $OCH_2CF_3$, with the proviso that said $C_3$-$C_{10}$ carbocycle can not be a phenyl group and $C_3$-$C_{10}$ carbocyclylalkyl can not be a benzyl group;

$R^3$ is H or $C_{1-6}$ alkyl $OR^a$, $NR^aR^{a1}$, and $S(O)_pR^a$, $R^4$ is selected from the group consisting of H, $C_{1-6}$ alkyl, $OR^a$, $NR^aR^{a1}$, and $S(O)_pR^a$, $R^5$ at each occurrence is selected from the group consisting of $C_{1-10}$ alkyl substituted with 0-2 $R^b$, and $C_{1-8}$ alkyl substituted with 0-2 $R^b$;

$R^e$ at each occurrence is selected from the group consisting of phenyl substituted with 0-2 $R^b$ and biphenyl substituted with 0-2 $R^b$;

$R^6$ at each occurrence is selected from the group consisting of phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$-$C_5$ alkyl)-1,3-dioxacyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7$ $R^{7a}$, —$CH(R^8)OC(O)R^9$, and —$CH(R^8)OC(O)OR^9$;

alternatively, $R^4$ and $R^6$ can be taken together to form a 5-10 membered ring optionally substituted with $R^c$;

$R^7$ is selected from the group consisting of H, $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from the group consisting of H, $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from the group consisting of H and $C_{1-4}$ linear alkyl;

$R^9$ is selected from the group consisting of H, $C_{1-8}$ alkyl substituted with 1-2 $R^f$, $C_{3-8}$ cycloalkyl substituted with 1-2 $R^f$, and phenyl substituted with 0-2 $R^b$;

$R^f$ at each occurrence is selected from the group consisting of H, $C_{1-4}$ alkyl, $C_{3-8}$ cycloalkyl, $C_{1-5}$ alkoxy, and phenyl substituted with 0-2 $R^b$;

p at each occurrence is 0, 1, and 2; and r at each occurrence is 0, or an integer from 1 to 10.

In a preferred embodiment, the present invention provides for a novel class of compounds according to the formula IIA:

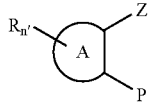

IIA wherein ring A is a 4-10 membered non-aromatic carbocycle or heterocycle comprising carbon atoms, 0-1 carbonyl groups and from 0-2 ring heteroatoms selected from the group consisting of O, N, NR, provided that ring A contains other than a O—O bond;

n' is 1 or 2;

Z is selected from the group consisting of —$CO_2H$, —$CH_2CO_2H$, —CONHOH, —$CONHOR^5$, —$NHR^a$, —$N(OH)C(O)R^5$, —N(OH)CHO, —SH, —$CH_2SH$, and P is —D-E-G-Q-L-T-X-Y, wherein D is absent or is selected from the group consisting of O, $NR^{a1}$, C(O), C(O)O, OC(O), $C(O)NR^{a1}$, $NR^{a1}C(O)$, $OC(O)NR^{a1}$, $NR^{a1}C(O)O$, $NR^{a1}C(O)NR^{a1}$, $S(O)_p$, $S(O)_pNR^{a1}$, and $NR^{a1}S(O)_p$;

E is absent or is selected from the group consisting of $C_{1-10}$alkylene, $C_{2-10}$ alkenylene, and $C_{2-10}$ alkynylene;

G is absent or is selected from the group consisting of O, $NR^{a1}$, $S(O)_p$, and C(O);

Q is absent or is selected from the group consisting of a $C_{3-10}$ carbocycle substituted with 0-5 $R^b$, and a 5-10 membered heterocycle comprising carbon atoms and 1-4 heteroatoms selected from the group consisting of N, O, and $S(O)_p$, and said heterocycle being substituted with 0-5 $R^b$;

L is absent or is selected from the group consisting of O, $NR^{a1}$, C(O), C(O)O, OC(O), $C(O)NR^{a1}$, $NR^{a1}C(O)$, $OC(O)NR^{a1}$, $NR^{a1}C(O)O$, $S(O)_p$, $S(O)_pNR^{a1}$, and $NR^{a1}S(O)_p$;

T is absent or is selected from the group consisting of $C_{1-10}$ alkylene, $C_{2-10}$ alkenylene, and $C_{2-10}$ alkynylene;

X is absent or is selected from the group consisting of O, $NR^{a1}$, $S(O)_p$, and C(O);

Y is selected from the group consisting of H, a $C_{3-10}$ carbocycle substituted with 0-5 $R^c$ and a 5-10 membered heterocycle comprising carbon atoms and 1-4 heteroatoms selected from the group consisting of N, O, and $S(O)_p$, and said heterocycle being substituted with 0-5 $R^c$; provided that D, E, G, Q, L, T, X and Y do not combine to form a N—N, N—O, O—N, O—O, $S(O)_p$—O, O—$S(O)_p$ or $S(O)_p$—$S(O)_p$ group;

R, at each occurrence, is independently selected from ($C_{10}$ alkylene substituted with 1-3 $R^{b1}$)-M, ($C_{2-10}$ alkenylene substituted with 1-3 $R^{b1}$)-M, ($C_{2-10}$ alkynylene substituted with 1-3 $R^{b1}$)-M, OH, Cl, F, Cl, —CN, $NO_2$, $CF_3$, $CF_2CF_3$, $CH_2F$, $CHF_2$, $CF_2CH_3$, $C(CH_3)_2F$, $OCF_3$, $OCHF_2$, $O(CR^dR^{d1})_r$-M, $NR^a(CR^dR^{d1})_r$-M, $OC(O)(CR^dR^{d1})_r$-M, $NR^aC(O)(CR^dR^{d1})_r$-M, $OC(O)O(CR^dR^{d1})_r$-M, $OC(O)NR^a(CR^dR^{d1})_r$-M, $NR^aC(O)O(CR^dR^{d1})_r$-M, $NR^aC(O)NR^{a1}(CR^dR^{d1})_r$-M, $S(O)_p(CR^dR^{d1})_r$-M, $S(O)_2NR^a(CR^dR^{d1})_r$-M, $NR^aS(O)_2(CR^dR^{d1})_r$-M, C(=NCN)$NR^{a1}R^{a2}$; C(=C(H)($NO_2$))$NR^{a1}R^{a2}$; a $C_{3-10}$ carbocycle substituted with 0-5 $R^d$ and a 5-10 membered heterocycle comprising carbon atoms and 1-4 heteroatoms selected from the group consisting of N, O, $S(O)_p$ and said heterocycle being substituted with 0-5 $R^d$;

alternatively, two R, together with a carbon atom on A, form the group $C_A$=$CR^dR^{d1}$, where the atom $C_A$ is said atom on A;

M is selected from the group consisting of H, $C_{2-10}$ alkenylene substituted with 0-3 $R^{b1}$, $C_{2-10}$ alkynylene substituted with 0-3 $R^{b1}$, $OR^a$, Cl, F, Br, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^a$, $NR^aC(O)OR^a$, $NR^aC(O)R^a$, $S(O)_2NR^aR^{a1}$, $NR^aS(O)_2R^{a2}$, $S(O)_pR^{a2}$, $CF_3$, $CF_2CF_3$, $CH_2F$, $CHF_2$, $CF_2CH_3$, $C(CH_3)_2F$, $OCF_3$, $OCHF_2$, a $C_{3-10}$ carbocycle substituted with 0-5 $R^d$, and a 5-10 membered heterocycle comprising carbon atoms and 1-4 heteroatoms selected from the group consisting of N, O, $S(O)_p$ and said heterocycle being substituted with 0-5 $R^d$;

alternatively, R, at each occurrence, is independently selected from $C_{1-10}$ alkylene-$M^1$, $C_{2-10}$ alkenylene-$M^1$, $C_{2-10}$ alkynylene-$M^1$, $(CR^dR^{d1})_rO(CR^dR^{d1})_r$-$M^1$, $(CR^dR^{d1})_rNR^a(CR^dR^{d1})_r$-$M^1$, $(CR^dR^{d1})_rC(O)(CR^dR^{d1})_r$-$M^1$, $(CR^dR^{d1})_rC(O)O(CR^dR^{d1})_r$-M, $(CR^dR^{d1})_rOC(O)(CR^dR^{d1})_r$-$M^1$, $(CR^dR^{d1})_rC(O)NR^a(CR^dR^{d1})_r$-$M^1(CR^dR^{d1})_rNR^aC(O)(CR^dR^{d1})_r$-$M^1$, $(CR^dR^{d1})_rOC(O)O(CR^dR^{d1})_r$-$M^1$, $(CR^dR^{d1})_rOC(O)NR^a(CR^dR^{d1})_r$-$M^1$, $(CR^dR^{d1})_rNR^aC(O)O(CR^dR^{d1})_r$-$M^1$, $(CR^dR^{d1})_rNR^aC(O)NR^{a1}(CR^dR^{d1})_r$-$M^1$, $(CR^dR^{d1})_rS(O)_p(CR^dR^{d1})_r$-$M^1$, $(CR^dR^{d1})_rS(O)_2NR^a(CR^dR^{d1})_r$-$M^1$, and $(CR^dR^{d1})_rNR^aS(O)_2(CR^dR^{d1})_r$-$M^1$;

$M^1$ is selected from the group consisting of $OR^a$, Cl, F, Br, —CN, $NO_2$, $NR^aR^{a1}$, $C(O)R^a$, $C(O)OR^a$, $C(O)NR^8R^{a1}$, $R^aNC(O)NR^aR^{a1}$, $OC(O)NR^aR^{a1}$, $R^aNC(O)OR^a$, $S(O)_2NR^aR^{a1}$, $NR^aS(O)_2R^{a2}$, $NR^aS(O)_2NR^aR^{a1}$, $OS(O)_2NR^aR^{a1}$, $S(O)_pR^{a2}$, $CF_3$, $CF_2CF_3$, $CH_2F$, $CHF_2$, $CF_2CH_3$, $C(CH_3)_2F$, $OCF_3$, and a 5-10 membered non-aromatic heterocycle comprising carbon atoms and 1-4 heteroatoms selected from the group consisting of N, O, $S(O)_p$ and said heterocycle being substituted with 0-5 $R^d$; a $C_3$-$C_{10}$ carbocycle, $C_5$-$C_{10}$ heterocycle and wherein said $C_3$-$C_{10}$ carbocycle and $C_5$-$C_{10}$ heterocycle are substituted with 1-3 $R^h$, and $CF_3$, $CF_2CF_3$, $CH_2F$, $CHF_2$, $CF_2CH_3$, $C(CH_3)_2F$, $OCF_3$, $OCHF_2$, $OCF_2CF_3$ and $OCH_2CF_3$;

alternatively, when two R groups are attached to adjacent ring A atoms, together with the atoms to which they are attached they may form a 3-8 membered saturated, partially saturated or unsaturated ring comprised of carbon atoms and 0-3 heteroatoms selected from the group consisting of N, $NR^a$, O, and $S(O)_p$, wherein said ring may be benzene-fused and/or substituted with $R^d$;

alternatively, when two R groups are attached to the same ring A carbon, together with the carbon to which they are attached they may form a 3-8 membered saturated, partially saturated or unsaturated spiro-ring comprised of carbon atoms and 0-3 heteroatoms selected from the group consisting of N, $NR^a$, O, and $S(O)_p$, wherein said spiro-ring may be benzene-fused and/or substituted with $R^d$;

provided that either two R or M, $M^1$ and the atom to which they are attached do not combine to form a N—N, N—O, O—N, O—O, N-halogen, O-halogen, S-halogen, $S(O)_p$—O, O—$S(O)_p$, $S(O)_p$—$S(O)_p$ group, or C(O)F, C(O)Cl, C(O)Br, or C(O)I reactive group;

$R^a$, $R^{a1}$, and $R^{a2}$ at each occurrence are independently selected from the group consisting of H, $C_1$-$C_8$ alkyl, $C_2$-$C_8$ alkenyl, $C_2$-$C_8$ alkynyl, wherein said alkyl, alkenyl and alkynyl groups are optionally substituted with O(primary, secondary, or tertiary)$C_1$-$C_8$, OH, Cl, F, —CN, alkylamino, dialkylamino, alkarylamino, arylamino, alkylcarbonyl, aralkylcarbonyl, arylcarbonyl, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamidoalkyl, N-alkylsufonamidodialkyl, alkylamidosulfonate, dialkylamidosulfonate, alkylsulfinyl, alkylsulfonyl, $CF_3$, $CF_2CF_3$, $CH_2F$, $CHF_2$, $CF_2CH_3$, $C(CH_3)_2F$, $OCF_3$, and $OCH_2CF_3$; $C_3$-$C_{10}$ carbocycle, heterocycles, $C_3$-$C_{10}$ carbocyclylalkyl, heterocyclylalkyl and wherein said $C_3$-$C_{10}$ carbocycle, heterocycles, $C_3$-$C_{10}$ carbocyclylalkyl, and heterocyclylalkyl may be optionally substituted with one or more substituents selected from the group consisting of $C_1$-$C_8$ alkyl, O(primary, secondary, or tertiary)$C_1$-$C_8$, OH, Cl, F, Br, =O, —CN, $NO_2$, alkylamino, dialkylamino, alkarylamino, arylamino, alkylcarbonyl, aralkylcarbonyl, arylcarbonyl, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamido-alkyl, N-alkylsufonamidodialkyl, alkylamidosulfonate, dialkylamidosulfonate, alkylsulfinyl, alkylsulfonyl, $CF_3$, $CH_2F$, $CHF_2$, $CF_2CH_3$, $C(CH_3)_2F$, $OCF_3$, and $OCH_2CF_3$;

alternatively, $R^a$ and $R^{a1}$ taken together with the nitrogen to which they are attached form a 3 to 8 membered ring containing from 0-1 additional heteroatoms selected from the group consisting of N, O, and S, wherein said ring may be substituted with $R^d$;

$R^b$ at each occurrence is independently selected from the group consisting of $C_{1-6}$ alkyl optionally substituted with $R^{c1}$, O(primary, secondary, or tertiary)$C_1$-$C_8$, OH, Cl, F, —CN, $NO_2$, $NR^aR^{a1}$, $C(O)R^a$, $C(O)OR^a$, $C(O)NR^aR^{a1}$, $R^aNC(O)NR^aR^a$, $OC(O)NR^aR^{a1}$, $R^aNC(O)OR^{a1}$, $S(O)_2 NR^aR^{a1}$, $NR^aS(O)_2R^{a2}$, $NR^aS(O)_2 NR^aR^{a1}$, $OS(O)_2 NR^aR^{a1}$, $S(O)_pR^{a2}$, $CF_3$, $CH_2F$, $CHF_2$, $CF_2CH_3$, $C(CH_3)_2F$, $OCF_3$, $OCHF_2$, and $OCH_2CF_3$; $C_{3-10}$ carbocyclic residue, and a 5-10 membered heterocyclic system containing from 1-4 heteroatoms selected from the group consisting of N, O, and S, $C_3$-$C_{10}$ carbocyclyl($C_{1-8}$)alkyl, and 5-10 heterocyclyl-($C_{1-8}$)alkyl and said $C_{3-10}$ carbocyclic residue, heterocyclic system, $C_3$-$C_{10}$ carbocyclyl($C_{1-8}$)alkyl, and 5-10 heterocyclyl($C_{1-8}$)alkyl are optionally substituted with $R^{c1}$;

$R^{b1}$ at each occurrence is independently selected from the group consisting of $OR^a$, F, =O, —CN, $NO_2$, $NR^aR^{a1}$ and $S(O)_pR^a$, $R^c$ at each occurrence is independently selected from the group consisting of $C_{1-6}$ alkyl optionally substituted with $R^{c1}$, $OR^a$, Cl, F, —CN, $NO_2$, $NR^aR^{a1}$, $C(O)R^a$, $C(O)OR^a$, $C(O)NR^aR^{a1}$, $R^aNC(O)NR^aR^a$, $OC(O)NR^aR^{a1}$, $R^aNC(O)OR^{a1}$, $S(O)_2 NR^aR^{a1}$, $NR^aS(O)_2R^{a2}$, $NR^aS(O)_2NR^aR^{a1}$, $S(O)_pR^{a2}$, $CF_3$, $CH_2F$, $CHF_2$, $CF_2CH_3$, $C(CH_3)_2F$, $OCF_3$, $OCHF_2$, and $OCH_2CF_3$; a $C_{3-0}$ carbocyclic residue, and a 5-10 membered heterocyclic system containing from 1-4 heteroatoms selected from the group consisting of N, O, and S, $C_3$-$C_{10}$ carbocyclyl($C_{1-8}$)alkyl, and 5-10 heterocyclyl($C_{1-8}$)alkyl; said $C_{3-10}$ carbocyclic residue, heterocyclic system, $C_3$-$C_{10}$ carbocyclyl($C_{1-8}$)alkyl, and 5-14 heterocyclyl($C_{1-8}$)alkyl are optionally substituted with $R^{c1}$.

$R^{c1}$ at each occurrence is independently selected from the group consisting of $C_{1-6}$ alkyl, $OR^a$, Cl, F, Br, =O, —CN, $NO_2$, $NR^aR^{a1}$, $C(O)R^a$, $C(O)OR^a$, $C(O)NR^aR^{a1}$, $OC(O)NR^aR^{a1}$, $R^aNC(O)OR^a$, $S(O)_2NR^aR^{a1}$, $NR^aS(O)_2R^{a2}$, $S(O)_pR^{a2}$, $CF_3$, and $CH_2F$, and $CHF_2$;

$R^d$ at each occurrence is independently selected from the group consisting of H, $C_{1-6}$ alkyl optionally substituted with $R^{c1}$, $OR^a$, Cl, F, Br, =O, —CN, $NO_2$, $NR^aR^{a1}$, $C(O)R^a$, $C(O)OR^a$, $C(O)NR^aR^{a1}$, $R^aNC(O)NR^aR^a$, $OC(O)NR^aR^{a1}$, $R^aNC(O)OR^{a1}$, $S(O)_2 NR^aR^{a1}$, $NR^aS(O)_2 R^{a2}$, $OS(O)_2 NR^aR^{a1}$, $S(O)_pR^{a2}$, $CF_3$, $CF_2CF_3$, $CH_2F$, $CHF_2$, $CF_2CH_3$, $C(CH_3)_2F$, $OCF_3$, $OCHF_2$, and $OCH_2CF_3$; $C_{3-10}$ carbocyclic residue, and a 5-10 membered heterocyclic system containing from 1-4 heteroatoms selected from the group consisting of N, O, and S, $C_3$-$C_{10}$ carbocyclyl($C_{1-8}$)alkyl, and 5-14 heterocyclyl($C_{1-8}$)alkyl; said $C_{3-10}$ carbocyclic residue, heterocyclic system $C_3$-$C_{10}$ carbocyclyl ($C_{1-8}$)alkyl, and 5-10 heterocyclyl($C_{1-8}$)alkyl optionally substituted with $R^{c1}$.

$R^{d1}$ at each occurrence is independently selected from the group consisting of H, $C_{1-6}$ alkyl optionally substituted with $R^c$, $OR^a$, Cl, F, —CN, $NR^aR^{a1}$, $C(O)R^a$, $C(O)OR^a$, $C(O)NR^aR^{a1}$, $R^aNC(O)NR^aR^a$, $OC(O)NR^aR^{a1}$, $R^aNC(O)OR^{a1}$, $S(O)_2 NR^aR^{a1}$, $NR^aS(O)_2R^{a2}$, $S(O)_pR^{a2}$, $CF_3$, $CH_2F$, $CHF_2$, $CF_2CH_3$, $C(CH_3)_2F$, $OCF_3$, $OCHF_2$, and $OCH_2CF_3$; $C_{3-10}$ carbocyclic residue, and a 5-10 membered heterocyclic system containing from 1-4 heteroatoms selected from the group consisting of N, O, and S, $C_3$-$C_{10}$ carbocyclyl($C_{1-8}$)alkyl, and 5-10 heterocyclyl ($C_{1-8}$)alkyl; said $C_{3-10}$ carbocyclic residue, heterocyclic system $C_3$-$C_{10}$ carbocyclyl($C_{1-8}$)alkyl, and 5-14 heterocyclyl($C_{1-8}$)alkyl optionally substituted with $R^{c1}$.

alternatively, $R^d$ and $R^{d1}$ taken together with the atom to which they are attached form a 4 to 8 membered ring containing from 0-1 heteroatoms selected from the group consisting of N, O, and S, wherein said ring may be substituted with $R^d$;

$R^h$ at each occurrence is independently selected from the group consisting of $OR^j$, $NR^jR^a$, $COR^j$, $C(O)OR^j$, $C(O)NR^jR^a$, $NR^aC(O)NR^jR^{a1}$, $OC(O)NR^jR^a$, $S(O)_pNR^jR^{a1}$, $NR^aS(O)_pR_1$, $C_1$, alkyl substituted with $R^c$.

$R^j$ at each occurrence is independently selected from the group consisting of $CF_3$, $CH_2F$, $CF_2H$, $CF_2CF_3$, $C_1$-$C_8$ alkyl substituted with O(primary, secondary, or tertiary) $C_1$-$C_8$, OH, Cl, F, —CN, alkylamino, dialkylamino, alkarylamino, arylamino, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamidoalkyl, N-alkylsufonamidodialkyl, alkylamidosulfonate, dialkylamidosulfonate, alkylsulfonyl, $CF_3$, $CH_2F$, $CHF_2$, $CF_2CH_3$, $C(CH_3)_2F$, $OCF_3$, $OCHF_2$, and $OCH_2CF_3$; $C_2$-$C_8$ alkenyl, $C_2$-$C_8$ alkynyl, wherein said alkenyl and alkynyl groups are optionally substituted with $C_1$-$C_8$ alkyl, O(primary, secondary, or tertiary)$C_1$-$C_8$, OH, Cl, F, —CN, alkylamino, dialkylamino, alkarylamino, arylamino, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamidoalkyl, N-alkylsufonamidodialkyl, alkylamidosulfonate, dialkylamidosulfonate, $CF_3$, $CH_2F$, $CHF_2$, $CF_2CH_3$, $C(CH_3)_2F$, $OCF_3$, $OCHF_2$, and $OCH_2CF_3$; $C_3$-$C_{10}$ carbocycle, 5-10 membered heterocycles, $C_3$-$C_{10}$ carbocyclylalkyl, heterocyclylalkyl and wherein said $C_3$-$C_{10}$ carbocycle, heterocycles, $C_3$-$C_{10}$ carbocyclylalkyl, and heterocyclylalkyl may be optionally substituted with one or more substituents selected from the group consisting of O(primary, secondary, or tertiary)$C_1$-$C_8$, OH, Cl, F, —CN, $NO_2$, alkylamino, dialkylamino, alkarylamino, arylamino, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamido-alkyl, N-alkylsufonamidodialkyl, alkylamidosulfonate, dialkylamidosulfonate, alkylsulfonyl, $CF_3$, $CH_2F$, $CHF_2$, $CF_2CH_3$, $C(CH_3)_2F$, $OCF_3$, and $OCH_2CF_3$, with the proviso that said $C_3$-$C_{10}$ carbocycle can not be a phenyl group and $C_3$-$C_{10}$ carbocyclylalkyl can not be a benzyl group;

$R^5$ at each occurrence is selected from the group consisting of $C_{1-10}$ alkyl substituted with 0-2 $R^b$, and $C_{1-8}$ alkyl substituted with 0-2 $R^e$;

$R^e$ at each occurrence is selected from the group consisting of phenyl substituted with 0-2 $R^b$ and biphenyl substituted with 0-2 $R^b$;

p at each occurrence is 0, 1, and 2; and r at each occurrence is 0, or an integer from 1 to 10.

In an even more preferred embodiment, the present invention provides potent matrix metalloprotease inhibitors which are cyclic hydroxamate derivatives according to the formula IIIA or IVA:

IIIA

IVA wherein ring A is a 5-7 membered non-aromatic carbocycle or heterocycle comprising carbon atoms, 0-1 carbonyl groups and from 0-2 ring heteroatoms selected from the group consisting of O, N, NR, provided that ring A contains other than a O—O bond;

n' is 1 or 2;

P is -D-E-G-Q-L-T-X-Y, wherein

D is absent or is selected from the group consisting of O, $NR^{a1}$, C(O), C(O)$NR^{a1}$, $NR^{a1}$C(O), OC(O)$NR^{a1}$, $NR^{a1}$C(O)O, $NR^{a1}$C(O)$NR^{a1}$, S(O)$_p$, S(O)$_p$$NR^{a1}$, and $NR^{a1}$S(O)$_p$;

E is absent or is selected from the group consisting of $C_{1-10}$alkylene, $C_{2-10}$ alkenylene, and $C_{2-10}$ alkynylene;

G is absent or is selected from the group consisting of O, $NR^{a1}$, S(O)$_p$, and C(O);

Q is absent or is selected from the group consisting of a $C_{5-7}$ carbocycle substituted with 0-5 $R^b$, and a 5-7 membered heterocycle comprising carbon atoms and 1-4 heteroatoms selected from the group consisting of N, O, and S(O)$_p$, and said heterocycle being substituted with 0-5 $R^b$;

L is absent or is selected from the group consisting of O, $NR^{a1}$, C(O), C(O)$NR^{a1}$, $NR^{a1}$C(O), OC(O)$NR^{a1}$, $NR^{a1}$C(O)O, S(O)$_p$, S(O)$_p$$NR^{a1}$, and $NR^{a1}$S(O)$_p$;

T is absent or is selected from the group consisting of $C_{1-10}$ alkylene, $C_{2-10}$ alkenylene, and $C_{2-10}$ alkynylene;

X is absent or is selected from the group consisting of O, $NR^a$, S(O)$_p$, and C(O);

Y is selected from the group consisting of H, a $C_{5-7}$ carbocycle substituted with 0-5 $R^c$ and a 5-6 membered heterocycle comprising carbon atoms and 1-4 heteroatoms selected from the group consisting of N, O, and S(O)$_p$, and said heterocycle being substituted with 0-5 $R^c$;

provided that D, E, G, Q, L, T, X and Y do not combine to form a N—N, N—O, O—N, O—O, S(O)$_p$—O, O—S(O)$_p$ or S(O)$_n$—S(O)$_p$ group;

R, at each occurrence, is independently selected from ($C_{1-10}$ alkylene substituted with 1-3 $R^{b1}$)-M, ($C_{2-10}$ alkenylene substituted with 1-3 $R^{b1}$)-M, ($C_{2-10}$ alkynylene substituted with 1-3 $R^{b1}$)-M, OH, F, Cl, —CN, $NO_2$, $CF_3$, $CH_2F$, $CHF_2$, $CF_2CH_3$, $C(CH_3)_2F$, $OCF_3$, $OCHF_2$, O($CR^dR^{d1}$)$_r$-M, $NR^a$($CR^dR^{d1}$)$_r$-M, OC(O)($CR^dR^{d1}$)$_r$-M, $NR^a$C(O)($CR^dR^{d1}$)$_r$-M, OC(O)O($CR^dR^{d1}$)$_r$-M, OC(O)$NR^a$($CR^dR^{d1}$)$_r$-M, $NR^a$C(O)O($CR^dR^{d1}$)$_r$-M, $NR^a$C(O)$NR^{a1}$($CR^dR^{d1}$)$_r$-M, S(O)$_p$($CR^dR^{d1}$)$_r$-M, S(O)$_2$$NR^a$($CR^dR^{d1}$)$_r$-M, $NR^a$S(O)$_2$($CR^dR^{d1}$)$_r$-M, C(=NCN)$NR^{a1}R^{a2}$; C(=C(H)(NO$_2$))$NR^aR^{a2}$; a $C_{3-10}$ carbocycle substituted with 0-5 $R^d$, and a 5-10 membered heterocycle comprising carbon atoms and 1-4 heteroatoms selected from the group consisting of N, O, S(O)$_p$ and said heterocycle being substituted with 0-5 $R^d$;

alternatively, two R, together with a carbon atom on A, form the group $C_A$=$CR^dR^{d1}$, where the atom $C_A$ is said atom on A;

M is selected from the group consisting of H, $C_{2-10}$ alkenylene substituted with 0-3 $R^{b1}$, $C_{2-10}$ alkynylene substituted with 0-3 $R^{b1}$, $OR^a$, Cl, F, —CN, $NO_2$, $NR^aR^{a1}$, C(O)$R^a$, C(O)$OR^a$, C(O)$NR^aR^{a1}$, $R^a$NC(O)$NR^aR^{a1}$, OC(O)$NR^aR^{a1}$, $NR^a$C(O)$OR^a$, $NR^a$C(O)$R^a$, S(O)$_2$$NR^aR$ $NR^a$S(O)$_2R^{a2}$, S(O)$_pR^{a2}$, $CF_3$, $CH_2F$, $CHF_2$, $CF_2CH_3$, $C(CH_3)_2F$, $OCF_3$, $OCHF_2$, a $C_{3-10}$ carbocycle substituted with 0-5 $R^d$, and a 5-10 membered heterocycle comprising carbon atoms and 1-4 heteroatoms selected from the group consisting of N, O, S(O)$_p$ and said heterocycle being substituted with 0-5 $R^d$;

alternatively, R, at each occurrence, is independently selected from $C_{1-10}$ to alkylene-$M^1$, $C_{2-10}$ alkenylene-$M^1$, $C_{2-10}$ alkynylene-$M^1$, ($CR^dR^{d1}$)$_r$O($CR^dR^{d1}$)$_r$-$M^1$, ($CR^dR^{d1}$)$_r$$NR^a$($CR^dR^{d1}$)$_{r-M^1}$, ($CR^dR^{d1}$)$_r$C(O)($CR^dR^{d1}$)$_r$-$M^1$, ($CR^dR^{d1}$)$_r$C(O)O($CR^dR^{d1}$)$_r$-$M^1$, ($CR^dR^{d1}$)$_r$OC(O)($CR^dR^{d1}$)$_r$-$M^1$, ($CR^dR^{d1}$)$_r$C(O)$NR^a$($CR^dR^{d1}$)$_r$-$M^1$, ($CR^dR^{d1}$)$_r$$NR^a$C(O)($CR^dR^{d1}$)$_r$-$M^1$, ($CR^dR^{d1}$)$_r$OC(O)O($CR^dR^{d1}$)$_r$-$M^1$, ($CR^dR^{d1}$)$_r$OC(O)$NR^a$($CR^dR^{d1}$)$_r$-$M^1$, ($CR^dR^{d1}$)$_r$$NR^a$C(O)O($CR^dR^{d1}$)$_r$-$M^1$, ($CR^dR^{d1}$)$_r$$NR^a$C(O)$NR^{a1}$($CR^dR^{d1}$)$_{r-M^1}$, ($CR^dR^{d1}$)$_r$S(O)$_p$($CR^dR^{d1}$)$_r$-$M^1$, ($CR^dR^{d1}$)$_r$S(O)$_2NR^a$($CR^dR^{d1}$)$_r$-$M^1$, and ($CR^dR^{d1}$)$_r$$NR^a$S(O)$_2$($CR^dR^{d1}$)$_r$-$M^1$;

$M^1$ is selected from the group consisting of $OR^a$, Cl, F, Br, —CN, $NO_2$, $NR^aR^{a1}$, C(O)$R^a$, C(O)$OR^a$, C(O)$NR^aR^{a1}$, $R^a$NC(O)$NR^aR^{a1}$, OC(O)$NR^aR^{a1}$, $R^a$NC(O)$OR^a$, S(O)$_2$$NR^aR^{a1}$, $NR^a$S(O)$_2R^{a2}$, OS(O)$_2NR^aR^{a1}$, S(O)$_pR^{a2}$, $CF_3$, $CF_2CF_3$, $CH_2F$, $CHF_2$, $CF_2CH_3$, $C(CH_3)_2F$, $OCF_3$, and a 5-10 membered non-aromatic heterocycle comprising carbon atoms and 1-4 heteroatoms selected from the group consisting of N, O, S(O)$_p$ and said heterocycle being substituted with 0-5 $R^d$; a $C_3$-$C_{10}$ carbocycle, $C_5$-$C_{10}$ heterocycle and wherein said $C_3$-$C_{10}$ carbocycle and $C_5$-$C_{10}$ heterocycle are substituted with 1-3 $R^h$, and $CF_3$, $CF_2CF_3$, $CH_2F$, $CHF_2$, $CF_2CH_3$, $C(CH_3)_2F$, $OCF_3$, $OCHF_2$, $OCF_2CF_3$ and $OCH_2CF_3$;

provided that either two R or M, $M^1$ and the atom to which they are attached do not combine to form a N—N, N—O, O—N, O—O, N-halogen, O-halogen, S-halogen, S(O)$_p$—O, O—S(O)$_p$, S(O)$_p$—S(O)$_p$ group, or C(O)F, C(O)Cl, C(O)Br, or C(O)I reactive group;

$R^a$, $R^{a1}$, and $R^{a2}$ at each occurrence are independently selected from the group consisting of H, $C_1$-$C_8$ alkyl, $C_2$-$C_8$ alkenyl, $C_2$-$C_8$ alkynyl; $C_3$-$C_{10}$ carbocycle, heterocycles, $C_3$-$C_{10}$ carbocyclylalkyl, heterocyclylalkyl;

alternatively, $R^a$ and $R^{a1}$ taken together with the nitrogen to which they are attached form a 3 to 8 membered ring containing from 0-1 additional heteroatoms selected from the group consisting of N, O, and S, wherein said ring may be substituted with $R^d$;

$R^b$ at each occurrence is independently selected from the group consisting of $C_{1-6}$ alkyl optionally substituted with $R^{c1}$, O(primary, secondary, or tertiary)$C_1$-$C_8$, OH, Cl, F, —CN, $NO_2$, $NR^aR^{a1}$, $C(O)R^a$, $C(O)OR^a$, $C(O)NR^aR^{a1}$, $R^aNC(O)NR^aR^{a1}$, $OC(O)NR^aR^{a1}$, $R^aNC(O)OR^a$, $S(O)_2$ $NR^aR^{a1}$, $NR^aS(O)_2R^{a2}$, $NR^aS(O)_2$ $NR^aR^{a1}$, $OS(O)_2$ $NR^aR^{a1}$, $S(O)_pR^{a2}$, $CF_3$, $CH_2F$, $CHF_2$, $CF_2CH_3$, $C(CH_3)_2$F, $OCF_3$, $OCHF_2$, and $OCH_2CF_3$; $C_{3-10}$ carbocyclic residue, and a 5-10 membered heterocyclic system containing from 1-4 heteroatoms selected from the group consisting of N, O, and S, $C_3$-$C_{10}$ carbocyclyl($C_{1-8}$)alkyl, and 5-10 heterocyclyl-($C_{1-8}$)alkyl and said $C_{3-10}$ carbocyclic residue, heterocyclic system, $C_3$-$C_{10}$ carbocyclyl($C_{1-8}$)alkyl, and 5-10 heterocyclyl($C_{1-8}$)alkyl are optionally substituted with $R^{c1}$;

$R^{b1}$ at each occurrence is independently selected from the group consisting of $OR^a$, F, —CN, $NR^aR^{a1}$ and $S(O)_pR^a$, $R^c$ at each occurrence is independently selected from the group consisting of $C_{1-6}$ alkyl optionally substituted with $R^{c1}$, $OR^a$, Cl, F, —CN, $NO_2$, $NR^aR^{a1}$, $C(O)R^a$, $C(O)OR^a$, $C(O)NR^aR^{a1}$, $R^aNC(O)NR^aR^a$, $OC(O)NR^aR^{a1}$, $R^aNC(O)OR^{a1}$, $S(O)_2$ $NR^aR^{a1}$, $NR^aS(O)_2R^{a2}$, $NR^aS(O)_2$ $NR^aR^{a1}$, $S(O)_pR^{a2}$, $CF_3$, $CH_2F$, $CHF_2$, $CF_2CH_3$, $C(CH_3)_2$F, $OCF_3$, $OCHF_2$, and $OCH_2CF_3$; a $C_{3-10}$ carbocyclic residue, and a 5-10 membered heterocyclic system containing from 1-4 heteroatoms selected from the group consisting of N, O, and S, $C_3$-$C_{10}$ carbocyclyl($C_{1-8}$)alkyl, and 5-10 heterocyclyl($C_{1-8}$)alkyl; said $C_{3-10}$ carbocyclic residue, heterocyclic system, $C_3$-$C_{10}$ carbocyclyl($C_{1-8}$)alkyl, and 5-14 heterocyclyl($C_{1-8}$)alkyl are optionally substituted with $R^{c1}$;

$R^{c1}$ at each occurrence is independently selected from the group consisting of $C_{1-6}$ alkyl, $OR^a$, Cl, F, —CN, $NO_2$, $NR^aR^{a1}$, $C(O)R^a$, $C(O)OR^a$, $C(O)NR^aR^{a1}$, $OC(O)$ $NR^aR^{a1}$, $R^aNC(O)OR^a$, $S(O)_2NR^aR^{a1}$, $NR^aS(O)_2R^{a2}$, $S(O)_pR^{a2}$, $CF_3$, and $CH_2F$, and $CHF_2$;

$R^d$ at each occurrence is independently selected from the group consisting of H, $C_{1-6}$ alkyl optionally substituted with $R^{c1}$, $OR^a$, Cl, F, —CN, $NO_2$, $NR^aR^{a1}$, $C(O)R^a$, $C(O)OR^a$, $C(O)NR^aR^{a1}$, $R^aNC(O)NR^aR^a$, $OC(O)NR^aR^{a1}$, $R^aNC(O)OR^{a1}$, $S(O)_2$ $NR^aR^{a1}$, $NR^aS(O)_2R^{a2}$, $S(O)_pR^{a2}$, $CF_3$, $CH_2F$, $CHF_2$, $CF_2CH_3$, $C(CH_3)_2$F, $OCF_3$, $OCHF_2$, and $OCH_2CF_3$; $C_{3-10}$ carbocyclic residue, and a 5-10 membered heterocyclic system containing from 1-4 heteroatoms selected from the group consisting of N, O, and S, $C_3$-$C_{10}$ carbocyclyl($C_{1-8}$)alkyl, and 5-14 heterocyclyl ($C_{1-8}$)alkyl; said $C_{3-10}$ carbocyclic residue, heterocyclic system $C_3$-$C_{10}$ carbocyclyl($C_{1-8}$)alkyl, and 5-10 heterocyclyl($C_{1-8}$)alkyl optionally substituted with $R^{c1}$.

$R^{d1}$ at each occurrence is independently selected from the group consisting of H, $C_{1-6}$ alkyl optionally substituted with $R^{c1}$, $OR^a$, Cl, F, —CN, $NR^aR^{a1}$, $C(O)R^a$, $C(O)OR^a$, $C(O)NR^aR^a$, $R^aNC(O)NR^aR^{a1}$, $OC(O)NR^aR^{a1}$, $R^aNC(O)OR^{a1}S(O)_2$ $NR^aR^{a1}$, $NR^aS(O)_2R^{a2}$, $S(O)_pR_2$, $CF_3$, $CH_2F$, $CHF_2$, $CF_2CH_3$, $C(CH_3)_2$F, $OCF_3$, $OCHF_2$, and $OCH_2CF_3$; $C_{3-10}$ carbocyclic residue, and a 5-10 membered heterocyclic system containing from 1-4 heteroatoms selected from the group consisting of N, O, and S, $C_3$-$C_{10}$ carbocyclyl($C_{1-8}$)alkyl, and 5-10 heterocyclyl ($C_{1-8}$)alkyl; said $C_3$ 10 carbocyclic residue, heterocyclic system $C_3$-$C_{10}$ carbocyclyl($C_{1-8}$)alkyl, and 5-14 heterocyclyl($C_{1-8}$)alkyl optionally substituted with $R^{c1}$.

alternatively, $R^d$ and $R^{d1}$ taken together with the atom to which they are attached form a 4 to 8 membered ring containing from 0-1 heteroatoms selected from the group consisting of N, O, and S, wherein said ring may be substituted with $R^d$;

$R^h$ at each occurrence is independently selected from the group consisting of $OR^j$, $NR^jR^a$, $COR^j$, $C(O)OR^j$, $C(O)$ $NR^jR^a$, $NR^aC(O)NR^jR^{a1}$, $OC(O)NR^jR^a$, $S(O)_pNR^jR^{a1}$, $NR^aS(O)pR^j$, $C_{1-6}$ alkyl substituted with $R^c$.

$R^j$ at each occurrence is independently selected from the group consisting of $CF_3$, $CF_2H$, $CFH_2$, $CF_2CF_3$, $C_1$-$C_8$ alkyl substituted with O(primary, secondary, or tertiary) $C_1$-$C_8$, OH, Cl, F, —CN, alkylamino, dialkylamino, alkarylamino, arylamino, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamidoalkyl, N-alkylsufonamidodialkyl, alkylamidosulfonate, dialkylamidosulfonate, alkylsulfonyl, $CF_3$, $CH_2F$, $CHF_2$, $CF_2CH_3$, $C(CH_3)_2$F, $OCF_3$, $OCHF_2$, and $OCH_2CF_3$; $C_2$-$C_8$ alkenyl, $C_2$-$C_8$ alkynyl, wherein said alkenyl and alkynyl groups are optionally substituted with $C_1$-$C_8$ alkyl, O(primary, secondary, or tertiary)$C_1$-$C_8$, OH, Cl, F, —CN, alkylamino, dialkylamino, alkarylamino, arylamino, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsufonamidodialkyl, alkylamidosulfonate, dialkylamidosulfonate, $CF_3$, $CH_2F$, $CHF_2$, $CF_2CH_3$, $C(CH_3)_2$F, $OCF_3$, $OCHF_2$, and $OCH_2CF_3$; $C_3$-$C_{10}$ carbocycle, 5-10 membered heterocycles, $C_3$-$C_{10}$ carbocyclylalkyl, heterocyclylalkyl and wherein said $C_3$-$C_{10}$ carbocycle, heterocycles, $C_3$-$C_{10}$ carbocyclylalkyl, and heterocyclylalkyl may be optionally substituted with one or more substituents selected from the group consisting of O(primary, secondary, or tertiary)$C_1$-$C_8$, OH, Cl, F, —CN, $NO_2$, alkylamino, dialkylamino, alkarylamino, arylamino, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamido-alkyl, N-alkylsufonamidodialkyl, alkylamidosulfonate, dialkylamidosulfonate, alkylsulfonyl, $CF_3$, $CH_2F$, $CHF_2$, $CF_2CH_3$, $C(CH_3)_2$F, $OCF_3$, and $OCH_2CF_3$, with the proviso that said $C_3$-$C_{10}$ carbocycle can not be a phenyl group and $C_3$-$C_{10}$ carbocyclylalkyl can not be a benzyl group;

p at each occurrence is 0, 1, and 2; and r at each occurrence is 0, or an integer from 1 to 10.

In a particular preferred embodiment, the compound is of the formula VA or VIA as shown below

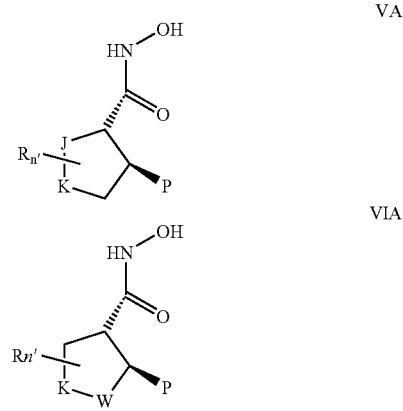

wherein J, K and W are independently selected from the group consisting of —(CH$_2$)$_n$—, NH, NR, O, n=1-3, and n'=1 or 2, with the proviso that J and K, and K and W can not be N—N, N—O or O—O;

P is -D-Q-L-Y, wherein

D is absent or is selected from the group consisting of C(O), C(O)NR$^{a1}$, NR$^{a1}$C(O), S(O)$_p$, S(O)$_p$NR$^{a1}$, and NR$^{a1}$S(O)$_p$;

Q is absent or is selected from the group consisting of a C$_{5-7}$ carbocycle substituted with 0-5 R$^b$, and a 5-7 membered heterocycle comprising carbon atoms and 1-4 heteroatoms selected from the group consisting of N, O, and S(O)$_p$, and said heterocycle being substituted with 0-5 R$^b$;

L is absent or is selected from the group consisting of 0;

Y is selected from the group consisting of H, a C$_{5-7}$ carbocycle substituted with 0-5 R$^c$ and a 5-6 membered heterocycle comprising carbon atoms and 1-4 heteroatoms selected from the group consisting of N, O, and S(O)$_p$, and said heterocycle being substituted with 0-5 R$^c$;

provided that D, Q, L and Y do not combine to form a N—N, N—O, O—N, O—O, S(O)$_p$—O, O—S(O)$_p$ or S(O)$_p$—S(O)$_p$ group;

R, at each occurrence, is independently selected from OH, F, Cl, —CN, NO$_2$, CF$_3$, CH$_2$F, CHF$_2$, CF$_2$CH$_3$, C(CH$_3$)$_2$F, OCF$_3$, OCHF$_2$, O(CR$^d$R$^{d1}$)$_r$-M, NR$^a$(CR$^d$R$^{d1}$)$_r$-M, NR$^a$C(O)(CR$^d$R$^{d1}$)$_r$-M, OC(O)O(CR$^d$R$^{d1}$)$_r$-M, OC(O)NR$^a$(CR$^d$R$^{d1}$)$_r$-M, NR$^a$C(O)O(CR$^d$R$^{d1}$)$_r$-M, NR$^a$C(O)NR$^{a1}$(CR$^d$R$^{d1}$)$_r$-M, S(O)$_p$(CR$^d$R$^{d1}$)$_r$-M, S(O)$_2$NR$^a$(CR$^d$R$^{d1}$)$_r$-M, NR$^a$S(O)$_2$(CR$^d$R$^{d1}$)$_r$-M, C(=NCN)NR$^{a1}$R$^{a2}$; C(=C(H)(NO$_2$))NR$^{a1}$R$^{a2}$; a C$_{3-10}$ carbocycle substituted with 0-5 R$^d$, and a 5-10 membered heterocycle comprising carbon atoms and 1-4 heteroatoms selected from the group consisting of N, O, S(O)$_p$ and said heterocycle being substituted with 0-5 R$^d$;

alternatively, two R, together with a carbon atom on the ring bearing J and K or K and W form the group C$_A$=CR$^d$R$^d$, where the atom C$_A$ is said atom on the ring bearing J and K or K and W;

M is selected from the group consisting of H, OR$^a$, Cl, F, —CN, NO$_2$, NR$^a$R$^a$, C(O)NR$^a$R$^{a1}$, R$^a$NC(O)NR$^a$R$^{a1}$, OC(O)NR$^a$R$^{a1}$, NR$^a$C(O)OR$^a$, NR$^a$C(O)R$^a$, S(O)$_2$NR$^a$R$^{a1}$, NR$^a$S(O)$_2$R$^{a2}$, S(O)$_p$R$^{a2}$, CF$_3$, CH$_2$F, CHF$_2$, CF$_2$CH$_3$, C(CH$_3$)$_2$F, OCF$_3$, OCHF$_2$, a C$_{3-10}$ carbocycle substituted with 0-5 R$^d$, and a 5-10 membered heterocycle comprising carbon atoms and 1-4 heteroatoms selected from the group consisting of N, O, S(O)$_p$ and said heterocycle being substituted with 0-5 R$^d$;

alternatively, R, at each occurrence, is independently selected C$_{1-10}$ alkylene-M$^1$, C$_{2-10}$ alkenylene-M$^1$, C$_{2-10}$ alkynylene-M$^1$, (CR$^d$R$^{d1}$)$_r$O(CR$^d$R$^{d1}$)$_r$-M$^1$, (CR$^d$R$^{d1}$)$_r$NR(CR$^d$R$^{d1}$)$_r$-M$^1$, (CR R$^{d1}$)$_r$C(O)(CR$^d$R$^{d1}$)$_r$-M$^1$, (CR$^d$R$^{d1}$)$_r$C(O)O(CR$^d$R$^{d1}$)$_r$-M$^1$ (CR$^d$R$^{d1}$)$_r$C(O)NR$^a$(CR$^d$R$^{d1}$)$_r$-M$^1$, (CR$^d$R$^{d1}$)$_r$NR$^a$C(O)(CR$^d$R$^{d1}$)$_r$-M$^1$, (CR$^d$R$^{d1}$)$_r$OC(O)O(CR$^d$R$^{d1}$)$_r$-M$^1$, (CR$^d$R$^{d1}$)$_r$OC(O)NR$^a$(CR$^d$R$^{d1}$)$_r$-M$^1$, (CR$^d$R$^{d1}$)$_r$NR$^a$C(O)O(CR$^d$R$^{d1}$)$_r$-M$^1$, (CR$^d$R$^{d1}$)$_r$NR$^a$C(O)NR$^a$(CR$^d$R$^{d1}$)$_r$-M$^1$, (CR$^d$R$^{d1}$)$_r$S(O)$_p$(CR$^d$R$^{d1}$)$_r$-M$^1$, (CR$^d$R$^{d1}$)$_r$S(O)$_2$NR$^a$(CR$^d$R$^{d1}$)$_r$-M$^1$, and (CR$^d$R$^{d1}$)$_r$NR$^a$S(O)$_2$(CR$^d$R$^{d1}$)$_r$-M$^1$;

M$^1$ is selected from the group consisting of OR$^a$, Cl, F, Br, —CN, NO$_2$, NR$^a$R$^{a1}$, C(O)NR$^a$R$^{a1}$, R$^a$NC(O)NR$^a$R$^{a1}$, OC(O)NR$^a$R$^{a1}$, R$^a$NC(O)OR$^a$, S(O)$_2$NR$^a$R$^{a1}$, NR$^a$S(O)$_2$R$^{a2}$, OS(O)$_2$NR$^a$R$^{a1}$, S(O)$_p$R$^{a2}$, CF$_3$, CF$_2$CF$_3$, CH$_2$F, CHF$_2$, CF$_2$CH$_3$, C(CH$_3$)$_2$F, OCF$_3$, and a 5-10 membered non-aromatic heterocycle comprising carbon atoms and 1-4 heteroatoms selected from the group consisting of N, O, S(O)$_p$ and said heterocycle being substituted with 0-5 R$^d$; a C$_3$-C$_{10}$ carbocycle, C$_5$-C$_{10}$ heterocycle and wherein said C$_3$-C$_{10}$ carbocycle and C$_5$-C$_{10}$ heterocycle are substituted with 1-3 R$^h$, and CF$_3$, CF$_2$CF$_3$, CH$_2$F, CHF$_2$, CF$_2$CH$_3$, C(CH$_3$)$_2$F, OCF$_3$, OCHF$_2$, OCF$_2$CF$_3$ and OCH$_2$CF$_3$;

provided that either two R or M, M$^1$ and the atom to which they are attached do not combine to form a N—N, N—O, O—N, O—O, N-halogen, O-halogen, S-halogen, S(O)$_p$—O, O—S(O)$_p$, S(O)$_p$—S(O)$_p$ group, or C(O)F, C(O)Cl, C(O)Br, or C(O)I reactive group;

R$^a$, R$^{a1}$, and R$^{a2}$ at each occurrence are independently selected from the group consisting of H, C$_1$-C$_8$ alkyl, C$_2$-C$_8$ alkenyl, C$_2$-C$_8$ alkynyl; C$_3$-C$_{10}$ carbocycle, heterocycles, C$_3$-C$_{10}$ carbocyclylalkyl, heterocyclylalkyl;

alternatively, R$^a$ and R$^{a1}$ taken together with the nitrogen to which they are attached form a 3 to 8 membered ring containing from 0-1 additional heteroatoms selected from the group consisting of N, O, and S, wherein said ring may be substituted with R$^d$;

R$^b$ at each occurrence is independently selected from the group consisting of C$_{1-6}$ alkyl optionally substituted with R$^{c1}$, O(primary, secondary, or tertiary)C$_1$-C$_8$, OH, Cl, F, —CN, NO$_2$, NR$^a$R$^{a1}$, C(O)NR$^a$R$^{a1}$, R$^a$NC(O)NR$^a$R$^a$, OC(O)NR$^a$R$^{a1}$, R$^a$NC(O)OR$^{a1}$, S(O)$_2$NR$^a$R$^{a1}$, NR$^a$S(O)$_2$R$^{a2}$, S(O)$_p$R$^{a2}$, CF$_3$, CH$_2$F, CHF$_2$, CF$_2$CH$_3$, C(CH$_3$)$_2$F, OCF$_3$, OCHF$_2$, and OCH$_2$CF$_3$;

R$^c$ at each occurrence is independently selected from the group consisting of C$_{1-6}$ alkyl optionally substituted with R$^{c1}$, OR$^a$, Cl, F, —CN, NO$_2$, NR$^a$R$^{a1}$, C(O)NR$^a$R$^{a1}$, R$^a$NC(O)NR$^a$, OC(O)NR$^a$R$^{a1}$, R$^a$NC(O)OR$^{a1}$, S(O)$_2$NR$^a$R$^{a1}$, NR$^a$S(O)$_2$R$^{a2}$, S(O)$_p$R$^{a2}$, CF$_3$, CH$_2$F, CHF$_2$, CF$_2$CH$_3$, C(CH$_3$)$_2$F, OCF$_3$, OCHF$_2$, and OCH$_2$CF$_3$; a C$_{3-10}$ carbocyclic residue, and a 5-10 membered heterocyclic system containing from 1-4 heteroatoms selected from the group consisting of N, O, and S, C$_3$-C$_{10}$ carbocyclyl(C$_{1-8}$)alkyl, and 5-10 heterocyclyl(C$_{1-8}$)alkyl; said C$_{3-10}$ carbocyclic residue, heterocyclic system, C$_3$-C$_{10}$ carbocyclyl(C$_{1-8}$) alkyl, and 5-14 heterocyclyl(C$_{1-8}$)alkyl are optionally substituted with R$^{c1}$;

R$^{c1}$ at each occurrence is independently selected from the group consisting of C$_{1-6}$ alkyl, OR$^a$, Cl, F, —CN, NO$_2$, NR$^a$R$^{a1}$; C(O)R$^a$, C(O)OR$^a$, C(O)N$^a$R$^{a1}$, OC(O)NR$^a$R$^{a1}$, R$^a$NC(O)OR$^a$, S(O)$_2$NR$^a$R$^{a1}$, NR$^a$S(O)$_2$R$^{a2}$, S(O)$_p$R$^{a2}$, CF$_3$, and CH$_2$F, and CHF$_2$;

R$^d$ at each occurrence is independently selected from the group consisting of H, C$_{1-6}$ alkyl optionally substituted with R$^{c1}$, OR$^a$, Cl, F, —CN, NO$_2$, NR$^a$R$^{a1}$, C(O)NR$^a$R$^{a1}$, R$^a$NC(O)NR$^a$R$^a$, OC(O)NR$^a$R$^{a1}$, R$^a$NC(O)OR$^{a1}$, S(O)$_2$NR$^a$R$^{a1}$, NR$^a$S(O)$_2$R$^a$, S(O)$_p$R$^{a2}$, CF$_3$, CH$_2$F, CHF$_2$, CF$_2$CH$_3$, C(CH$_3$)$_2$F, OCF$_3$, OCHF$_2$, and OCH$_2$CF$_3$; C$_{3-10}$ carbocyclic residue, and a 5-10 membered heterocyclic system containing from 1-4 heteroatoms selected from the group consisting of N, O, and S, C$_3$-C$_{10}$ carbocyclyl(C$_{1-8}$) alkyl, and 5-14 heterocyclyl(C$_{1-8}$)alkyl; said C$_{3-10}$ carbocyclic residue, heterocyclic system C$_3$-C$_{10}$ carbocyclyl (C$_{1-8}$)alkyl, and 5-10 heterocyclyl(C$_{1-8}$)alkyl optionally substituted with R$^{c1}$.

R$^{d1}$ at each occurrence is independently selected from the group consisting of H, C$_{1-6}$ alkyl optionally substituted with R$^{c1}$, OR$^a$, Cl, F, —CN, NR$^a$R$^{a1}$, C(O)NR$^a$R$^{a1}$, R$^a$NC(O)NR$^a$R$^a$, OC(O)NR$^a$R$^{a1}$, R$^a$NC(O)OR$^{a1}$, S(O)$_2$NR$^a$R$^{a1}$, NR$^a$S(O)$_2$R$^{a2}$, S(O)$_p$R$^{a2}$, CF$_3$, CH$_2$F, CHF$_2$, CF$_2$CH$_3$, C(CH$_3$)$_2$F, OCF$_3$, OCHF$_2$, and OCH$_2$CF$_3$; C$_{3-10}$ carbocyclic residue, and a 5-10 membered heterocyclic system containing from 1-4 heteroatoms selected from the group consisting of N, O, and S, C$_3$-C$_{10}$ carbocyclyl(C$_{1-8}$) alkyl, and 5-10 heterocyclyl(C$_{1-8}$)alkyl; said C$_{3-10}$ carbocyclic residue, heterocyclic system $C_3$-$C_{10}$ carbocyclyl $(C_{1-8})$alkyl, and 5-14 heterocyclyl$(C_{1-8})$alkyl optionally substituted with $R^{c1}$.

alternatively, $R^d$ and $R^{d1}$ taken together with the atom to which they are attached form a 4 to 8 membered ring containing from 0-1 heteroatoms selected from the group consisting of N, O, and S, wherein said ring may be substituted with $R^d$;

$R^h$ at each occurrence is independently selected from the group consisting of $OR^j$, $NR^jR^a$, $COR^j$, $C(O)OR^j$, $C(O)NR^jR^a$, $NR^aC(O)NR^jR^{a1}$, $OC(O)NR^jR^a$, $S(O)_pNR^jR^a$, $NR^aS(O)_pR^j$, $C_{1-6}$ alkyl substituted with $R^c$.

$R^j$ at each occurrence is independently selected from the group consisting of $CF_3$, $CHF_2$, $CH_2F$, $CF_2CF_3$, $C_1$-$C_8$ alkyl substituted with O(primary, secondary, or tertiary) $C_1$-$C_8$, OH, Cl, F, —CN, alkylamino, dialkylamino, alkarylamino, arylamino, alkylamido, dialkylamido, carbamoylalkyl, carbamoyldialkyl, alkylcarbamoyl, sulfonamidoalkyl, sulfonamidodialkyl, N-alkylsulfonamidoalkyl, N-alkylsulfonamidoalkyl, N-alkylsufonamidodialkyl, alkylsulfonyl, $CF_3$, $CH_2F$, $CHF_2$, $CF_2CH_3$, $C(CH_3)_2F$, $OCF_3$, $OCHF_2$, and $OCH_2CF_3$; $C_2$-$C_8$ alkenyl, $C_2$-$C_8$ alkynyl, wherein said alkenyl and alkynyl groups are optionally substituted with $C_1$-$C_8$ alkyl, O(primary, secondary, or tertiary)$C_1$-$C_8$, OH, Cl, F, —CN, alkylamino, dialkylamino, alkarylamino, arylamino, alkylamido, dialkylamido, carbamoylalkyl, carbamoyldialkyl, alkylcarbamoyl, sulfonamidoalkyl, sulfonamidodialkyl, N-alkylsulfonamidoalkyl, N-alkylsulfonamidoalkyl, N-alkylsufonamidodialkyl, $CF_3$, $CH_2F$, $CHF_2$, $CF_2CH_3$, $C(CH_3)_2F$, $OCF_3$, $OCHF_2$, and $OCH_2CF_3$; $C_3$-$C_{10}$ carbocycle, 5-10 membered heterocycles, $C_3$-$C_{10}$ carbocyclylalkyl, heterocyclylalkyl and wherein said $C_3$-$C_{10}$ carbocycle, heterocycles, $C_3$-$C_{10}$ carbocyclylalkyl, and heterocyclylalkyl may be optionally substituted with one or more substituents selected from the group consisting of O(primary, secondary, or tertiary)$C_1$-$C_8$, OH, Cl, F, —CN, $NO_2$, alkylamino, dialkylamino, alkarylamino, arylamino, alkylamido, dialkylamido, carbamoylalkyl, carbamoyldialkyl, alkylcarbamoyl, sulfonamidoalkyl, sulfonamidodialkyl, N-alkylsulfonamidoalkyl, N-alkylsulfonamido-alkyl, N-alkylsufonamidodialkyl; alkylsulfonyl, $CF_3$, $CH_2F$, $CHF_2$, $CF_2CH_3$, $C(CH_3)_2F$, $OCF_3$, and $OCH_2CF_3$, with the proviso that said $C_3$-$C_{10}$ carbocycle can not be a phenyl group and $C_3$-$C_{10}$ carbocyclylalkyl can not be a benzyl group;

p at each occurrence is 0, 1, and 2; and r at each occurrence is 0, or an integer from 1 to 10.

Additional embodiments associated with the particularly preferred compounds of formula III, IIIA, IV, IVA, V, VA, VI, or VIA include pharmaceutical compositions comprised of a compound of formula III, IIIA, IV, IVA, V, VA, VI, or VIA (inclusive of salts, enantiomer, diastereomers, prodrug forms and other derivatives as hereinabove described) in conjunction with at least one pharmaceutically acceptable carrier, and numerous therapeutic methods accomplished by administering these compositions to mammalian subjects in need of metalloprotease inhibition.

The term "alkyl" when used either alone or as a suffix includes straight chain and branched structures such as primary alkyl groups, secondary alkyl groups and tertiary alkyl groups. These groups may contain up to 15, preferably up to 8 and more preferably up to 4 carbon atoms. Similarly the terms "alkenyl" and "alkynyl" refer to unsaturated straight or branched structures containing for example from 2 to 12, preferably from 2 to 6 carbon atoms. Cyclic moieties such as cycloalkyl, cycloalkenyl and cycloalkynyl are similar in nature but have at least 3 carbon atoms. Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. In the present application, "cycloalkyl" is also intended to include adamantyl groups and other bridge compounds. The terms "alkoxy", "alkylamino" and "alkylthio" (or "thioalkoxy") are used in their conventional sense, and refer to those alkyl groups attached to the remainder of the molecule via an oxygen atom, an amino group, or a sulfur atom, respectively. Therefore, terms such as "alkoxy" and "thioalkyl" comprise alkyl moieties as defined above, attached to the appropriate functionality.

Other suitable substituents which can be used in the many carbon rings of the present invention (such as but not limited to cycloaliphatic, aromatic, non-aromatic heterocyclic rings or benzyl group) include, for example, —OH, halogen (—Br, —Cl, —I and —F)—O(aliphatic, substituted aliphatic, benzyl, substituted benzyl, aromatic or substituted aromatic group), —CN, —$NO_2$, —COOH, —NH2, —NH(aliphatic group, substituted aliphatic, benzyl, substituted benzyl, aromatic or substituted aromatic group), —N(aliphatic group, substituted aliphatic, benzyl, substituted benzyl, aromatic or substituted aromatic group)$_2$, —COO(aliphatic group, substituted aliphatic, benzyl, substituted benzyl, aromatic or substituted aromatic group), —$CONH_2$, —CONH(aliphatic, substituted aliphatic group, benzyl, substituted benzyl, aromatic or substituted aromatic group)), —SH, —S(aliphatic, substituted aliphatic, benzyl, substituted benzyl, aromatic or substituted aromatic group) and —NH—C=NH)—NH2. A substituted non-aromatic heterocyclic ring, benzylic group or aromatic group can also have an aliphatic or substituted aliphatic group as a substituent. A substituted alkyl or aliphatic group can also have a non-aromatic heterocyclic ring, benzyl, substituted benzyl, aromatic or substituted aromatic group as a substituent. A substituted non-aromatic heterocyclic ring can also have =O, =S, =NH or =N(aliphatic, aromatic or substituted aromatic group) as a substituent. A substituted aliphatic, substituted aromatic, substituted non-aromatic heterocyclic ring or substituted benzyl group can have more than one substituent.

The terms "halo" or "halogen", by themselves or as part of another substituent, mean, unless otherwise stated, a fluorine, chlorine, bromine, or iodine atom. Similarly, terms such as "haloalkyl", are meant to include monohaloalkyl and polyhaloalkyl. For example, the term "halo($C_1$-$C_4$)alkyl" is mean to include trifluoromethyl, 2,2,2-trifluoroethyl, 4-chlorobutyl, 3-bromopropyl, and the like.

The term "$C_3$-$C_{13}$ carbocyclic group" is intended to include all cycloaliphatic groups selected from the group consisting of cyclopropyl, cyclobutyl, cyclopentyl, cyclohexyl, cycloheptyl, cyclooctyl, cyclononyl all the way up to a cyclic $C_{13}$ group. The above cycloaliphatic groups may also have unsaturation where appropiate and where there is no high ring strain as a result of the double bond. Additionally, the term "$C_3$-$C_{13}$ carbocyclic group" is also intended to include bridged and fused ring systems such as adamantyl, [3.3.0]bicyclooctane, [4.3.0]bicyclononane, [4.4.0]bicyclodecane, [2.2.2]bicyclooctane, norbornyl, menthenyl, fluorenyl, phenyl, naphthyl, indanyl, indenyl, anthracenyl and hydrogenated derivatives, phenanthrenyl and hydrogenated derivatives and tetrahydronaphthyl. The $C_3$-$C_{13}$ carbocyclic group as defined above may also be substituted with —OH, halogen (—Br, —Cl, —I and —F) —O(aliphatic, substituted aliphatic, benzyl, substituted benzyl, aromatic or substituted aromatic group), —CN, —NO$_2$, —COOH, —NH2, —NH (aliphatic group, substituted aliphatic, benzyl, substituted benzyl, aromatic or substituted aromatic group), —N(aliphatic group, substituted aliphatic, benzyl, substituted benzyl, aromatic or substituted aromatic group)$_2$, —COO(aliphatic group, substituted aliphatic, benzyl, substituted benzyl, aromatic or substituted aromatic group), —CONH$_2$, —CONH(aliphatic, substituted aliphatic group, benzyl, substituted benzyl, aromatic or substituted aromatic group)), —SH, —S(aliphatic, substituted aliphatic, benzyl, substituted benzyl, aromatic or substituted aromatic group) and —NH—C=NH)—NH2.

The terms "3-13 membered heterocyclic system containing from 0-4 heteroatoms" and "5-14 membered heterocyclic system containing from 1-4 heteroatoms" are intended to include aromatic and non aromatic heterocyclic systems. The 3-13 membered heterocyclic is intended to include a 3, 4, 5, 6, or 7-membered monocyclic or bicyclic or 7, 8, 9, 10, 11, 12, or 13 membered bicyclic heterocyclic ring which is saturated, partially unsaturated or unsaturated (aromatic), and which consists of carbon atoms and 1 to 4 heteroatoms independently selected from the group consisting of O, N, NR, and S(O)$_p$, and including any bicyclic group in which any of the above-defined heterocyclic rings is fused to a benzene ring. The 5-14 membered heterocyclic system is intended to include a 5, 6, or 7-membered monocyclic or bicyclic or 7, 8, 9, 10, 11, 12, 13, or 14-membered bicyclic heterocyclic ring which is saturated, partially unsaturated or unsaturated (aromatic), and which consists of carbon atoms and 1 to 4 heteroatoms independently selected from the group consisting of O, N, NR, and S(O)$_p$, and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized.

Examples of heterocycles include, but are not limited to, pyrimidinyl, phenanthridinyl, phenanthrolinyl, phenazinyl, phenothiazinyl, phenoxathiinyl, phenoxazinyl, phthalazinyl, piperazinyl, piperidinyl, 1,2,3,6-tetrahydropyridyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrazolyl, 6H-1,2,5-thia-diazinyl, 1,2,3-thiadiazolyl, 1,2,4thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, quinazolinyl, quinolinyl, 4H-quinolizinyl, quinoxalinyl, quinuclidinyl, acridinyl, azocinyl, benzimidazolyl, benzofuranyl, benzothiofuranyl, benzo-thiophenyl, benzoxazolyl, benzthiazolyl, benztriazolyl, benztetrazolyl, benzisoxazolyl, benzisothiazolyl, benzimidazolinyl, methylenedioxyphenyl, morpholinyl, naphthyridinyl, deca-hydroquinolinyl, 2H, 6H-1,5,2dithiazinyl, dihydrofuro [2,3-b]tetrahydrofuran, furanyl, furazanyl, carbazolyl, 4aH-carbazolyl, carbolinyl, chromanyl, chromenyl, cinnolinyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl and isoxazolyl. Also included are fused ring and spiro compounds containing, for example, the above heterocycles.

Unless otherwise indicated, the compounds provided in the above formulae I-IV are meant to include pharmaceutically acceptable salts, prodrugs thereof, enantiomers, diastereomers, racemic mixtures thereof, crystalline forms, non-crystalline forms, amorphous forms thereof and solvates thereof.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, phosphoric, partially neutralized phosphoric acids, sulfuric, partially neutralized sulfuric, hydroiodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention may contain both basic and acidic functionalities that allow the compounds to be converted into either base or acid addition salts.

The neutral forms of the compounds of the present invention may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As noted above, some of the compounds of formulae I, IA, II, IIA, III, IIIA, IV, IVA, V, VA, VI, and VIA possess chiral or asymmetric carbon atoms (optical centers) or double bonds; the racemates, diastereomers, geometric isomers and individual optical isomers are all intended to be encompassed within the scope of the invention.

Some of the compounds of formulae I, IA, II, IIA, III, IIIA, IV, IVA, V, VA, VI, and VIA can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

In addition to the above-described salt forms, the present invention also embraces the compounds of formulae I-VI in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex-vivo environment. For example, prodrugs can be slowly converted to the compounds of the present invention when placed in a transdermal patch reservoir with a suitable enzyme or chemical reagent.

The novel compounds of the present invention may be prepared in a variety of ways well known to one skilled in the art of organic synthesis. The compounds of the present invention can be synthesized using the methods as hereinafter described below, together with synthetic methods known in the art of synthetic organic chemistry or variations thereon as appreciated by those skilled in the art. Preferred methods include, but are not limited to, those described below. The entire contents of all references cited herein are hereby incorporated by reference.

The novel compounds of this invention may be prepared using the reaction pathways and techniques as described below.

The inventive compounds, and the salts, solvates, and prodrugs thereof, may be prepared by employing the techniques available in the art using starting materials that are readily available. Exemplary methods of preparing the inventive compounds are described below. In the following schemes, unless otherwise indicated, Z, P, R, $R^1$, $R^2$, $R^3$, $R^4$, D, Q, L, T, X, and Y, etc. are as previously defined herein.

The inventive compounds of the formula I and IA wherein Z is hydroxamic acid group can be prepared by reacting a compound of the formula 1a (where Z is a carboxylic acid) with hydroxylamine in the presence of a suitable peptide coupling reagent. Illustrative examples of suitable coupling agents including 1,1'-carbonyl-diimidazole, N-(dimethylaminopropyl)-N'-ethyl carbodiimide, benzotriazol-1-yloxy-tris(dimethylamino)phosphonium hexafluoro-phosphate ("PyBOP"), or propanephosphonic anhydride in an inert polar solvent, such as dimethylformamide ("DMF").

Alternatively, the coupling reactions described above can be carried out with compounds of formula 1a and oxygen-protected compounds of hydroxylamine (i.e., a suitable protecting group known to those skilled in the art, such as benzyl, t-butyl, t-butyldimethylsilyl, or t-butyldiphenylilyl, and/or described in T. W. Green and P. G. M. Wuts, *Protective Groups in Organic Synthesis* (1991)) to give compounds of formula 2/Deprotection of compounds of the formula 2 provides compounds of formula (I). Suitable methods of deprotecting compounds of the formula 2 are known in the art, for example, as described in T. W. Green and P. G. M. Wuts, *Protective Groups in Organic Synthesis* (1991).

Compounds of the formula 1a can be prepared by alkaline hydrolysis of the corresponding ester 1b (where alkyl is a suitable group such as methyl, ethyl, allyl, benzyl- or t-butyl) using a suitable aqueous base, such as lithium hydroxide, sodium hydroxide, or potassium hydroxide, preferably in a homogeneous aqueous-organic solvent mixture. Alternatively, these compounds can also be prepared by acid hydrolysis of the corresponding ester using a suitable aqueous acid, such as hydrochloric acid in aqueous dioxane, at a suitable temperature. Other methods recognizable by those skilled in the art as suitable for converting esters to acids can also be employed, such as hydrogenolysis of the benzyl ester using hydrogen and palladium on carbon, acid-promoted cleavage of t-butyl esters under anhydrous conditions, and palladium-catalyzed cleavage of allyl esters.

Alternatively, compounds of formula I can also be prepared from the ester compound of formula 1b via several routes known in the literature, such as by treatment of the esters 1b with hydroxylamine under basic conditions such as KOH or NaOMe in solvents such as methanol, by converting the esters 1b to oxygen-protected hydroxyamic acid under similar conditions followed by subsequent deprotection as previously described or by using Weinreb's trimethylaluminum reaction conditions (J. I. Levin, E. Turos, S. M. Weinreb, *Syn. Comm.* 1982, 12, 989) or Roskamp's bis[bis(trimethylsilyl)amido] tin reagent (W.-B. Wang, E. J. Roskamp, *J. Org. Chem.* 1992, 57, 6101). The compounds of formula 1b with different substiutents R, $R^1$, and $R^2$ can be synthesized following a variety of literature routes by funtionalizing the corresponding ring A compounds of formula 3 or 16 as outlined in Scheme 2-5. One representative approach as shown in Scheme 2 is selective reduction of the ketone of formula 3 with appropriate metal-hydride system known in art, such as sodium borohydride in an aprotic solvent. Alkylation of the alcohol compound of formula 4 with the desired alkyl halide or alkyl sulfonate under basic conditions as reviewed in "Comprehensive Organic Transformations, A Guide to Funtional Group Preparations" (R. C. Larock, Wiley-VCH, 1999) provides ether compounds of formula 5. Alternatively, ether compound 5 may be prepared by Mitsnobu reaction as known in the art. The alcohol compounds of formula 4 can also be converted to carbonates of formula 6 or carbamates of formula 7 via several approaches known in the literatures, such as by reacting alcohol of formula 4 with desired chloroformates or carbamyl chlorides in the presence of a base, or by treatment of the alcohol of formula 4 with carbonyl diimidazole or p-nitrophenyl chloroformate followed by reaction of the resultant active carbamate or carbonate with desired alcohols or amines.

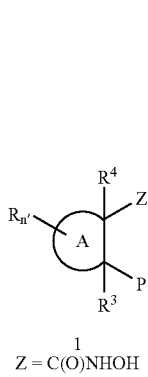

Scheme 1

Scheme 2

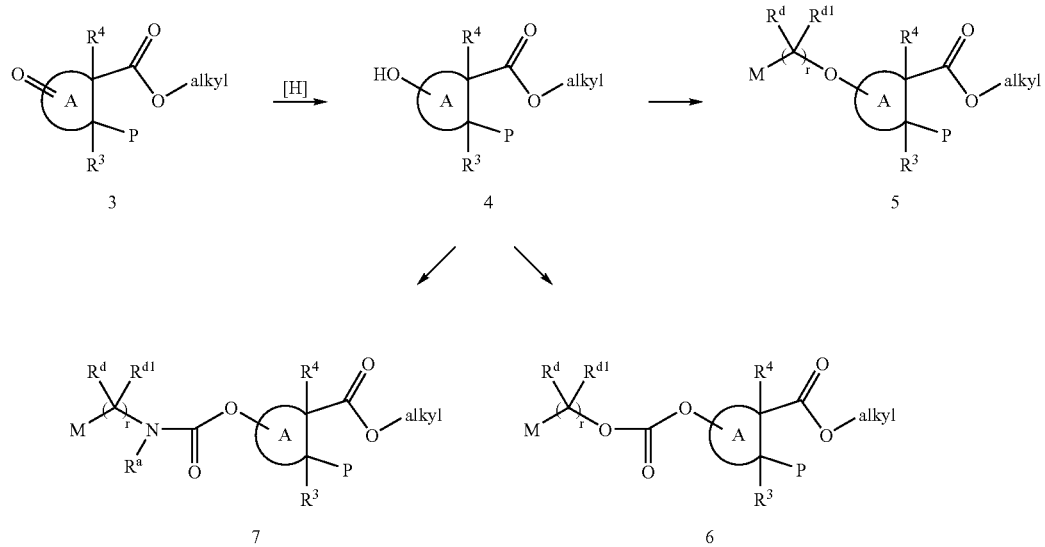

Alternatively, the ketone of formula 3 could be subjected to reductive amination with desired amines to afford the amines of formular 8 (Scheme 3) following a variety of literature procedures such as reviewed in "Comprehensive Organic Synthesis" (B. M. Trost, I. Fleming, Eds. Pergamon, 1991, Vol 8, Part 1.2, P25). The amines of formula 8 could then be further transformed into amides of formula 9, sulfonamides of formula 10, carbamates of formula 11, or ureas of formula 12 using methods known in the art.

Scheme 3

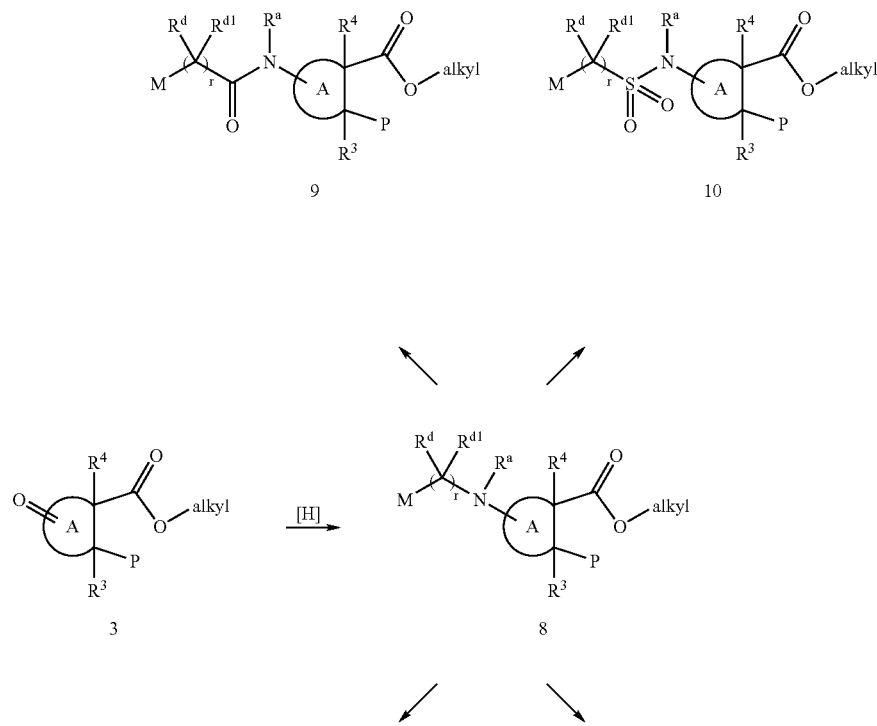

-continued

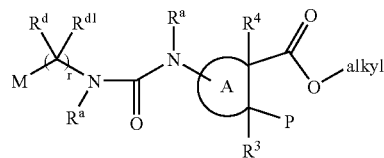

12

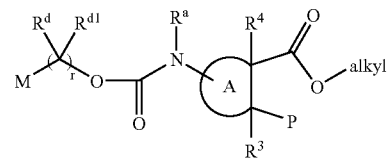

11

Alternatively, the ketones of formula 3 could be subjected to carbonyl homologation as outlines in Scheme 4 and reviewed in "Comprehensive Organic Transformations, A Guide to Funtional Group Preparations" (R. C. Larock, Wiley-VCH, 1999). For example, treatment of compounds of formula 3 with trimethylsilyl cyanide in the presence of tin (II) chloride followed by acid hydrolysis (*Syn. Commun.* of the ester followed by reduction of the resultant acid to form the corresponding alcohols with borane, then oxidation of the alcohol to form the corresponding aldehydes. The latter aldehydes can be further functionalized using reaction methodology in an analogous manner as those described in Schemes 2 and 3.

Scheme 4

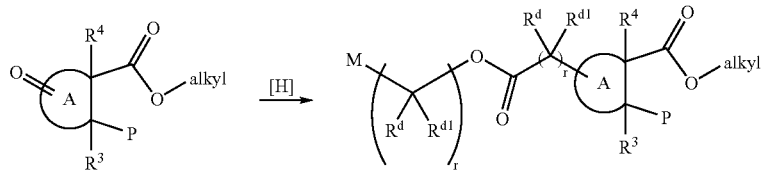

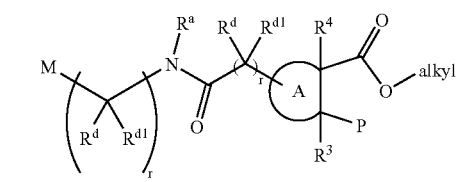

14

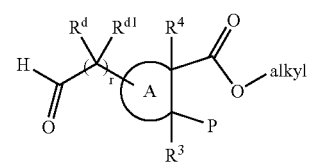

15

1982, 12, 763), or, by reacting with 1,3-dithianes anion followed by acid catalysis hydrolysis (*Tetrahedron Lett.* 1988, 29, 1493) or mecury salt catalyzed hydrolysis (*J. Org. Chem.* 1991, 56, 4499). Where desired, compounds of formula 3 can also be subjected to Wittig and related reaction conditions followed by catalytic hydrogenation to reduce the resultant double bond to provide compounds of formula 13 as shown in Scheme 4 (Comprehensive Organic Synthesis, B. M. Trost, I. Fleming, Eds. Pergamon, 1991, Vol 1, Part 3.1, P729). The esters of formula 13 can then be transformed to amides of formula 14 using the methods described in Scheme 1. On the other hand, the esters of formula 13 can be converted to aldehydes of formula 15 by methods recognizable by those skilled in the art; for example, such as by selective hydrolysis Alternatively, ketone of formula 3 can be subjected to Grignard or related lithium anion reaction conditions to generate a tertiary alcohol as depicted in Scheme 5. Or, ketone of formula 3 can also be subjected to reactions with allyltrimethylsilane catalyzed by lewis acid to generate corresponding tertiary alcohol. The tertiary alcohols can be further derivatized as described in Scheme 2. Alternatively, the ketone of formula 3 can also be subjected to Wittig reaction conditions to furnish a vinyl compound which can be oxidized to an epoxide (Scheme 5). The epoxide can be opened by HO(CR$^d$R$^{d1}$)$_r$M or HN(R$^a$)(CR$^d$R$^{d1}$)$_r$M to affored vicinal diol mono-ether or vicinal amino alcohol, respectively. The latter can be further modified as described in Scheme 2 and 3 when (CR$^d$R$^{d1}$)$_r$M is hydrogen.

Scheme 5

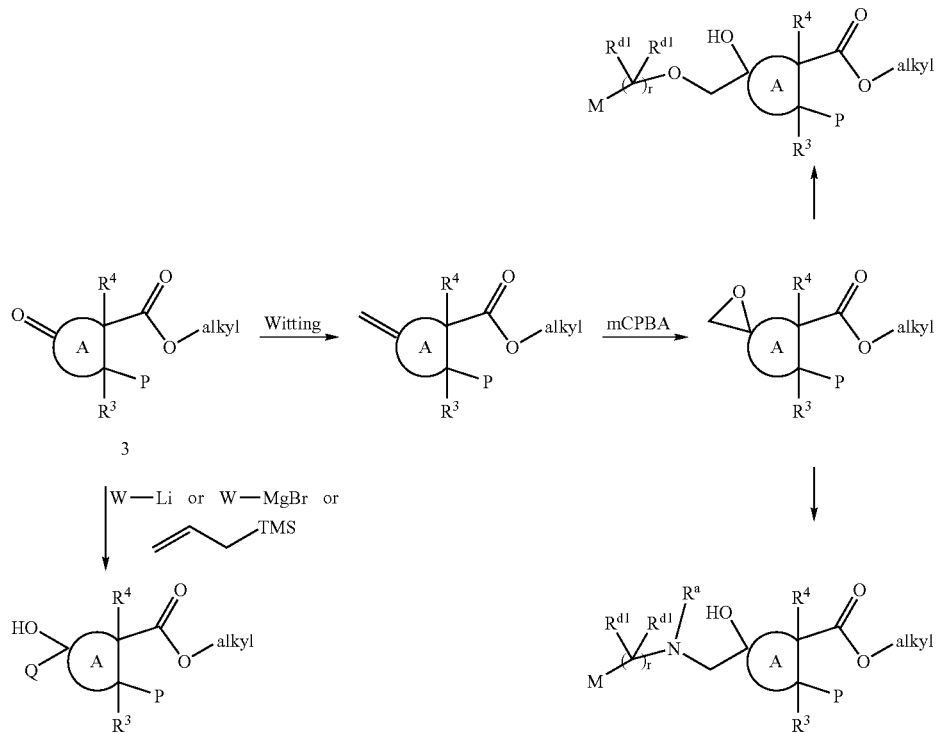

When the ring A is an aza-ring, as shown in formula 16 in Scheme 6, the compounds can be converted directly to formula 17, 18, 19, 20 and 21, for example by treatment with a suitable alkylating or acylating agent, such as an alkyl halide, sulfonyl chloride, carboxylic acid chloride, chloroformate or carbamyl chloride, respectively, in a suitable solvent at an appropriate temperature. Alternatively, the compounds of formula 16 can also be alkylated to yield formula 22, which could then be further functionalized as described in Scheme 4.

Scheme 6

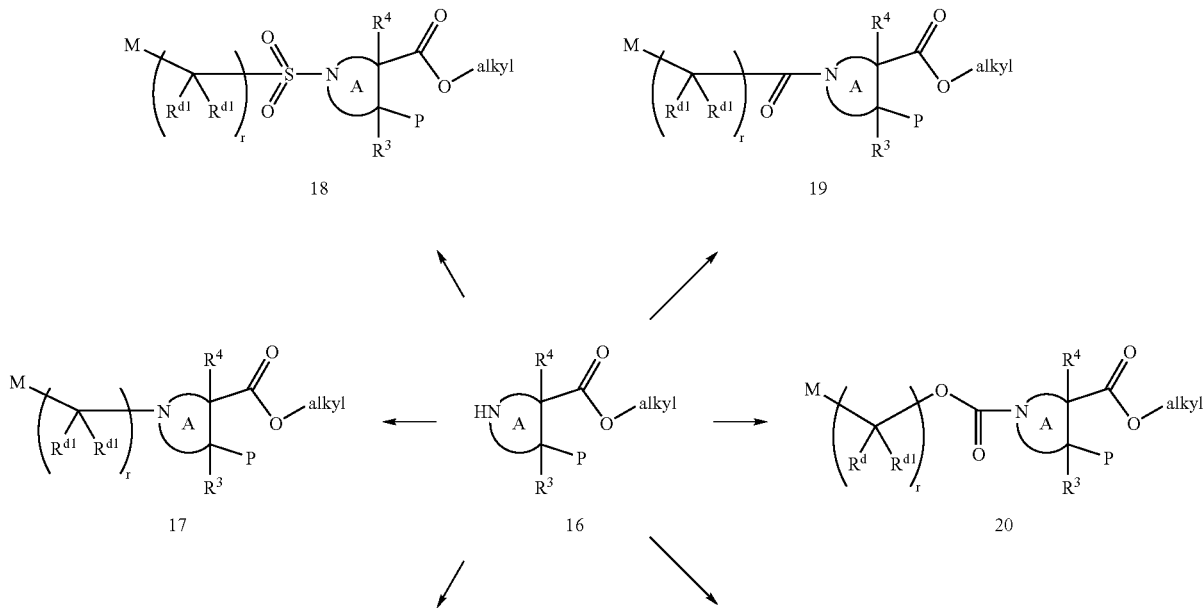

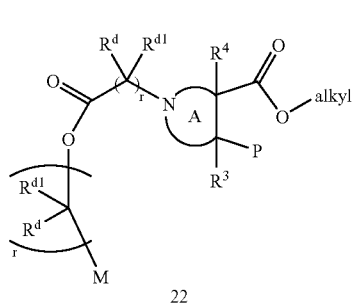

22

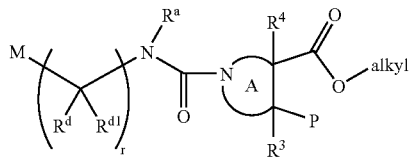

21

The ring A compounds of formula 3 and 16 can be synthesized using the methods outlined in Scheme 7-15, together with synthetic methods known in the art of synthetic organic chemistry, or variations therein as appreciated by those skilled in the art. Preferred methods include, but are not limited to, those described below.

The 5-oxo-piperidine of formula 30 and 31 can be prepared using the procedures described in Scheme 7. L-Aspartic acid β-tert-butyl ester monohydrate is treated with 2 equivalents of benzyl bromide in the presence of DBU in toluene to afford mono-benzyl amine 23. Alkylation of 23 with 1'-chloro-2-chloromethyl-1-propene gives allyl chloride 24, which is converted to the corresponding allyl iodide 25 by the treatment with sodium iodide in acetone. The latter is reacted with LiHMDS to yield the piperidine ring compound 26. After changing the benzyl protection in 26 to Cbz protection, the resultant alkene 27 was subjected to ozonelization to provide the ketone compound 28. The latter can be de-protected by catalyzed hydrogenation and then reacts with an appropriate amines to generate the corresponding ketone 30. Alternatively, the amino acid 29 can be subjected to coupling with benzyl protected hydroxylamine in the presence of BOP to furnish benzyl protected hydroxyamide 31, which could then be converted to ketone 32.

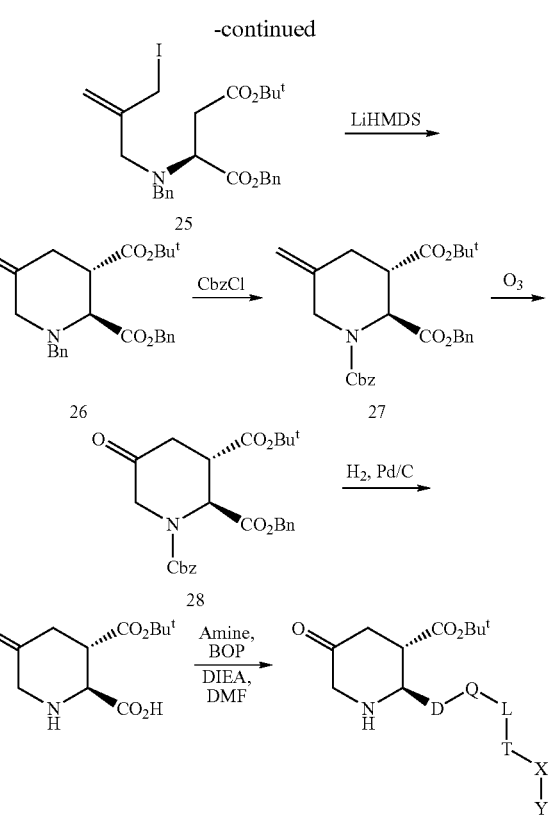

Scheme 7

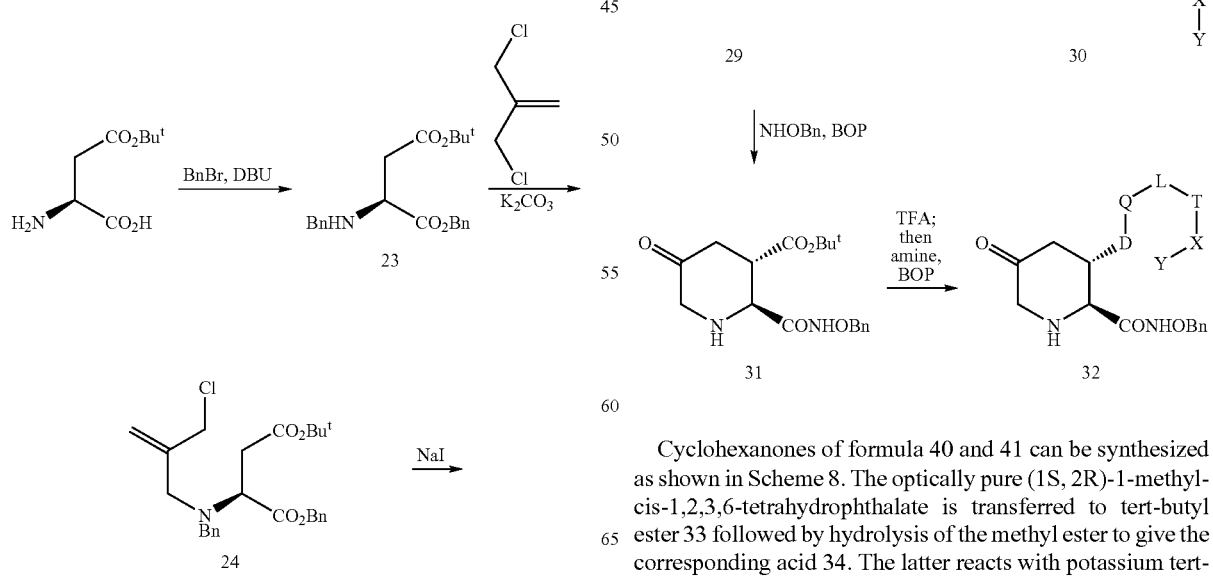

Cyclohexanones of formula 40 and 41 can be synthesized as shown in Scheme 8. The optically pure (1S, 2R)-1-methyl-cis-1,2,3,6-tetrahydrophthalate is transferred to tert-butyl ester 33 followed by hydrolysis of the methyl ester to give the corresponding acid 34. The latter reacts with potassium tert-butoxide to yield the trans-compound 35. Treatment of 35 with iodine affords lactone 36. After removal of the iodide by treatment with tris(trimethylsilyl)silane, the lactone 37 is treated with benzyl alcohol to provide a differentiated bis-ester 38, which can be oxidazided to give ketone 39 under Dess-Martin oxidation or Swern oxidation conditions. Ketone 39 can then be transformed selectively to ketone 40 or 41 by deprotection and coupling with desired amines, respectively. Alternatively, ketone 39 can be prepared from corresponding cyclohexene directly via Wacker oxidation.

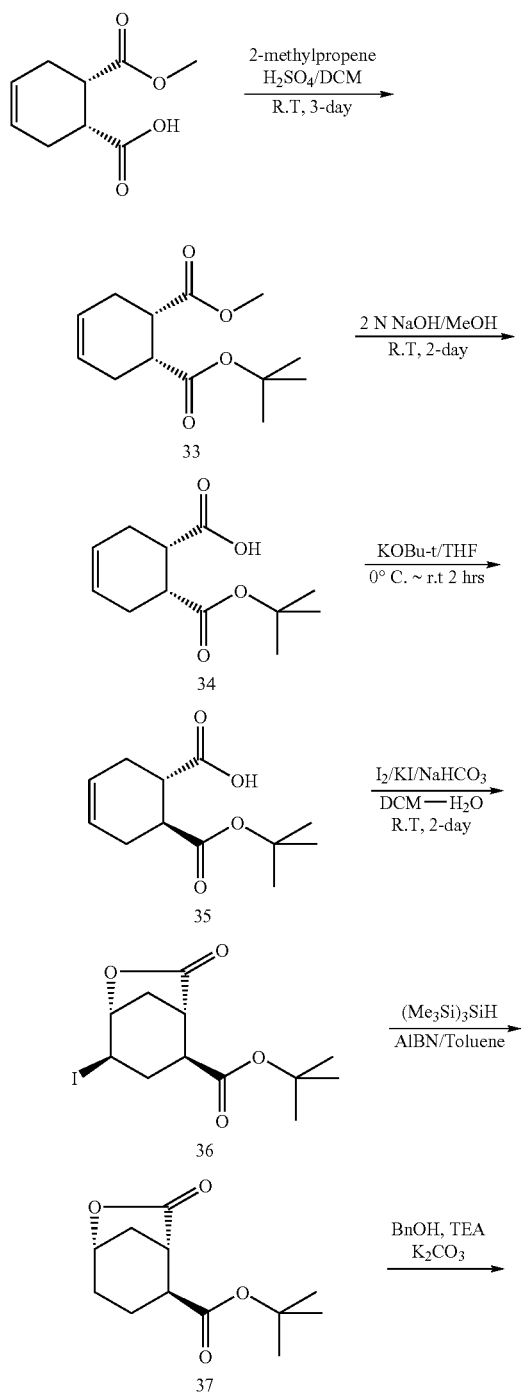

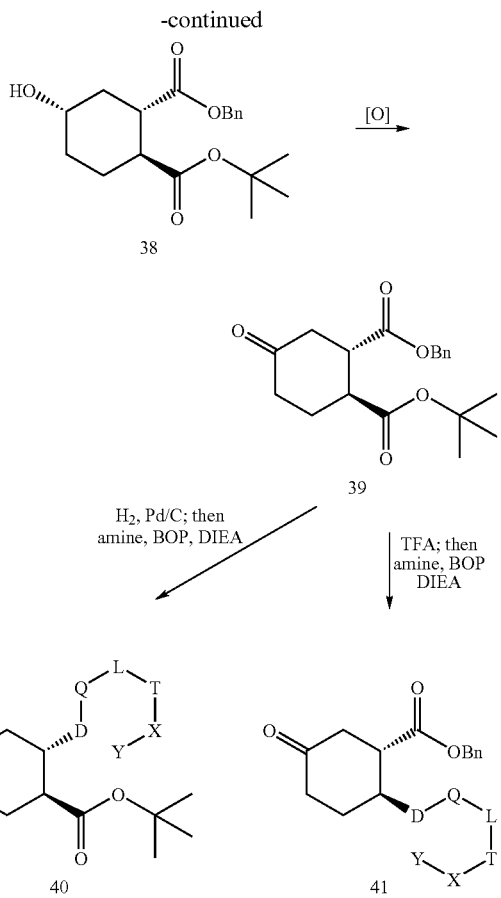

The cyclopentanones of formula 46 and 47 can be synthesized as illustrated in Scheme 9. The optically pure (1S, 2R)-1-methyl-cis-1,2,3,6-tetrahydrophthalate is converted to trans-isomer 42, followed by treatment with 2-methylpropene in the presence of sulfuric acid to furnish diester 43. The cyclohexene 43 is oxidized to the bis-acid and cyclized to the ketone 45 (for a related example refer to: Gais et al. *J. Org. Chem.* 1989, 54, 5115). The ketone 45 is then converted to 46 or 47 as shown in Scheme 9.

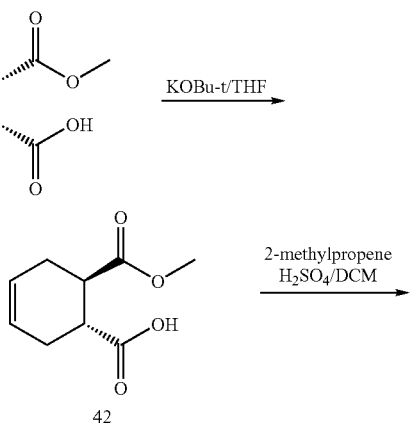

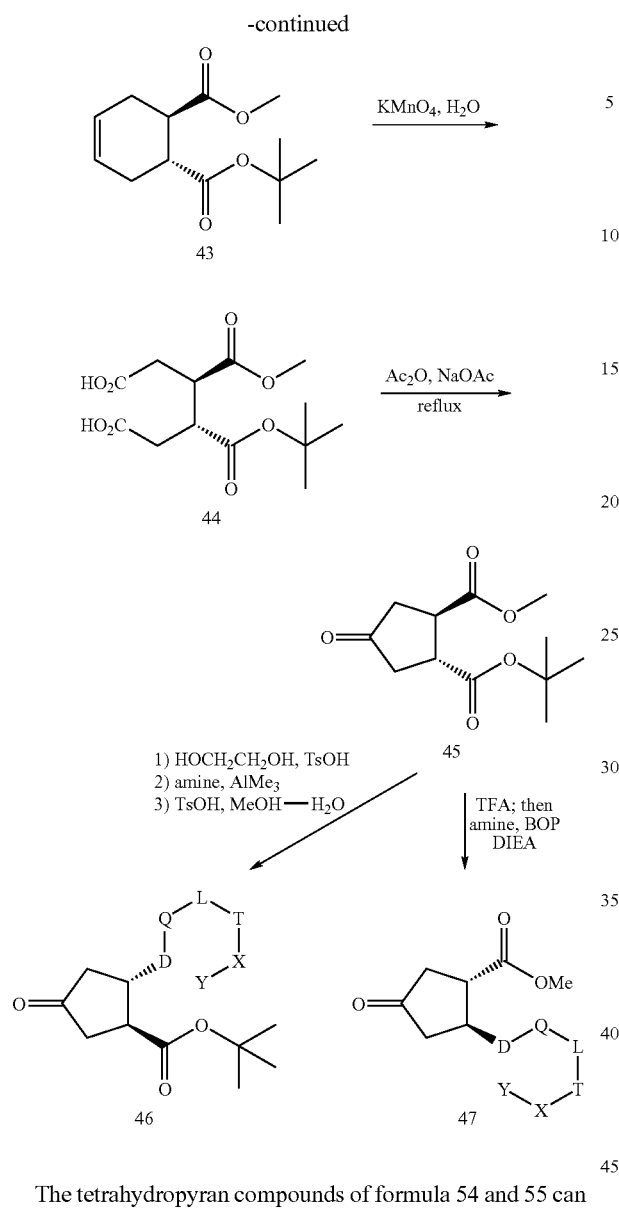
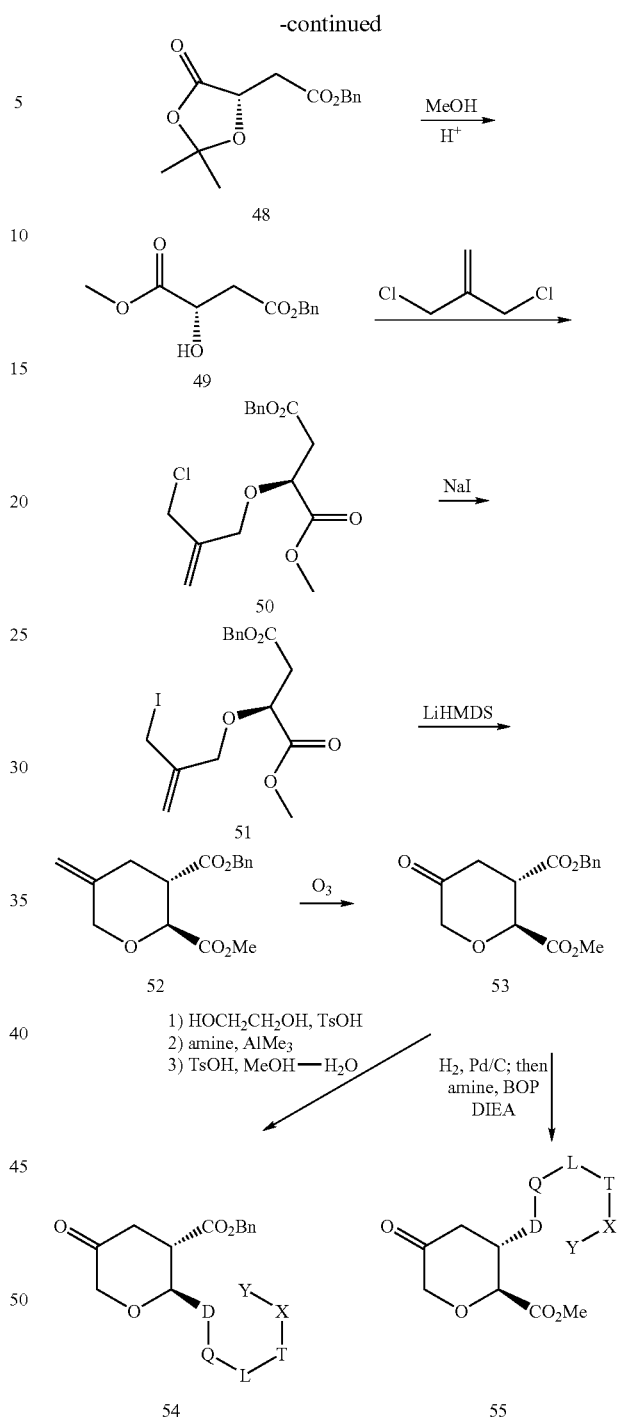

The tetrahydropyran compounds of formula 54 and 55 can be prepared starting from (S)-(+)-2,2-dimethyl-5-oxo-1,3-dioxolane-4-acetic acid as illustrated in Scheme 10. After being protected as benzyl ester 48, the dioxolane ring is hydrolyzed to give methyl ester 49. Reaction of 49 with 1-chloro-2-chloromethyl-1-propene under basic conditions provides allyl chloride 50, which is converted to iodide 51. Treatment of 51 with LiHMDS yields tetrahydropyran 52. The latter can then be ozonized to give ketone 53 and subsequently 54 and 55 as shown in Scheme 10.

Scheme 10

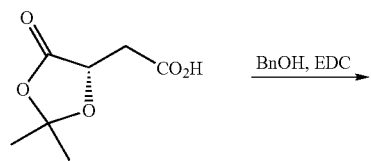

The tetrahydrofuran compounds of formula 62 and 63 can be obtained as described in Scheme 11. Protection of hydroxy compound 49 as silyl ether 56 followed by reaction of the latter with allyl iodide in the presence of KHMDS generates compound 57 as a major diastereoisomer. After deprotection, the hydroxy compound 58 is treated with iodine to furnish 59. Iodide 59 can then be converted to aldehyde 61 via an alcohol intermediate 60. The coupling of the aldehyde 60 with the desired amines as shown in Scheme 111 then provides tetrahydrofuran compounds of formula 62 and 63.

Scheme 11

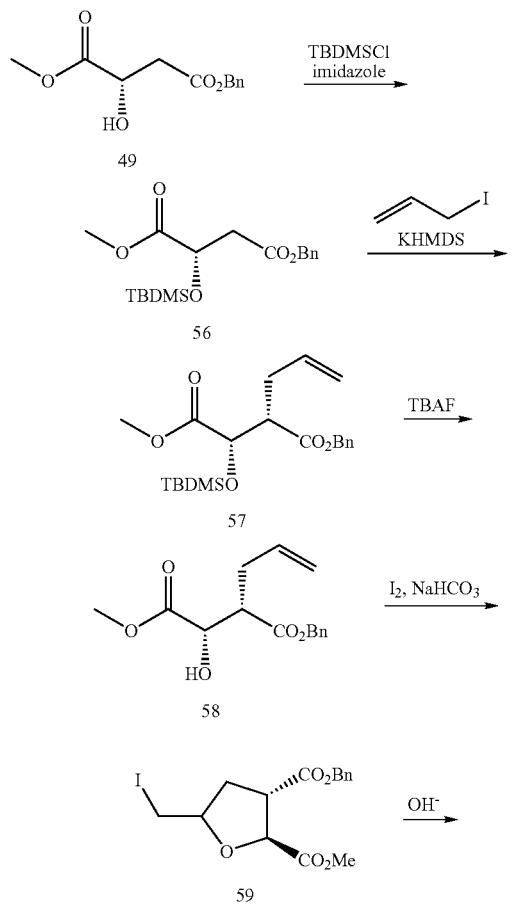

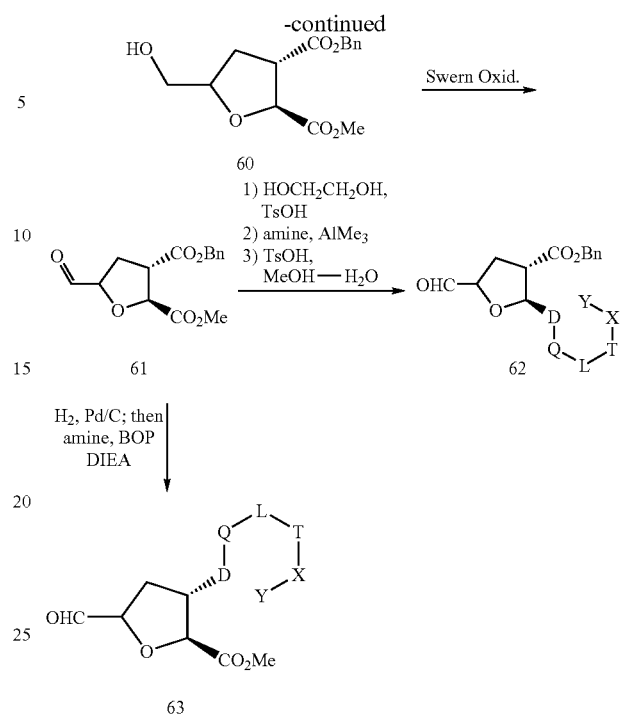

A series of trans-2,3-pyrrolidinedicarboxylate of formula 68 and 69 can be prepared using the sequence shown in Scheme 12. Alkylation of Cbz-protected L-aspartic acid ester with allyl iodide using LiHMDS as a base followed by chromatography to separate the two produced diastereoisomers yields the desired syn-diastereoisomer 64. Ozonolysis of 64 converts it to an aldehyde 65. Hydrogenation of 65 leads to a ring closure to generate a pyrrolidine 66. Derivatization at the dicarboxylic acid as described in Scheme 7 affords compounds of formula 68 and 69.

Scheme 12

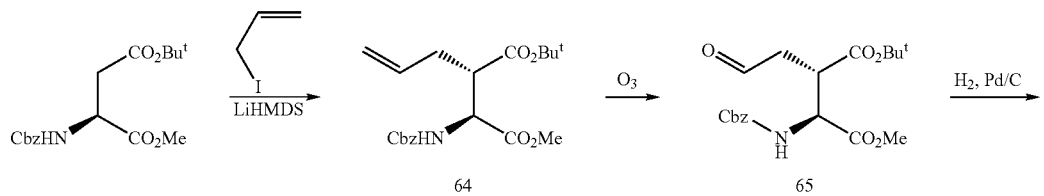

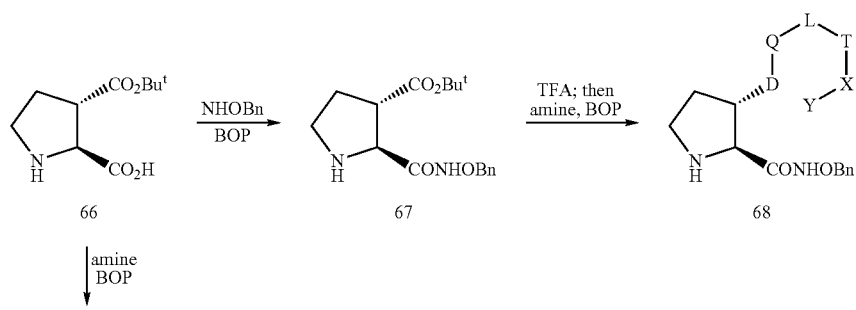

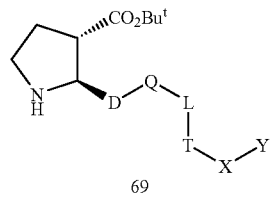
-continued
The 5-formyl pyrrolidine compounds of formula 76 and 77 can be obtained in analogue to the preparation of 5-formyl tetrahydrofuran as described in Scheme 10 and is illustrated in Scheme 13.
Scheme 13
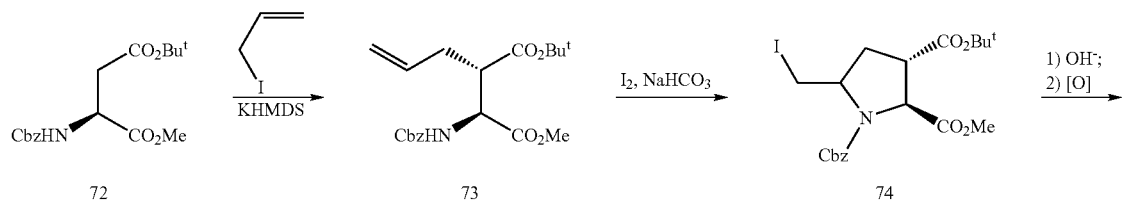
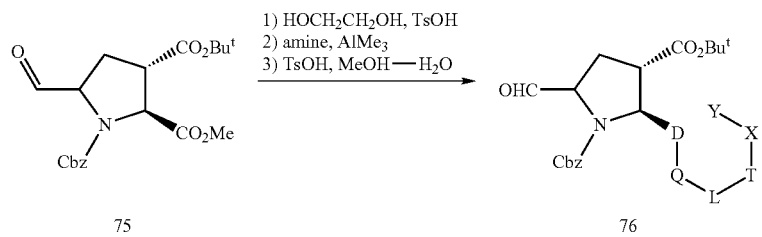
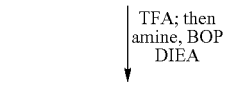
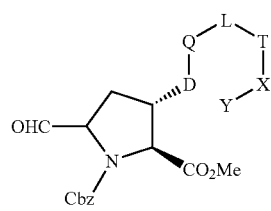

A series of compounds of formula 81 and 82 are prepared following the sequence outlined in Scheme 14. Pyrrolidine 79 is prepared following a dipolar addition procedure documented in the literature (M. Joucla, J. Mortier, *Chem. Commun.* 1985, 1566). After Boc-pretection of the pyrrolidine, compound 80 can be transformed to the desired compounds of formula 81 and 82, respectively.

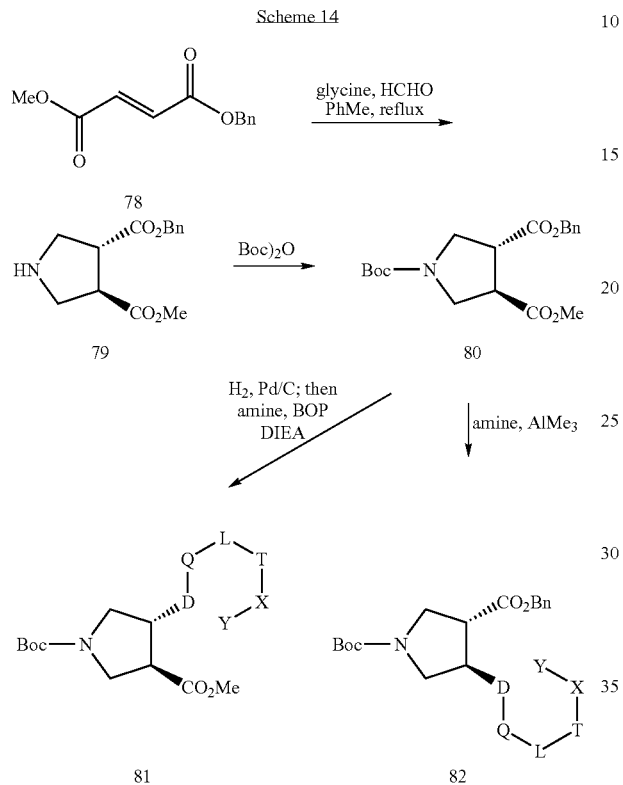

Compounds of formula (I) wherein ring A is piperidine (shown below) can be prepared following literature procedures (C.-B. Xue, X. He, J. Roderick, R. L. Corbertt, C. P. Decicco, *J. Org. Chem.* 2002, 67, 865).

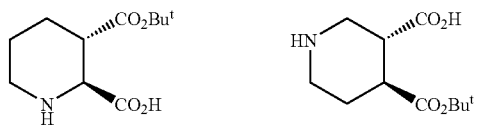

It should be noted that the synthesis shown above could be modified to construct the R, $R^1$ and $R^2$ before coupling of ring A with amines to form the —D-E-G-Q-L-T-X-Y fragment. One stereomer of a compound of formula (I) may display better activity compared with the others. Thus the following stereochemistries are considered to be a part of the present invention.

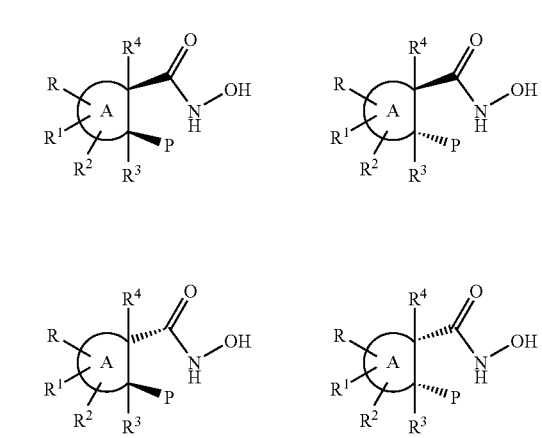

When required, separation of the racemic material can be achieved by HPLC using a chiral column or by a resolution using a resolving agent such as camphonic chloride as documented in literature (S. H. Wilen, "Tables of Resolving Agents and Optical Resolutions, 1972) or using enantiomerically pure acids and bases. A chiral compounds of Formula (I) may also be directly synthesized using a chiral catalyst or a chiral ligand (E. Jacobsen, *Acc. Chem. Res.* 2000, 33, 421) or using other enantio- and diastereo-selective reactions and reagents known to one skilled in the art of asymmetric synthesis.

For example, the axial hydroxy compound shown in Scheme 15 could be prepared by reduction with L-Selectride in THF. The axial and equatorial hydroxy isomers were obtained in a ratio of 15:1. On the other hand, the equatorial hydroxy compound could be obtained, by reduction with sodium boronhydride in methanol, as a separable 11:1 mixture of equatorial and axial diastereoisomers.

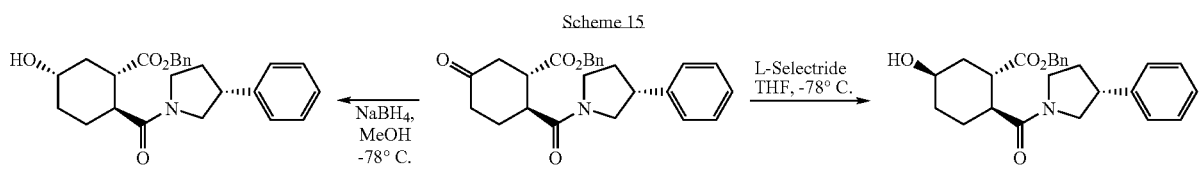

The alkene compound in Scheme 16 could be selective reduced to axial isomer in 92% d.e. under homogeneous conditions.

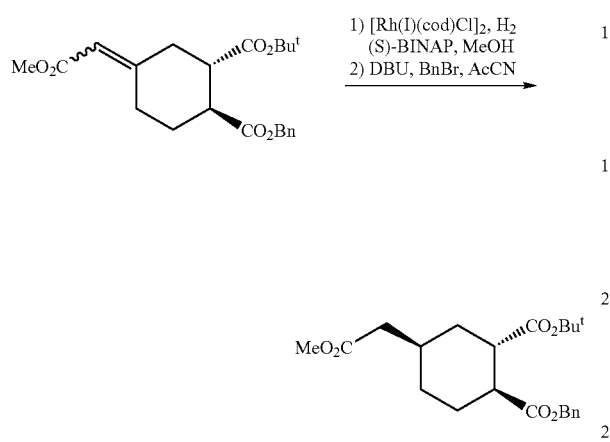

Scheme 16

Intermediates of the present invention with a formula -Q-Y (P, wherein E, G, L, T, and X are absent) can be synthesized using strategies loosely grouped into three types: synthesis in which the ring Q is attached to the ring Y through the ring nitrogen; carbon-carbon bond formation between the two cyclic structures; and synthesis in which the ring Q is formed during synthesis. This is illustrated in Scheme 15-18 using aryl piperazine and aryl piperidine and aryl pyrrolidine as examples, respectively (wherein Q is piperazine, piperidine or pyrroline; and Y is aryl).

Aryl piperazines can be prepared by reacting Boc-piperazine with a variety of boronic acid under the catalysis of copper (II) acetate (Combs, A. P.; Tadesse, S.; Rafalski, M.; Haque, T. S.; Lam, P. Y. S. *Journal of Combinatorial Chemistry* 2002, 4, 179), or by reacting with a variety of aryl halide using Hartwig's catalyst (Louie, J; Hartwig, J. F. *Tetrahedron Lett.* 1995, 36, 3609). After removal of the Boc group, compound 90 can be coupled with ring A compounds to furnish compounds of formula 91 (Scheme 17). It should be noted that the arylpiprazine can also be prepared through classical ring closure of appropriately substituted anilines and bis(2-chloroethyl)amine hydrochloride in the presence of base (E. Mishani, et. al. *Tetrahedron Lett.* 1996, 37, 319), or through direct nucleophilic aromatic substitution of the piperazine (S. M. Dankwardt, et al, *Tetrahedron Lett.* 1995, 36, 4923).

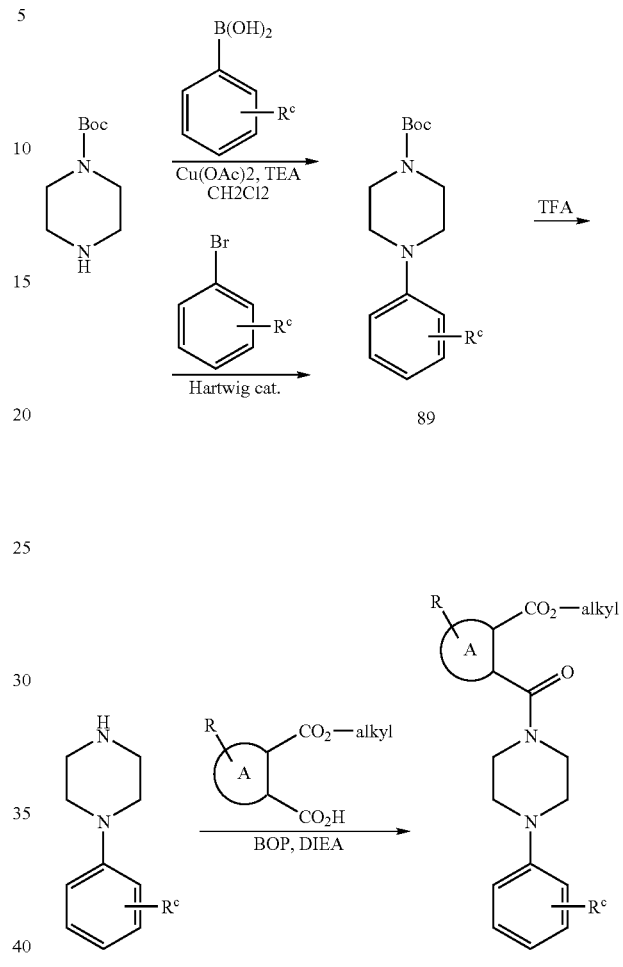

Scheme 17

Aryl piperidines such as 36 may be synthesized as described in Scheme 18. tert-Butoxycarbonylpiperid-4-one is converted to the enol triflate 92 using LDA and N-phenyltrifluoromethanesulfonamide. Suzuki-type coupling with arylboronic acid then produces the aryltetrahydropyridine 94 (M. G. Bursavich, D. H. Rich, *Org. Lett.* 2001, 3, 2625). Compound 94 can also be prepared from Suzuki-type coupling of aryl halide with enol boronate 93. After deprotection, compound 95 can be converted to formula 96. The aryltetrahydropyridine can be reduced to saturated aryl piperidine under catalytic hydrogenation condition where desired. It should be noted that compound 94 can also be prepared though classic direct nucleaphilic addition of aryl anion to a piperidone followed by dehydration of the resultant alcohol compound.

Scheme 18

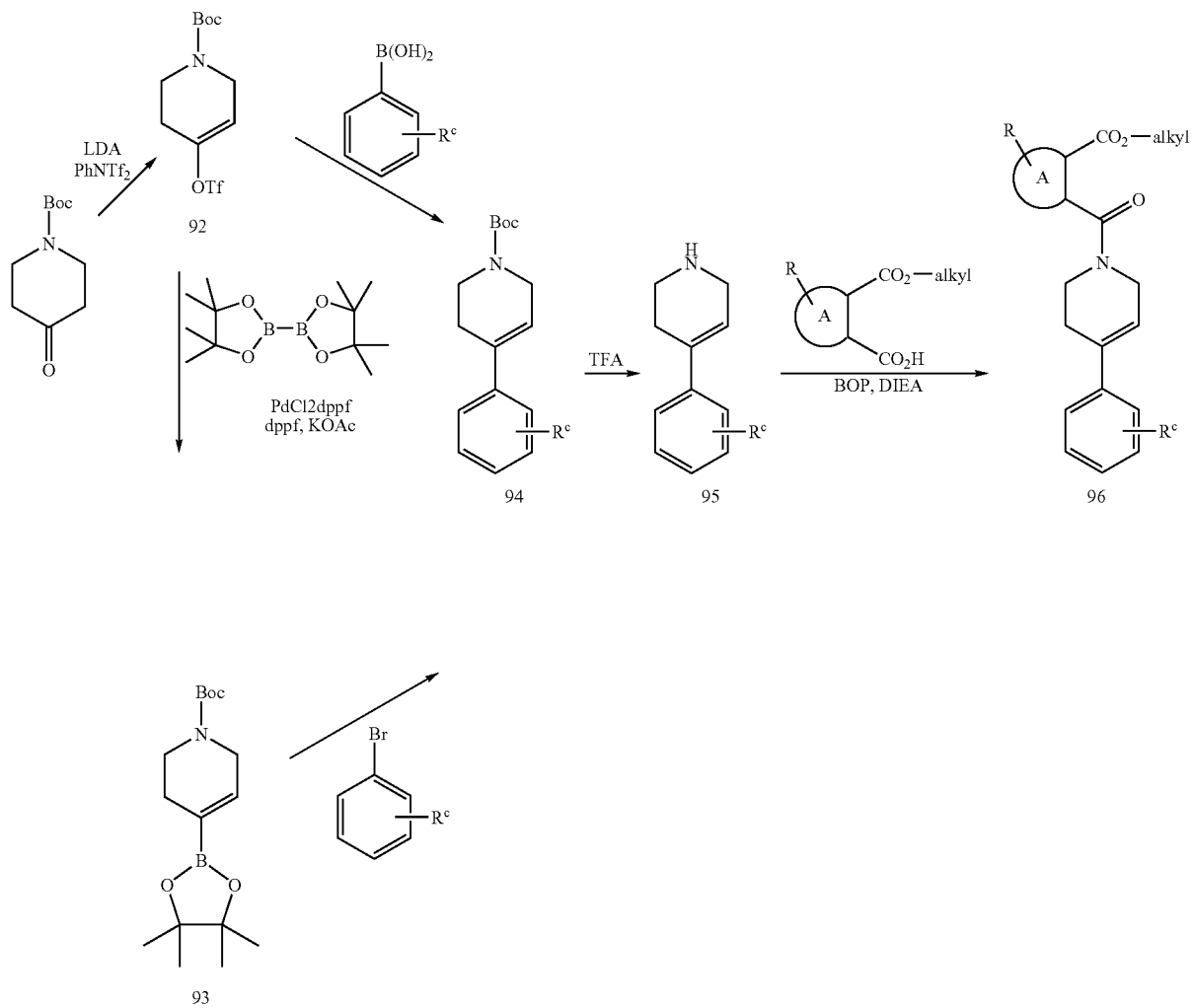

Alternatively, aryl piperidine derivatives can be prepared by coupling of 4-bromopyridine with a boronic acid using Pd(PPh$_3$)$_4$ as a catalyst followed by hydrogenation as shown in Scheme 19.

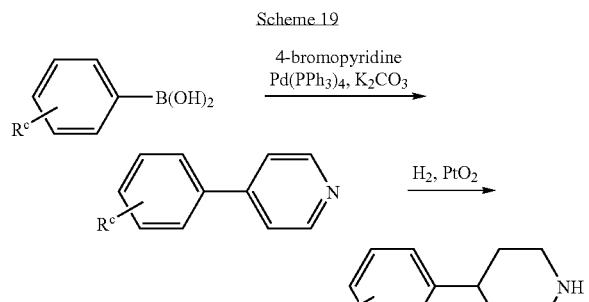

Scheme 19

Phenylpyrrolidine 100 can be prepared as illustrated in Scheme 20. Optical pure (R)-phenylsuccinic acid is reduced to diol 97 followed by mesylation to afford di-mesylate 98. Treatment of 98 with benzylamine in the presence of triethylamine provides pyrrolidine 99, which after hydrogenation provides 100. Alternatively, refluxing of (R)-phenylsuccinic acid in acetyl chloride affords the corresponding anhydride 102. After treatment with ammonia and reflux in acetyl chloride again, imide 103 is obtained and then subjects to LAH reduction to give the phenylpyrrolidine 100. Reaction of 100 with ring A compound generated formula 101. It should be noted that aryl pyrrolidine compounds also can be synthesized through Suzuki-type coupling via an enol triflate or enol boronate intermediates as described in Scheme 16. It also can be prepared through classic direct nucleaphilic addition of aryl anion to a pyrrolidone followed by dehydration of the resultant alcohol compound and then asymmetric hydrogenation.

Scheme 20

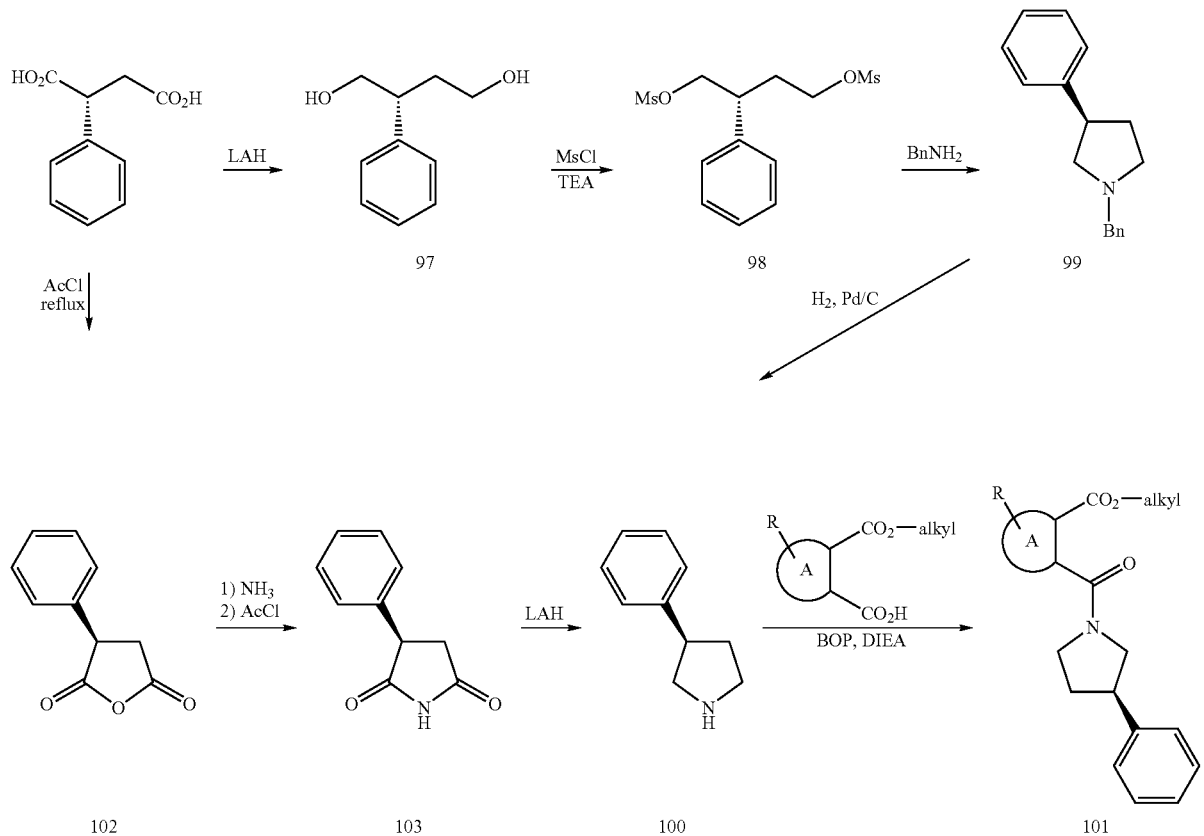

Intermediates of the present invention with a formula -Q-L-T-Y (P, wherein E, G, and X are absent) can be synthesized as exemplified in Scheme 21 (wherein Q is phenyl, L is oxygen, T is methylene, and Y is methylquilonine). The starting material 2-methylquilonine is converted to alcohol 104 followed by treatment with thionyl chloride to yield 105. Reaction of 105 with phenol 106 under basic conditions provides 107. The latter can be de-protected by treating with TFA to afford aniline 108, which can then be transformed to intermediate of formula 109.

Scheme 21

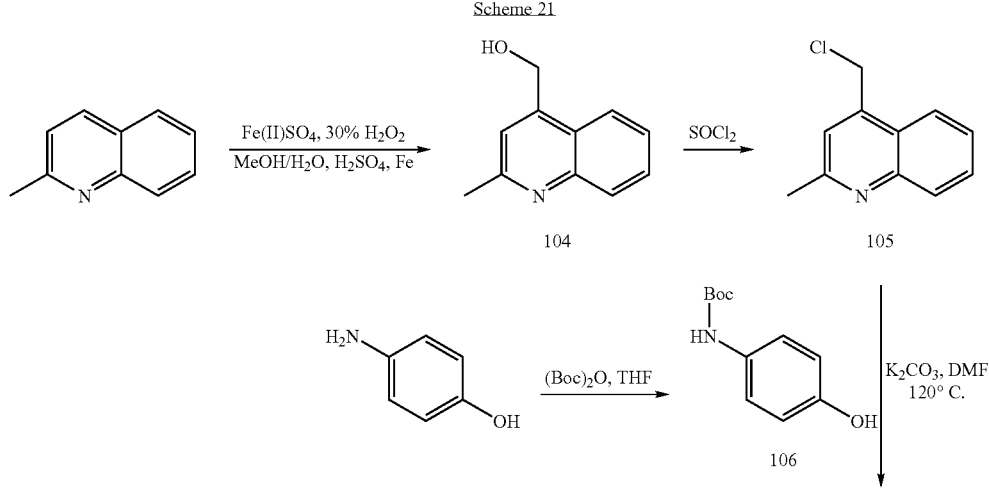

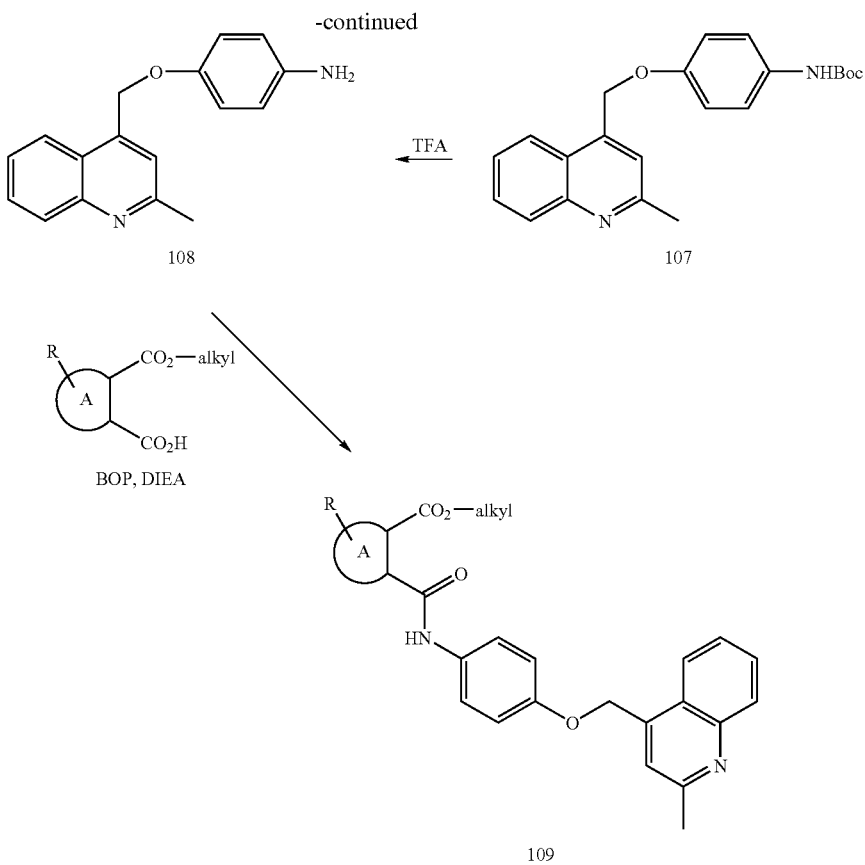

Other possible P groups (wherein -D-E-G-Q-L-T-X-Y are as previously defined herein) can be prepared using methodologies known in the art. Specific examples of methods used to prepare the inventive compounds are described below along with illustrative preferred embodiments of the inventive compounds of the formulae (I), (II), and (III) or their pharmaceutically acceptable prodrugs, salts or solvates.

The following specific examples are intended to be illustrative of the invention and should not be construed as limiting the scope of the invention as defined by the appended claims. These examples include preferred embodiments of the inventive compounds.

EXAMPLES

Reagents and solvents used below can be obtained from commercial sources such as Aldrich Chemical Co. (Milwaukee, Wis., USA). Mass spectrometry results are reported as the ratio of mass over charge. In tables, a single m/e value is reported for the M+H (or, as noted, M-H) ion containing the most common atomic isotopes. Isotope patterns correspond to the expected formula in all cases.

Example 1

(2S,3S,5R)-2-{[4-(4-cyano-2-methylphenyl)-3,6-dihydropyridin-1(2H)-yl]carbonyl}-N-hydroxy-5-[(3R)-3-hydroxypyrrolidin-1-yl]piperidine-3-carboxamide Part 1: To a mixture of L-aspartic acid β-tert-butyl ester monohydrate (22 g, 106 mmol) and benzyl bromide (35 g, 205 mmol) in toluene (600 mL) was added DBU (33 g, 217 mmol) dropwise, at 0° C., under nitrogen. The mixture was allowed to warm to rt and stirred overnight. The crude reaction mixture was filtered through a glass filter and concentrated under reduced pressure. The residue was purified by Combiflash (hexane and ethyl acetate: gradient 0 to 10% in 12 min) to afford 12.1 g (30.9%) of (2S)-benzylamino-succinic acid 1-benzyl ester 4-tert-butyl ester. MS (ESI): 370 (M+H$^+$).

Part 2: A mixture of (2S)-benzylamino-succinic acid 1-benzyl ester 4-tert-butyl ester (12.1 g, 32.6 mmol), K$_2$CO$_3$ (14 g, 3 equiv.), NaI (3.0 g, 20 mmol) and 3-chloro-2-chloromethyl-1-propene (5.1 g, 40.8 mmol) in MeCN (150 mL) was stirred at 81° C. for 16 h. After cooling, the reaction mixture was filtered and the filtrate was concentrated under reduced pressure. Purification by Combiflash (hexane and ethyl acetate: gradient 0 to 8% during 12 min) afforded (2S)-[benzyl-(2-chloromethyl-allyl)-amino]-succinic acid 1-benzyl ester 4-tert-butyl ester (8.7 g, 58%). MS (ESI): 458 (M+H$^+$).

Part 3: A mixture of the chloride made above (8.7 g, 19.0 mmol) and NaI (8.0 g, 53.3 mmol) in acetone (100 mL) was stirred at rt overnight. The heterogeous mixture was filtered and the filtrate was concentrated under reduced pressure. The residue was treated with methylene chloride and filtered through a pad of silica gel to give the corresponding iodide compound (9.2 g, 88.2%). MS (ESI): 550 (M+H$^+$).

Part 4: To a solution of the iodo-compound made above (9.2 g, 16.76 mmol) in anhydrous THF (50 mL) was added dropwise LiHMDS (1.0 M in THF, 20.2 mL) at –78° C., under nitrogen, during a period of 30 min. The mixture was stirred at –78° C. for 1 h, and then was allowed to warm to –30° C.

during a period of 3 h. The reaction mixture was quenched with 10% citric acid (10 mL), diluted with brine (100 mL) and extracted with ethyl acetate (4×75 mL). The combined organic layers were dried over $MgSO_4$ and concentrated under reduced pressure. The residue was purified using Combiflash (eluting with hexane and ethyl acetate: gradient 0 to 5% during 12 min) to give (2S,3S)-1-benzyl-5-methylene-piperidine-dicarboxylic acid 2-benzyl ester 3-tert-butyl ester (3.45 g, 48.9%). MS (ESI): 422 ($M+H^+$).

Part 5: A mixture of the N-benzylpiperidine made above (2.3 g, 5.46 mmol) and benzyl chloroformate (3 mL) was stirred at 65° C. for 28 h. The excess of the benzyl chloroformate was removed under reduced pressure and the residue was purified by Combiflash (hexane and ethyl acetate: gradient 0 to 10% during 12 min) to give the corresponding N-Cbz protected piperidine compound (1.40 g, 52.6%). MS (ESI): 488 ($M+Na^+$); 366 ($M+2H^+$—COO(t-Bu)).

Part 6: Ozone was passed through a solution of the alkene compound made above (6.0 g, 12.9 mmol) in methylene chloride (250 mL), at −78° C., until the color of the solution remained blue. After the addition of dimethyl sulfide (1.2 mL. 16.1 mmol), the resultant mixture was allowed to warm to rt and stirred overnight. The mixture was then concentrated under reduced pressure, redissolved in methylene chloride and washed with brine. After drying the organic layer with $MgSO_4$ and removal of the volatiles in-vacuo, the crude product was purified by chromatography (hexane and ethyl acetate: gradient 0 to 30%) to give (2S,3S)-5-oxo-piperidine-tricarboxylic acid 1,2-dibenzyl ester 3-tert-butyl ester (5.2 g, 86.2%). MS (ESI): 468 ($M+H^+$).

Part 7: A mixture of (R)-pyrrolinol (140 mg, 1.60 mmol) and the ketone made above (250 mg, 0.53 mmol) in of methylene chloride (5 mL) was treated with $NaBH(OAc)_3$ (339 mg, 1.60 mmol) and stirred at rt overnight. The reaction was quenched with satd. $NaHCO_3$ and extracted with methylene chloride. The organic layers were combined and dried with sodium sulfate. After evaporation of the solvent, the resultant residue was purified by flash chromatography (eluting with 0 to 10% MeOH in $CH_2Cl_2$) to afford a mixture of (R)-[(R)-hydroxypyrrolidine] substituted piperidine compound (115 mg, 39.9%) and its diastereoisomer, (S)-[(R)-hydroxypyrrolidine]substituted piperidine compound (64 mg, 22.2%). MS (ESI): 539 ($M+H^+$).

Part 8: A solution of the (R)-[(R)-hydroxypyrrolidine]substituted isomer made above (230 mg, 0.43 mmol) in methanol (5 mL) was hydrogenated in the presence of 10% Pd/C, under balloon pressure of hydrogen, overnight. The heterogeous reaction mixture was filtered through a pad of celite and concentrated under reduced pressure to afford the corresponding desired amino acid (133 mg, 99%), which was used directly in the coupling reaction in Part 13.

Part 9: To a solution of tert-butyl-4-oxopiperidine-1-carboxylate (5.21 g, 26.16 mmol) in anhydrous THF (26 mL) was added dropwise LiHMDS (1.0 M in THF, 28.7 mL, 28.7 mmol) at −78° C., under nitrogen. After 20 min, a solution of N-phenyl trifluoromethanesulfonimide (10.0 g, 27.99 mmol) in THF (26 mL) was added and the reaction was allowed to gradually warm to 0° C. and stirred for 3 h. The reaction was quenched with a minimum amount of saturated $NaHCO_3$ and the resultant mixture was concentrated under reduced pressure. Flash chromatography on neutral $Al_2O_3$ afforded the desired enol triflate (8.67 g, 100%).

Part 10: A flask charged with bis(pinacolato)diboron (3.37 g, 13.28 mmol), sodium acetate (2.97 g, 36.22 mmol), [1,1'-bis(diphenylphosphino)ferrocene]dichloropalladium (II)] ($PdCl_2$dppf) (0.296 g, 0.36 mmol), dppf (0.20 g, 0.36 mmol) and 1,4-dioxane (30 mL) was flushed with nitrogen. To the flask was added a solution of the enol triflate (4.0 g, 12.07 mmol) in 1,4-dioxane (30 mL) and the resultant mixture was stirred at 80° C. overnight. The reaction was quenched by the dropwise addition of water and aqueous layer was extracted with ethyl acetate. The combined organic layers were washed with brine, dried over $MgSO_4$ and concentrated under reduced pressure. The residue was purified by flash chromatography, eluting with 0 to 10% ethyl acetate in hexane, to give the boronate as a white wax-like solid (3.14 g, 84%). MS (ESI): 210 ($M+2H^+$−Boc), 332 ($M+Na^+$).

Part 11: To a nitrogen flushed flask containing the above boronate (2.0 g, 6.47 mmol), $K_2CO_3$ (2.68 g, 19.40 mmol) and $PdCl_2$dppf (317 mg, 0.38 mmol) was added a solution of 4-bromo-3-methylbenzonitrile (1.40 g, 7.12 mmol) in DMF (33 mL). The resultant mixture was heated to 80° C. and vigorously stirred overnight under nitrogen. The reaction was quenched with water and extracted with ethyl acetate. The combined organic layers were combined and washed with brine, dried ($MgSO_4$) and concentrated under reduced pressure. The residue was purified by flash chromatography, eluting with 0 to 30% ethyl acetate in hexane, to provide the desired biaryl product (1.5 g, 77.7%).

Part 12: The above tetrahydropyridine compound (1.3 g, 4.36 mmol) was treated with HCl/dioxane solution (4N, 5 mL) at rt for 1 h. The mixture was concentrated under reduced pressure to afford 3-methyl-4-(1,2,3,6-tetrahydropyridin-4-yl)-benzonitrile HCl salt (1.02 g, 100%). MS (ESI): 199 ($M+H^+$).

Part 13: A mixture of the amino acid made in part 8 (53 mg, 0.17 mmol), 3-methyl-4-(1,2,3,6-tetrahydropyridin-4-yl)-benzonitrile HCl salt (40 mg, 0.17 mmol) and BOP (82 mg, 0.19 mmol) in DMF (0.2 mL) was treated with diisopropylethylamine (0.065 mL, 0.37 mmol) at rt, under nitrogen, for 2 h. The reaction was quenched with saturated $NaHCO_3$ and extracted with ethyl acetate. The combined organic layers were washed with brine, dried over $MgSO_4$ and concentrated under reduced pressure. The resultant residue was used directly in next step without further purification. MS (ESI): 495 ($M+H^+$).

Part 14: The above-titled compound was dissolved in $CH_2Cl_2$ (1 mL) and treated with TFA (1 mL) at rt for 3 h. The mixture was concentrated under reduced pressure to afford the crude piperidine 3-carboxylic acid, which was used directly in next step without purification. MS (ESI): 439 ($M+H^+$).

Part 15: A mixture of the above crude piperidine 3-carboxylic acid was dissolved in DMF (0.2 mL) and to this was added sequentially: hydroxylamine HCl salt (19 mg, 0.27 mmol), BOP (73 mg, 0.16 mmol), and diisopropylethylamine (0.072 mL, 0.41 mmol) at rt, under nitrogen. After 2 h, the reaction mixture was applied directly on RP-HPLC to provide the title compound as a TFA salt (29 mg, 35% in 3 steps). MS (ESI): 454.1 ($M+H^+$).

Example 2

(2S,3S)-2-{[4-(4-cyano-2-methylphenyl)-3,6-dihydropyridin-1(2H)-yl]carbonyl}-5-(2-{[2-(dimethylamino)ethyl]amino}-2-oxoethyl)-N-hydroxypiperidine-3-carboxamide Part 1: To a flask charged with methyl(triphenylphosphoranylidene)acetate (787 mg, 2.35 mmol) was added a solution of (1,2S,3S)-5-oxo-piperidine-tricarboxylic acid 1,2-dibenzyl ester 3-tert-butyl ester (500 mg, 1.07 mmol) in toluene (5.4 mL). The resultant mixture was heated to reflux and stirred overnight. After cooling the reaction mixture to rt, the volatiles were removed under reduced pressure. Purification by flash chromatography, eluting with 0 to 30% ethyl acetate in hexane, afforded the Wittig products as a separable trans- and cis-mixture (257 mg, 45.9%, 7:1, stereochemistry not determined). MS (ESI): 546 (M+Na$^+$).

Part 2: A solution of the alkene mixture (257 mg, 0.49 mmol) in methanol (3 mL) was hydrogenated in the presence of 10% Pd/C (60 mg), under balloon pressure of hydrogen, for 2 h. The heterogeneous mixture was filtered through a pad of celite and the volatiles were removed under reduced pressure to afford (5)-methoxycarbonylmethyl-piperidine-(2S, 3S)-dicarboxylic acid 3-tert-butyl ester (148 mg, 100%) as an inseparable mixture of diastereoisomers. MS (ESI): 302 (M+H$^+$).

Part 3: The amino acid made above (148 mg, 0.49 mmol) was coupled with 3-methyl-4-(1,2,3,6-tetrahydropyridin-4-yl)-benzonitrile HCl salt (115 mg, 0.49 mmol) as described in Example 1, Part 13 to provide the corresponding amide compound. MS (ESI): 482 (M+H$^+$).

Part 4: To a solution of the crude product made above (115 mg, 0.49 mmol) in THF (1 mL) was added a solution of LiOH solution (3 N, 0.049 mL, 1.47 mmol) at 0° C. The resultant mixture was stirred at rt for 1 h, then 3 mL of 1N HCl was added at 0° C. The mixture was lyophilized to afford (5)-carboxylmethyl-(2S)-[4-(4-cyano-2-methyl-phenyl)-3,6-dihydro-2H-pyridine-1-carbonyl]-piperidine-(3S)-carboxylic acid tert-butyl ester lithium salt, which was used directly in the following step. MS (ESI): 468 (M+H$^+$).

Part 5: The lithium salt made above (50 mg, 0.099 mmol) was coupled with N,N-dimethylethylenediamine (0.011 mL, 0.099 mmol) as described in Example 1, Part 13 to provide the corresponding amide compound. MS (ESI): 538 (M+1$^+$).

Part 6: Using procedures analogous to Part 14 and Part 15 in Example 1, the tert-butyl ester from above was converted to the desired hydroxyamide as an inseparable mixture of diastereoisomers at C-5 of the piperidine ring (3.1 mg). MS (ESI): 497 (M+1+).

Example 3

(2S,3S,5S)-2-{[4-(4-cyano-2-methylphenyl)-3,6-dihydropyridin-1(2H)-yl]carbonyl}-N-hydroxy-5-{2-[(3R)-3-hydroxypyrrolidin-1-yl]-2-oxoethyl}piperidine-3-carboxamide and (2S,3S,5R)-2-{[4-(4-cyano-2-methylphenyl)-3,6-dihydropyridin-1(2H)-yl]carbonyl}-N-hydroxy-5-{2-[(3R)-3-hydroxypyrrolidin-1-yl]-2-oxoethyl}piperidine-3-carboxamide The two titled compounds were prepared using procedures analogous to those for Example 2. The two diastereoisomers were separated by RP-HPLC.

Example 4

(2S,3S,5S)-2-{[4-(4-cyano-2-methylphenyl)-3,6-dihydropyridin-1(2H)-yl]carbonyl}-N-hydroxy-5-(2-morpholin-4-yl-2-oxoethyl)piperidine-3-carboxamide and (2S,3S,5R)-2-{[4-(4-cyano-2-methylphenyl)-3,6-dihydropyridin-1(2H)-yl]carbonyl}-N-hydroxy-5-(2-morpholin-4-yl-2-oxoethyl)piperidine-3-carboxamide The two titled compounds were prepared using procedures analogous to those for Example 2. The two diastereoisomers were separated by RP-HPLC.

Example 5

(2S,3S,5S)-2-{[4-(4-cyano-2-methylphenyl)-3,6-dihydropyridin-1(2H)-yl]carbonyl}-N-hydroxy-5-[2-(4-hydroxypiperidin-1-yl)-2-oxoethyl]piperidine-3-carboxamide and (2S,3S,5R)-2-{[4-(4-cyano-2-methylphenyl)-3,6-dihydropyridin-1(2H)-yl]carbonyl}-N-hydroxy-5-[2-(4-hydroxypiperidin-1-yl)-2-oxoethyl]piperidine-3-carboxamide The two titled compounds were prepared using procedures analogous to those for Example 2. The two diastereoisomers were separated by RP-HPLC.

Example 6

(2S,3S,5R)-2-{[4-(4-cyano-2-methylphenyl)piperazin-1-yl]carbonyl}-N-hydroxy-5-[(methoxyacetyl)(methyl)amino]piperidine-3-carboxamide and (2S,3S,5S)-2-{[4-(4-cyano-2-methylphenyl)piperazin-1-yl]carbonyl}-N-hydroxy-5-[(methoxyacetyl)(methyl)amino]piperidine-3-carboxamide Part 1: A mixture of methylamine hydrochloride (216.6 mg, 3.21 mmol) and 5-oxo-piperidine-(2S, 3S)-1,2,3-tricarboxylic acid 1,2-dibenzyl ester 3-tert-butyl ester (500 mg, 1.07 mmol) in 1,2-dichloroethane (3.6 mL) was treated with NaBH(OAc)$_3$ (680 mg, 3.21 mmol) and stirred at rt overnight. The reaction was quenched with saturated NaHCO$_3$ and extracted with ethyl acetate. The combined organic layers were dried over magnesium sulfate and concentrated in-vacuo to afford the (5)-methylamino-piperidine-(1,2S, 3S)-tricarboxylic acid 1,2-dibenzyl ester 3-tert-butyl ester, which was used directly in the following step without further purification. MS (ESI): 483.1 (M+H$^+$).

Part 2: To a solution of the above crude product in CH$_2$Cl$_2$ (3.6 ml) was added methoxyacetyl chloride and Et$_3$N. After vigorously stirring the reaction mixture at rt for 30 min, the volatiles were removed in-vacuo. Purification by flash chromatography (0~10% ethyl acetate in hexane) afforded (5R)-[(2-methoxy-acetyl)-methyl-amino]-piperidine-(1,2S,3S)-tricarboxylic acid 1,2-dibenzyl ester 3-tert-butyl ester (190 mg) and (5S)-[(2-methoxy-acetyl)-methyl-amino]-piperidine-(1,2S,3S)-tricarboxylic acid 1,2-dibenzyl ester 3-tert-butyl ester (170 mg) as pure diastereoisomers. The less polar diastereoisomer was assigned to be the (5R)-isomer and was the more polar diasteoisomer. MS (ESI): 555.1 (M+H$^+$).

Part 3: A solution of (5R)-[(2-methoxy-acetyl)-methyl-amino]-piperidine-(1,2S,3S)-tricarboxylic acid 1,2-dibenzyl ester 3-tert-butyl ester (190 mg, 0.343 mmol) in methanol (2 mL) was hydrogenated in the presence of 10% Pd/C (40 mg), under balloon pressure of hydrogen, for 1 h. The heterogeneous mixture was filtered through a pad of celite and the volatiles were removed to afford (5R)-[(2-methoxy-acetyl)-methyl-amino]-piperidine-(2S,3S)-dicarboxylic acid 3-tert-butyl ester (102.4 mg, 90%) as a white solid. MS (ESI): 331.2 (M+H$^+$).

(5S)-[(2-methoxy-acetyl)-methyl-amino]-piperidine-(2S, 3S)-dicarboxylic acid 3-tert-butyl ester was made in an analogous manner.

Part 4: To a nitrogen flushed flask containing PdCl₂dppf (65.8 mg, 0.081 mmol), dppf (44.6 mg, 0.081 mmol) and 4-bromo-3-methylbenzonitrile (631 mg, 3.22 mmol) in THF (5 mL) at −78° C. was added tert-butyl 1-piperazinecarboxylate (500 mg, 2.68 mmol) as a solid. The resultant mixture was heated to 100° C. and vigorously stirred overnight under nitrogen. The reaction was quenched with water and extracted with ethyl acetate. The combined organic layers were washed with brine, dried (MgSO₄) and concentrated under reduced pressure. The residue was purified by flash chromatography (eluting with 0 to 30% ethyl acetate in hexane) to afford 4-(4-cyano-2-methyl-phenyl)-piperazine-1-carboxylic acid tert-butyl ester (702 mg, 86.9%). MS (ESI): 302.0 (M+H⁺).

Part 5: The titled compound above (702 mg, 2.33 mmol) was dissolved in CH₂Cl₂ (2 mL) and treated with TFA. (2 mL) After stirring the reaction mixture at rt for 1 h, the volatiles were removed under reduced pressure to provide 4-(4-cyano-2-methyl-phenyl)-piperazine TFA salt.

Part 6: A mixture of (5R)-[(2-methoxy-acetyl)-methyl-amino]-piperidine-(2S,3S)-dicarboxylic acid 3-tert-butyl ester (69 mg, 0.21 mmol), 4-(4-cyano-2-methyl-phenyl)-piperazine TFA salt (89.7 mg, 0.21 mmol) and BOP (102 mg, 0.23 mmol) in anhydrous DMF (0.4 mL) was treated with diisopropylethylamine (0.12 mL, 0.69 mmol) at rt, under nitrogen, for 2 h. The reaction was quenched with saturated NaHCO₃ and extracted with ethyl acetate. The combined organic layers were washed with brine, dried over MgSO₄ and concentrated to dryness under reduced pressure. The resultant residue was used directly in the next step without further purification. MS (ESI): 514.2 (M+H⁺). (2S)-[4-(4-cyano-2-methyl-phenyl)-piperazine-1-carbonyl]-(5S)-[(2-methoxy-acetyl)-methyl-amino]-piperidine-(3S)-carboxylic acid tert-butyl ester was made in an analogous manner.

Part 7: The crude product made above was dissolved in CH₂Cl₂ (1.5 mL) and treated with TFA (1.5 mL) at rt for 3 h. The mixture was concentrated to dryness under reduced pressure to afford piperidine 3-carboxylic acid, which was used directly in the next step without purification. MS (ESI): 458.1 (M+H⁺).

Part 8: A solution of the above crude piperidine 3-carboxylic acid, hydroxyamine HCl salt (29 mg, 0.42 mmol) and BOP (111 mg, 0.25 mmol) in DMF (0.42 mL) was treated with diisopropylethylamine (0.11 mL, 0.63 mmol) at rt, under nitrogen, for 2 h. The reaction mixture was applied directly on RP-HPLC to provide (2S)-[4-(4-cyano-2-methyl-phenyl)-piperazine-1-carbonyl]-(5R)-[(2-methoxy-acetyl)-methyl-amino]-piperidine-(3S)-carboxylic acid hydroxyamide as a TFA salt (6.8 mg, 6.9% in 3 steps). MS (ESI): 473.2 (M+H⁺).

(2S)-[4-(4-cyano-2-methyl-phenyl)-piperazine-1-carbonyl]-(5S)-[(2-methoxy-acetyl)-methyl-amino]-piperidine-(3S)-carboxylic acid hydroxyamide TFA salt was made in analogous manner.

Example 7

(2S,3S,5S)-2-{[4-(4-cyano-2-methylphenyl)-3,6-dihydropyridin-1(2H)-yl]carbonyl}-N-hydroxy-5-{2-[(2-methoxyethyl)amino]-2-oxoethyl}piperidine-3-carboxamide and (2S,3S,5R)-2-{[4-(4-cyano-2-methylphenyl)-3,6-dihydropyridin-1(2H)-yl]carbonyl}-N-hydroxy-5-{2-[(2-methoxyethyl)amino]-2-oxoethyl}piperidine-3-carboxamide The two titled compounds were prepared using procedures analogous to those for Example 2. The two diastereoisomers were separated by RP-HPLC.

Example 8

(2S,3S,5S)-2-{[4-(4-cyano-2-methylphenyl)-3,6-dihydropyridin-1(2H)-yl]carbonyl}-N-hydroxy-5-{2-oxo-2-[(3R)-tetrahydrofuran-3-ylamino] ethyl}piperidine-3-carboxamide and (2S,3S,5R)-2-{[4-(4-cyano-2-methylphenyl)-3,6-dihydropyridin-1(2H)-yl]carbonyl}-N-hydroxy-5-{2-oxo-2-[(3R)-tetrahydrofuran-3-ylamino]ethyl}piperidine-3-carboxamide The two titled compounds were prepared using procedures analogous to those for Example 2. The two diastereoisomers were separated by RP-HPLC.

Example 9

Methyl(3R,5S,6S)-5-[(hydroxyamino)carbonyl]-6-{[(3R)-3-phenylpyrrolidin-1-yl]carbonyl}piperidin-3-yl carbonate and Methyl(3S,5S,6S)-5-[(hydroxyamino)carbonyl]-6-{[(3R)-3-phenylpyrrolidin-1-yl]carbonyl}piperidin-3-yl carbonate Part 1: A suspension of lithium aluminum hydride in 80 mL of THF was cooled at 0° C. and (R)-phenylsuccinic acid solid was added portionwise through a flexible plastic sleeve so as that not to produce too vigorous an evolution of hydrogen. After addition, the reaction was warmed to rt and then refluxed overnight. The reaction was then cooled again to 0° C. and diluted with ether (80 mL). The reaction is quenched over a 30 min period with water (3.2 mL), aq. 15% NaOH (3.2 mL, over 20 min), and water (9.6 mL, over 30 min). The solution was stirred for 30 min and the white precipitate was filtered. The filter cake was washed with ether (3×) and the filtrates combined, dried with sodium sulfate and concentrated to dry. The residue was purified on silica gel, eluting with 0 to 100% EtOAc in hexane, to give 5.45 g (91%) of the corresponding diol.

To a solution of the diol made above in 100 mL of dry methylene chloride at −78° C. was added triethylamine followed by MsCl. The mixture was allowed to warm up to rt gradually and stirred at rt overnight. The reaction was quenched with aq. Sodium bicarbonate, extracted with methylene chloride, dried (MgSO₄), evaporated to dry. The crude residue was used directly in next step without further purification.

The bis-mesylate, benzylamine and triethylamine in 120 mL of dioxane were refluxed for 12 h. The crude mixture was concentrated in vacuo, and the residue was dissolved in methylene chloride, washed with 5% HCl, dried. After evaporated to dry, the residue was purified on silica gel, eluting with 5% MeOH in methylene chloride, to give 1-benzyl-(3R)-phenylpyrrolidine (6.6 g, 84.8% in 2 step). LCMS (M+H) 238.1.

1-Benzyl-(3R)-phenylpyrrolidine (500 mg, 2.11 mmol) was hydrogenated in the presence of 20% Pd(OH)₂/C in ethanol, under 50 psi of hydrogen overnight. After filtered off the catalyst, the filtration was evaporated to dry to provide (3R)-phenylpyrrolidine (310 mg, 100%), LCMS (M+H) 148.0.

Part 2: To a solution of 5-oxo-piperidine-(1,2S,3S)-tricarboxylic acid 1,2-dibenzyl ester 3-tert-butyl ester (200 mg, 0.43 mmol) in MeOH (7 ml) and CH₂Cl₂ (7 ml) was added NaBH₄ (97 mg, 2.6 mmol) at −78° C. under a nitrogen atmosphere. The resulting mixture was stirred at −78° C. for 1 h, then quenched with acetone (2 ml) and allowed to gradually warm to ambient temperature over 30 min. The volatiles were removed under reduced pressure and the resulting residue was dissolved in ethyl acetate (10 ml), washed with brine, and dried over MgSO$_4$. Purification by Combiflash (ethyl acetate in hexane: gradient 0 to 30% in 25 min) afforded 152 mg (75.7%) of (5R/S)-hydroxy-piperidine-(1,2S,3S)-tricarboxylic acid 1,2-dibenzyl ester 3-tert-butyl ester. MS (ESI): 492.2 (M+Na$^+$).

Part 3: To a solution of the above made hydroxy-piperidine (200 mg, 0.426 mmol) in CH$_2$Cl$_2$ (1.4 ml) was added methyl chloroformate (48.3 mg, 0.51 mmol), followed by Et$_3$N (43 mg, 0.43 mmol) and DMAP (2.6 mg) at 0° C. The resulting mixture was stirred overnight and then concentrated in vacuo. The crude product was purified by Combiflash (ethyl acetate in hexane: gradient 0 to 40% in 25 min) to afford 49 mg (21.8%) of (5RIS)-methoxycarbonyloxy-piperidine-(1,2S, 3S)-tricarboxylic acid 1,2-dibenzyl ester 3-tert-butyl ester. MS (ESI): 550.1 (M+Na$^+$).

Part 4: (5R/S)-methoxycarbonyloxy-piperidine-(1,2S,3S)-tricarboxylic acid 1,2-dibenzyl ester 3-tert-butyl ester was coupled with (3R)-phenylpyrrolidine made in Part 1, then carried through to generate the titled two compounds, using procedures analogous to Part 3, 6, 7 and Part 8 in Example 6. The two diastereoisomers were separated by RP-HPLC. MS (ESI): 392.2 (M+H$^+$).

Example 10

(2S,3S)-N,5-dihydroxy-2-{[(3R)-3-phenylpyrrolidin-1-yl]carbonyl}piperidine-3-carboxamide The titled compound was prepared using procedures analogous to those of Example 9 as an inseparable mixture of diastereoisomers at C-5 on the piperidine ring (2.4 mg). MS (ESI): 334.2 (M+H$^+$).

Example 11

(5S,6S)-5-[(hydroxyamino)carbonyl]-6-{[(3R)-3-phenylpyrrolidin-1-yl]carbonyl}piperidin-3-yl methylcarbamate Part 1: To a solution of (5R/S)-hydroxy-piperidine-(1,2S, 3S)-tricarboxylic acid 1,2-dibenzyl ester 3-tert-butyl ester (200 mg, 0.426 mmol) in CH$_2$Cl$_2$ (1.4 ml) was added methyl isocyanate (29 mg, 0.51 mmol), followed by Et$_3$N (43 mg, 0.43 mmol) at 0° C. The resulting mixture was stirred at rt overnight and then concentrated in vacuo. The crude product was purified by Combiflash (ethyl acetate in hexane: gradient 0 to 40% in 25 min) to afford 44 mg (19.6%) of (5R/S)-methylcarbamoyloxy-piperidine-(1,2S,3S)-tricarboxylic acid 1,2-dibenzyl ester 3-tert-butyl ester.

Part 2: The titled compound was prepared using procedures analogous to Part 3 in Example 9 as an inseperable diastereo isomer mixtures at piperidine 5-position (6.7 mg). MS (ESI): 391.2 (M+H$^+$).

Example 12

Tetrahydro-2H-pyran-4-yl(3R,4S)-3-[(hydroxyamino)carbonyl]-4-{[(3R)-3-phenylpyrrolidin-1-yl]carbonyl}piperidine-1-carboxylate (1a) To a stirred solution of N-benzyloxycarbonyl-β-alanine (11.16 g, 50.00 mmol) in anhydrous THF (160 mL) and DMF (40 mL) at 0° C. was slowly added NaH (60% in oil, 6.000 g, 150.0 mmol). After stirring at 0° C. for 15 min, benzyl bromide (9.10 mL, 75.00 mmol) was added. The reaction mixture was stirred at rt for 22 h. It was quenched with water (90 mL), followed by 1 N HCl (110 mL), and extracted three times with ethyl acetate. The combined organic layers were washed with brine, dried over MgSO$_4$, filtered and concentrated under reduced pressure. The residue was purified by Combiflash (40-60% EtOAc/hexane) to afford 3-{benzyl[(benzyloxy)cabonyl]amino}propanoic acid as a viscous pale yellow oil (14.2 g, 91% in yield). MS (ESI): 312.0 (M–H).

(1b) To a stirred solution of 3-{benzyl[(benzyloxy)cabonyl]amino}propanoic acid (13.80 g, 44.04 mmol) and triethylamine (18.5 mL, 132.1 mmol) in anhydrous THF (220 mL) at –25° C. was slowly added pivaloyl chloride (6.03 mL, 48.44 mmol) to immediately form a white precipitate. The reaction mixture was stirred at –20° C. for 1 h, prior to the sequential addition of LiCl and (R)-(+)-4-benzyl-2-oxazolidinone. After stirring the reaction mixture at rt for 16 h, the reaction was quenched with saturated aqueous NaHCO$_3$ (80 mL) and water (80 mL). The aqueous phase was extracted twice with ethyl acetate and the combined organic layers were washed with brine, dried over MgSO$_4$, filtered and concentrated under reduced pressure. The residue was purified by Combiflash (20-40% EtOAc/hexane) to give benzyl-{3-[(4R)-benzyl-2-oxo-1,3-oxazolidin-3-yl)-3-oxo-propyl]-carbamic acid phenyl ester as a colorless semi-solid (17.00 g, 82% in yield). MS (ESI): 473.1 (M+H$^+$).

(1c) To a stirred solution of diisopropylamine (5.96 mL, 42.16 mmol) in anhydrous THF (70 mL) at –78° C. was added n-butyllithium (1.6 M in Hexane, 26.4 mL, 42.16 mmol). After stirring at 0° C. for 30 min, the LDA was added to a solution of benzyl-{3-[(4R)-benzyl-2-oxo-1,3-oxazolidin-3-yl)-3-oxo-propyl]-carbamic acid phenyl ester (16.60 g, 35.13 mmol) in anhydrous THF (70 mL) at –78° C. via cannula. After stirring at –78° C. for 1 h, tert-butyl bromoacetate (6.35 mL, 42.16 mmol) was added. The reaction mixture was slowly warmed to –30° C. over 1 h, and stirred at –30° C. for 4 h. It was quenched with water (70 mL) and saturated aqueous ammonium chloride (70 mL) and extracted twice with ethyl acetate. The combined organic layers were washed with brine, dried over MgSO$_4$, filtered and concentrated under reduced pressure. The residue was purified by Combiflash (15-35% EtOAc/hexane) to provide 7.547 g (37%) of tert-butyl(3R)-({benzyl[(benzyloxy)carbonyl]amino}methyl)-4-[(4R)-benzyl-2-oxo-1,3-oxazolidin-3-yl]-4-oxo-butanoate. MS (ESI): 609.2 (M+Na$^+$).

(1d) To a solution of tert-butyl(3R)-({benzyl[(benzyloxy)carbonyl]amino}methyl)-4-[(4R)-benzyl-2-oxo-1,3-oxazolidin-3-yl]-4-oxo-butanoate (6.703 g, 11.43 mmol) in THF (57 mL) and water (37 mL) at 0° C. was added 30% hydrogen peroxide (4.67 mL, 45.72 mmol). After 5 min at 0° C., a solution of LiOH (559 mg, 22.86 mmol) in water (20 mL) was added and the reaction mixture was stirred at 0° C. for 1.5 h. and then at rt for 1 h. The reaction was quenched with 10% sodium thiosulfate (70 mL), acidified with 1 N HCl (30 mL) to pH 3, and extracted three times with ethyl acetate. The combined organic layers were washed with brine, dried over MgSO$_4$, filtered and concentrated under reduced pressure. The residue was purified by Combiflash (30-60% EtOAc/hexane) to provide 4.642 g (95%) of (2R)-({benzyl[(benzyloxy)cabonyl]amino}methyl)-4-tert-butoxy-4-oxobutanoic acid. MS (ESI): 426.2 (M–H$^+$).

(1e) To a stirred solution of diisopropylamine (3.67 mL, 26.06 mmol) in anhydrous THF (27 mL) at –78° C. was added n-butyllithium (1.6 M in Hexane, 16.3 mL, 26.06 mmol). After stirring at 0° C. for 30 min, it was added to a solution of (2R)-({benzyl[(benzyloxy)cabonyl]amino}methyl-4-tert-butoxy-4-oxobutanoic acid (4.642 g, 10.86 mmol) in anhydrous THF (27 mL) at –78° C. via cannula. After stirring at –78° C. for 1 h, allyl iodide (1.32 mL, 14.12 mmol) was added and the reaction mixture was slowly warmed to −30° C. over 3.5 h and stirred at −30° C. for 2.5 h. The reaction was quenched with water (50 mL) and 1 N HCl (50 mL), extracted three times with ethyl acetate. The combined organic layers were washed with brine, dried over $MgSO_4$, filtered and concentrated under reduced pressure. The residue was purified by Combiflash (20-60% EtOAc/hexane) to afford 3.256 g (64%) of (2R,3S)-2-({benzyl[(benzyloxy)cabonyl]amino}methyl)-4-(tert-butoxycarbonyl)-5-hexenoic acid. MS (ESI): 466.2 (M−H$^+$).

(1f) To a stirred solution of (2R,3S)-2-({benzyl[(benzyloxy)cabonyl]amino}methyl)-4-(tert-butoxycarbonyl)-5-hexenoic acid (2.930 g, 6.267 mmol) in anhydrous acetonitrile (15 mL) at rt was added DBU (1.91 mL, 12.53 mmol), followed by methyl iodide (0.98 mL, 15.67 mmol). After stirring at rt for 3 h, the reaction was quenched with water (60 mL) and extracted twice with ethyl acetate. The combined organic layers were washed with brine, dried over $MgSO_4$, filtered and concentrated under reduced pressure. The residue was purified by Combiflash (10-20% EtOAc/hexane) to provide 2.523 g (84%) 4-methyl 1-tert-butyl (2S,3R)-2-allyl-3-({benzyl[(benzyloxy)cabonyl]amino}methyl)butanedioate as a colorless viscous oil (. MS (ESI): 504.2 (M+Na$^+$).

(1g) To a stirred solution of 4-methyl 1-tert-butyl(2S,3R)-2-allyl-3-({benzyl[(benzyloxy)cabonyl]amino}methyl)butanedioate (2.336 g, 4.851 mmol) in dichloromethane (97 mL) at −78° C. was bubbled ozone. After the solution turned blue, ozone bubbling continued for additional 15 min. Nitrogen was then bubbled into the mixture until the blue color disappeared. The reaction was quenched with dimethyl sulfide (1.78 mL, 24.26 mmol) and the solution was stirred at rt for 2 h. The solvent was removed under reduced pressure and the residue was purified by Combiflash (15-25% EtOAc/hexane) to provide 1.853 g (79%) of 1-methyl 4-tert-butyl (2R,3S)-2-({benzyl[(benzyloxy)cabonyl]amino}methyl)-3-(2-oxoethyl)butanedioate as a colorless viscous oil (1.853 g, 79% in yield). MS (ESI): 506.1 (M+Na$^+$).

(1 h) To a solution of 1-methyl 4-tert-butyl(2R,3S)-2-({benzyl[(benzyloxy)cabonyl]amino}methyl)-3-(2-oxoethyl)butanedioate (836 mg, 1.729 mmol) in methanol (17 mL) was added 10% palladium on carbon (251 mg). The reaction mixture was stirred under 55 psi hydrogen at rt for 15.5 h. The reaction mixture was diluted with methanol, filtered through a pad of Celite and washed with methanol. The filtrate was concentrated under reduced pressure to provide 417 mg (99%) of piperidine-(3R,4S)-3,4-dicarboxylic acid 4-tert-butyl ester 3-methyl ester. MS (ESI): 244.2 (M+H$^+$).

(1i) To a stirred solution of piperidine-(3R,4S)-3,4-dicarboxylic acid 4-tert-butyl ester 3-methyl ester (415 mg, 1.706 mmol) in anhydrous dichloromethane (11 mL) at rt was added 4-methylmorpholine (0.474 mL, 4.265 mmol) and N-(benzyloxycarbonyloxy) succinimide (651 mg, 2.559 mmol). After stirring the reaction mixture at rt for 25 h, the reaction was quenched with saturated aqueous $NaHCO_3$ (30 mL) and extracted twice with ethyl acetate. The combined organic layers were washed with brine, dried over $MgSO_4$, filtered and concentrated under reduced pressure. The residue was purified by Combiflash (15-25% EtOAc/hexane) to afford 490 mg (76%) of piperidine-(3R,4S)-1,3,4-tricarboxylic acid 1-benzyl ester 4-tert-butyl ester 3-methyl ester as a colorless solid. MS (ESI): 400.0 (M+Na$^+$).

(1j) To a stirred solution of piperidine-(3R,4S)-1,3,4-tricarboxylic acid 1-benzyl ester 4-tert-butyl ester 3-methyl ester (465 mg, 1.232 mmol) in dichloromethane (12 mL) at rt was added trifluoroacetic acid (12 mL) and water (0.6 mL). The reaction mixture was stirred at rt for 5 h. The reaction mixture was concentrated under reduced pressure and the residue was azeotropically washed with toluene (3×) to provide 396 mg (100%) of piperidine-(3R,4S)-1,3,4-tricarboxylic acid 1-benzyl ester 3-methyl ester. MS (ESI): 320.1 (M−H$^+$).

(1k) To a stirred solution of piperidine-(3R,4S)-1,3,4-tricarboxylic acid 1-benzyl ester 3-methyl ester (208 mg, 0.647 mmol) in anhydrous DMF (6 mL) at rt was added (3R)-3-phenyl-pyrrolidine hydrochloride (178 mg, 0.971 mmol), PyBOP (382 mg, 0.712 mmol), followed by diisopropylethyl amine (0.566 mL, 3.235 mmol). After stirring the reaction mixture at rt overnight, the reaction was quenched with saturated aqueous $NaHCO_3$ (20 mL) and extracted twice with ethyl acetate. The combined organic layers were washed with brine, dried over $MgSO_4$, filtered and concentrated under reduced pressure. The residue was purified by Combiflash (40-60% EtOAc/hexane) to provide 200 mg (69%) of (4S)-[(3R)-3-phenyl-pyrrolidine-1-carbonyl]-piperidine-(3R)-1,3-dicarboxylic acid 1-benzyl ester 3-methyl ester MS (ESI): 451.1 (M+H$^+$).

(1l) To a solution of (4S)-[(3R)-3-phenyl-pyrrolidine-1-carbonyl]-piperidine-(3R)-1,3-dicarboxylic acid 1-benzyl ester 3-methyl ester (143 mg, 0.317 mmol) in methanol (8 mL) was added 10% palladium on carbon (29 mg). The reaction mixture was stirred under 1 atm hydrogen balloon at rt for 21 h. Upon completion the reaction mixture was diluted with methanol, filtered through a pad of Celite and washed with methanol. The filtrate was concentrated under reduced pressure to afford 100 mg (100%) (4S)-[(3R)-3-phenyl-pyrrolidine-1-carbonyl]-piperidine-(3R)-carboxylic acid 3-methyl ester. MS (ESI): 317.2 (M+H$^+$).

(1m) To a stirred solution of (4S)-[(3R)-phenyl-pyrrolidine-1-carbonyl]-piperidine-(3R)-carboxylic acid 3-methyl ester (23 mg, 0.0727 mmol) in anhydrous dichloromethane (2 mL) at rt was added diisopropylethyl amine (0.038 mL, 0.218 mmol) and carbonic acid 4-nitro-phenyl ester tetrahydro-pyran-4-yl ester (29 mg, 0.109 mmol, prepared using procedure analogous to example 34, step 1). The reaction mixture was stirred at rt for 22 h and then purified directly by Combiflash (60-90% EtOAc/hexane) to afford 27 mg (84%) of (4S)-[(3R)-phenyl-pyrrolidine-1-carbonyl]-piperidine-(3R)-1,3-dicarboxylic acid 3-methyl ester 1-(tetrahydro-pyran-4-yl)ester MS (ESI): 445.1 (M+H$^+$).

(1n) Preparation of $NH_2OH/NaOMe$ (1.5 M in MeOH): To a stirred solution of hydroxylamine hydrochloride (702 mg, 10.00 mmol) in anhydrous methanol (3 mL) at rt was added NaOMe (25 wt % in MeOH, 3.43 mL, 15.00 mmol). The reaction mixture was heated at 55° C. for 5 min and then allowed to gradually warm to rt before cooling to 0° C. Filtration of the crude mixture afforded a clear solution assumed to be a ca. 1.5 M solution of $NH_2OH/NaOMe$ in MeOH.

To a stirred solution of (4S)-[(3R)-phenyl-pyrrolidine-1-carbonyl]-piperidine-(3R)-1,3-dicarboxylic acid 3-methyl ester 1-(tetrahydro-pyran-4-yl)ester (24 mg, 0.054 mmol) in anhydrous methanol (1.5 mL) at rt was added the above $NH_2OH/NaOMe$ (1.5 M in MeOH, 0.72 mL, 1.08 mmol). After stirring the reaction mixture at rt for 16 h, the reaction was quenched with 1 N HCl (1 mL) and saturated aqueous ammonium chloride (10 mL) and extracted twice with ethyl acetate. The combined organic layers were washed with brine, dried over $NaSO_4$, filtered and concentrated under reduced pressure. The residue was purified by reverse phase HPLC (eluting with 5-95% acetonitrile/water (0.05% TFA)) to afford 6.8 mg (28%) of (3R)-hydroxycarbomoyl-4-[(3R)-phenyl-pyrrolidine-1-carbonyl)]-piperidine-1-carboxylic acid tetrahydro-pyran-4-yl ester as a colorless semi-solid. MS (ESI): 446.1 (M+H$^+$).

Example 13

(3R)-tetrahydrofuran-3-yl(3R,4S)-3-[(hydroxyamino)carbonyl]-4-{[(3R)-3-phenylpyrrolidin-1-yl]carbonyl}piperidine-1-carboxylate The titled compound was prepared using procedures analogous to those in Example 12. ESI MS: m/z 432.1 (M+H)+.

Example 14

(3S)-tetrahydrofuran-3-yl(3R,4S)-3-[(hydroxyamino)carbonyl]-4-{[(3R)-3-phenylpyrrolidin-1-yl]carbonyl}piperidine-1-carboxylate The titled compound was prepared using procedures analogous to those in Example 12. ESI MS: m/z 432.1 (M+H)+.

Example 15

2-methoxyethyl(3R,4S)-3-[(hydroxyamino)carbonyl]-4-{[(3R)-3-phenylpyrrolidin-1-yl]carbonyl}piperidine-1-carboxylate The titled compound was prepared using procedures analogous to those in Example 12. ESI MS: m/z 420.1 (M+H)+.

Example 16

Tetrahydro-2H-pyran-4-yl(3R,4S)-3-[(hydroxyamino)carbonyl]-4-[(4-phenylpiperazin-1-yl)carbonyl]piperidine-1-carboxylate The titled compound was prepared using procedures analogous to those in Example 12. ESI MS: m/z 461.1 (M+H)+.

Example 17

(3R)-tetrahydrofuran-3-yl(3R,4S)-3-[(hydroxyamino)carbonyl]-4-[(4-phenylpiperazin-1-yl)carbonyl]piperidine-1-carboxylate The titled compound was prepared using procedures analogous to those in Example 12. ESI MS: m/z 447.1 (M+H)+.

Example 18

(3S)-tetrahydrofuran-3-yl(3R,4S)-3-[(hydroxyamino)carbonyl]-4-[(4-phenylpiperazin-1-yl)carbonyl]piperidine-1-carboxylate The titled compound was prepared using procedures analogous to those in Example 12. ESI MS: m/z 447.2 (M+H)+.

Example 19

2-methoxyethyl(3R,4S)-3-[(hydroxyamino)carbonyl]-4-[(4-phenylpiperazin-1-yl)carbonyl]piperidine-1-carboxylate The titled compound was prepared using procedures analogous to those in Example 12. ESI MS: m/z 435.1 (M+H)+.

Example 20

Tetrahydro-2H-pyran-4-yl(3R,4S)-3-[(hydroxyamino)carbonyl]-4-[(4-phenylpiperidin-1-yl)carbonyl]piperidine-1-carboxylate The titled compound was prepared using procedures analogous to those in Example 12. ESI MS: m/z 460.2 (M+H)+.

Example 21

(3R)-tetrahydrofuran-3-yl(3R,4S)-3-[(hydroxyamino)carbonyl]-4-[(4-phenylpiperidin-1-yl)carbonyl]piperidine-1-carboxylate The titled compound was prepared using procedures analogous to those in Example 12. ESI MS: m/z 446.2 (M+H)+.

Example 22

(3S)-tetrahydrofuran-3-yl(3R,4S)-3-[(hydroxyamino)carbonyl]-4-[(4-phenylpiperidin-1-yl)carbonyl]piperidine-1-carboxylate The titled compound was prepared using procedures analogous to those in Example 12. ESI MS: m/z 446.2 (M+H)+.

Example 23

2-methoxyethyl(3R,4S)-3-[(hydroxyamino)carbonyl]-4-[(4-phenylpiperidin-1-yl)carbonyl]piperidine-1-carboxylate The titled compound was prepared using procedures analogous to those in Example 12. ESI MS: m/z 444.2 (M+H)+.

Example 24

(1S,2S,4S)-N,4-dihydroxy-2-{[(3R)-3-phenylpyrrolidin-1-yl]carbonyl}cyclohexanecarboxamide Part 1: Starting material 3a, 4, 7, 7a-tetrahydro-isobenzofuran-1,3-dione (30.4 g, 0.2 mole) was suspended in methanol (40 mL) and the mixture was stirred at room temperature overnight to form a homogenous mixture. The reaction mixture was cooled to 0° C. and thionyl chloride (14.6 ml) was added dropwise. After completion of the addition, the cold bath was removed and the mixture was stirred at room temperature for 3 hours. The volatiles were then removed in-vacuo and the resulting residue was neutralized with saturated sodium bicarbonate solution. The product was extracted with ethyl acetate (×3) and the combined extracts were washed with water (×1), brine (×1), dried over $MgSO_4$, filtered and concentrated under reduced pressure. The resulting residue was purified by distillation to obtain 37.06 g (93%) of pure product.

Part 2: To a solution of diester from Part 1(37 g, 187 mmole) in acetone (127 ml) was added a solution of LE (25 mg, 1025 units, 41 unit/mg) in a premade phosphate buffer solution (4 ml) (Phosphate buffer solution (pH 8.0) was prepared by adding $KH_2PO_4$ (34.43 g, 252 mmole) and NaOH (9.30 g, 233 mmole) to distilled water (2530 ml)) The homogenous reaction mixture was gently stirred at rt, while maintaining a pH between 7 and 8 by the occasional addition of aqueous NaOH. After 8 days, the solution was saturated with NaCl and acidified to pH 3.0 with a solution of HCl. The mixture was extracted with EtOAc (600 ml×3) and the combined extracts were washed with water (×1), brine (×1), dried over MgSO$_4$, filtered, and concentrated in-vacuo to afford the desired product.

Part 3: A mixture of optically pure mono acid made above (25 g), 2-methyl propene (100 ml), concentrated H$_2$SO$_4$ (1.63 ml) in methylene chloride (40 ml) in a sealed reaction vessel was stirred at room temperature for 3 days. The mixture was poured into saturated sodium bicarbonate solution, and extracted with hexane-diethyl ether (×2). The combined extracts were washed with water (×1), brine (×1), dried over MgSO$_4$, filtered and concentrated under reduced pressure to afford 30.3 g (91%) of the desired product as an oil.

Part 4: The tert-butyl ester made above was dissolved in methanol (82 ml) and cooled to 0° C., before slowly adding 2 N NaOH (NaOH, 13.12 g in distilled water 164 ml). After stirring the reaction mixture at rt for 2 d, the mixture was acidified with 1 N HCl solution, extracted with EtOAc (×3). The combined extracts were washed with water (×1), brine (×1), dried over MgSO4, filtered and concentrated in-vacuo to afford the desired product in quantitative yield.

Part 5: To a 0° C. solution of KOBu-t (10.61 mL, 1.0 M KOBu-t THF and 6.1 mL of THF) was added slowly cyclohex-4-ene-(1R,2S)-dicarboxylic acid-tert-butyl ester (1.6 g, 7.07 mmole) in THF (12.2 ml). The reaction mixture was stirred at 0° C. for 10 to 15 min and then at rt for 1 to 2 hours. After the reaction was complete, 1 N HCl was carefully added until the pH was ca. 2 and the product was extracted with EtOAc (×2). The combined extracts were washed with water (×1), brine (×1), dried over MgSO$_4$, filtered and concentrated under reduced pressure. The resulting residue was purified by flash column to afford 1.56 g (97%) of the desired product.

Part 6: To a solution of the epimerized compound from Part 5 (5.5 g, 24.3 mmol) dissolved in methylene chloride (60 ml) was added 12 (18.5 g, 72.9 mmol), KI (24.2 g, 145.6 mmol), and NaHCO$_3$ (6.1 g, 72.9 mmol) successively, followed by distilled water (90 mL). The mixture was stirred in the absence of light at rt for 2 days. At this time saturated Na$_2$S$_2$O$_3$ solution was added and the product was extracted with methylene chloride. The extract was washed with water (×1), brine (×1), dried over MgSO$_4$, filtered and concentrated under reduced pressure. The crude material was purified by flash column to afford 6.21 g (82%) of the desired product.

Part 7: To a solution of iodo compound made above (6.6 g, 18.7 mmol) in toluene (55 mL) was added tris(trimethylsilyl) silane (6.94 mL, 22.5 mmol), followed by AIBN (0.31 g, 1.87 mmol). The mixture was heated at 90° C. for 1.5 hours. After cooling, the reaction mixture to ambient temperature the reaction was quenched with 10% citric acid and extracted with EtOAc. The organic phase was washed with water (×1), saturated NaHCO3 solution (×1), water (×1), brine (×1), dried over MgSO$_4$, and concentrated in-vacuo. The residue was purified by flash column to afford 3.42 g (80%) of the desired product.

Part 8: A solution (R)-3-phenylpyrrolidine (234 mg, 1.59 mmol) and 2 M AlMe$_3$ in toluene (0.86 mL) was stirred at rt for 30 min. To the solution was added the lactone compound (300 mg, 1.33 mmol) in THF (0.5 ml). The mixture was stirred at 40° C. overnight. After cooling to rt, the reaction mixture was extracted with EtOAc. The organic layers were washed with 10% citric acid (×1), water (×1), brine (×1), dried over MgSO$_4$, filtered, and concentrated under reduced pressure. The resulting crude product was purified by flash chromatography to afford 180 mg (36%) of desired product.

Part 9: The compound made above was stirred in methylene chloride-TFA-H$_2$O (45:50:5) for 3 hours. After the reaction was complete according to HPLC analysis, the volatiles were removed in-vacuo to afford the desired product in quantitative yield.

Part 10: A solution of compound from Part 9 (12 mg, 0.038 mmol), NH$_2$OH.HCl (7.9 mg, 0.113 mmol), BOP (17.6 mg, 0.039 mmol) and DIEA (22.1 mg, 0.17 mmol) in DMF (0.4 mL) was stirred at room temperature for 3 hours. The crude reaction mixture was directly purified by preparative HPLC To afford 4 mg (32%) of desired product was obtained. MS m/z: 333.1 (M+H$^+$); 687.3 (2×M+Na$^+$).

Example 25

(1S,2S,5S)-N,5-dihydroxy-2-{[4-phenyl-3,6-dihydropyridin-1(2H)-yl]carbonyl}cyclohexanecarboxamide Part 1: The mixture of 7-oxo-6-oxa-bicyclo [3.2.1]octane-2-carboxylic acid tert-butyl ester from Experiment 24, Part 7 (0.92 g, 4.07 mmol) in methylene chloride (3 ml) and TFA (3 mL) was stirred a room temperature for 1.5 hours. After the reaction was complete according to TLC analysis the volatiles were removed in-vacuo to afford 0.67 (97%) of the desired product.

Part 2: To a 0° C. solution of the acid made above (30 mg, 0.176 mmol) in DMF (0.4 mL) was added 4-phenyl-1,2,5,6-tetrahydropyridine (41 mg, 0.212 mmol) and BOP (82 mg, 0.185 mmol). After stirring for 5 minDIEA (69 mg, 0.529 mmol) was added And the mixture was allowed to gradually warm to ambient temperature and stirred overnight. The reaction was quenched with saturated sodium bicarbonate solution and extracted with EtOAc (×3). The combined extracts were washed with water (×1), brine (×1), dried over MgSO$_4$, filtered and concentrated under reduced pressure to provide the product in quantitative yield.

Part 3: A solution of compound made from Part 2 and LiOH.H$_2$O (22 mg, 0.529 mmol) in THF (0.5 mL) and H$_2$O (0.1 mL) was stirred at rt for 2 h. After the TLC indicated that the start material was completely consumed, 1 N HCl was carefully added until the pH was ca. 2. The reaction mixture was extracted with EtOAc (×3) and the combined extracts were washed with water (×1), brine (×1), dried over MgSO$_4$ filtered, and concentrated under reduced pressure to provide the desired 5-hydroxy-2-(-phenyl-3,6-dihydro-2H-pyridine-1-carbonyl)-cyclohexanecarboxylic acid.

Part 4: To a solution of the compound made above (24 mg, 0.07 mmol) and NH$_2$OH.H$_2$O in DMF (0.4 ml) was added BOP (34 mg, 0.077 mmol). After stirring for 5 min, DIEA (33 mg, 0.255 mmol) was added. The mixture was stirred at rt for 3 h. After HPLC analysis indicated that the starting material was completely consumed the crude reaction mixture was purified by preparative HPLC to afford 16 mg (63%) of the desired product. MS m/z 345.1 (M+H$^+$); 367.1 (M+Na$^+$); 711.2 (2×M+Na$^+$).

Example 26

(1S,2S,5S)-N,5-dihydroxy-2-[(4-phenylpiperidin-1-yl)carbonyl]cyclohexanecarboxamide To a solution of (5S)-hydroxy-(2S)-(4-phenyl-3,6-dihydro-2H-pyridine-1-carbonyl)-cyclohexane-(1S)-carboxylic acid hydroxyamide (5 mg) in methanol (1 mL) was added 5% Pd on BaSO$_4$. The mixture was stirred under hydrogen 1 atm at room temperature for 2 h. Upon completion of the reaction, the reaction mixture was filtered through a pad of celite and the filtrate was concentrated to afford 2.5 mg (50%) of the desired product. MS m/z 347.1 (M+H$^+$); 369.1 (M+Na$^+$); 715.3 (2×M+Na$^+$)$^+$.

Example 27

(1S,2S,5S)-N,5-dihydroxy-2-[(4-phenylpiperazin-1-yl)carbonyl]cyclohexanecarboxamide The titled compound was prepared using procedures analogous to those in Example 25.

Example 28

(1S,2S,5S)-N,5-dihydroxy-2-[(3-phenyl-2,5-dihydro-1H-pyrrol-1-yl)carbonyl]cyclohexanecarboxamide Part 1. Tert-butyl 3-hydroxy-3-phenylpyrrolidine-1-carboxylate To a solution of tert-butyl 3-oxopyrrolidine-1-carboxylate (1 g, 5.40 mmol) in ether (20 ml) was added dropwise phenylmagnesium bromide (10.3 mL, 3.0 M in ether, 6.21 mmol) at rt under nitrogen. The reaction was heated to reflux for 15 min, then cooled to rt, poured into sat. NH4Cl, extracted with ether (3×). The combined organic layers were dried over Na$_2$SO$_4$, concentrated in vacuo. The crude residue was purified by flash column chromatography to yield the desired product (700 mg, 49.24%). LCMS (M+H) 264.160.

Part 2. 3-phenyl-2,5-dihydro-1H-pyrrole

A mixture of tert-butyl 3-hydroxy-3-phenylpyrrolidine-1-carboxylate (0.36 g, 0.0014 mol) and trifluoroacetic acid (2.0 mL, 0.026 mol) was stirred under nitrogen at room temp for 1 h. The volatile was removed under vacuum and evaporated with toluene twice. The residue was used in next step w/o further purification. LCMS: 146.1 (M+H)$^+$.

Part 3.

The titled compound was then prepared using procedures analogous to those in Example 25.

Example 29

(1S,2S)-N-hydroxy-2-{[(3R)-3-phenylpyrrolidin-1-yl]carbonyl}-5-pyrrolidin-1-ylcyclohexanecarboxamide Step 1: Preparation of 2-(3-Phenyl-pyrrolidine-1-carbonyl)-6-oxa bicyclo[3.2.1]octan-7-one To a solution of 7-oxo-6-oxa-bicyclo[3.2.1]octane-2-carboxylic acid tert-butyl ester (500 mg) in methylene chloride (3 mL was added TFA (3 mL). After stirring the mixture at rt for 2 h, the solution was concentrated under reduced pressure. The residue was azeotropically washed with methylene chloride (×3) and redissolved in DMF (3 mL). To this solution was added (R)-3-phenylpyrrolidine and the resultant mixture was cooled to 0° C., prior to the sequential addition of PyBOP (1.25 g) and diisopropylethylamine (0.42 ml). After stirring the mixture at rt overnight, the reaction solution was diluted with EtOAc and washed with saturated NaHCO$_3$ aqueous solution (×3), water, and brine. The organic phase was dried over MgSO$_4$, filtered and concentrated under reduced pressure. The residue was purified by flash chromatography (eluting with 8% methanol in methylene chloride). MS (ESI): 300.1 (M+H$^+$).

Step 2: Preparation of 5-Hydroxy-2-(3-phenyl-pyrrolidine-1-carbonyl)-cyclohexanecarboxylic acid benzyl ester To a solution of the compound made above (400 mg) in THF (4 mL) was added lithium hydroxide (302 mg), followed by water (1 mL). After 3 h, the reaction mixture was diluted with 1N HCl and extracted with EtOAc (3×30 mL). The organic phases were washed with brine, dried over MgSO$_4$, filtered, and concentrated under reduced pressure. The residue was used without further purification in the following step.

To a solution of the above residue in acetonitrile (10 mL) was added benzyl bromide (0.41 mL), followed by DBU (0.51 mL). After stirring the reaction mixture at rt overnight the reaction mixture was concentrated under reduced pressure and then the residue was dissolved in EtOAc, followed by washing with 10% citric acid aqueous solution and brine. The organic phases were dried over MgSO$_4$, filtered, and concentrated under reduced pressure. The residue was purified by flash chromatography (eluting with 5% methanol in methylene chloride). MS (ESI): 408.2 (M+H$^+$).

Step 3: Preparation of 5-oxo-2-(3-phenyl-pyrrolidine-1-carbonyl)-cyclohexanecarboxylic acid benzyl ester To a solution of alcohol compound from Step 2 (400 mg) was added Dess-Martin reagent (500 mg) and the mixture was stirred at rt for 3 h. After the reaction was complete the mixture was diluted with methylene chloride followed by the addition of 0.1 N NaOH aqueous solution (12 mL) and the stirring was continued for about 20 min. The organic phases were washed with 0.1 N NaOH solution, brine, dried over MgSO$_4$, and concentrated under reduced pressure. The residue was purified by flash chromatographed (eluting with 5% methanol in methylene chloride). MS (ESI): 406.1 (M+H$^+$).

Step 4: Preparation of 2-(3-Phenyl-pyrrolidine-1-carbonyl)-5-pyrrolidin-1-yl-cyclohexanecarboxylic acid benzyl ester To a solution of the ketone compound made above (30 mg) in 1,2-dichloroethane was added pyrrolidine (6 μL). The mixture was stirred at rt about 10 min, prior to the addition of NaBH(OAc)$_3$ (24 mg). The resultant mixture was stirred for an additional hour and then diluted with EtOAc and washed with saturated NaHCO$_3$, and brine. The organic phases were dried over MgSO$_4$, filtered and concentrated to dry under reduced pressure. MS (ESI): 461.2 (M+H$^+$).

Step 5: Preparation of 2-(3-Phenyl-pyrrolidine-1-carbonyl)-5-pyrrolidin-1-yl-cyclohexanecarboxylic acid hydroxyamide To a solution of the above made compound (30 mg, crude) in methanol (1 mL) was added palladium on carbon (20 mg). The suspension was stirred under hydrogen balloon overnight. The mixture was filter through a pad of celite and concentrated in-vacuo. The residue was used in the next step without further purification. MS (ESI): 371.2 (M+H$^+$).

To a solution of the above residue in DMF (0.3 mL) was added hydroxylamine (14 mg) and the mixture was cooled to 0° C., prior to the sequential addition of PyBOP (34 mg) and NMM (18 μL). The mixture was stirred at rt for about 3 h and then applied directly on preparative HPLC to afford the final product. MS (ESI): 386.2 (M+H$^+$).

Example 30

(1S,2S,5S)-N-hydroxy-2-{[(3R)-3-phenylpyrrolidin-1-yl]carbonyl}-5-morpholin-4-ylcyclohexanecarboxamide This compound was prepared using procedures analogous to those for Example 29. MS (ESI): 402.2 (M+H$^+$).

Example 31

(1S,2S,5R)-N-hydroxy-2-{[(3R)-3-phenylpyrrolidin-1-yl]carbonyl}-5-morpholin-4-ylcyclohexanecarboxamide This compound was prepared using procedures analogous to those for Example 29. MS (ESI): 402.2 (M+H$^+$).

Example 32

(1S,2S)-N-hydroxy-5-[(3R)-3-hydroxypyrrolidin-1-yl]-2-{[(3R)-3-phenylpyrrolidin-1-yl]carbonyl}cyclohexanecarboxamide This compound was prepared using procedures analogous to those for Example 29. MS (ESI): 402.2 (M+H$^+$).

Example 33

(1S,2S,5S)-2-{[4-(4-tert-butylphenyl)piperazin-1-yl]carbonyl}-N,5-dihydroxycyclohexanecarboxamide Step 1: Preparation of 2-[4-(4-tert-Butyl-phenyl)-piperazine-1-carbonyl]-6-oxa-bicyclo[3.2.1]octan-7-one This compound was prepared using procedures analogous to Example 29, Step 1. MS (ESI): 371.1 (M+H$^+$).

Step 2: Preparation of 2-[4-(4-tert-Butyl-phenyl)-piperazine-1-carbonyl]-5-hydroxy-cyclohexanecarboxylic acid hydroxyamide To a solution of the above made compound (130 mg) in THF (2 mL) was added lithium hydroxide (45 mg), followed by water (0.5 mL). After stiirring at rt for 3 h, the reaction mixture was diluted with 1N HCl solution and extracted with EtOAc (3×15 mL). The organic phases were washed with brine, dried over MgSO$_4$, and concentrated to dry under reduced pressure. The residue was used in next step without further purification.

The crude residue (45 mg) was dissolved in DMF (0.3 mL), and hydroxylamine HCl salt (25 mg) was added. The mixture was cooled to 0° C. and PyBOP (68 mg) was added, followed by DIEA (93 μL). After stirring the reaction mixture at rt for 3 h, the crude reaction mixture was applied directly on preparative HPLC to afford the final product. MS (ESI): 404.2 (M+H$^+$).

Example 34

(3S)-tetrahydrofuran-3-yl((3S,4S)-3-[(hydroxyamino)carbonyl]-4-{[(3R)-3-phenylpyrrolidin-1-yl]carbonyl}cyclohexyl)methylcarbamate Step 1: Preparation of Carbonic acid 4-nitro-phenyl ester tetrahydro-furan-3-yl ester To a solution of p-nitrophenyl chloroformate (1.21 g) in methylene chloride at 0° C. was added S-(+)-3-hydoxytetrahydrofuran (0.51 g), followed by NMM (0.66 mL). After stirring the mixture at rt for 2 h the volatiles were removed under reduced pressure and the resulting residue was dissolved in a small amount of methylene chloride and filtered. The filtrate was concentrated under reduced pressure and subjected to flash chromatography (eluting with 30% ethyl acetate in methylene chloride) to afford the titled compound.

Step 2: Preparation of 5-Methylamino-2-(3-phenyl-pyrrolidine-1-carbonyl)-cyclohexanecarboxylic acid benzyl ester This compound was prepared using procedures analogous to Step 4 in Example 29. MS (ESI): 421.2 (M+H$^+$).

Step 3: Preparation of 5-[Methyl-(tetrahydro-furan-3-yloxycarbonyl)-amino]-2-(3-phenyl-pyrrolidine-1-carbonyl)-cyclohexanecarboxylic acid benzyl ester To a solution of the compound made above (37 mg) in THF (0.3 mL) was added DIEA (31 μL), followed by carbonic acid 4-nitro-phenyl ester tetrahydro-furan-3-yl ester (25 mg) in THF (0.3 mL). After stirring the mixture at rt for 24 hours, the volatiles were removed under reduced pressure. The residue was purified by flash chromatography (eluting with 5% methanol in methylene chloride) to provide the desired product. MS (ESI): 535.2 (M+H$^+$).

Step 4: Preparation of [3-Hydroxycarbamoyl-4-(3-phenyl-pyrrolidine-1-carbonyl)-cyclohexyl]-methyl-carbamic acid tetrahydro-furan-3-yl ester This compound was prepared using procedures analogous to those for Example 29 in step 5. MS (ESI): 460.2 (M+H$^+$).

Example 35

(3R)-tetrahydrofuran-3-yl((3S,4S)-3-[(hydroxyamino)carbonyl]-4-{[(3R)-3-phenylpyrrolidin-1-yl]carbonyl}cyclohexyl)methylcarbamate This compound was prepared using procedures analogous to those for Example 34. MS (ESI): 460.2 (M+H$^+$).

Example 36

Tetrahydro-2H-pyran-4-yl((3S,4S)-3-[(hydroxyamino)carbonyl]-4-{[(3R)-3-phenylpyrrolidin-1-yl]carbonyl}cyclohexyl)methylcarbamate This compound was prepared using procedures analogous to those for Example 34. MS (ESI): 474.2 (M+H$^+$).

Example 37

(1S,3S,4S)-3-[(hydroxyamino)carbonyl]-4-{[(3R)-3-phenylpyrrolidin-1-yl]carbonyl}cyclohexyl pyrrolidine-1-carboxylate Step 1: Preparation of 5-(4-Nitro-phenoxycarbonyloxy)-2-(3-phenyl-pyrrolidine-1-carbonyl)-cyclohexa-2,3-dicarboxylic acid benzyl ester.

To a solution of p-nitrophenyl chloroformate (181 mg) in methylene chloride was added 5-hydroxy-2-(3-phenyl-pyrrolidine-1-carbonyl)-cyclohexanecarboxylic acid benzyl ester (183 mg), followed by NMM (99 μL). After stirring the reaction condition for 60 h the volatiles were removed in-vacuo. The residue was purified by flash chromatography (eluting with 5% methanol in methylene chloride) to provide the carbamate compound. MS (ESI): 573.2 (M+H$^+$).

Step 2: Preparation of Pyrrolidine-1-carboxylic Acid 3-benzyloxycarbonyl-4-(3-phenyl-pyrrolidine-1-carbonyl)-cyclohexyl ester This compound was prepared using procedures analogous to Example 34, step 3. MS (ESI): 505.2 (M+H$^+$).

Step 3: Preparation of Pyrrolidine-1-carboxylic acid 3-hydroxycarbamoyl-4-(3-phenyl-pyrrolidine-1-carbonyl)-cyclohexyl ester This compound was prepared using procedures analogous to those for Example 29 in step 5. MS (ESI): 430.3 (M+H$^+$) 315.2 (M−114)$^+$.

Example 38

(1S,3S,4S)-3-[(hydroxyamino)carbonyl]-4-{[(3R)-3-phenylpyrrolidin-1-yl]carbonyl}cyclohexyl methylcarbamate This compound was prepared using procedures analogous to those for Example 37. MS (ESI): 390.2 (M+H$^+$) 315.2 (M−114)$^+$.

Example 39

(1S,3S,4S)-3-[(hydroxyamino)carbonyl]-4-{[(3R)-3-phenylpyrrolidin-1-yl]carbonyl}cyclohexyl dimethylcarbamate This compound was prepared using procedures analogous to those for Example 37. MS (ESI): 404.3 (M+H$^+$) 315.2 (M−114)$^+$.

Example 40

(1S,3S,4S)-3-[(hydroxyamino)carbonyl]-4-{[(3R)-3-phenylpyrrolidin-1-yl]carbonyl}cyclohexyl morpholine-4-carboxylate This compound was prepared using procedures analogous to those for Example 37. MS (ESI): 446.2 (M+H$^+$) 315.2 (M−114)$^+$.

Example 41

(1S,3S,4S)-3-[(hydroxyamino)carbonyl]-4-[([(3R)-3-phenylpyrrolidin-1-yl]carbonyl}cyclohexyl(3R)-3-hydroxypyrrolidine-1-carboxylate This compound was prepared using procedures analogous to those for Example 37. MS (ESI): 446.3 (M+H$^+$) 315.2 (M−114)$^+$.

Example 42

(3S)-tetrahydrofuran-3-yl(2S,3S)-3-[(hydroxyamino)carbonyl]-2-{[4-(3-isopropylphenyl)piperidin-1-yl]carbonyl}piperidine-1-carboxylate Step 1. Tert-Butyl 4-[(trifluoromethyl)sulfonyl]oxy-3,6-dihydropyridine-1(2H)-carboxylate To a solution of tert-butyl 4-oxo-1-piperidinecarboxylate (10.50 g, 0.05270 mol) in tetrahydrofuran (200.0 mL, 2.466 mol) at −78 Celsius, under nitrogen, was added 1.00 M of lithium hexamethyldisilazide in tetrahydrofuran (55.96 mL). After stirred at −78 Celsius for 1 h, to the resultant mixture was added solid N-phenylbis(trifluoromethane-sulphonimide) (20.00 g, 0.05598 mol). The reaction mixture was stirred at −78 Celsius for 2 h, then allowed to warm to rt gradually and stirred at rt overnight. After evaporation of THF under reduced pressure, the residue was diluted with ether. The mixture was washed with 1N HCl, 1N NaOH, and brine, successively. The organic layers were then dried and evaporated to dry. The residue was applied on silica gel column, eluting 0 to 20% ethyl acetate in hexane, to provide the enol triflate (17.46 g, 84%). MS (ESI): (−Boc) 232.0.

Step 2. Tert-Butyl 4-(3-isopropylphenyl)-3,6-dihydropyridine-1(2H)-carboxylate

A mixture of tert-butyl 4-[(trifluoromethyl)sulfonyl]oxy-3,6-dihydropyridine-1(2H)-carboxylate (11.0 g, 0.0332 mol), (3-isopropylphenyl)boronic acid (5.44 g, 0.0332 mol) and potassium phosphate (21.1 g, 0.0996 mol) in tetrahydrofuran (150.0 mL, 1.849 mol) was degassed for 15 min, then tetrakis(triphenylphosphine)palladium(0) (2 g, 0.002 mol) was added and the resulting mixture was refluxed overnight. After evaporation of most of THF, the residue was diluted with water, extracted with EtOAc. The combined organic layers were washed with brine, dried and evaporated to dry. The residue was applied on silica gel column, eluting with 0 to 20% EtOAc in hexane (9.1 g, 91%). MS (ESI): (M−Bu) 246.1.

Step 3: De-Boc tert-Butyl 4-(3-isopropylphenyl)-3,6-dihydropyridine-1(2H)-carboxylate (2.54 g, 0.00844 mol) was treated with 10 mL of TFA at rt for 30 min. After evaporation of TFA, the residue was exposed on high vacuum and then used directly in next step.

Step 4: Preparation of 2-[4-(3-Isopropyl-phenyl)-3,6-dihydro-2H-pyridine-1-carbonyl]-piperidine-3-carboxylic acid tert-butyl ester To a 0° C. solution of piperidine-2,3-dicarboxylic acid 3-tert-butyl ester (100 mg) in DMF (0.6 mL) was added sequentially, 4-(3-isopropyl-phenyl)-1,2,3,6-tetrahydro-pyridine (97 mg), PyBOP (232 mg), and diisopropylethylamine (0.152 mL). The resultant mixture was stirred at rt overnight. The reaction solution was diluted with EtOAc and washed with saturated NaHCO$_3$ solution (×3), water, and brine. The organic layers were dried over MgSO$_4$, filtered, and concentrated to dry under reduced pressure. The residue was used in next step without further purifications. MS (ESI): 413.2 (M+H$^+$).

Step 5: Preparation of 2-[4-(3-Isopropyl-phenyl)-3,6-dihydro-2H-pyridine-1-carbonyl]-piperidine-3-carboxylic acid benzyloxy-amide To a solution of the crude product made above in methylene chloride (1.3 mL) was added TFA (3.5 mL) followed by water (0.3 mL). The mixture was stirred at rt overnight and then concentrated to dry under reduced pressure. The residue was co-evaporated several times with benzene to remove water. The residue was dissolved in DMF (1 mL) and cooled to 0° C., prior to the sequential addition of O-benzylhydroxyamine (83 mg), PyBOP (249 mg), and diisopropylethylamine (0.31 mL). The resultant mixture was stirred at rt overnight. The reaction solution was diluted with EtOAc and washed with saturated NaHCO$_3$ solution (×3), water, and brine. The organic layers were dried over MgSO$_4$, filtered and concentrated to dry under reduced presure. The residue was purified by flash chromatography (eluting with 10% methanol in methylene chloride) to provide the desired product. MS (ESI): 462.2 (M+H$^+$).

Step 6: Preparation of 3-Benzyloxycarbamoyl-2-[4-(3-isopropyl-phenyl)-3,6-dihydro-2H-pyridine-1-carbonyl]-piperidine-1-carboxylic acid tetrahydro-furan-3-yl ester To a solution of the compound made above (50 mg) in THF (0.5 mL) was added DIEA (40 µL) and carbonic acid 4-nitrophenyl ester tetrahydro-furan-3-yl ester (30 mg) in THF (0.5 mL). After stirring the reaction mixture at rt for 24 h, the volatiles were removed under reduced pressure. The residue was purified by flash chromatography (eluting with 7% methanol in methylene chloride) to provide the titled compound. MS (ESI): 576.3 (M+H$^+$).

Step 7: Preparation of 3-Hydroxycarbamoyl-2-[4-(3-isopropyl-phenyl)-piperidine-1-carbonyl]-piperidine-1-carboxylic acid tetrahydro-furan-3-yl ester To a solution of the compound made above in methanol (1 mL) was added palladium on carbon (20 mg). The suspension was stirred under hydrogen balloon for 3 h. The mixture was filtered and concentrated to dry under reduced pressure. The residue was purified by prepative HPLC to afford the final product. MS (ESI): 488.2 (M+H$^+$).

Example 43

(3R)-tetrahydrofuran-3-yl(2S,3S)-3-[(hydroxyamino)carbonyl]-2-{[4-(3-isopropylphenyl)piperidin-1-yl]carbonyl}piperidine-1-carboxylate This compound was prepared using procedures analogous to those for Example 42. MS (ESI): 488.2 (M+H$^+$).

Example 44

Tetrahydro-2H-pyran-4-yl(2S,3S)-3-[(hydroxyamino)carbonyl]-2-{[4-(3-isopropylphenyl)piperidin-1-yl]carbonyl}piperidine-1-carboxylate This compound was prepared using procedures analogous to those for Example 42. MS (ESI): 502.2 (M+H$^+$).

Example 45

(3R)-tetrahydrofuran-3-yl(2S,3S)-3-[(hydroxyamino)carbonyl]-2-[(4-phenylpiperazin-1-yl)carbonyl]piperidine-1-carboxylate This compound was prepared using procedures analogous to those for Example 42. MS (ESI): 447.2 (M+H$^+$).

Example 46

(3S)-tetrahydrofuran-3-yl(2S,3S)-3-[(hydroxyamino)carbonyl]-2-[(4-phenylpiperazin-1-yl)carbonyl]piperidine-1-carboxylate This compound was prepared using procedures analogous to those for Example 42. MS (ESI): 447.2 (M+H$^+$).

Example 47

Tetrahydro-2H-pyran-4-yl(2S,3S)-3-[(hydroxyamino)carbonyl]-2-[(4-phenylpiperazin-1-yl)carbonyl]piperidine-1-carboxylate This compound was prepared using procedures analogous to those for Example 42. MS (ESI): 461.2 (M+H$^+$).

Example 48

Benzyl {5-[({(5S,6S)-5-[(hydroxyamino)carbonyl]-6-[(3-phenylpyrrolidin-1-yl)carbonyl]piperidin-3-yl}acetyl)amino]pentyl}carbamate Part 1: 1,2-dibenzyl 3-tert-butyl(2S,3S)-5-oxopiperidine-1,2,3-tricarboxylate. To an oven-dried 5 mL conical vial equipped with a magnetic stir bar and under a nitrogen gas atmosphere was placed oxalyl chloride (0.080 mL, 0.92 mmol) and methylene chloride (0.7 mL). The solution was cooled to −78° C. prior to the dropwise addition of dimethyl sulfoxide (0.080 mL, 1.13 mmol) in methylene chloride (0.3 mL). After stirring the solution for 45 min, a solution of 1,2-dibenzyl 3-tert-butyl(2S,3S)-5-hydroxypiperidine-1,2,3-tricarboxylate (266 mg, 0.567 mmol) in methylene chloride (1 mL) was added dropwise and the solution was allowed to gradually warm to ca. 0° C. over 1.5 h. The reaction mixture was cooled to −78° C. prior to the dropwise addition of triethylamine (0.240 mL, 1.72 mmol) and stirring was continued for 3 h with gradual warming to ca. 0° C. The reaction was quenched by the dropwise addition of 5% citric acid (2 mL) and diluted with methylene chloride (15 mL). The organic layer was washed with brine (2×5 mL), dried (NaSO$_4$), and concentrated in-vacuo to afford 264 mg (100%) of the desired ketone as a sticky yellow oil. LCMS (ESI): 490 (M+Na$^+$).

Part 2: 1,2-dibenzyl 3-tert-butyl(2S,3S)-5-(2-methoxy-2-oxoethylidene)piperidine-1,2,3-tricarboxylate: To an oven-dried 25 mL round-bottomed flask equipped with a magnetic stir bar and under a nitrogen gas atmosphere was placed methyl(triphenylphosphoranylidene) acetate (199 mg, 0.597 mmol) and toluene (5 mL). To this heterogeneous solution was added a solution of 1,2-dibenzyl 3-tert-butyl(2S,3S)-5-oxopiperidine-1,2,3-tricarboxylate (93 mg, 0.199 mmol) in toluene (3 mL). The reaction mixture was heated to reflux and stirred overnight. The volatiles were then removed in-vacuo and the yellow oil was purified by Combiflash (10 to 30% ethyl acetate in hexanes) to afford 83 mg (80%) of 1,2-dibenzyl 3-tert-butyl(2S,3S)-5-(2-methoxy-2-oxoethylidene)piperidine-1,2,3-tricarboxylate. LCMS (ESI): 424 (M−CO$_2$t-Bu+2H$^+$), 468 (M−t-Bu+2H$^+$), 524 (M+H$^+$).

Part 3: (2S,3S)-3-(tert-butoxycarbonyl)-5-(2-methoxy-2-oxoethyl)piperidine-2-carboxylic acid. A solution of 1,2-dibenzyl 3-tert-butyl(2S,3S)-5-(2-methoxy-2-oxoethylidene)piperidine-1,2,3-tricarboxylate (98 mg, 0.188) in methanol (5 mL) was hydrogenated in the presence of 10% palladium on carbon (100 mg, 0.094), under balloon pressure of hydrogen, overnight. The resulting reaction mixture was filtered through a pad of celite and the precipitate was washed with methanol (2×5 mL). The volatiles were removed in-vacuo to afford 50 mg (88%) of (2S,3S)-3-(tert-butoxycarbonyl)-5-(2-methoxy-2-oxoethyl)piperidine-2-carboxylic acid as a sticky amorphous solid, which was used directly in the following coupling without further purification. LCMS (ESI): 246 (M−t-Bu+H+), 302 (M+H$^+$).

Part 4: tert-butyl(2S,3S)-5-(2-methoxy-2-oxoethyl)-2-[(3-phenylpyrrolidin-1-yl)carbonyl]piperidine-3-carboxylate.
To an oven-dried 5 mL conical vial equipped with a magnetic stir bar and under a nitrogen gas atmosphere was placed sequentially: (2S,3S)-3-(tert-butoxycarbonyl)-5-(2-methoxy-2-oxoethyl)piperidine-2-carboxylic acid (50 mg, 0.166 mmol), anhydrous DMF (2 mL), BOP reagent (100 mg, 0.226 mmol), 3-phenyl-pyrrolidine (25 mg, 0.17 mmol), and N,N-diisopropyl ethylamine (0.086 mL, 0.49 mmol). After stirring the reaction mixture overnight, the reaction was quenched with 5% citric acid (1 mL) and the reaction mixture was diluted with ethyl acetate (15 mL) and water (4 mL). The aqueous layer was extracted with ethyl acetate (3×3 mL) and the combined organic phases were washed with saturated sodium bicarbonate (3×5 mL), brine (5 mL), dried (NaSO4), and concentrated in-vacuo to afford 75 mg of crude product that was used directly in the following hydrolysis. LCMS (ESI): 431 (M+H), 375 (M−t-Bu+2H$^+$).

Part 5: {(5S,6S)-5-(tert-butoxycarbonyl)-6-[(3-phenylpyrrolidin-1-yl)carbonyl]piperidin-3-yl}acetic acid. A solution of tert-butyl(2S,3S)-5-(2-methoxy-2-oxoethyl)-2-[(3-phenylpyrrolidin-1-yl)carbonyl]piperidine-3-carboxylate in THF (3 mL) was cooled to 0° C. prior to the addition of lithium hydroxide (7 mg, 0.16 mmol). After warming to ambient temperature, the reaction mixture-was stirred overnight. The volatiles were removed in-vacuo to afford 60 mg (87%) of {(5S,6S)-5-(tert-butoxycarbonyl)-6-[(3-phenylpyrrolidin-1-yl)carbonyl]piperidin-3-yl}acetic acid as an off-white solid that was used without neutralization and purification in the following coupling reaction. MS (ESI): 417 (M+H$^+$).

Part 6: Tert-Butyl(2S,3S)-5-{2-[(5-{[(benzyloxy)carbonyl]amino}pentyl)amino]-2-oxoethyl}-2-[(3-phenylpyrrolidin-1-yl)carbonyl]piperidine-3-carboxylate. To an oven-dried 5 mL conical vial equipped with a magnetic stir bar and under a nitrogen gas atmosphere was placed sequentially: {(5S,6S)-5-(tert-butoxycarbonyl)-6-[(3-phenylpyrrolidin-1-yl)carbonyl]piperidin-3-yl}acetic acid (60 mg, 0.144 mmol), anhydrous DMF (2 mL), BOP reagent (100 mg, 0.226 mmol), N,N-Cbz-1,5-diaminopentane hydrochloride (45 mg, 0.17 mmol), and N,N-diisopropyl ethylamine (0.086 mL, 0.49 mmol). After stirring the reaction mixture overnight, the reaction was quenched with 5% citric acid (1 mL) and the reaction mixture was diluted with ethyl acetate (15 mL) and water (4 mL). The aqueous layer was extracted with ethyl acetate (3×3 mL) and the combined organic phases were washed with saturated sodium bicarbonate (3×5 mL), brine (5 mL), dried (NaSO4), and concentrated in-vacuo. Purification by Combiflash (0 to 10% methanol in methylene chloride over 25 min) to afford 56 mg (62%) of tert-butyl(2S,3S)-5-{2-[(5-{[(benzyloxy)carbonyl]amino}pentyl)amino]-2-oxoethyl}-2-[(3-phenylpyrrolidin-1-yl)carbonyl]piperidine-3-carboxylate. LCMS (ESI): 635 (M+H$^+$), 636 (M+2H$^+$).

Part 7: (2S,3S)-5-{2-[(5-{[(benzyloxy)carbonyl]amino}pentyl)amino]-2-oxoethyl}-2-[(3-phenylpyrrolidin-1-yl)carbonyl]piperidine-3-carboxylic acid. A solution of tert-butyl (2S,3S)-5-{2-[(5-{[(benzyloxy)carbonyl]amino}pentyl)amino]-2-oxoethyl}-2-[(3-phenylpyrrolidin-1-yl)carbonyl]piperidine-3-carboxylate (40 mg, 0.063 mmol) in methylene chloride (2 mL) was added a drop of water and trifluoroacetic acid (4 mL). After stirring the reaction mixture overnight, the volatiles were removed in-vacuo and the residue was azeotropically washed with benzene (2×3 mL) and heptane (2×3 mL). The crude product was dried under high vacuum and used directly in the following coupling reaction without purification. MS (ESI): 579 (M+H).

Part 8: Benzyl {5-[({(5S,6S)-5-[(hydroxyamino)carbonyl]-6-[(3-phenylpyrrolidin-1-yl)carbonyl]piperidin-3-yl}acetyl)amino]pentyl}carbamate. To an oven-dried 5 mL conical vial equipped with a magnetic stir bar and under a nitrogen gas atmosphere was placed sequentially: (2S,3S)-5-{2-[(5-{[(benzyloxy)carbonyl]amino}pentyl)amino]-2-oxoethyl}-2-[(3-phenylpyrrolidin-1-yl)carbonyl]piperidine-3-carboxylic acid (0.063 mmol), anhydrous DMF (1.5 mL), PyBOP reagent (40 mg, 0.076 mmol), hydroxylamine hydrochloride (20 mg, 0.289 mmol), and 4-methyl morpholine (0.046 mL, 0.42 mmol). After stirring overnight, the crude reaction mixture was directly applied to preparative HPLC purification to afford 14 mg (38% for 2 steps) of pure {7-[5-(S)-hydroxycarbomyl-6-(R)-(3-phenyl-pyrrolidine-1-carbonyl)-piperidine-3-yl]-6-oxo-heptyl}-carbamic acid benzyl ester. LCMS (ESI): 594 (M+H$^+$), 595 (M+2H$^+$).

Example 49

(2S,3S)-5-{2-[(5-aminopentyl)amino]-2-oxoethyl}-N-hydroxy-2-[(3-phenylpyrrolidin-1-yl)carbonyl]piperidine-3-carboxamide A solution of {7-[5-(S)-hydroxycarbomyl-6-(R)-(3-phenyl-pyrrolidine-1-carbonyl)-piperidine-3-yl]-6-oxo-heptyl}-carbamic acid benzyl ester (10 mg, 0.0169 mmol) in methanol (2 mL) was hydrogenated using palladium on barium sulfate (5%) (10 mg, 0.0047 mmol) and under balloon pressure of hydrogen. After stirring for 4 h, the reaction mixture was filtered through a pad of celite and the precipitate was washed with methanol (2×5 mL). The volatiles were removed in-vacuo to afford 6.5 mg (84%) of 5-(7-amino-2-oxo-heptyl)-2-(R)-(3-phenyl-pyrrolidine-1-carbonyl)-piperidine-3-(S)-carboxylic acid hydroxyamide. LCMS (ESI): 460 (M+H$^+$).

Example 50

(1S,2S)-N-Hydroxy-5-(2-oxo-2-piperidin-1-ylethyl)-2-[(4-phenylpiperazin-1-yl)carbonyl]cyclohexanecarboxamide Part 1: 4-Methoxycarbonylmethylidene-cyclohexane-1-(S)-2-(S)-dicarboxylic acid 2-(S)-benzyl ester]-(S)-tert-butyl ester. To an oven-dried 50 mL round-bottomed flask equipped with a magnetic stir bar and under a nitrogen gas atmosphere was placed 4-oxo-cyclohexane-1-(S)-2-(S)-dicarboxylic acid 2-(S)-benzyl ester 1-(S)-tert-butyl ester (470 mg, 1.42 mmol), toluene (35 mL), and methyl(triphenylphosphoranylidene)acetate (2.4 g, 7.2 mmol). The heterogeneous mixture was heated to reflux and stirred overnight. The volatiles were then removed in-vacuo and the yellow oil was purified by Combiflash (10 to 30% ethyl acetate in hexanes) to afford 496 mg (85%) of 4-methoxycarbonyl-methylene-cyclohexane-1-(S)-2-(S)-dicarboxylic acid 2-(S)-benzyl ester 1-(S)-tert-butyl ester. LCMS (ESI): 301 (M−CO$_2$(t-Bu)−Me+3H$^+$), 411 (M+Na$^+$).

Part 2: 4-Methoxycarbonylmethylidene-cyclohexane-1-(S)-2-(S)-dicarboxylic acid 2-(S)-benzyl ester. A solution of 4-methoxycarbonyl-methylidene-cyclohexane-1-(S)-2-(S)-dicarboxylic acid 2-benzyl ester 1-tert-butyl ester (496 mg, 1.21 mmol) in methylene chloride (8 mL) was added a couple of drops of water and trifluoroacetic acid (16 mL). After stirring the reaction mixture for 3 h, the volatiles were removed in-vacuo and the residue was azeotropically washed with benzene (2×5 mL), heptane (2×5 mL), and toluene (2×5 mL). The crude product was dried under high vacuum and used directly in the following coupling reaction without further purification. MS (ESI): 355 (M+Na$^+$).

Part 3: 5-Methoxycarbonylmethylidene-2-(S)-(4-phenyl-piperazine-1-carbonyl)-cyclohexane-(S)-carboxylic acid benzyl ester. To an oven-dried 10 mL conical vial equipped with a magnetic stir bar and under a nitrogen gas atmosphere was placed sequentially: 4-methoxycarbonylmethylidene-cyclohexane-1-(S)-2-(S)-dicarboxylic acid 2-(S)-benzyl ester (172 mg, 0.52 mmol), anhydrous DMF (4 mL), PyBOP reagent (324 mg, 0.62 mmol), N-phenyl piperazine (0.10 mL, 0.655 mmol), and 4-methyl morpholine (0.220 mL, 2.02 mmol). After stirring the reaction mixture overnight, the reaction was quenched with 5% citric acid (1 mL) and the reaction mixture was diluted with ethyl acetate (15 mL) and water (4 mL). The aqueous layer was extracted with ethyl acetate (3×3 mL) and the combined organic phases were washed with saturated sodium bicarbonate (3×5 mL), brine (5 mL), dried (Na$_2$SO4), and concentrated in-vacuo. Purification by Combiflash (0 to 10% methanol in methylene chloride over 30 min) to afford 233 mg (94%) of pure 5-methoxycarbonylmethylidene-2-(S)-(4-phenyl-piperazine-1-carbonyl)-cyclohexane-(S)-carboxylic acid benzyl ester. LCMS (ESI): 477 (M+H$^+$).

Part 4: 5-Methoxycarbonylmethylidene-2-(S)-(4-phenyl-piperazine-1-carbonyl)-cyclohexane-(S)-carboxylic acid. A solution of 5-methoxycarbonylmethylidene-2-(S)-(4-phenyl-piperazine-1-carbonyl)-cyclohexane-(S)-carboxylic acid benzyl ester (233 mg, 0.49) in methanol (5 mL) was hydrogenated in the presence of 10% palladium on carbon (150 mg, 0.14), under balloon pressure of hydrogen, for 2 h. The resulting reaction mixture was filtered through a pad of celite and the precipitate was washed with methanol (2×5 mL). The volatiles were removed in-vacuo to afford 172 mg (90%) of 5-methoxy-carbonylmethylidene-2-(S)-(4-phenyl-piperazine-1-carbonyl)-cyclohexane-(S)-carboxylic acid as a sticky oil, which was used directly in the following coupling without further purification. LCMS (ESI): 389 (M+H$^+$).

Part 5: [3-(S)-Benyloxycarbamoyl-4-(S)-(4-phenyl-piperazine-1-carbonyl)-cyclohexyl]-acetic acid methyl ester. To an oven-dried 5 mL conical vial equipped with a magnetic stir bar and under a nitrogen gas atmosphere was placed sequentially: 5-methoxy carbonyl-methylene-2-(S)-(4-phenyl-piperazine-1-carbonyl)-cyclohexane-(S)-carboxylic acid (172 mg, 0.44 mmol), anhydrous DMF (3 mL), PyBOP reagent (320 mg, 0.61 mmol), O-benzyl-hydroxylamine hydrochloride (100 mg, 0.627 mmol), and 4-methyl morpholine (0.160 mL, 1.47 mmol). After stirring the reaction mixture overnight, the reaction was quenched with 5% citric acid (1 mL) and the reaction mixture was diluted with ethyl acetate (15 mL) and water (4 mL). The aqueous layer was extracted with ethyl acetate (3×3 mL) and the combined organic phases were washed with saturated sodium bicarbonate (3×5 mL), brine (5 mL), dried (NaSO4), and concentrated in-vacuo. Purification by Combiflash (0 to 15% methanol in methylene chloride over 30 min) to afford 213 mg (98%) of pure [3-(S)-benyloxycarbamoyl-4-(S)-(4-phenyl-piperazine-1-carbonyl)-cyclohexyl]-acetic acid methyl ester. LCMS (ESI): 494 (M+H$^+$).

Part 6: [3-(S)-Benyloxycarbamoyl-4-(S)-(4-phenyl-piperazine-1-carbonyl)-cyclohexyl]-acetic acid. To a solution of [3-(S)-benyloxycarbamoyl-4-(S)-(4-phenyl-piperazine-1-carbonyl)-cyclohexyl]-acetic acid methyl ester (213 mg, 0.432 mmol) in THF (5 mL) was added water (3 mL) and lithium hydroxide (40 mg, 0.95 mmol). After stirring at ambient temperature for 4 h, the reaction mixture was acidified with 1 N HCl to a pH of ca. 5. The product was extracted with ethyl acetate (4×5 mL) and the combined organic layers were washed with brine (5 mL), dried (NaSO4), and the volatiles were removed in-vacuo to afford 154 mg (87%) of [3-(S)-benyloxycarbamoyl-4-(S)-(4-phenyl-piperazine-1-carbonyl)-cyclohexyl]-acetic acid as a sticky oil that was used without further purification in the following coupling reaction. MS (ESI): 480 (M+H$^+$).

Part 7: 5-(2-Oxo-2-piperidiin-1-yl-ethyl)-2-(S)-(4-phenyl-piperazine-1-carbonyl)-cyclohexan-(S)-carboxylic acid benzyloxy-amide. To an oven-dried 5 mL conical vial equipped with a magnetic stir bar and under a nitrogen gas atmosphere was placed sequentially: [3-(S)-benyloxycarbamoyl-4-(S)-(4-phenyl-piperazine-1-carbonyl)-cyclohexyl]-acetic acid (16 mg, 0.033 mmol), anhydrous DMF (1 mL), PyBOP reagent (20 mg, 0.038 mmol), piperidine (0.010 mL, 0.101 mmol), and 4-methyl morpholine (0.01 mL, 0.092 mmol). After stirring the reaction mixture overnight, the reaction was quenched with 5% citric acid (1 mL) and the reaction mixture was diluted with ethyl acetate (15 mL) and water (4 mL). The aqueous layer was extracted with ethyl acetate (3×3 mL) and the combined organic phases were washed with saturated sodium bicarbonate (3×5 mL), brine (5 mL), dried (NaSO4), and concentrated in-vacuo. Purification by Combiflash (0 to 10% methanol in methylene chloride over 30 min) to afford 17 mg (94%) of pure 5-(2-oxo-2-piperidin-1-yl-ethyl)-2-(S)-(4-phenyl-piperazine-1-carbonyl)-cyclohexan-(S)-carboxylic acid benzyloxy-amide. LCMS (ESI): 547 (M+H$^+$).

Part 8: 5-(2-Oxo-2-piperidin-1-yl-ethyl)-2-(S)-(4-phenyl-piperazine-1-carbonyl-cyclohexan-(S)-carboxylic acid hydroxyamide. A solution of 5-(2-oxo-2-piperidin-1-yl-ethyl)-2(S)-(4-phenyl-piperazine-1-carbonyl-cyclohexan-(S)-carboxylic acid benzyloxy-amide (16 mg, 0.029 mmol) in methanol (2 mL) was hydrogenated using palladium on barium sulfate (5%) (40 mg, 0.018 mmol) and under balloon pressure of hydrogen. After stirring for 6 h, the reaction mixture was filtered through a pad of celite and the precipitate was washed with methanol (2×5 mL). The volatiles were removed in-vacuo and the residue was purified by preparative HPLC (gradient of 0 to 40% of 0.1% TFA in acetonitrile to 0.1% TFA in water over 30 min) to afford 6 mg (46%) of 5-(2-oxo-2-piperidin-1-yl-ethyl)-2-(S)-(4-phenyl-piperazine-1-carbonyl-cyclohexan-(S)-carboxylic acid hydroxyamide as a white solid. LCMS (ESI): 457 (M+H$^+$).

Example 51

(1S,2S)-N-Hydroxy-5-(2-oxo-2-pyrrolidin-1-yl-ethyl)-2-[(4-phenylpiperazin-1-yl)carbonyl]cyclohexanecarboxamide The title compound was prepared using the general procedure that was outlined above. The amide coupling, described above in part 7 for the analogous compound, afforded 18 mg (100%) of 5-(2-oxo-2-pyrrolidin-1-yl-ethyl)-2-(S)-(4-phenyl-piperazine-1-carbonyl-cyclohexancarboxylic acid benzyloxy-amide LCMS (ESI): 533 (M+H$^+$). Subsequent hydrogenation to remove the benzyl group, described above in part 8 for the analogous compound, afforded 7 mg (46%) of 5-(2-oxo-2-pyrrolidin-1-yl-ethyl)-2-(S)-(4-phenyl-piperazine-1-carbonyl-cyclohexan-(S)-carboxylic acid hydroxyamide as a white solid. LCMS (ESI): 443 (M+H$^+$).

Example 52

(1S,2S)-N-hydroxy-5-{2-[(3R)-3-hydroxypyrrolidin-1-yl]-2-oxoethyl}-2-[(4-phenylpiperazin-1-yl)carbonyl]cyclohexanecarboxamide The title compound was prepared using the general procedure that was outlined above. The amide coupling, described above in part 7 for the analogous compound, afforded 13 mg (72%) of 5-[2-oxo-2-(3-R-hydroxypyrrolidin-1-yl-ethyl]-2-(S)-(4-phenyl-piperazine-1-carbonyl-cyclohexan-(S)-carboxylic acid benzyloxy-amide LCMS (ESI): 549 (M+H$^+$). Subsequent hydrogenation to remove the benzyl group, described above in part 8 for the analogous compound, afforded 5 mg (45%) of 5-[2-oxo-2-(3-(R)-hydroxypyrrolidin-1-yl-ethyl)-2-(S)-(4-phenyl-piperazine-1-carbonyl-cyclohexan-(S)-carboxylic acid hydroxyamide as a white solid. LCMS (ESI): 459 (M+H$^+$).

Example 53

(1S,2S)-N(2)-hydroxy-N(1)-{4-[(2-methylquinolin-4-yl)methoxy]phenyl}-4-(2-oxo-2-piperidin-1-yl-ethyl)cyclohexane-1,2-dicarboxamide Part 1: 4-Hydroxymethyl-2-methyl quinoline. To a 25 mL round-bottomed flask equipped with a magnetic stirrer and under a N$_2$ (g) purge was placed sequentially: quinaldine (0.57 g, 4.0 mmol), methanol (8 mL), and water (4 mL). The solution was cooled to 0° C. prior to the sequential addition of: concentrated sulfuric acid (0.2 mL, 4 mmol), iron (II) sulfate heptahydrate (0.33 g, 1.2 mmol), and iron powder (0.067 g, 1.2 mmol). After stirring the heterogeneous mixture for 10 min, hydroxylamine-O-sulfonic acid (HOSA) (1.36 g, 12 mmol) was added and the resulting mixture was stirred for 6 h prior to quenching the reaction with 50% NaOH until the pH was ca. 10. The brown solution was filtered through a pad of celite and then extracted with methylene chloride (4×15 mL). The combined organic phases were washed with water (20 mL), brine (15 mL), dried (NaSO$_4$), and concentrated in-vacuo to afford a brown solid that was purified by Combiflash (0 to 60% ethyl acetate in hexanes over 30 min) to afford 360 mg (52%) of pure 4-hydroxymethyl-2-methyl quinoline. LCMS (ESI): 174 (M+H$^+$).

Part 2: 4-Chloromethyl-2-methyl quinoline. 4-hydroxymethyl-2-methyl quinoline (7.0 g, 40 mmol) was dissolved in chloroform (150 mL) and cooled to 0° C., thionyl chloride (15.0 mL) was added slowly at this temperature and then the reaction mixture was allowed to warm up to room temperature and stirred overnight. The solvent was removed in-vacuo and the residue was titureted with ethyl acetate/ethyl ether to provide 9.0 g (100%) of 4-chloromethyl-2-methyl quinoline as an HCl salt. MS (ESI): 191.9 (M+H$^+$).

Part 3: Tert-Butyl N-(4-hydroxyphenyl) carbamate. To a dry 250 mL round-bottomed flask equipped with a magnetic stir bar and rubber septa with N$_2$ (g) inlet was placed 4-aminophenol (5.0 g, 45.8 mmol) and THF (50 mL). The heterogeneous solution was cooled to 0° C. prior to the addition of di-tert-butyl dicarbonate (12 g, 55 mmol). Upon addition heat was observed and the cloudy solution became translucent. The solution was allowed to gradually warm to ambient temperature and stirred overnight. The volatiles were removed in-vacuo to afford tert-butyl N-(4-hydroxyphenyl) carbamate (11.3 g). LCMS (ESI): 154 (M−t-Bu+2H$^+$), 232 (M+Na$^+$).

Part 4: [4-(2-methyl-quinolin-4-ylmethoxy)-phenyl]-carbamic acid tert-butyl ester. To a 500 mL round-bottomed flask equipped with magnetic stir bar was placed 4-chloromethyl-2-methyl quinoline (6.84 g, 30.0 mmol), tert-butyl N-(4-hydroxyphenyl) carbamate (6.24 g, 30.0 mmol), CS$_2$CO$_3$ (20.0 g, 60.0 mmol), and n-Bu$_4$NI (11.1 g, 30.0 mmol) in DMSO (150 mL). The solution was stirred at 80° C. for 3 h. After cooling to ambient temperature, cold water was added and the product was extracted with ethyl acetate. The combined extract was washed with water, brine, dried and concentrated. Combiflash chromatography with CH$_2$Cl$_2$/EtOAc afforded 8.0 g (73%) of the desired product. MS (ESI): 365.3 (M+H$^+$).

Part 5: 4-(2-methyl-quinolin-4-ylmethoxy)-phenylamine hydrochloride. To a solution of [4-(2-methyl-quinolin-4-ylmethoxy)-phenyl]-carbamic acid tert-butyl ester (1.5 g, 4.1 mmol) in ethyl acetate (5 mL) was added 4 N HCl in dioxane (20 mL) and the mixture was stirred at room temperature for 3 h. Ethyl ether was then added and the precipitate was filtered and washed with ethyl ether to provide 1.3 g of the desired free amine as an HCl salt, which was used in the following reaction without further purification. MS (ESI): 265.0 (M+H$^+$).

Part 6: 5-Methoxycarbonylmethylene-2-(S)-[4-(2-methyl-quinolin-4-ylmethoxy)-phenylcarbamoyl]-cyclohexanecarboxylic acid]-(S)-benzyl ester. To an oven-dried 10 mL conical vial equipped with a magnetic stir bar and under a nitrogen gas atmosphere was placed sequentially: 4-methoxycarbonylmethylene-cyclohexane-1-(S), 2-(S)-dicarboxylic acid 2-(S)-benzyl ester (172 mg, 0.52 mmol), anhydrous DMF (4 mL), PyBOP reagent (324 mg, 0.62 mmol), 4-(2-methyl-quinolin-4-ylmethoxy)-phenylamine hydrochloride (172 mg, 0.655 mmol), and 4-methyl morpholine (0.30 mL, 2.76 mmol). After stirring the reaction mixture overnight, the reaction was quenched with 5% citric acid (1 mL) and the reaction mixture was diluted with ethyl acetate (15 mL) and water (4 mL). The aqueous layer was extracted with ethyl acetate (3×3 mL) and the combined organic phases were washed with saturated sodium bicarbonate (3×5 mL), brine (5 mL), dried (NaSO4), and concentrated in-vacuo. Purification by Combiflash (0 to 10% methanol in methylene chloride over 30 min) to afford 267 mg (89%) of pure product. LCMS (ESI): 579 (M+H$^+$).

Part 7: 5-Methoxycarbonylmethyl-2-(S)-[4-(2-methylquinolin-4-ylmethoxy)-phenylcarbamoyl]-cyclohexane-(S)-carboxylic acid. A solution of benzyl methyl ester (267 mg, 0.46) in methanol (5 mL) was hydrogenated in the presence of 10% palladium on carbon (150 mg, 0.14), under balloon pressure of hydrogen, for 2 h. The resulting reaction mixture was filtered through a pad of celite and the precipitate was washed with methanol (2×5 mL). The volatiles were removed in-vacuo to afford 212 mg (94%) of the desired carboxylic acid as a sticky oil, which was used directly in the following coupling without further purification. LCMS (ESI): 491 (M+H$^+$).

Part 8: {3-(S)-Benzyloxycarbamoyl-4-(S)-[4-(2-methyl-quinolin-4-ylmethoxy)-phenylcarbamoyl]-cyclohexyl}-acetic acid methyl ester. To an oven-dried 5 mL conical vial equipped with a magnetic stir bar and under a nitrogen gas atmosphere was placed sequentially: 5-methoxycarbonylmethyl-2-(S)-[4-(2-methylquinolin-4-ylmethoxy)-phenylcarbamoyl]-cyclohexane-(S)-carboxylic acid (212 mg, 0.43 mmol), anhydrous DMF (3 mL), PyBOP reagent (320 mg, 0.61 mmol), O-benzylhydroxylamine hydrochloride (100 mg, 0.627 mmol), and 4-methyl morpholine (0.160 mL, 1.47 mmol). After stirring the reaction mixture overnight, the reaction was quenched with 5% citric acid (1 mL) and the reaction mixture was diluted with ethyl acetate (15 mL) and water (4 mL). The aqueous layer was extracted with ethyl acetate (3×3 mL) and the combined organic phases were washed with saturated sodium bicarbonate (3×5 mL), brine (5 mL), dried (NaSO4), and concentrated in-vacuo. Purification by Combiflash (0 to 15% methanol in methylene chloride over 30 min) to afford 238 mg (93%) of the pure amide. LCMS (ESI): 596 (M+H$^+$).

Part 9: {3-(S)-Benzyloxycarbamoyl-4-(S)-[4-(2-methyl-quinolin-4-ylmethoxy)-phenylcarbamoyl]-cyclohexyl}-acetic acid. To a solution of {3-(S)-benzyloxy carbamoyl-4-(S)-[4-(2-methyl-quinolin-4-ylmethoxy)-phenylcarbamoyl]-cyclohexyl}-acetic acid methyl ester (238 mg, 0.40 mmol) in THF (5 mL) was added water (3 mL) and lithium hydroxide (40 mg, 0.95 mmol). After stirring at ambient temperature for 4 h, the reaction mixture was acidified with 1 N HCl to a pH of ca. 5. The product was extracted with ethyl acetate (4×5 mL) and the combined organic layers were washed with brine (5 mL), dried (NaSO4), and the volatiles were removed in-vacuo to afford 210 mg (90%) of the desired carboxylic acid as a sticky oil that was used without further purification in the following coupling reaction. MS (ESI): 582 (M+H$^+$).

Part 10: 4-(2-Oxo-2-piperidin-1-yl-ethyl)-cyclohexan-1-(S)-,2-(S)-dicarboxylic acid 2-(S)-(benzyloxy-amide)1-(S)-{[4-(2-methyl-quinolin-4-ylmethoxy)-phenyl]-amide. To an oven-dried 5 mL conical vial equipped with a magnetic stir bar and under a nitrogen gas atmosphere was placed sequentially: {3-(S)-benzyloxycarbamoyl-4-(S)-[4-(2-methyl-quinolin-4-ylmethoxy)-phenylcarbamoyl]-cyclohexyl}-acetic acid (20 mg, 0.034 mmol), anhydrous DMF (1 mL), PyBOP reagent (20 mg, 0.038 mmol), piperidine (0.010 mL, 0.101 mmol), and 4-methyl morpholine (0.01 mL, 0.092 mmol). After stirring the reaction mixture overnight, the reaction was quenched with 5% citric acid (1 mL) and the reaction mixture was diluted with ethyl acetate (15 mL) and water (4 mL). The aqueous layer was extracted with ethyl acetate (3×3 mL) and the combined organic phases were washed with saturated sodium bicarbonate (3×5 mL), brine (5 mL), dried (NaSO4), and concentrated in-vacuo. Purification by Combiflash (0 to 10% methanol in methylene chloride over 30 min) to afford 21 mg (95%) of the desired amide. LCMS (ESI): 649 (M+1H).

Part 11: 4-(2-Oxo-2-piperidin-1-yl-ethyl)-cyclohexane-1-(S)—, 2-(S)-dicarboxylic acid 2-(S)-hydroxyamide 1-{[4-(2-methyl-quinolin-4-ylmethoxy)-phenyl]-amide}. A solution of 4-(2-oxo-2-piperidin-1-yl-ethyl)-cyclohexan-1-(S), 2-(S)-dicarboxylic acid 2-(S)-(benzyloxy-amide) 1-(S)-{[4-(2-methyl-quinolin-4-ylmethoxy)-phenyl]-amide (18 mg, 0.028 mmol) in methanol (2 mL) was hydrogenated using palladium on barium sulfate (5%) (40 mg, 0.018 mmol) and under balloon pressure of hydrogen. After stirring for 6 h, the reaction mixture was filtered through a pad of celite and the precipitate was washed with methanol (2×5 mL). The volatiles were removed in-vacuo and the residue was purified by preparative HPLC (gradient of 0 to 40% of 0.1% TFA in acetonitrile to 0.1% TFA in water over 30 min) to afford 10 mg (64%) of the desired hydroxomic acid as a white solid. LCMS (ESI): 559 (M+H$^+$).

The following compounds were made using the methods described and exemplified above.

Example 54

(2S,3S,5R)-2-{[4-(3-isopropylphenyl)-3,6-dihydropyridin-1(2H)-yl]carbonyl)-N,5-dihydroxypiperidine-3-carboxamide and (2S,3S,5S)-2-{[4-(3-isopropylphenyl)-3,6-dihydropyridin-1(2H)-yl]carbonyl}-N,5-dihydroxypiperidine-3-carboxamide These compounds were prepared using procedures analogous to those for example 10. Ms(ESI): (M+H)$^+$=388.3.

Example 55

(2S,3S,5R)-N,5-dihydroxy-2-[(4-phenylpiperazin-1-yl)carbonyl]piperidine-3-carboxamide and (2S,3S,5S)-N,5-dihydroxy-2-[(4-phenylpiperazin-1-yl)carbonyl]piperidine-3-carboxamide These compounds were prepared using procedures analogous to those for example 10. Ms(ESI): (M+H)$^+$=349.3.

Example 56

(2S,3S,5R)-N-Hydroxy-5-(2-morpholin-4-yl-2-oxoethyl)-2-[(4-phenylpiperazin-1-yl)carbonyl]piperidine-3-carboxamide and (2S,3S,5S)-N-Hydroxy-5-(2-morpholin-4-yl-2-oxoethyl)-2-[(4-phenylpiperazin-1-yl)carbonyl]piperidine-3-carboxamide These compounds were prepared using procedures analogous to those for example 2. Ms(ESI): (M+H)$^+$=460.3.

Example 57

(2S,3S,5S)-N,5-dihydroxy-2-{[4-(3-isopropylphenyl)piperidin-1-yl]carbonyl}piperidine-3-carboxamide and (2S,3S,5R)-N,5-dihydroxy-2-{[4-(3-isopropylphenyl)piperidin-1-yl]carbonyl}piperidine-3-carboxamide These compounds were prepared using procedures analogous to those for example 10. Ms(ESI): (M+H)$^+$=390.2.

Example 58

(2S,3S,5R)-N-hydroxy-2-{[4-(3-isopropylphenyl)piperidin-1-yl]carbonyl}-5-(2-morpholin-4-yl-2-oxoethyl)piperidine-3-carboxamide and (2S,3S,5S)-N-hydroxy-2-{[4-(3-isopropylphenyl)piperidin-1-yl]carbonyl}-5-(2-morpholin-4-yl-2-oxoethyl)piperidine-3-carboxamide These compounds were prepared using procedures analogous to those for example 2. Ms(ESI): (M+H)$^+$=501.3.

Example 59

(1S,2S)-N-Hydroxy-5-[2-(4-methylpiperazin-1-yl)-2-oxoethyl]-2-[(4-phenylpiperazin-1-yl)carbonyl]cyclohexanecarboxamide This compound was prepared using procedures analogous to those for example 50. Ms(ESI): (M+H)$^+$=472.2.

Example 60

(1S,2S)-N-Hydroxy-5-(2-morpholin-4-yl-2-oxoethyl)-2-[(4-phenylpiperazin-1-yl)carbonyl]cyclohexanecarboxamide This compound was prepared using procedures analogous to those for example 50. Ms(ESI): (M+H)$^+$=459.2.

Example 61

(1S,2S)-N-Hydroxy-5-(2-[(2-methoxyethyl)amino]-2-oxoethyl}-2-[(4-phenylpiperazin-1-yl)carbonyl]cyclohexanecarboxamide This compound was prepared using procedures analogous to those for example 50. Ms(ESI): (M+H)$^+$=447.2.

Example 62

(1S,3S,4S)-3-[(Hydroxyamino)carbonyl]-4-[(4-phenylpiperazin-1-yl)carbonyl]cyclohexyl methylcarbamate This compound was prepared using procedures analogous to those for example 37. Ms(ESI): $(M+H)^+=405.1$.

Example 63

(1S,3S,4S)-3-[(Hydroxyamino)carbonyl]-4-[(4-phenylpiperazin-1-yl)carbonyl]cyclohexyl dimethylcarbamate This compound was prepared using procedures analogous to those for example 37. Ms(ESI): $(M+H)^+=419.1$.

Example 64

(1S,3S,4S)-3-[(Hydroxyamino)carbonyl]-4-[(4-phenylpiperazin-1-yl)carbonyl]cyclohexyl pyrrolidine-1-carboxylate This compound was prepared using procedures analogous to those for example 37. Ms(ESI): $(M+H)^+=445.1$.

Example 65

(1S,3S,4S)-3-[(Hydroxyamino)carbonyl]-4-[(4-phenylpiperazin-1-yl)carbonyl]cyclohexyl piperidine-1-carboxylate This compound was prepared using procedures analogous to those for example 37. Ms(ESI): $(M+H)^+=459.2$.

Example 66

(1S,3S,4S)-3-[(Hydroxyamino)carbonyl]-4-[(4-phenylpiperazin-1-yl)carbonyl]cyclohexyl morpholine-4-carboxylate This compound was prepared using procedures analogous to those for example 37. Ms(ESI): $(M+H)^+=461.1$.

Example 67

(1S,3S,4S)-3-[(Hydroxyamino)carbonyl]-4-[(4-phenylpiperazin-1-yl)carbonyl]cyclohexyl (3R)-3-hydroxypyrrolidine-1-carboxylate This compound was prepared using procedures analogous to those for example 37. Ms(ESI): $(M+H)^+=461.1$.

Example 68

(1S,3S,4S)-3-[(Hydroxyamino)carbonyl]-4-[(4-phenylpiperazin-1-yl)carbonyl]cyclohexyl cyclopropylcarbamate This compound was prepared using procedures analogous to those for example 37. Ms(ESI): $(M+H)^+=431.1$.

Example 69

(3R,4S)-N-Hydroxy-1-(morpholin-4-ylcarbonyl)-4-[(4-phenylpiperidin-1-yl)carbonyl]piperidine-3-carboxamide This compound was prepared using procedures analogous to those for example 12. Ms(ESI): $(M+H)^+=445.2$.

Example 70

(3S,5S,6S)-5-[(Hydroxyamino)carbonyl]-1-methyl-6-{[(3R)-3-phenylpyrrolidin-1-yl]carbonyl}piperidin-3-yl pyrrolidine-1-carboxylate and (3R,5S,6S)-5-[(Hydroxyamino)carbonyl]-1-methyl-6-{[(3R)-3-phenylpyrrolidin-1-yl]carbonyl}piperidin-3-yl pyrrolidine-1-carboxylate These compounds were prepared using procedures analogous to those for example 11. Ms(ESI): $(M+H)^+=445.2$.

Example 71

(3S)-tetrahydrofuran-3-yl(2S,3S)-2-{[4-(4-tert-butylphenyl)piperazin-1-yl]carbonyl}-3-[(hydroxyamino)carbonyl]piperidine-1-carboxylate This compound was prepared using procedures analogous to those for example 42. Ms(ESI): $(M+H)^+=503.3$.

Example 72

(1R,3S,4S)-3-[(Hydroxyamino)carbonyl]-4-{[(3R)-3-phenylpyrrolidin-1-yl]carbonyl}cyclohexyl pyrrolidine-1-carboxylate To a solution of 5-oxo-(2S)-[(3R)-phenyl-pyrrolidine-1-carbonyl]-cycloheane-(1S)-carboxylic acid benzyl ester (94 mg) in THF (2 mL) at −78° C. was added a solution of L-Selectride in THF (1.5 mL, 1.0M). The solution was stirred at −78° C. for 30 min, then poured into ice-water, extracted with ethyl acetate (30 mL ×2). The combined organic phases were dried with MgSO$_4$. After removal of the solvent under reduced pressure, the residue was subjected to HPLC analysis and found to be a mixture of two isomers in a 1:15 ratio. Chromatography on silica gel afforded the major isomer at 90% yield, which was found to be the axial-hydroxy isomer. MS (ESI): 408.1 (M+H$^+$).

Starting from the pure axial-hydroxy compound, the titled compound was prepared using procedures analogous to those for example 37. Ms(ESI): $(M+H)^+=430.2$.

Example 73

(1R,3S,4S)-3-[(Hydroxyamino)carbonyl]-4-{[(3R)-3-phenylpyrrolidin-1-yl]carbonyl}cyclohexyl morpholine-4-carboxylate This compound was prepared using procedures analogous to those for example 72. Ms(ESI): $(M+H)^+=446.2$.

Example 74

(1R,3S,4S)-3-[(Hydroxyamino)carbonyl]-4-{[(3R)-3-phenylpyrrolidin-1-yl]carbonyl}cyclohexyl dimethylcarbamate This compound was prepared using procedures analogous to those for example 72. Ms(ESI): $(M+H)^+=404.2$.

Example 75

(1R,3S,4S)-3-[(Hydroxyamino)carbonyl]-4-{[(3R)-3-phenylpyrrolidin-1-yl]carbonyl}cyclohexyl methylcarbamate This compound was prepared using procedures analogous to those for example 72. Ms(ESI): (M+H)$^+$=390.2.

Example 76

Methyl((1R,3S,4S)-3-[(Hydoxyamino)carbonyl]-4-{[(3R)-3-phenylpyrrolidin-1-yl]carbonyl}cyclohexyl)carbamate Part 1: (4S)-Hydroxy-cyclohexane-(1S, 2S)-dicarboxylic acid 2-benzyl ester 1-tert-butyl ester (320 mg) was dissolved in DCM (5 ml). To the resulting solution was added triethylamine (1.5 eq. 0.20 ml) at rt, followed by methanesulfonyl chloride (1.55 eq. 0.115 ml), and DMAP (0.12 eq. 14 mg). The mixture was stirred at r.t. for 3 hours. The reaction mixture was quenched with saturated NH$_4$Cl solution, extracted with ethyl acetate (×2). The combined extracts were washed with water, brine successively, dried over MgSO$_4$. After filtration, the filtrate was concentrated under reduced pressure to yield an oil which was further purified by combi-flash. Quantitative product (400 mg) was obtained.

Part 2: The mesylate compound made above (390 mg) was dissolved in DMF (8.0 ml). To the solution, NaN$_3$ (10 eq., 615 mg) was added. The mixture was heated at 80° C. with stirring over night. After cooling, the reaction was quenched with saturated NaHCO$_3$ solution, extracted with ethyl acetate (×2). The combined extracts were washed with water (×1), brine (×1), dried over MgSO$_4$. After filtration, the filtrate was concentrated under reduced pressure. The resulting residue was purified with combi-flash to afford 330 mg (95%) of azide product.

Part 3: The azide compound (320 mg) was stirred with DCM (2 ml)-TFA (2 ml) solution at r.t. for 1.5 hours. The mixture was concentrated to dry to yield quantitative of the corresponding acid.

Part 4: The acid made above (100 mg) was dissolved in DMF (1 ml). To the solution, (R)-3-phenylpyrrolidine hydrochloride (67 mg) was added, followed by BOP (153 mg). After stirring at r.t. for 5 min, to the mixture was added DIEA (0.144 ml). The resultant reaction mixture was stirred at r.t. for 4 hours. The reaction was quenched with saturated KH$_2$PO$_4$ solution, extracted with ethyl acetate (×2). The combined extracts were washed with water (×1), brine (×1); dried over MgSO$_4$. After filtration, the filtrate was concentrated under reduced pressure. The resulting residue was purified by combi-flash to yield 80 mg (56%) of (5R)-azido-(2S)-[(3R)-phenyl-pyrrolidine-1-carbonyl]-cyclohexane-(1S)-carboxylic acid benzyl ester.

Part 5: The azido compound (80 mg) was dissolved in a mixture of methanol (5 ml) and conc. HCl (0.1 mL) solution. After the addition of 10% Pd on carbon, the mixture was stirred at r.t. under hydrogen atmosphere for 2 hours. The reaction mixture was filtered, and concentration under reduced pressure to give the corresponding amino acid in quantitative yield (60 mg).

Part 6: A mixture of the amino acid made above (21 mg), methyl chloroformate (6.2 mg), and DIEA (26 ul) in acetonitrile (0.4 ml) was stirred at r.t. overnight. The reaction was quenched with 1 N HCl solution, extracted with ethyl acetate. The combined organic phases were washed with brine (×1), dried over MgSO$_4$. After filtration, the filtrate was concentrated under reduced pressure to provide (5R)-Methoxycarbonylamino-(2S)-[(3R)-phenyl-pyrrolidine-1-carbonyl]-cyclohexane-(1S)-carboxylic acid methyl ester.

Part 7: The crude methyl ester was stirred with LiOH in THF-water over night. The reaction was acidified with 1 N HCl solution, extracted with ethyl acetate. The combined organic layers were washed with brine (×1), dried over MgSO$_4$. After filtration, the filtrate was concentrated under reduced pressure to afford 14 mg (62% in 2 step) of the corresponding acid.

Part 8: A mixture of the crude acid made above (14 mg), hydroxylamine hydrochloride (8 mg), BOP (18 mg) in DMF (0.2 ml) was stirred at rt for 5 min. To the resultant mixture was added DIEA (26 ul). After being stirred for 1.5 hours, the reaction mixture was subjected to HPLC purification to generate the titlted compound as a solid (3.1 mg, 21%). MS: M/Z 390.1 (M+H)$^+$; 801.3 (2M+Na)$^+$; 357.1 (M−NHOH)$^+$.

Example 77

(1S,2S,5R)-N-Hydroxy-5-[(methylsulfonyl)amino]-2-{[(3R)-3-phenylpyrrolidin-1-yl]carbonyl}cyclohexanecarboxamide This compound was prepared using procedures analogous to those for example 76. Ms(ESI): (M+H)$^+$=410.1.

Example 78

(1S,2S,5R)-5-(acetylamino)-N-hydroxy-2-[([(3R)-3-phenylpyrrolidin-1-yl]carbonyl}cyclohexanecarboxamide This compound was prepared using procedures analogous to those for example 76. Ms(ESI): (M+H)$^+$=374.2.

Example 79

(3R,4S)-N-Hydroxy-4-[(4-phenylpiperidin-1-yl)carbonyl]-1-(piperidin-1-ylcarbonyl)piperidine-3-carboxamide This compound was prepared using procedures analogous to those for example 12. Ms(ESI): (M+H)$^+$=443.2.

Example 80

(3R,4S)-N-Hydroxy-4-[(4-phenylpiperidin-1-yl)carbonyl]-1-(pyrrolidin-1-ylcarbonyl)piperidine-3-carboxamide This compound was prepared using procedures analogous to those for example 12. Ms(ESI): (M+H)$^+$=429.2.

Example 81

(5S,6S)-5-[(Hydroxyamino)carbonyl]-6-[(4-phenyl-3,6-dihydropyridin-1(2H)-yl)carbonyl]piperidin-3-yl pyrrolidine-1-carboxylate This compound was prepared using procedures analogous to those for example 11. Ms(ESI): (M+H)$^+$=443.2.

Example 82

(5S,6S)-5-[(Hydroxyamino)carbonyl]-6-[(4-phenylpiperidin-1-yl)carbonyl]piperidin-3-yl pyrrolidine-1-carboxylate This compound was prepared using procedures analogous to those for example 11. Ms(ESI): $(M+H)^+=445.5$.

Example 83

(1S,2S,5R)-N-Hydroxy-2-{[4-(3-isopropylphenyl)piperidin-1-yl]carbonyl}-5-(2-oxo-2-piperidin-1-ylethyl)cyclohexanecarboxamide and (1S,2S,5S)-N-Hydroxy-2-{[4-(3-isopropylphenyl)piperidin-1-yl]carbonyl}-5-(2-oxo-2-piperidin-1-ylethyl)cyclohexanecarboxamide These compounds were prepared using procedures analogous to those for example 50. Ms(ESI): $(M+H)^+=498.3$.

Example 84

(2S,3S)-N-Hydroxy-5-(2-oxo-2-piperidin-1-ylethyl)-2-{[(3R)-3-phenylpyrrolidin-1-yl]carbonyl}piperidine-3-carboxamide This compound was prepared using procedures analogous to those for example 2. Ms(ESI): $(M+H)^+=443.3$.

Example 85

(2S,3S,5R)-N-Hydroxy-5-(2-oxo-2-pyrrolidin-1-ylethyl)-2-{[(3R)-3-phenylpyrrolidin-1-yl]carbonyl}piperidine-3-carboxamide and (2S,3S,5S)-N-Hydroxy-5-(2-oxo-2-pyrrolidin-1-ylethyl)-2-{[(3R)-3-phenylpyrrolidin-1-yl]carbonyl}piperidine-3-carboxamide These compounds were prepared using procedures analogous to those for example 2. Ms(ESI): $(M+H)^+=429.3$.

Example 86

(2S,3S)-N-Hydroxy-5-(2-oxo-2-pyrrolidin-1-ylethyl)-2-[(4-phenylpiperazin-1-yl)carbonyl]piperidine-3-carboxamide This compound was prepared using procedures analogous to those for example 2. Ms(ESI): $(M+H)^+=444.0$.

Example 87

(2S,3S)-N-Hydroxy-5-(2-oxo-2-piperidin-1-ylethyl)-2-[(4-phenylpiperazin-1-yl)carbonyl]piperidine-3-carboxamide This compound was prepared using procedures analogous to those for example 2. Ms(ESI): $(M+H)^+=458.2$.

Example 88

(2S,3S)-N-Hydrooxy-1-methyl-5-(2-oxo-2-piperidin-1-ylethyl)-2-[(4-phenylpiperazin-1-yl)carbonyl]piperidine-3-carboxamide This compound was prepared using procedures analogous to those for example 2. Ms(ESI): $(M+H)^+=472.1$.

Example 89

(2S,3S)-N-Hydroxy-1-methyl-5-(2-oxo-2-pyrrolidin-1-ylethyl)-2-[(4-phenylpiperazin-1-yl)carbonyl]piperidine-3-carboxamide This compound was prepared using procedures analogous to those for example 2. Ms(ESI): $(M+H)^+=458.2$.

Example 90

(2S,3S)-N-Hydroxy-1-methyl-5-(2-oxo-2-piperidin-1-ylethyl)-2-{[(3R)-3-phenylpyrrolidin-1-yl]carbonyl}piperidine-3-carboxamide This compound was prepared using procedures analogous to those for example 2. Ms(ESI): $(M+H)^+=457.1$.

Example 91

(2S,3S)-N-Hydroxy-1-methyl-5-(2-oxo-2-pyrrolidin-1-ylethyl)-2-{[(3R)-3-phenylpyrrolidin-1-yl]carbonyl}piperidine-3-carboxamide This compound was prepared using procedures analogous to those for example 2. Ms(ESI): $(M+H)^+=443.0$.

Example 92

Stereoselective synthesis of (1S,2S,5R)-N-Hydroxy-5-(2-oxo-2-piperidin-1-ylethyl)-2-[(4-phenylpiperazin-1-yl)carbonyl]cyclohexanecarboxamide To an oven-dried 25 mL round bottomed flask equipped with a magnetic stir bar and under a nitrogen gas atmosphere was placed sequentially: (S)-(−)-2,2'-bis(diphenylphosphino)-1,1'-binaphthylbenzylbromide (12.5 mg, 0.0201 mmol), rhodium (I) 1,5-cyclooctadiene chloride dimer (9.5 mg, 0.019 mmol), and deoxygenated anhydrous methanol (5 mL). After stirring the resulting yellow solution for 1 h, a solution of 4-methoxycarbonylmethylidene-cyclohexane-1-(S)-2-(S)-dicarboxylic acid 2-(S)-benzyl ester 1-(S)-tert-butyl ester (135 mg, 0.348 mmol) in deoxygenated anhydrous methanol (3 mL) was added via cannula. The reaction mixture was then purged with hydrogen gas and stirred under a hydrogen balloon atmosphere for 3 d. The volatiles were then removed from the heterogeneous mixture in-vacuo to afford a yellow solid. The LCMS data suggested that the starting material had been completely consumed and that a 30:70 mixture of the desired product and the debenzylated desired product was formed. For the desired product LCMS (ESI): 413 $(M+Na^+)$, 335 $(M-t-Bu+2H^+)$, 803 $(dimer+Na^+)$. For the debenzylated desired product LCMS (ESI): 323 $(M+Na^+)$, 227 (M−Ot-Bu), 153 (M−Ot-Bu, $CO_2H$, OMe, $+2H^+$), 623 $(dimer+Na^+)$.

Without further purification or analysis, anhydrous acetonitrile (1 mL) was added to the flask and upon vigorous stirring a hetereogeneous mixture was formed. The suspended dark solid was assumed to be inorganic byproduct. To this solution was added 1,8-diazabicyclo[5.4.0]undec-7-ene (50 μL, 0.33 mmol) and benzylbromide (50 μL, 0.41 mmol). The resulting solution was stirred under a nitrogen gas atmosphere for 13 h. The heterogeneous mixture was filtered through a pad of celite, which was subsequently washed with ethyl actetate (3×5 mL). The filtrate was then washed sequentially with 5% citric acid (2×3 mL), water (1×3 mL), brine (2×3 mL), dried (Na$_2$SO$_4$), and concentrated in-vacuo. Purification by Combiflash (0 to 60% ethyl acetate in hexanes over 30 min) afforded 91 mg (67%) of pure product and 10 mg (7%) of the pure minor isomer. LCMS (ESI): 413 (M+Na$^+$), 335 (M−t-Bu+2H$^+$), 803 (dimer+Na$^+$). Chiral HPLC analysis of the isomers confirmed the optical purity and the following NMR experiments were conducted to elucidate the absolute stereochemistry at C4 of the major isomer: $^1$H, COSY, HSQC, HMBC, and NOE.

The remainder of the synthesis of 5-(2-oxo-2-piperazin-1-yl-ethyl)-2-(S)-(4-phenyl-piperazine-1-carbonyl-cyclohexan-(S)-carboxylic acid hydroxyamide followed the general procedure outlined in the above synthesis of the racemic compound (Example 50).

Example 93

(2S,3S)-N-Hydroxy-5-[isobutyryl(methyl)amino]-2-{[((3R)-3-phenylpyrrolidin-1-yl]carbonyl}piperidine-3-carboxamide This compound was prepared using procedures analogous to those for example 6. Ms(ESI): (M+H)$^+$=417.2.

Example 94

(2S,3S)-N-Hydroxy-5-[isobutyryl(methyl)amino]-2-[(3-phenyl-2,5-dihydro-1H-pyrrol-1-yl)carbonyl]piperidine-3-carboxamide This compound was prepared using procedures analogous to those for example 6. Ms(ESI): (M+H)$^+$=415.2.

Example 95

(2S,3S)-N-Hydroxy-5-[isobutyryl(methyl)amino]-2-[(4-phenyl-3,6-dihydropyridin-1(2H)-yl)carbonyl]piperidine-3-carboxamide This compound was prepared using procedures analogous to those for example 6. Ms(ESI): (M+H)$^+$=429.2.

Example 96

(2S,3S)-N-Hydroxy-5-[isobutyryl(methyl)amino]-2-[(4-phenylpiperidin-1-yl)carbonyl]piperidine-3-carboxamide This compound was prepared using procedures analogous to those for example 6. Ms(ESI): (M+H)$^+$=431.3.

Example 97

(2S,3S)-N-Hydroxy-5-[isobutyryl(methyl)amino]-2-[(4-phenylpiperazin-1-yl)carbonyl]piperidine-3-carboxamide This compound was prepared using procedures analogous to those for example 6. Ms(ESI): (M+H)$^+$=432.3.

Example 98

(3R,4S)-N-Hydroxy-4-{[(3S)-3-phenylpyrrolidin-1-yl]carbonyl}-1-4-(trifluoromethoxy)benzoyl]piperidine-3-carboxamide This compound was prepared using procedures analogous to those for example 12. Ms(ESI): (M+H)$^+$=506.2.

Example 99

(3R,4S)-N-Hydroxy-4-{[(3S)-3-phenylpyrrolidin-1-yl]carbonyl}-1-{[4-(trifluoromethoxy)phenyl]sulfonyl}piperidine-3-carboxamide This compound was prepared using procedures analogous to those for example 12. Ms(ESI): (M+H)$^+$=542.0.

Example 100

(3R,4S)-N-Hydroxy-4-{[(3S)-3-phenylpyrrolidin-1-yl]carbonyl}-1-[3-(trifluoromethoxy)benzoyl]piperidine-3-carboxamide This compound was prepared using procedures analogous to those for example 12. Ms(ESI): (M+H)$^+$=506.2.

Example 101

(3R,4S)-N-Hydroxy-4-{[(3S)-3-phenylpyrrolidin-1-yl]carbonyl}-1-[2-(trifluoromethoxy)benzoyl]piperidine-3-carboxamide This compound was prepared using procedures analogous to those for example 12. Ms(ESI): (M+H)$^+$=506.0.

Example 102

(3R,4S)-N-Hydroxy-1-[4-(difluoromethoxy)benzoyl]-4-{[(3S)-3-phenylpyrrolidin-1-yl]carbonyl}piperidine-3-carboxamide This compound was prepared using procedures analogous to those for example 12. Ms(ESI): (M+H)$^+$=488.2.

Example 103

(5S,6S)-5-[(Hydroxyamino)carbonyl]-6-{[(3S)-3-phenylpyrrolidin-1-yl]carbonyl}piperidin-3-yl pyrrolidine-1-carboxylate This compound was prepared using procedures analogous to those for example 11. Ms(ESI): (M+H)$^+$=431.2.

Example 104

(5S,6S)-5-[(Hydroxyamino)carbonyl]-6-[(4-phenylpiperazin-1-yl)carbonyl]piperidin-3-yl pyrrolidine-1-carboxylate This compound was prepared using procedures analogous to those for example 11. Ms(ESI): (M+H)$^+$=446.2.

Example 105

(5S,6S)-5-[(Hydroxyamino)carbonyl]-6-[(3-phenyl-2,5-dihydro-1H-pyrrol-1-yl)carbonyl]piperidin-3-yl pyrrolidine-1-carboxylate This compound was prepared using procedures analogous to those for example 11. Ms(ESI): (M+H)$^+$=429.2.

Example 106

Methyl(2S,3S)-3-[(Hydroxyamino)carbonyl]-2-[(3-phenyl-2,5-dihydro-1H-pyrrol-1-yl)carbonyl]-5-[(pyrrolidin-1-ylcarbonyl)oxy]piperidine-1-carboxylate This compound was prepared using procedures analogous to those for example 11. Ms(ESI): (M+H)$^+$=487.2.

Example 107

Methyl(2S,3S)-3-[(hydroxyamino)carbonyl]-2-{[(3S)-3-phenylpyrrolidin-1-yl]carbonyl}-5-[(pyrrolidin-1-ylcarbonyl)oxy]piperidine-1-carboxylate This compound was prepared using procedures analogous to those for example 11. Ms(ESI): (M+H)$^+$=489.2.

Example 108

Methyl(2S,3S)-3-[(hydroxyamino)carbonyl]-2-[(4-phenylpiperidin-1-yl)carbonyl]-5-[(pyrrolidin-1-ylcarbonyl)oxy]piperidine-1-carboxylate This compound was prepared using procedures analogous to those for example 11. Ms(ESI): (M+H)$^+$=503.3.

Example 109

Methyl(2S,3S)-3-[(hydroxyamino)carbonyl]-2-[(4-phenyl-3,6-dihydropyridin-1(2H)-yl)carbonyl]-5-[(pyrrolidin-1-ylcarbonyl)oxy]piperidine-1-carboxylate This compound was prepared using procedures analogous to those for example 11. Ms(ESI): (M+H)$^+$=501.2.

Example 110

Methyl(2S,3S)-3-[(hydroxyamino)carbonyl]-2-[(4-phenylpiperazin-1-yl)carbonyl]-5-[(pyrrolidin-1-ylcarbonyl)oxy]piperidine-1-carboxylate This compound was prepared using procedures analogous to those for example 11. Ms(ESI): (M+H)$^+$=504.3.

Example 111

(2S,3S)-5-[benzoyl(methyl)amino]-N-hydroxy-2-[(4-phenyl-3,6-dihydropyridin-1 (2H)-yl)carbonyl]piperidine-3-carboxamide This compound was prepared using procedures analogous to those for example 6. Ms(ESI): (M+H)$^+$=463.2.

Example 112

(2S,3S)-5-[benzoyl(methyl)amino]-N-hydroxy-2-[(4-phenylpiperazin-1-yl)carbonyl]piperidine-3-carboxamide This compound was prepared using procedures analogous to those for example 6. Ms(ESI): (M+H)$^+$=466.2.

Example 113

Isopropyl {(5S,6S)-5-[(hydroxyamino)carbonyl]-6-[(4-phenylpiperazin-1-yl)carbonyl]piperidin-3-yl}methylcarbamate This compound was prepared using procedures analogous to those for example 6. Ms(ESI): (M+H)$^+$=448.3.

Example 114

Isopropyl {(5S,6S)-5-[(hydroxyamino)carbonyl]-6-[(4-phenyl-3,6-dihydropyridin-1(2H)-yl)carbonyl]piperidin-3-yl}methylcarbamate This compound was prepared using procedures analogous to those for example 6. Ms(ESI): (M+H)$^+$=445.2.

Example 115

(1S,2S,5R)-N,5-dihydroxy-2-{[(3R)-3-phenylpyrrolidin-1-yl]carbonyl}-5-propylcyclohexanecarboxamide and (1S,2S,5S)-N,5-dihydroxy-2-{[(3R)-3-phenylpyrrolidin-1-yl]carbonyl}-5-propylcyclohexanecarboxamide To a solution of 5-oxo-(2S)-[(3R)-phenyl-pyrrolidine-1-carbonyl]-cycloheane-(1S)-carboxylic acid benzyl ester (120 mg, 0.296 mMol) in methylene chloride at 0° C. was added allyltrimethyl silane (0.94 mL) followed by titanium tetrachloride (1.48 mL, 1.0 M in CH$_2$Cl$_2$) dropwise. After being stirred at 0° C. for about 20 minutes, the mixture was allowed to warm up to room temperature and stirred at rt for about 3 hours. The reaction was poured into ice-water and extracted with ethyl acetate. The combined organic phases were washed with water, brine, and then dried with MgSO$_4$. After filtration, the filtrate was concentrated under reduced pressure. The residue was purified with Combiflash using 7% methanol in methylene chloride to afford 5-Hydroxy-(2S)-[(3R)-phenyl-pyrrolidine-1-carbonyl]-5-propyl-cyclohexane-(1S)-carboxylic acid benzyl ester as a diastereoisomer mixtures (48 mg, 37%).

The remainder of the synthesis (5R)-5-Hydroxy-(2S)-[(3R)-phenyl-pyrrolidine-1-carbonyl]-5-propyl-cyclohexane-(1S)-carboxylic acid hydroxyamide and (5S)-5-Hydroxy-(2S)-[(3R)-phenyl-pyrrolidine-1-carbonyl]-5-propyl-cyclohexane-(1S)-carboxylic acid hydroxyamide followed the general procedure outlined in Example 25. The two isomers were separated by HPLC at the final step. Ms(ESI): (M+H)$^+$=375.2.

Example 116

(1S,3S,4S)-4-{[4-(4-tert-butylphenyl)piperazin-1-yl]carbonyl}-3-[(hydroxyamino)carbonyl]cyclohexyl methylcarbamate This compound was prepared using procedures analogous to those for example 37. Ms(ESI): (M+H)$^+$=461.3.

Example 117

(1S,3S,4S)-4-{[4-(4-tert-butylphenyl)piperazin-1-yl]carbonyl}-3-[(hydroxyamino)carbonyl]cyclohexyl dimethylcarbamate This compound was prepared using procedures analogous to those for example 37. Ms(ESI): (M+H)$^+$=475.3.

Example 118

(1S,3S,4S)-4-{[4-(4-tert-butylphenyl)piperazin-1-yl]carbonyl}-3-[(hydroxyamino)carbonyl]cyclohexyl cyclopropylcarbamate This compound was prepared using procedures analogous to those for example 37. Ms(ESI): (M+H)$^+$=487.3.

Example 119

(1S,3S,4S)-4-{[4-(4-tert-butylphenyl)piperazin-1-yl]carbonyl}-3-[(hydroxyamino)carbonyl]cyclohexyl pyrrolidine-1-carboxylate This compound was prepared using procedures analogous to those for example 37. Ms(ESI): (M+H)$^+$=501.3.

Example 120

(1S,3S,4S)-4-{[4-(4-tert-butylphenyl)piperazin-1-yl]carbonyl}-3-[(hydroxyamino)carbonyl]cyclohexyl (3R)-3-hydroxypyrrolidine-1-carboxylate This compound was prepared using procedures analogous to those for example 37. Ms(ESI): (M+H)$^+$=517.3.

Example 121

(1S,3S,4S)-4-{[4-(4-tert-butylphenyl)piperazin-1-yl]carbonyl}-3-[(hydroxyamino)carbonyl]cyclohexyl morpholine-4-carboxylate This compound was prepared using procedures analogous to those for example 37. Ms(ESI): (M+H)$^+$=517.3.

Example 122

(1S,3S,4S)-4-{[4-(4-tert-butylphenyl)piperazin-1-yl]carbonyl}-3-[(hydroxyamino)carbonyl]cyclohexyl piperidine-1-carboxylate This compound was prepared using procedures analogous to those for example 37. Ms(ESI): (M+H)$^+$=515.3.

Example 123

(1R,3S,4S)-3-[(hydroxyamino)carbonyl]-4-[(4-phenyl-3,6-dihydropyridin-1(2H)-yl)carbonyl]cyclohexyl methylcarbamate This compound was prepared using procedures analogous to those for example 72. Ms (ESI): (M+H$^+$)=402.1.

Example 124

(1R,3S,4S)-3-[(hydroxyamino)carbonyl]-4-[(4-phenyl-3,6-dihydropyridin-1(2H)-yl)carbonyl]cyclohexyl dimethylcarbamate This compound was prepared using procedures analogous to those for example 72. Ms (ESI): (M+H$^+$)=416.1.

Example 125

(1R,3S,4S)-3-[(Hydroxyamino)carbonyl]-4-[(4-phenyl-3,6-dihydropyridin-1(2H)-yl)carbonyl]cyclohexyl pyrrolidine-1-carboxylate This compound was prepared using procedures analogous to those for example 72. Ms (ESI): (M+H$^+$)=442.1.

Example 126

Methyl(2S,3S,5S)-5-(3-fluorophenoxy)-3-[(hydroxyamino)carbonyl]-2-[(4-phenylpiperazin-1-yl)carbonyl]piperidine-1-carboxylate Part 1. (S)-2-Benzylamino-succinic acid 1-benzyl ester 4-methyl ester: To a suspension of L-Aspartic acid β-methyl ester HCl salt (50.00 g, 0.2704 mol) in acetonitrile (500.00 mL, 9.5732 mol) was added 1,8-diazabicyclo[5.4.0]undec-7-ene (124 mL, 0.811 mol) at 0 Celsius, followed by benzyl bromide (65.6 mL, 0.541 mol) at one portion. The reaction mixture was allowed to warm up to rt and stirred at rt overnight. The resultant mixture was concentrated to almost dry, diluted with EtOAc, then filtered through Celite to remove the DBU HCl salt. The filtration was concentrated under reduced pressure. The residue was applied on silica gel chromatography, eluting with 0 to 20% EtOAc in hexane to afford the desired product (30.20 g, 34.1%).

Part 2. 1-benzyl 4-methyl(2S)-2-[benzyl((2S)-2-hydroxy-3-[(4-methylphenyl)sulfonyl]oxypropyl)amino]succinate:
To a solution of (2S)-(+)-glycidyl tosylate (23.0 g, 0.101 mol) in 500 mL of methylene chloride was added 2.00 M of trimethylaluminum in toluene (50.4 mL) at −78 Celsius, under an atmosphere of nitrogen. After stirred at −78 Celsius for 10 min, to the mixture was added a solution of (S)-2-benzylamino-succinic acid 1-benzyl ester 4-methyl ester (30.0 g, 0.0916 mol) in 150 mL of methylene chloride. The resulting reaction mixture was stirred at −78 Celsius for 30 min. The dry ice-acetone bath was changed to an ice-water bath to warm the mixture up to 0 Celsius. The mixture was stirred at 0Celsius for 30 min. To the reaction mixture was added sodium fluoride (16.2 g, 0.385 mol) followed by water (10.4 mL, 0.577 mol) at 0 Celsius. The resulting suspension was rapidly stirred for 1 h at 0 Celsius and filtered through a short column of of celite and the cloumn was subsequently washed with 600 mL of methylene chloride. The combined filtrates were dried over sodium sulfate, concentrated to dry and purified by column purification (eluting with 0 to 20% EtOAc in hexane) to yield the titled compound (46.7 g, 91.7%). MS(ESI): (M+H)$^+$=556.2.

Part 3. 1-benzyl 4-methyl(2S)-2-[benzyl((2S)-2-(1-ethoxyethoxy)-3-[(4-methylphenyl)sulfonyl]oxypropyl)amino]succinate: To a mixture of 1-benzyl 4-methyl(2S)-2-[benzyl((2S)-2-hydroxy-3-[(4-methylphenyl)sulfonyl]oxypropyl)amino]succinate (43.0 g, 0.0774 mol) in methylene chloride (600.0 mL, 9.360 mol) was added ethyl vinyl ether (14.8 mL, 0.155 mol) followed by pyridinium p-toluenesulfonate (1 g, 0.004 mol). The mixture was stirred at rt for 1 h, concentrated to dry and purified on silical gel (eluting with 0 to 20% EtOAc in hexane) to afford the ether compound (39.7 g, 81.7%). MS(ESI): (M+H)$^+$=628.1.

Part 4. 2-benzyl 3-methyl(2S, 3S, 5R)-1-benzyl-5-(1-ethoxyethoxy)piperidine-2,3-dicarboxylate: To a solution of 1-benzyl 4-methyl(2S)-2-[benzyl((2S)-2-(1-ethoxyethoxy)-3-[(4-methylphenyl)sulfonyl]oxypropyl)amino]succinate (35.7 g, 0.0569 mol) in a mixture of tetrahydrofuran (95.5 mL, 1.18 mol) and toluene (490 mL, 4.6 mol) at −78 Celsius was was added 1.00 M of Lithium hexamethyldisilazide in tetrahydrofuran (68.2 mL). The reaction was stirred at −78 Celsius overnight then allowed to warm up to −20 Celsius and stirred at −20 Celsius for 3 h. After quenched with aq. ammonium chloride, the mixture was extracted with ethyl acetate. The combined organic layers were washed with brine, dried and concentrated to dry. The residue was applied on silica gel column, eluting with 0 to 20% EtOAc in hexane, to afford the product (18.1 g, 69.9%). MS(ESI): (M+H)$^+$=456.2. The corresponding diastereoisomer was also obtained (4.52 g, 17.5%).

Part 5. 2-benzyl 3-methyl(2S,3S,5R)-1-benzyl-5-hydroxypiperidine-2,3-dicarboxylate: To a solution of 2-benzyl 3-methyl(2S,3S,5R)-1-benzyl-5-(1-ethoxyethoxy)piperidine-2,3-dicarboxylate (5.70 g, 0.0125 mol) in 100 mL of THF was added 20 mL of water followed by 20 mL of 1N HCl. The mixture was stirred at rt fro 1 h. After diluted with EtOAc, the mixture was neutralized with 1N NaOH, washed with brine, dried. The residure obtained after concentration was applied on silical, eluting with 0 to 50% EtOAc in hexane, to provide the alcohol compound (4.80 g, 89.6%). MS(ESI): (M+H)$^+$=384.2.

Part 6. (2S,3S, R)-5-hydroxy-3-(methoxycarbonyl)piperidine-2-carboxylic acid: A mixture of 2-benzyl 3-methyl(2S,3S,5R)-1-benzyl-5-hydroxypiperidine-2,3-dicarboxylate (1.00 g, 0.00261 mol) in 10 mL of methanol was hydrogenated in the presence of 10% Pd/C, under a balloon pressure of hydrogen, for 3 h. After filtered off the catalyst, the filtration was concentrated to dry in vacuo and used directly in next step. MS(ESI): (M+H)$^+$=204.0.

Part 7. dimethyl(2S,3S,5R)-5-hydroxy-2-[(4-phenylpiperazin-1-yl)carbonyl]piperidine-1,3-dicarboxylate: To a mixture of (2S,3S,5R)-5-hydroxy-3-(methoxycarbonyl)piperidine-2-carboxylic acid (3.140 g, 0.01545 mol), 1-phenylpiperazine (2.597 mL, 0.01700 mol) and benzotriazol-1-yloxytris(dimethylamino)phosphonium hexafluorophosphate (7.518 g, 0.01700 mol) in N,N-dimethylformamide (10.00 mL, 0.1291 mol) was added N,N-diisopropylethylamine (3.230 mL, 0.01854 mol) at 0 Celsius. After stirred at rt overnight, the reaction mixture was diluted with methylene chloride (90.0 mL, 1.40 mol) and then cooled to 0 Celsius. To the mixture was added N,N-diisopropylethylamine (5.38 mL, 0.0309 mol) followed by methyl chloroformate (2.39 mL, 0.0309 mol). The mixture was stirred at rt for 2 h and then concentrated to dry. The residue was diluted with water and extracted with ethyl acetate. The combined organic layers were washed with brine, dried and concentrated to dry. The residue was purified on silica gel, eluting with 0 to 100% EtOAc in hexane, to give the titled compound (5.20 g, 83.0%). MS(ESI): (M+H)$^+$=406.1.

Part 8. dimethyl(2S, 3S, 5S)-5-(3-fluorophenoxy)-2-[(4-phenylpiperazin-1-yl)carbonyl]piperidine-1,3-dicarboxylate: To a solution of dimethyl(2S,3S,5R)-5-hydroxy-2-[(4-phenylpiperazin-1-yl)carbonyl]piperidine-1,3-dicarboxylate (50.0 mg, 0.000123 mol) in tetrahydrofuran (0.50 mL, 0.00617 mol) was added 3-fluoro-phenol (0.0134 mL, 0.000148 mol), triphenylphosphine (38.8 mg, 0.000148 mol), followed by diethyl azodicarboxylate (0.0233 mL, 0.000148 mol). The mixture was heated at 70 Celsius overnight. After concentrated to dry, the mixture was purified on silica gel, eluting with 0 to 40% EtOAc in hexane, to generate the phenyl ether compound (27 mg, 44%). MS (ESI): (M+H)$^+$=500.05.

Part 9. Methyl(2S, 3S, 5S)-5-(3-fluorophenoxy)-3-[(hydroxyamino)carbonyl]-2-[(4-phenylpiperazin-1-yl)carbonyl]piperidine-1-carboxylate: To a solution of dimethyl (2S, 3S,5S)-5-(3-fluorophenoxy)-2-[(4-phenylpiperazin-1-yl)carbonyl]piperidine-1,3-dicarboxylate (27 mg, 0.000054 mol) in methanol (0.2189 mL, 0.005405 mol) was added 1.640 M of N-hydroxyamine in Methanol (0.659 mL) made from the corresponding HCl salt and sodium methoxide. After stirred at rt for 1 h, the mixture was acidified with 1N HCl. The resultant mixture was applied directly on RP-HPLC to afford the product as a TFA salt (18 mg 54.5%). MS (ESI): (M+H)$^+$=501.2.

Example 127

Methyl(2S,3S,5S)-3-[(hydroxyamino)carbonyl]-2-[(4-phenylpiperazin-1-yl)carbonyl]-5-[3-(trifluoromethyl)phenoxy]piperidine-1-carboxylate This compound was prepared using procedures analogous to those for example 126. MS (ESI): (M+H)$^+$=551.1.

Example 128

Methyl(2S,3S,5S)-5-(2,4-difluorophenoxy)-3-[(hydroxyamino)carbonyl]-2-[(4-phenylpiperazin-1-yl)carbonyl]piperidine-1-carboxylate This compound was prepared using procedures analogous to those for example 126. MS (ESI): (M+H)$^+$=519.0.

Example 129

Methyl(2S,3S,5S)-5-(3-chloro-4-fluorophenoxy)-3-[(hydroxyamino)carbonyl]-2-[(4-phenylpiperazin-1-yl)carbonyl]piperidine-1-carboxylate This compound was prepared using procedures analogous to those for example 126. MS (ESI): (M+H)$^+$=535.0.

Example 130

Methyl(2S,3S,5S)-5-[(5-chloropyridin-3-yl)oxy]-3-[(hydroxyamino)carbonyl]-2-[(4-phenylpiperazin-1-yl)carbonyl]piperidine-1-carboxylate This compound was prepared using procedures analogous to those for example 126. MS (ESI): (M+H)$^+$=518.1.

Example 131

Methyl(2S,3S,5S)-5-(3-bromophenoxy)-3-[(hydroxyamino)carbonyl]-2-[(4-phenylpiperazin-1-yl)carbonyl]piperidine-1-carboxylate This compound was prepared using procedures analogous to those for example 126. MS (ESI): (M+H)$^+$=561.0.

Example 132

Methyl(2S,3S,5S)-3-[(hydroxyamino)carbonyl]-2-[(4-phenylpiperazin-1-yl)carbonyl]-5-(pyridin-3-yloxy)piperidine-1-carboxylate This compound was prepared using procedures analogous to those for example 126. MS (ESI): (M+H)$^+$=484.1.

Example 133

Methyl(2S,3S,5S)-3-[(hydroxyamino)carbonyl]-2-[(4-phenylpiperazin-1-yl)carbonyl]-5-(quinolin-6-yloxy)piperidine-1-carboxylate This compound was prepared using procedures analogous to those for example 126. MS (ESI): $(M+H)^+=534.1$.

Example 134

Methyl(2S,3S,5S)-3-[(hydroxyamino)carbonyl]-5-(3-methylphenoxy)-2-[(4-phenylpiperazin-1-yl)carbonyl]piperidine-1-carboxylate This compound was prepared using procedures analogous to those for example 126. MS (ESI): $(M+H)^+=497.1$.

Example 135

Methyl(2S,3S,5S)-3-[(hydroxyamino)carbonyl]-5-(3-methoxyphenoxy)-2-[(4-phenylpiperazin-1-yl)carbonyl]piperidine-1-carboxylate This compound was prepared using procedures analogous to those for example 126. MS (ESI): $(M+H)^+=513.1$.

Example 136

Methyl(2S,3S,5S)-3-[(hydroxyamino)carbonyl]-5-[(6-methylpyridin-2-yl)oxy]-2-[(4-phenylpiperazin-1-yl)carbonyl]piperidine-1-carboxylate This compound was prepared using procedures analogous to those for example 126. MS (ESI): $(M+H)^+=498.1$.

Example 137

Methyl(2S,3S,5S)-3-[(hydroxyamino)carbonyl]-5-[(2-methylquinolin-4-yl)oxy]-2-[(4-phenylpiperazin-1-yl)carbonyl]piperidine-1-carboxylate This compound was prepared using procedures analogous to those for example 126. MS (ESI): $(M+H)^+=548.15$.

Example 138

Methyl(2S,3S,5S)-3-[(hydroxyamino)carbonyl]-5-phenoxy-2-[(4-phenylpiperazin-1-yl)carbonyl]piperidine-1-carboxylate This compound was prepared using procedures analogous to those for example 126. MS (ESI): $(M+H)^+=483.2$.

Example 139

Methyl(2S,3S,5S)-5-(3-chlorophenoxy)-3-[(hydroxyamino)carbonyl]-2-[(4-phenylpiperazin-1-yl)carbonyl]piperidine-1-carboxylate This compound was prepared using procedures analogous to those for example 126. MS (ESI): $(M+H)^+=517.0$.

Example 140

Methyl(2S,3S,5S)-5-(2,3-difluorophenoxy)-3-[(hydroxyamino)carbonyl]-2-[(4-phenylpiperazin-1-yl)carbonyl]piperidine-1-carboxylate This compound was prepared using procedures analogous to those for example 126. MS (ESI): $(M+H)^+=519.1$.

Example 141

Methyl(2S,3S,5S)-3-[(hydroxyamino)carbonyl]-2-[(4-phenylpiperazin-1-yl)carbonyl]-5-(pyridin-2-yloxy)piperidine-1-carboxylate This compound was prepared using procedures analogous to those for example 126. MS (ESI): $(M+H)^+=484.1$.

Example 142

Methyl(2S,3S,5S)-3-[(hydroxyamino)carbonyl]-2-[(4-phenylpiperazin-1-yl)carbonyl]-5-(quinolin-4-yloxy)piperidine-1-carboxylate This compound was prepared using procedures analogous to those for example 126. MS (ESI): $(M+H)^+=534.1$.

Example 143

Methyl(2S,3S,5S)-3-[(hydroxyamino)carbonyl]-2-[(4-phenylpiperazin-1-yl)carbonyl]-5-(pyridin-4-yloxy)piperidine-1-carboxylate This compound was prepared using procedures analogous to those for example 126. MS (ESI): $(M+H)^+=484.05$.

Example 144

Methyl(2S,3S,5S)-3-[(hydroxyamino)carbonyl]-5-[(4-methylpyridin-2-yl)oxy]-2-[(4-phenylpiperazin-1-yl)carbonyl]piperidine-1-carboxylate This compound was prepared using procedures analogous to those for example 126. MS (ESI): $(M+H)^+=498.2$.

Example 145

Methyl(2S,3S,5S)-5-(2-fluorophenoxy)-3-[(hydroxyamino)carbonyl]-2-[(4-phenylpiperazin-1-yl)carbonyl]piperidine-1-carboxylate This compound was prepared using procedures analogous to those for example 126. MS (ESI): $(M+H)^+=501.1$.

Example 146

Methyl(2S,3S,5S)-3-[(hydroxyamino)carbonyl]-5-(2-methylphenoxy)-2-[(4-phenylpiperazin-1-yl)carbonyl]piperidine-1-carboxylate This compound was prepared using procedures analogous to those for example 126. MS (ESI): $(M+H)^+=497.1$.

Example 147

Methyl(2S,3S,5S)-5-(4-fluorophenoxy)-3-[(hydroxyamino)carbonyl]-2-[(4-phenylpiperazin-1-yl)carbonyl]piperidine-1-carboxylate This compound was prepared using procedures analogous to those for example 126. MS (ESI): (M+H)$^+$=501.1.

Example 148

Methyl(2S,3S,5S)-5-(3,5-difluorophenoxy)-3-[(hydroxyamino)carbonyl]-2-[(4-phenylpiperazin-1-yl)carbonyl]piperidine-1-carboxylate This compound was prepared using procedures analogous to those for example 126. MS (ESI): (M+H)$^+$=519.0.

Example 150

Methyl(2S,3S,5S)-5-(1,3-benzothiazol-2-yloxy)-3-[(hydroxyamino)carbonyl]-2-[(4-phenylpiperazin-1-yl)carbonyl]piperidine-1-carboxylate This compound was prepared using procedures analogous to those for example 126. MS (ESI): (M+H)$^+$=540.1.

Example 151

Methyl(2S,3S,5S)-5-(3,4-difluorophenoxy)-3-[(hydroxyamino)carbonyl]-2-[(4-phenylpiperazin-1-yl)carbonyl]piperidine-1-carboxylate This compound was prepared using procedures analogous to those for example 126. MS (ESI): (M+H)$^+$=519.0.

Example 152

(2S,3S,5S)-N-hydroxy-1-methyl-2-[(4-phenyl-3,6-dihydropyridin-1(2H)-yl)carbonyl]-5-(pyridin-4-yloxy)piperidine-3-carboxamide Part 1. 1-tert-butyl 3-methyl(2S,3S,5R)-5-hydroxy-2-[(4-phenyl-3,6-dihydropyridin-1(2H)-yl)carbonyl]piperidine-1,3-dicarboxylate: A mixture of (2S,3S,5R)-5-hydroxy-3-(methoxycarbonyl)piperidine-2-carboxylic acid (1.851 g, 0.009110 mol), 4-phenyl-1,2,3,6-tetrahydropyridine hydrochloride (2.14 g, 0.0109 mol) and benzotriazol-1-yloxytris(dimethylamino)phosphonium hexafluorophosphate (4.83 g, 0.0109 mol) in N,N-dimethylformamide (15.0 mL, 0.194 mol) was stirred at rt for 5 min, then treated with N,N-diisopropylethylamine (3.81 mL, 0.0219 mol) at rt for 2 h. The reaction mixture was diluted with methylene chloride (10.0 mL, 0.156 mol). The resultant mixture was then treated with N,N-diisopropylethylamine (3.17 mL, 0.0182 mol), followed by di-tert-butyldicarbonate (3.98 g, 0.0182 mol) at rt overnight. The reaction was diluted with water, extracted with EtOAc. The combined orgnica layers were washed with brine, dried, and concentrated to dry in vacuo. The residue was applied on silica gel, eluting with 0 to 80% EtOAc in hexane, to give the titled compound (2.10 g, 51.9%). MS (ESI): (M+H−Boc)$^+$=345.1.

Part 2. 1-tert-butyl 3-methyl(2S, 3S, 5S)-2-[(4-phenyl-3,6-dihydropyridin-1(2H)-yl)carbonyl]-5-(pyridin-4-yloxy)piperidine-1,3-dicarboxylate: To a solution of 1-tert-butyl 3-methyl (2S,3S,5R)-5-hydroxy-2-[(4-phenyl-3,6-dihydropyridin-1 (2H)-yl)carbonyl]piperidine-1,3-dicarboxylate (100 mg, 0.0002 mol) in tetrahydrofuran (0.912 mL, 0.0112 mol) was added 4-pyridinol (25.7 mg, 0.000270 mol), triphenylphosphine (70.8 mg, 0.000270 mol), followed by diisopropyl azodicarboxylate (0.0532 mL, 0.000270 mol). The mixture was heated at 70 Celsius overnight. After concentrated to dry, the mixture was purified on silica gel, eluting with 0 to 40% EtOAc in hexane, to afford the desired ether compound (56 mg, 50%). MS (ESI): (M+H)$^+$=522.1.

Part 3. methyl(2S, 3S, 5S)—-methyl-2-[(4-phenyl-3,6-dihydropyridin-1(2H)-yl)carbonyl]-5-(pyridin-4-yloxy)piperidine-3-carboxylate: 1-tert-butyl 3-methyl(2S,3S,5S)-2-[(4-phenyl-3,6-dihydropyridin-1 (2H)-yl)carbonyl]-5-(pyridin-4-yloxy)piperidine-1,3-dicarboxylate (0.09 g, 0.0002 mol) was treated with trifluoroacetic acid (1.0 mL, 0.013 mol) at rt for 1 h. The mixture was then concentrated to dry. The crude secondary amine made above was dissolved in tetrahydrofuran (0.80 mL, 0.0099 mol) and acetonitrile (0.80 mL, 0.015 mol). The mixture was then treated with N,N-diisopropylethylamine (0.061 mL, 0.00035 mol) to adjust the pH to around 7. To the resultant mixture was then added 12.32 M of formaldehyde in water (0.071 mL) followed by sodium triacetoxyborohydride (180 mg, 0.00087 mol). After stirred at rt overnight, the mixture was concentrated to dry in vacuo, diluted with with aq. sodium bicarbonate, extracted with EtOAc. The combined organic layers were washed with brine, dried, and evaporated to dry in vacuo. The residue was exposed in high vacuum and then used directly in next step. MS (ESI): (M+H)$^+$=436.1.

Part 4. (2S,3S, 5S)-N-hydroxy-1-methyl-2-[(4-phenyl-3,6-dihydropyridin-1 (2H)-yl)carbonyl]-5-(pyridin-4-yloxy)piperidine-3-carboxamide: To a solution of methyl(2S,3S,5S)-1-methyl-2-[(4-phenyl-3,6-dihydropyridin-1 (2H)-yl)carbonyl]-5-(pyridin-4-yloxy)piperidine-3-carboxylate (70 mg, 0.0002 mol) in methanol (0.6674 mL, 0.01648 mol) was added 1.640 M of N-hydroxyamine in Methanol (2.01 mL) made from the corresponding HCl salt and sodium methoxide. After stirred at rt for 1 h, the mixture was acidified with 1N HCl. The resultant mixture was applied directly on RP-HPLC to afford the product as a TFA salt (56 mg, 63.4%). MS (ESI): (M+H)$^+$=437.1.

Example 153

(2S,3S,5S)-N-hydroxy-1-methyl-5-[(4-methylpyridin-2-yl)oxy]-2-[(4-phenyl-3,6-dihydropyridin-1 (2H)-yl)carbonyl]piperidine-3-carboxamide This compound was prepared using procedures analogous to those for example 152. MS (ESI): (M+H)$^+$=451.1.

Example 154

(2S,3S,5S)-N-hydroxy-1-methyl-5-phenoxy-2-[(4-phenyl-3,6-dihydropyridin-1(2H)-yl)carbonyl]piperidine-3-carboxamide This compound was prepared using procedures analogous to those for example 152. MS (ESI): (M+H)$^+$=436.0.

Example 155

(2S,3S,5S)-5-(3-fluorophenoxy)-N-hydroxy-1-methyl-2-[(4-phenyl-3,6-dihydropyridin-1(2H)-yl)carbonyl]piperidine-3-carboxamide This compound was prepared using procedures analogous to those for example 152. MS (ESI): (M+H)$^+$=454.1.

Example 156

(2S,3S,5S)-N-hydroxy-1-methyl-2-[(4-phenyl-3,6-dihydropyridin-1(2H)-yl)carbonyl]-5-(quinolin-6-yloxy)piperidine-3-carboxamide This compound was prepared using procedures analogous to those for example 152. MS (ESI): $(M+H)^+ = 487.0$.

Example 157

(2S,3S,5S)-N-hydroxy-1-methyl-5-[(2-methylquinolin-4-yl)oxy]-2-[(4-phenyl-3,6-dihydropyridin-1(2H)-yl)carbonyl]piperidine-3-carboxamide This compound was prepared using procedures analogous to those for example 152. MS (ESI): $(M+H)^+ = 501.1$.

Example 158

(2S,3S,5S)-N-hydroxy-1-methyl-2-[(4-phenyl-3,6-dihydropyridin-1(2H)-yl)carbonyl]-5-(pyridin-2-yloxy)piperidine-3-carboxamide This compound was prepared using procedures analogous to those for example 152. MS (ESI): $(M+H)^+ = 437.0$.

Example 159

(2S,3S,5S)-5-(3,5-difluorophenoxy)-N-hydroxy-1-methyl-2-[(4-phenyl-3,6-dihydropyridin-1(2H)-yl)carbonyl]piperidine-3-carboxamide This compound was prepared using procedures analogous to those for example 152. MS (ESI): $(M+H)^+ = 472.1$.

Example 160

(2S,3S,5S)-N-hydroxy-1-methyl-2-[(4-phenyl-3,6-dihydropyridin-1(2H)-yl)carbonyl]-5-(quinolin-4-yloxy)piperidine-3-carboxamide This compound was prepared using procedures analogous to those for example 152. MS (ESI): $(M+H)^+ = 486.9$.

Example 161

(2S,3S,5S)-N-hydroxy-1-methyl-2-[(4-phenylpiperidin-1-yl)carbonyl]-5-(pyridin-4-yloxy)piperidine-3-carboxamide (1a)

A mixture of (2S,3S,5S)-N-hydroxy-1-methyl-2-[(4-phenyl-3,6-dihydropyridin-1(2H)-yl)carbonyl]-5-(pyridin-4-yloxy)piperidine-3-carboxamide TFA salt (4 mg, 0.00001 mol) in 1 mL of MeOH was hydrogenated in the presence of 5% Pd/BaSO4, under balloon pressure of hydrogen, for 2 h. After filtered off the catalyst, the filtration was concentrated to dry to yield the titled compound (4 mg, 100%). MS (ESI): $(M+H)^+ = 439.2$.

Example 162

(2S,3S,5S)-N-hydroxy-1-methyl-5-[(2-methyl-1,2,3,4-tetrahydroquinolin-4-yl)oxy]-2-[(4-phenylpiperidin-1-yl)carbonyl]piperidine-3-carboxamide This compound was prepared using procedures analogous to those for example 161. MS (ESI): $(M+H)^+ = 507.2$.

Example 163

(2S,3S,5S)-N-hydroxy-1-methyl-5-[(4-methylpyridin-2-yl)oxy]-2-[(4-phenylpiperidin-1-yl)carbonyl]piperidine-3-carboxamide This compound was prepared using procedures analogous to those for example 161. MS (ESI): $(M+H)^+ = 453.0$.

Example 164

(2S,3S,5S)-N-hydroxy-1-methyl-2-[(4-phenylpiperidin-1-yl)carbonyl]-5-(pyridin-2-yloxy)piperidine-3-carboxamide This compound was prepared using procedures analogous to those for example 161. MS (ESI): $(M+H)^+ = 439.1$.

Example 165

(2S,3S,5S)-N-hydroxy-1-(methylsulfonyl)-5-phenoxy-2-[(4-phenylpiperazin-1-yl)carbonyl]piperidine-3-carboxamide This compound was prepared using procedures analogous to those for example 126. MS (ESI): $(M+H)^+ = 503.2$.

Example 166

(3S)-tetrahydrofuran-3-yl(2S,3S,5S)-3-[(hydroxyamino)carbonyl]-5-phenoxy-2-[(4-phenylpiperazin-1-yl)carbonyl]piperidine-1-carboxylate This compound was prepared using procedures analogous to those for example 126. MS (ESI): $(M+H)^+ = 539.2$.

Example 167

Methyl(2S,3S,5S)-5-(2-bromophenoxy)-3-[(hydroxyamino)carbonyl]-2-[(4-phenylpiperazin-1-yl)carbonyl]piperidine-1-carboxylate This compound was prepared using procedures analogous to those for example 126.

Example 168

Methyl(2S,3S,5S)-5-(2-chlorophenoxy)-3-[(hydroxyamino)carbonyl]-2-[(4-phenylpiperazin-1-yl)carbonyl]piperidine-1-carboxylate This compound was prepared using procedures analogous to those for example 126. MS (ESI): $(M+H)^+ = 517.2$.

Example 169

Tetrahydro-2H-pyran-4-yl(2S,3S,5S)-3-[(hydroxyamino)carbonyl]-5-phenoxy-2-[(4-phenylpiperazin-1-yl)carbonyl]piperidine-1-carboxylate This compound was prepared using procedures analogous to those for example 126. MS (ESI): $(M+H)^+ = 553.2$.

Example 170

Ethyl(2S,3S,5S)-3-[(hydroxyamino)carbonyl]-5-phenoxy-2-[(4-phenylpiperazin-1-yl)carbonyl]piperidine-1-carboxylate This compound was prepared using procedures analogous to those for example 126. MS (ESI): (M+H)$^+$=497.2.

Example 171

(2S,3S,5S)-N-hydroxy-5-(3-methylphenoxy)-2-[(4-phenylpiperazin-1-yl)carbonyl]piperidine-3-carboxamide This compound was prepared using procedures analogous to those for example 152. MS (ESI): (M+H)$^+$=439.1.

Example 172

(2S,3S,5S)-N-hydroxy-2-[(4-phenylpiperazin-1-yl)carbonyl]-5-[3-(trifluoromethyl)phenoxy]piperidine-3-carboxamide This compound was prepared using procedures analogous to those for example 152. MS (ESI): (M+H)$^+$=493.2.

Example 173

(2S,3S,5S)-5-(3-chlorophenoxy)-N-hydroxy-2-[(4-phenylpiperazin-1-yl)carbonyl]piperidine-3-carboxamide This compound was prepared using procedures analogous to those for example 152. MS (ESI): (M+H)$^+$=459.2.

Example 174

(2S,3S,5S)-N-hydroxy-5-(3-methoxyphenoxy)-2-[(4-phenylpiperazin-1-yl)carbonyl]piperidine-3-carboxamide This compound was prepared using procedures analogous to those for example 152. MS (ESI): (M+H)$^+$=455.0.

Example 175

(2S,3S,5S)-5-(3-fluorophenoxy)-N-hydroxy-2-[(4-phenylpiperazin-1-yl)carbonyl]piperidine-3-carboxamide This compound was prepared using procedures analogous to those for example 152. MS (ESI): (M+H)$^+$=443.2.

Example 176

(3S,5S,6S)-5-[(hydroxyamino)carbonyl]-1-methyl-6-[(4-phenyl-3,6-dihydropyridin-1(2H)-yl)carbonyl]piperidin-3-yl piperidine-1-carboxylate Part 1. 1-benzyl 4-methyl(2S)-2-[benzyl((2R)-2-hydroxy-3-[(4-methylphenyl)sulfonyl]oxypropyl)amino]succinate: To a solution of (2R)-oxiran-2-ylmethyl 4-methylbenzenesulfonate (23.0 g, 0.101 mol) in 500 mL of methylene chloride was added 2.000 M of trimethylaluminum in Toluene (50.4 mL) at −78 Celsius, under an atmosphere of nitrogen. After stirred at −78 Celsius for 10 min, to the mixture was added a solution of (S)-2-benzylamino-succinic acid 1-benzyl ester 4-methyl ester (30.0 g, 0.0916 mol) in 150 mL of methylene chloride. The resulting reaction mixture was stirred at −78 Celsius for 30 min. The dry ice-acetone bath was changed to an ice-water bath to warm the mixture up to 0 Celsius. The mixture was stirred at 0 Celsius for 30 min. To the reaction mixture was added sodium fluoride (16.2 g, 0.385 mol) followed by Water (10.4 mL, 0.577 mol) at 0 Celsius. The resulting suspension was rapidly stirred for 1 h at 0 Celsius and filtered through a short column of of Celite and the cloumn was subsequently washed with 600 mL of methylene chloride. The combined filtrates were dried over sodium sulfate, concentrated to dry and purified by column purification (eluting with 0 to 30% EtOAc in hexane) to give the titled compound (43.0 g, 84.4%). MS (ESI): (M+H)$^+$=556.1.

Part 2. 1-benzyl 4-methyl(2S)-2-[benzyl((2R)-2-(1-ethoxyethoxy)-3-[(4-methylphenyl)sulfonyl]oxypropyl)amino]succinate: To a solution of 1-benzyl 4-methyl(2S)-2-[benzyl((2R)-2-hydroxy-3-[(4-methylphenyl)sulfonyl]oxypropyl)amino]succinate (43.0 g, 0.0774 mol) in methylene chloride (500.0 mL, 7.800 mol) was added ethyl vinyl ether (15.0 mL, 0.157 mol) followed by pyridinium p-toluenesulfonate (4.0 g, 0.016 mol). The mixture was stirred at rt for 3 g. After concentrated to dry, the residue was purified by silical gel column (eluting with 0 to 20% EtOAc in hexane) to provide the ether compound (38.1 g, 78.4%). MS (ESI): (M+H)$^+$=628.1.

Part 3. 2-benzyl 3-methyl(2S,3S,5S)-1-benzyl-5-(1-ethoxyethoxy)piperidine-2,3-dicarboxylate: To a solution of 1-benzyl 4-methyl(2S)-2-[benzyl((2R)-2-(1-ethoxyethoxy)-3-[(4-methylphenyl)sulfonyl]oxypropyl)amino]succinate (34.30 g, 0.05464 mol) in a mixture of tetrahydrofuran (90.0 mL, 1.11 mol) and toluene (470.0 mL, 4.412 mol) at −78 Celsius was added 1.00 M of Lithium hexamethyldisilazide in tetrahydrofuran (65.6 mL). The resulting mixture was stirred at −78 Celsius overnight, and then allowed to warm up to at 0 Celsius gradually and stirred at 0 Celsius for 30 min. After quenched with aq. ammonium chloride, the mixture was extracted with ethyl acetate. The combined orgnic layers were washed with water, brine, and dried (sodium sulfate), and concentrated to dry. The residue was purified on silica gel columnn, eluting with 0 to 20% EtOAc in hexane, to yield the cyclized product (19.47 g, 78.2%). MS (ESI): (M+H)$^+$=456.0.

Part 4. 2-benzyl 3-methyl(2S,3S,5S)-1-benzyl-5-hydroxypiperidine-2,3-dicarboxylate: To a solution of 2-benzyl 3-methyl(2S,3S,5S)-1-benzyl-5-(1-ethoxyethoxy)piperidine-2,3-dicarboxylate (3.80 g, 0.00834 mol) in 67 mL of THF was added 13 mL of water followed by 13 mL of 1 N HCl. The mixture was stirred at rt for 1 h. After diluted with ethyl acetate, the mixture was neutralized with 1N NaOH, washed with brine, dried. The residue after concentration was purified on cloumn, eluting with 0 to 50% EtOAc in hexane, to generate the corresponding alcohol compound (2.90 g, 90.6%). MS (ESI): (M+H)$^+$=384.1.

Part 5. (2S,3S,5S)-5-hydroxy-3-(methoxycarbonyl)piperidine-2-carboxylic acid: A solution of 2-benzyl 3-methyl(2S,3S,5S)-1-benzyl-5-hydroxypiperidine-2,3-dicarboxylate (2.00 g, 0.00522 mol) in 30 mL of methanol was hydrogenated in the presence of 10% Pd/C, under a balloon pressure of hydrogen, overnight. After filtered off the catalyst, the filtration was conetrated to dry and used directly in next step.

Part 6. methyl(2S, 3S, 5S)-5-hydroxy-1-methyl-2-[(4-phenyl-3,6-dihydropyridin-1(2H)-yl)carbonyl]piperidine-3-carboxylate: A mixture of (2S,3S,5S)-5-hydroxy-3-(methoxycarbonyl)piperidine-2-carboxylic acid (0.309 g, 0.00152 mol), 4-phenyl-1,2,3,6-tetrahydropyridine hydrochloride (0.357 g, 0.00182 mol) and benzotriazol-1-yloxytris(dimethylamino)phosphonium hexafluorophosphate (0.807 g, 0.00182 mol) in N, N-dimethylformamide (2.50 mL, 0.0323 mol) was stirred at rt for 5 min, then treated with N, N-diisopropylethylamine (0.636 mL, 0.00365 mol) at rt for 2 h. The reaction mixture was diluted with acetonitrile (5.0 mL, 0.096 mol) and tetrahydrofuran (5.0 mL, 0.062 mol). To the mixture was added 12.32 M of formaldehyde in Water (0.41 mL) followed by sodium triacetoxyborohydride (1.1 g, 0.0051 mol). After stirred at rt overnight, the mixture was concentrated to dry, then diluted with aq. sodium bicarbonate, extracted with EtOAc. The combined organic layers were washed with brine, dried and concentrated to dry. The residue was applied on silica gel, eluting with 0 to 100% EtOAc in hexane, to yield the methyl amine compound (0.31 g, 85%). MS (ESI): (M+H)$^+$=358.1.

Part 7. (3S, 5S, 6S)-5-(methoxycarbonyl)-1-methyl-6-[(4-phenyl-3,6-dihydropyridin-1 (2H)-yl)carbonyl]piperidin-3-yl piperidine-1-carboxylate: A solution of methyl(2S,3S,5S)-5-hydroxy-1-methyl-2-[(4-phenyl-3,6-dihydropyridin-1 (2H)-yl)carbonyl]piperidine-3-carboxylate (72 mg, 0.00020 mol) in methylene chloride (2.0 mL, 0.031 mol) was treated with N, N-carbonyldiimidazole (50 mg, 0.0003 mol) at rt for 2 h. To the mixture was added piperidine (0.060 mL, 0.00060 mol). After tirred at rt overnight, the mixture was cocnentrated to dry and used directly in next step.

Part 8. (3S, 5S, 6S)-5-[(hydroxyamino)carbonyl]-1-methyl-6-[(4-phenyl-3,6-dihydropyridin-1 (2H)-yl)carbonyl]piperidin-3-yl piperidine-1-carboxylate: To a solution of (3S, 5S,6S)-5-(methoxycarbonyl)-1-methyl-6-[(4-phenyl-3,6-dihydropyridin-1 (2H)-yl)carbonyl]piperidin-3-yl piperidine-1-carboxylate (94 mg, 0.00020 mol) in methanol (0.8109 mL, 0.02002 mol) was added 1.640 M of N-hydroxyamine in methanol (2.44 mL) made from the corresponding salt and sodium methoxide. After stirred at rt for 1 h, the mixture was acidified with 1N HCl. The resultant mixture was applied directly on RP-HPLC to afford the product as a TFA salt (56 mg, 48%). MS (ESI): (M+H)$^+$=471.1.

Example 177

(3S,5S,6S)-5-[(hydroxyamino)carbonyl]-1-methyl-6-[(4-phenyl-3,6-dihydropyridin-1(2H)-yl)carbonyl]piperidin-3-yl(2S)-2-(hydroxymethyl)pyrrolidine-1-carboxylate This compound was prepared using procedures analogous to those for example 176. MS (ESI): (M+H)$^+$=487.15.

Example 178

(3S,5S,6S)-5-[(hydroxyamino)carbonyl]-1-methyl-6-[(4-phenyl-3,6-dihydropyridin-1(2H)-yl)carbonyl]piperidin-3-yl azepane-1-carboxylate This compound was prepared using procedures analogous to those for example 176. MS (ESI): (M+H)$^+$=485.2.

Example 179

(3S,5S,6S)-5-[(hydroxyamino)carbonyl]-1-methyl-6-[(4-phenyl-3,6-dihydropyridin-1(2H)-yl)carbonyl]piperidin-3-yl azetidine-1-carboxylate This compound was prepared using procedures analogous to those for example 176. MS (ESI): (M+H)$^+$=443.2.

Example 180

(3S,5S,6S)-5-[(hydroxyamino)carbonyl]-1-methyl-6-[(4-phenyl-3,6-dihydropyridin-1(2H)-yl)carbonyl]piperidin-3-yl dimethylcarbamate This compound was prepared using procedures analogous to those for example 176. MS (ESI): (M+H)$^+$=431.1.

Example 181

(3S,5S,6S)-5-[(hydroxyamino)carbonyl]-1-methyl-6-[(4-phenyl-3,6-dihydropyridin-1(2H)-yl)carbonyl]piperidin-3-yl 2,5-dihydro-1H-pyrrole-1-carboxylate This compound was prepared using procedures analogous to those for example 176. MS (ESI): (M+H)$^+$=455.1.

Example 182

(3S,5S,6S)-5-[(hydroxyamino)carbonyl]-1-methyl-6-[(4-phenyl-3,6-dihydropyridin-1(2H)-yl)carbonyl]piperidin-3-yl pyrrolidine-1-carboxylate This compound was prepared using procedures analogous to those for example 176. MS (ESI): (M+H)$^+$=457.1.

Example 183

(3S,5S,6S)-5-[(hydroxyamino)carbonyl]-1-methyl-6-[(4-phenylpiperazin-1-yl)carbonyl]piperidin-3-yl azetidine-1-carboxylate This compound was prepared using procedures analogous to those for example 176. MS (ESI): (M+H)$^+$=446.2.

Example 184

(3S,5S,6S)-5-[(hydroxyamino)carbonyl]-1-methyl-6-[(3-phenyl-2,5-dihydro-1H-pyrrol-1-yl)carbonyl]piperidin-3-yl azetidine-1-carboxylate This compound was prepared using procedures analogous to those for example 176. MS (ESI): (M+H)$^+$=429.2.

Example 185

(3S,5S,6S)-6-(1,3-dihydro-2H-benzo [e]isoindol-2-ylcarbonyl)-5-[(hydroxyamino)carbonyl]-1-methylpiperidin-3-yl azetidine-1-carboxylate This compound was prepared using procedures analogous to those for example 176. MS (ESI): (M+H)$^+$=453.2.

Example 186

(3S,5S,6S)-5-[(hydroxyamino)carbonyl]-1-methyl-6-[(4-phenylpiperazin-1-yl)carbonyl]piperidin-3-yl pyrrolidine-1-carboxylate This compound was prepared using procedures analogous to those for example 176. MS (ESI): (M+H)$^+$=460.2.

Example 187

(3S,5S,6S)-5-[(hydroxyamino)carbonyl]-1-methyl-6-[(3R)-3-phenylpyrrolidin-1-yl]carbonylpiperidin-3-yl azetidine-1-carboxylate This compound was prepared using procedures analogous to those for example 176. MS (ESI): (M+H)$^+$=431.2.

Example 188

(3S,5S,6S)-5-[(hydroxyamino)carbonyl]-1-methyl-6-[(4-phenylpiperazin-1-yl)carbonyl]piperidin-3-yl piperidine-1-carboxylate This compound was prepared using procedures analogous to those for example 176. MS (ESI): (M+H)$^+$=474.2.

Example 189

(3S,5S,6S)-6-(1,3-dihydro-2H-isoindol-2-ylcarbonyl)-5-[(hydroxyamino)carbonyl]-1-methylpiperidin-3-yl azetidine-1-carboxylate This compound was prepared using procedures analogous to those for example 176. MS (ESI): (M+H)$^+$=403.2.

Example 190

(3S,5S,6S)-5-[(hydroxyamino)carbonyl]-1-methyl-6-[(3-phenyl-2,5-dihydro-1H-pyrrol-1-yl)carbonyl]piperidin-3-yl pyrrolidine-1-carboxylate This compound was prepared using procedures analogous to those for example 176. MS (ESI): (M+H)$^+$=443.05.

Example 191

(3S,5S,6S)-5-[(hydroxyamino)carbonyl]1-methyl-6-[(4-phenylpiperidin-1-yl)carbonyl]piperidin-3-yl pyrrolidine-1-carboxylate A solution of (3S,5S,6S)-5-[(hydroxyamino)carbonyl]-1-methyl-6-[(4-phenyl-3,6-dihydropyridin-1(2H)-yl)carbonyl]piperidin-3-yl pyrrolidine-1-carboxylate (5.0 mg, 0.000011 mol) TFA salt in 1 mL of MeOH was hydrogenated in the presence of 5% Pd/BaSO4, under a balloon pressure of hydrogen, for 2 h. After filtered off the catalyst, the filtration was concentrated to dry to give the product (5.0 mg, 100%). MS (ESI): (M+H)$^+$=459.15.

Example 192

(3S,5S,6S)-5-[(hydroxyamino)carbonyl]-1-methyl-6-[(4-phenylpiperidin-1-yl)carbonyl]piperidin-3-yl azepane-1-carboxylate This compound was prepared using procedures analogous to those for example 191. MS (ESI): (M+H)$^+$=487.2.

Example 193

(3S,5S,6S)-5-[(hydroxyamino)carbonyl]-1-methyl-6-[(4-phenylpiperidin-1-yl)carbonyl]piperidin-3-yl (2S)-2-(hydroxymethyl)pyrrolidine-1-carboxylate This compound was prepared using procedures analogous to those for example 191. MS (ESI): (M+H)$^+$=489.2.

Example 194

(3S,5S,6S)-5-[(hydroxyamino)carbonyl]-1-methyl-6-[(4-phenylpiperidin-1-yl)carbonyl]piperidin-3-yl piperidine-1-carboxylate This compound was prepared using procedures analogous to those for example 191. MS (ESI): (M+H)$^+$=473.2.

Example 195

(3S,5S,6S)-5-[(hydroxyamino)carbonyl]-1-methyl-6-[(4-phenylpiperidin-1-yl)carbonyl]piperidin-3-yl dimethylcarbamate This compound was prepared using procedures analogous to those for example 191. MS (ESI): (M+H)$^+$=433.1.

Example 196

Methyl(2S,3S,5S)-3-[(hydroxyamino)carbonyl]-5-([(2S)-2-(hydroxymethyl)pyrrolidin-1-yl]carbonyloxy)-2-[(4-phenylpiperazin-1-yl)carbonyl]piperidine-1-carboxylate Part 1 dimethyl(2S,3S,5S)-5-hydroxy-2-[(4-phenylpiperazin-1-yl)carbonyl]piperidine-1,3-dicarboxylate: To a mixture of (2S,3S,5S)-5-hydroxy-3-(methoxycarbonyl)piperidine-2-carboxylic acid (1.10 g, 0.00541 mol), 1-phenylpiperazine, (0.910 mL, 0.00595 mol) and benzotriazol-1-yloxytris(dimethylamino)phosphonium hexafluorophosphate (2.63 g, 0.00595 mol) in N,N-dimethylformamide (6.00 mL, 0.0775 mol) was added N,N-diisopropylethylamine (1.04 mL, 0.00595 mol) at 0 Celsius. The reaction was stirred at rt for 3 h. To the reaction mixture was added methylene chloride (40.00 mL, 0.6240 mol), cat. amount of DMAP, N,N-diisopropylethylamine (2.36 mL, 0.0135 mol), followed by methyl chloroformate (0.836 mL, 0.0108 mol) at 0 Celsius. The resulting reaction mixture was stirred at rt overnight. After quenched with water, the mixture was extracted with ethyl acetate. The combined organic layers were washed with brine, dried and concentrated to dry. The residue was purified on silica gel, eluting with 0 to 100% EtOAc in hexane, to give the titled compound (1.88 g, 85.7%). MS (ESI): (M+H)$^+$=406.2.

Part 2. dimethyl(2S,3S,5S)-5-([(2S)-2-(hydroxymethyl)pyrrolidin-1-yl]carbonyloxy)-2-[(4-phenylpiperazin-1-yl)carbonyl]piperidine-1,3-dicarboxylate: To a solution of dimethyl (2S,3S,5S)-5-hydroxy-2-[(4-phenylpiperazin-1-yl)carbonyl]piperidine-1,3-dicarboxylate (0.050 g, 0.00012 mol) in methylene chloride (1.00 mL, 0.0156 mol) was added N,N-carbonyldiimidazole (0.024 g, 0.0001480 mol). The reaction was stirred at rt for 2 h. To the resultant mixture was added L-prolinol (0.01704 mL, 0.0001726 mol) and the reaction was stirred at rt overnight. The mixture was concentrated to dry in vacuo and used directly in next step. MS (ESI): (M+H)$^+$=533.2.

Part 3. methyl(2S, 3S, 5S)-3-[(hydroxyamino)carbonyl]-5-([(2S)-2-(hydroxymethyl)pyrrolidin-1-yl]carbonyloxy)-2-[(4-phenylpiperazin-1-yl)carbonyl]piperidine-1-carboxylate: To a solution of dimethyl(2S,3S,5S)-5-([(2S)-2-(hydroxymethyl)pyrrolidin-1-yl]carbonyloxy)-2-[(4-phenylpiperazin-1-yl)carbonyl]piperidine-1,3-dicarboxylate (66 mg, 0.00012 mol) in methanol (0.57 mL, 0.014 mol) was added 1.640 M of N-hydroxyamine in methanol solution (1.511 mL), made from the hydroxylamine HCl salt and sodium methoxide freshly. The mixture was stirred at rt for 1 h and acidified with 1N HCl. The resulting mixture was applied directly on RP-HPLC to yield the desired compound (61 mg, 76%). MS (ESI): (M+H)$^+$=534.2.

Example 197

Methyl(2S,3S,5S)-2-(1,3-dihydro-2H-isoindol-2-ylcarbonyl)-3-[(hydroxyamino)carbonyl]-5-[(pyrrolidin-1-ylcarbonyl)oxy]piperidine-1-carboxylate This compound was prepared using procedures analogous to those for example 196. MS (ESI): (M+H)$^+$=461.2.

Example 198

Methyl(2S,3S,5S)-3-[(hydroxyamino)carbonyl]-2-[(4-phenylpiperazin-1-yl)carbonyl]-5-[(piperidin-1-ylcarbonyl)oxy]piperidine-1-carboxylate This compound was prepared using procedures analogous to those for example 196. MS (ESI): (M+H)$^+$=518.15.

Example 199

Methyl(2S, 3S, 5S)-3-[(hydroxyamino)carbonyl]-2-[(4-phenylpiperazin-1-yl)carbonyl]-5-[(pyrrolidin-1-ylcarbonyl)oxy]piperidine-1-carboxylate This compound was prepared using procedures analogous to those for example 196. MS (ESI): (M+H)$^+$=504.2.

Example 200

Methyl(2S, 3S, 5S)-3-[(hydroxyamino)carbonyl]-2-[(3-phenylpyrrolidin-1-yl)carbonyl]-5-[(pyrrolidin-1-ylcarbonyl)oxy]piperidine-1-carboxylate This compound was prepared using procedures analogous to those for example 196. MS (ESI): (M+H)$^+$=489.2.

Example 201

Methyl(2S,3S,5S)-5-[(dimethylamino)carbonyl]oxy-3-[(hydroxyamino)carbonyl]-2-[(4-phenylpiperazin-1-yl)carbonyl]piperidine-1-carboxylate This compound was prepared using procedures analogous to those for example 196. MS (ESI): (M+H)$^+$=478.1.

Example 202

Methyl(2S,3S,5S)-3-[(hydroxyamino)carbonyl]-2-[(4-phenyl-3,6-dihydropyridin-1(2H)-yl)carbonyl]-5-[(pyrrolidin-1-ylcarbonyl)oxy]piperidine-1-carboxylate This compound was prepared using procedures analogous to those for example 196. MS (ESI): (M+H)$^+$=501.2.

Example 203

Methyl(2S,3S,5S)-3-[(hydroxyamino)carbonyl]-2-[(4-phenylpiperidin-1-yl)carbonyl]-5-[(pyrrolidin-1-ylcarbonyl)oxy]piperidine-1-carboxylate This compound was prepared using procedures analogous to those for example 191. MS (ESI): (M+H)$^+$=503.2.

Example 204

(3S,5S,6S)-5-[(hydroxyamino)carbonyl]-6-[(4-phenyl-3,6-dihydropyridin-1(2H)-yl)carbonyl]piperidin-3-yl pyrrolidine-1-carboxylate Part 1. 2-benzyl 3-methyl(2S, 3S, 5S)-1-benzyl-5-[(pyrrolidin-1-ylcarbonyl)oxy]piperidine-2,3-dicarboxylate: To a solution of 2-benzyl 3-methyl(2S,3S,5S)-1-benzyl-5-hydroxypiperidine-2,3-dicarboxylate (144 mg, 0.000376 mol) in methylene chloride (2.0 mL, 0.031 mol) was added N, N-carbonyldiimidazole (73.1 mg, 0.000451 mol). The reaction was stirred at rt for 2 h. To the resulting mixture was added pyrrolidine (0.0470 mL, 0.000563 mol) and the reaction was stirred at rt overnight. The reaction was quenched with aq sodium bicarbonate, extracted with methylene chloride. The combined organic layers were dried, purified on silica gel (eluting with 0 to 40% EtOAc in hexane) to provide the carbamate compound (160 mg, 88.7%). MS (ESI): (M+H)$^+$=481.2.

Part 2. (2S, 3S, 5S)-3-(methoxycarbonyl)-5-[(pyrrolidin-1-ylcarbonyl)oxy]piperidine-2-carboxylic acid: A solution of 2-benzyl 3-methyl(2S,3S,5S)-1-benzyl-5-[(pyrrolidin-1-ylcarbonyl)oxy]piperidine-2,3-dicarboxylate (144 mg, 0.000300 mol) in methanol (3.0 mL, 0.074 mol) was hydrogenated in the presence of 10% Pd/C, under balloon pressure of hydrgen, overnight. After filtered off the catalyst, the filtration was concentrated to dry to provide crude product, which was used directly in next step.

Part 3. methyl(2S, 3S, 5S)-2-[(4-phenyl-3,6-dihydropyridin-1(2H)-yl)carbonyl]-5-[(pyrrolidin-1-ylcarbonyl)oxy]piperidine-3-carboxylate: To a mixture of (2S,3S,5S)-3-(methoxycarbonyl)-5-[(pyrrolidin-1-ylcarbonyl)oxy]piperidine-2-carboxylic acid (90.1 mg, 0.000300 mol) and 4-phenyl-1,2,3,6-tetrahydropyridine (64.6 mg, 0.000330 mol) HCl salt, benzotriazol-1-yloxytris(dimethylamino)phosphonium hexafluorophosphate (146 mg, 0.000330 mol) in N, N-dimethylformamide (0.44 mL, 0.0057 mol) was added N, N-diisopropylethylamine (0.115 mL, 0.000660 mol) at rt. The mixture was stirred at rt overnight, then quenched with aq. sodium bicarbonate. After seperation of the organic layers, the aq. layer was extracted with EtOAc. The combined organic layers were washed with brine, dried, and concentrated to dry. The crude material was used directly in next step.

Part 4. (3S, 5S, 6S)-5-[(hydroxyamino)carbonyl]-6-[(4-phenyl-3,6-dihydropyridin-1(2H)-yl)carbonyl]piperidin-3-yl pyrrolidine-1-carboxylate: A mixture of N-hydroxyamine hydrochloride (1.20 g, 0.0173 mol) in 4.5 mL of methanol was heated to at 55 Celsius. Sodium methoxide, 25 wt. % solution in methanol (5.925 mL, 0.06506 mol) was added. The resulting mixture was stirred at 55 Celsius for 5 min, then cooled to rt then at 0 Celsius. Filtered off insolubles afforded a clear solution assumed to be c.a. 1.64 M of hydroxyamine in MeOH. The solution was prepared and used fresh.

1.90 mL of the above prepared solution was added to a mixture of crude methyl(2S,3S,5S)-2-[(4-phenyl-3,6-dihydropyridin-1(2H)-yl)carbonyl]-5-[(pyrrolidin-1-ylcarbonyl)

oxy]piperidine-3-carboxylate (132.5 mg, 0.0003001 mol) in 1.43 mL of methanol. After stirred at rt for 1 h, the mixture was adjusted to pH7 with 1N HCl (c.a.1.9 mL). The resulting mixture was applied directly on RP-HPLC to afford the targeted product (65 mg, 39%). MS (ESI): (M+H)$^+$=443.2.

Example 205

(3S,5S,6S)-6-(1,3-dihydro-2H-benzo[e]isoindol-2-ylcarbonyl)-5-[(hydroxyamino)carbonyl]piperidin-3-yl azetidine-1-carboxylate This compound was prepared using procedures analogous to those for example 204. MS (ESI): (M+H)$^+$=439.2.

Example 206

(3S,5S,6S)-6-(1,3-dihydro-2H-isoindol-2-ylcarbonyl)-5-[(hydroxyamino)carbonyl]piperidin-3-yl azetidine-1-carboxylate This compound was prepared using procedures analogous to those for example 204. MS (ESI): (M+H)$^+$=389.2.

Example 207

(3S,5S,6S)-5-[(hydroxyamino)carbonyl]-6-[(4-phenyl-3,6-dihydropyridin-1(2H)-yl)carbonyl]piperidin-3-yl azetidine-1-carboxylate This compound was prepared using procedures analogous to those for example 204. MS (ESI): (M+H)$^+$=429.2.

Example 208

(3S,5S,6S)-5-[(hydroxyamino)carbonyl]-6-[(3R)-3-phenylpyrrolidin-1-yl]carbonylpiperidin-3-yl azetidine-1-carboxylate This compound was prepared using procedures analogous to those for example 204. MS (ESI): (M+H)$^+$=417.2.

Example 209

(3S,5S,6S)-5-[(hydroxyamino)carbonyl]-6-[(4-phenylpiperazin-1-yl)carbonyl]piperidin-3-yl azetidine-1-carboxylate This compound was prepared using procedures analogous to those for example 204. MS (ESI): (M+H)$^+$=432.2.

Example 210

(3S,5S,6S)-5-[(hydroxyamino)carbonyl]-6-[(3-phenyl-2,5-dihydro-1H-pyrrol-1-yl)carbonyl]piperidin-3-yl azetidine-1-carboxylate This compound was prepared using procedures analogous to those for example 204. MS (ESI): (M+H)$^+$=415.2.

Example 211

(3S,5S,6S)-5-[(hydroxyamino)carbonyl]-6-[(4-phenylpiperidin-1-yl)carbonyl]piperidin-3-yl azetidine-1-carboxylate This compound was prepared using procedures analogous to those for example 191. MS (ESI): (M+H)$^+$=431.3.

Example 212

(3S,5S,6S)-5-[(hydroxyamino)carbonyl]-6-[(4-phenylpiperidin-1-yl)carbonyl]piperidin-3-yl pyrrolidine-1-carboxylate This compound was prepared using procedures analogous to those for example 191. MS (ESI): (M+H)$^+$=445.2.

Example 213

Methyl(2S,3S,5S)-3-[(hydroxyamino)carbonyl]-5-(2-oxo-2-pyrrolidin-1-ylethoxy)-2-[(4-phenylpiperazin-1-yl)carbonyl]piperidine-1-carboxylate Part 1. dimethyl(2S,3S,5S)-5-(2-tert-butoxy-2-oxoethoxy)-2-[(4-phenylpiperazin-1-yl)carbonyl]piperidine-1,3-dicarboxylate: To a solution of dimethyl(2S,3S,5S)-5-hydroxy-2-[(4-phenylpiperazin-1-yl)carbonyl]piperidine-1,3-dicarboxylate (50.0 mg, 0.000123 mol) in tetrahydrofuran (0.50 mL, 0.0062 mol) was added 1.00 M of potassium tert-butoxide in tetrahydrofuran (0.150 mL). After stirred at rt for 30 min, to the mixture was added bromo-acetic acid 1,1-dimethylethyl ester (0.0228 mL, 0.000154 mol). The resulting mixture was stirred at rt overnight and then concentrated to dry.

Part 2. ((3S, 5S, 6S)-1,5-bis(methoxycarbonyl)-6-[(4-phenylpiperazin-1-yl)carbonyl]piperidin-3-yloxy)acetic acid: The crude mixture made above was treated with 1 mL of TFA at rt for 30 min. After concentrated to dry, the crude residue was used directly in next step.

Part 3. dimethyl(2S, 3S, 5S)-5-(2-oxo-2-pyrrolidin-1-ylethoxy)-2-[(4-phenylpiperazin-1-yl)carbonyl]piperidine-1,3-dicarboxylate: To a mixture of ((3S,5S,6S)-1,5-bis(methoxycarbonyl)-6-[(4-phenylpiperazin-1-yl)carbonyl]piperidin-3-yloxy)acetic acid (57 mg, 0.00012 mol), pyrrolidine (0.0308 mL, 0.000369 mol), and benzotriazol-1-yloxytris(dimethylamino)phosphonium hexafluorophosphate (163 mg, 0.000369 mol) in N, N-dimethylformamide (0.50 mL, 0.0064 mol) was added N, N-diisopropylethylamine (0.0857 mL, 0.000492 mol). The mixture was stirred at rt for 2 h, then diluted with ethyl acetate, washed with water, brine and dired. After concentrated to dry, the residue was used directly in next step.

Part 4. methyl(2S, 3S, 5S)-3-[(hydroxyamino)carbonyl]-5-(2-oxo-2-pyrrolidin-1-ylethoxy)-2-[(4-phenylpiperazin-1-yl)carbonyl]piperidine-1-carboxylate: To the reaction mixture of dimethyl(2S,3S,5S)-5-(2-oxo-2-pyrrolidin-1-ylethoxy)-2-[(4-phenylpiperazin-1-yl)carbonyl]piperidine-1,3-dicarboxylate (64 mg, 0.00012 mol) in methanol (0.5018 mL, 0.01239 mol) was added 1.640 M of N-hydroxamine in methanol solution (1.51 mL) made from the corresponding salt and sodium methoxide. After stirred at rt for 1 h, the mixture was acidified with 1N HCl. The resultant mixture was applied directly on RP-HPLC to afford the product as a TFA salt (14 mg, 18%). MS (ESI): (M+H)$^+$=518.2.

Example 214

Methyl(2S,3S,5S)-3-[(hydroxyamino)carbonyl]-2-[(4-phenylpiperazin-1-yl)carbonyl]-5-(phenylthio)piperidine-1-carboxylate Part 1. dimethyl(2S,3S,5R)-5-[(methylsulfonyl)oxy]-2-[(4-phenylpiperazin-1-yl)carbonyl]piperidine-1,3-dicarboxylate: To a stirred solution of dimethyl(2S,3S,5R)-5-hydroxy-2-[(4-phenylpiperazin-1-yl)carbonyl]piperidine-1,3-dicarboxylate (1.00 g, 0.00247 mol) and triethylamine (0.412 mL, 0.00296 mol) in methylene chloride (20.00 mL, 0.3120 mol) was added methanesulfonyl chloride (0.210 mL, 0.00271 mol). The mixture was stirred at rt overnight. After quenched with MeOH, the mixture was evaporated to dry in vacuo and diluted with ethyl acetate. The organic layers were washed with water, brine and dried, concentrated to dry. The rsidue was purified on silica gel, eluting with 0 to 80% EtOAc in hexane, to generate the mesylate compound (0.98 g, 82%). MS (ESI): $(M+H)^+=484.1$.

Part 2. dimethyl(2S,3S,5S)-2-[(4-phenylpiperazin-1-yl)carbonyl]-5-(phenylthio)piperidine-1,3-dicarboxylate: To a mixture of dimethyl(2S,3S,5R)-5-[(methylsulfonyl)oxy]-2-[(4-phenylpiperazin-1-yl)carbonyl]piperidine-1,3-dicarboxylate (50.0 mg, 0.000103 mol) and benzenethiol (0.0149 mL, 0.000145 mol) in tetrahydrofuran (0.50 mL, 0.0062 mol) was added 1.00 M of potassium tert-butoxide in tetrahydrofuran (0.150 mL). The mixture was stirred at rt overnight. The reaction mixture was carried directly into next step.

Part 3. methyl(2S, 3S, 5S)-3-[(hydroxyamino)carbonyl]-2-[(4-phenylpiperazin-1-yl)carbonyl]-5-[(phenylthio)piperidine-1-carboxylate: To the reaction mixture of dimethyl (2S,3S,5S)-2-[(4-phenylpiperazin-1-yl)carbonyl]-5-(phenylthio)piperidine-1,3-dicarboxylate (51 mg, 0.00010 mol) in tetrahydrofuran (0.50 mL, 0.0062 mol) was added 1.640 M of N-hydroxyamine in methanol (1.25 mL) made from the corresponding salt and sodium methoxide. After stirred at rt for 1 h, the mixture was acidified with 1N HCl. The resultant mixture was applied directly on RP-HPLC to afford the product as a TFA salt (39 mg, 63%). MS (ESI): $(M+H)^+=499.1$.

Example 215

Methyl(2S,3S,5S)-5-(allyloxy)-3-[(hydroxyamino)carbonyl]-2-[(4-phenylpiperazin-1-yl)carbonyl]piperidine-1-carboxylate Part 1. dimethyl(2S, 3S, 5S)-5-[(allyloxy)carbonyl]oxy-2-[(4-phenylpiperazin-1-yl)carbonyl]piperidine-1,3-dicarboxylate: To a solution of dimethyl(2S,3S,5S)-5-hydroxy-2-[(4-phenylpiperazin-1-yl)carbonyl]piperidine-1,3-dicarboxylate (0.1000 g, 0.0002466 mol) in methylene chloride (1.00 mL, 0.0156 mol) was added triethylamine (0.04469 mL, 0.0003206 mol), catalytic amount of DAMP, followed by allyl chloroformate (0.03146 mL, 0.0002960 mol). The mixture was stirred at rt overnight, then quenched with aq. sodium bicarbonate and extracted with methylene chloride. The combined organic layers were dried and concentrated to dry. The residue was purified on column, eluting with 0 to 100% EtOAc in hexane, to yield the corresponding carbonate (0.11 g, 91%). MS (ESI): $(M+H)^+=490.2$.

Part 2. dimethyl(2S, 3S,5S)-5-(allyloxy)-2-[(4-phenylpiperazin-1-yl)carbonyl]piperidine-1,3-dicarboxylate: A mixture of dimethyl(2S,3S,5S)-5-[(allyloxy)carbonyl]oxy-2-[(4-phenylpiperazin-1-yl)carbonyl]piperidine-1,3-dicarboxylate (100 mg, 0.0002 mol) and tetrakis(triphenylphosphine)palladium(0) (24 mg, 0.000020 mol) in tetrahydrofuran (5.00 mL, 0.0616 mol) was refluxed for 2 h. The mixture was concentrated to dry and used directly in next step.

Part 3. methyl(2S, 3S, 5S)-5-(allyloxy)-3-[(hydroxyamino)carbonyl]-2-[(4-phenylpiperazin-1-yl)carbonyl]piperidine-1-carboxylate: To a solution of dimethyl(2S,3S,5S)-5-(allyloxy)-2-[(4-phenylpiperazin-1-yl)carbonyl]piperidine-1,3-dicarboxylate (80 mg, 0.0002 mol) in methanol (0.79 mL, 0.020 mol) was added 1.640 M of N-hydroxyamine in Methanol (2 mL), made by treatment of the corresponding hydroxylamine HCl salt with sodium methoxide. The mixture was stirred at rt for 1 h, then acidified with 1N HCl and applied on RP-HPLC directly to give the titled compound as a TFA salt (23 mg, 23%). MS (ESI): $(M+H)^+=447.1$.

Example 216

Methyl(2S,3S,5S)-3-[(hydroxyamino)carbonyl]-2-[(4-phenylpiperazin-1-yl)carbonyl]-5-propoxypiperidine-1-carboxylate This compound was prepared using procedures analogous to those for example 191. MS (ESI): $(M+H)^+=449.2$.

Example 217

Methyl(2S,3S,5S)-3-[(hydroxyamino)carbonyl]-5-methoxy-2-[(4-phenylpiperazin-1-yl)carbonyl]piperidine-1-carboxylate Part 1. 2-benzyl 3-methyl(2S, 3S, 5S)-1-benzyl-5-methoxypiperidine-2,3-dicarboxylate: Diazomethane was generated (from 5 g of Diazald) and distilled together with ether into a mixture of 2-benzyl 3-methyl(2S,3S,5S)-1-benzyl-5-hydroxypiperidine-2,3-dicarboxylate (0.60 g, 0.0016 mol) and around 1 g of silica gel in 10 mL of ether. After distillation, the mixture was stirred at rt overnight. The mixture was diluted with methylene chloride, filtered to remove silica gel. The filtration was concentrated to dry and the resulting residue was applied on column, eluting with 0 to 40% EtOAc in Hexane, to yield the methyl ether compound (20 mg, 3.2%). MS (ESI): $(M+H)^+=398.1$.

Part 2. (2S,3S,5S)-5-methoxy-3-(methoxycarbonyl)piperidine-2-carboxylic acid: A solution of 2-benzyl 3-methyl (2S,3S,5S)-1-benzyl-5-methoxypiperidine-2,3-dicarboxylate (30.0 mg, 0.0000755 mol) in 2 mL of MeOH was hydrogenated in the presence of 10% Pd/C, under a balloon pressure of hydrogen, for 1 h. The catalyst was filtered off and the filtration was concentrated to dry. The residue was used directly in next step (16 mg, 97.6%). MS (ESI): $(M+H)^+=218.0$.

Part 3. methyl(2S, 3S, 5S)-5-methoxy-2-[(4-phenylpiperazin-1-yl)carbonyl]piperidine-3-carboxylate: To a mixture of (2S,3S,5S)-5-methoxy-3-(methoxycarbonyl)piperidine-2-carboxylic acid (14.0 mg, 0.0000644 mol), 1-phenyl-piperazine (0.01231 mL, 8.056E-5 mol) and benzotriazol-1-yloxy-tris(dimethylamino)phosphonium hexafluorophosphate (35.63 mg, 8.056E-5 mol) in N, N-dimethylformamide (0.20 mL, 0.0026 mol) was added N, N-diisopropylethylamine (0.01403 mL, 8.056E-5 mol). The mixture was stirred at rt for 2 h. After quenched with water, the mixture was extracted with ethyl acetate. The combine organic lyers were washed with brine, dried and concentrated to dry. The residue was used directly in next step without further purification. MS (ESI): $(M+H)^+=362.1$.

Part 4. dimethyl(2S, 3S, 5S)-5-methoxy-2-[(4-phenylpiperazin-1-yl)carbonyl]piperidine-1,3-dicarboxylate: To a mixture of methyl(2S,3S,5S)-5-methoxy-2-[(4-phenylpiperazin-1-yl)carbonyl]piperidine-3-carboxylate (0.0233 g, 0.0000645 mol) and 4-dimethylaminopyridine (0.0118 g, 0.0000967 mol) in methylene chloride (1.00 mL, 0.0156 mol) was added methyl chloroformate (0.00648 mL, 0.0000838 mol). The reaction was stirred at rt overnight. After quenched with aq. sodium bicaronate, the reaction was extracted with ethyl acetate. The combined organic layers were washed with brine, dried, concentrated to dry. The resulting residue was used directly in next step. MS (ESI): (M+H)$^+$=420.2.

Part 5. methyl(2S,3S,5S)-3-[(hydroxyamino)carbonyl]-5-methoxy-2-[(4-phenylpiperazin-1-yl)carbonyl]piperidine-1-carboxylate: To a solution of dimethyl(2S,3S,5S)-5-methoxy-2-[(4-phenylpiperazin-1-yl)carbonyl]piperidine-1,3-dicarboxylate (0.027 g, 0.000064 mol) in methanol (0.30 mL, 0.0074 mol) was added 1.640 M of N-hydroxyamine in methanol (0.7850 mL), freshly made from the corresponding hydroxylamine HCl salt and sodium methoxide. The mixture was stirred at rt for 1 h, then acidified with 1N HCl. The crude mixture was applied directly on RP-HPLC to afford the product as a TFA salt (23 mg, 68%). MS (ESI): (M+H)$^+$=421.2.

Example 218

(2S,3S,5S)-5-tert-butoxy-N-hydroxy-2-[(4-phenylpiperazin-1-yl)carbonylpiperidine-3-carboxamide Part 1. 2-benzyl 3-methyl(2S, 3S, 5S)-1-benzyl-5-tert-butoxypiperidine-2,3-dicarboxylate: Isobutylene (2.96 mL, 0.0313 mol) was collected at –78 Celsius. To the cold isobutylene was added 2-benzyl 3-methyl(2S,3S,5S)-1-benzyl-5-hydroxypiperidine-2,3-dicarboxylate (0.60 g, 0.0016 mol) tetrahydrofuran (3.00 mL, 0.0370 mol), sulfuric acid (0.021 mL, 0.00039 mol). The reaction was sealed and allowed to warm up to rt and stirred at rt overnight. The mixture was cooled to –78 Celsius again. The seal was replaced with a septa connecting with a balloon. The reaction was then allowed to warm up to rt gradually to allow the evaporating of excess isobutylene. The residue was diluted with EtOAc, neutralized with aq. sodium hydroxide. The organic layers were washed with brine, dried. The residue was purified on silica gel, eluting with 0 to 30% EtOAc in hexane, to afford the tert-butyl ether (0.35 g, 51%). MS (ESI): (M+H)$^+$= 440.25.

Part 2. (2S,3S,5S)-5-tert-butoxy-3-(methoxycarbonyl)piperidine-2-carboxylic acid: A solution of 2-benzyl 3-methyl (2S,3S,5S)-1-benzyl-5-tert-butoxypiperidine-2,3-dicarboxylate (80.0 mg, 0.000182 mol) in 5 mL of MeOH was hydrogenated in the presence of 10% Pd/C, under a balloon pressure of hydrogen, overnight. After filter off the catalyst, the filtration was concentrated to dry and used directly in next step (43 mg, 91.1%). MS (ESI): (M+H)$^+$=260.1.

Part 3. methyl(2S, 3S, 5S)-5-tert-butoxy-2-[(4-phenylpiperazin-1-yl)carbonyl]piperidine-3-carboxylate: To a mixture of (2S,3S,5S)-5-tert-butoxy-3-(methoxycarbonyl)piperidine-2-carboxylic acid (43.0 mg, 0.000166 mol), 1-phenylpiperazine (0.03166 mL, 0.0002073 mol) and benzotriazol-1-yloxytris(dimethylamino)phosphonium hexafluorophosphate (0.09168 g, 0.0002073 mol) in N,N-dimethylformamide (0.40 mL, 0.0052 mol) was added N,N-diisopropylethylamine (0.03611 mL, 0.0002073 mol). The reaction was stirred at rt for 2 h, then quenched with water. The mixture was extracted with ethyl acetate. The combined organic layers were washed with brine, dried and concentrated to dry. The residue was used directly in next step. MS (ESI): (M+H)$^+$=404.2.

Part 4. (2S, 3S, 5S)-5-tert-butoxy-N-hydroxy-2-[(4-phenylpiperazin-1-yl)carbonyl]piperidine-3-carboxamide (3a): To a solution of methyl(2S,3S,5S)-5-tert-butoxy-2-[(4-phenylpiperazin-1-yl)carbonyl]piperidine-3-carboxylate (0.03345 g, 8.290E-5 mol) in Methanol (0.30 mL, 0.0074 mol) was added 1.640 M of N-hydroxyamine in Methanol (1.011 mL), freshly made from the corresponding HCl salt and sodium methoxide. The mixture was stirred at rt for 1 h then acidified with 1N HCl. The resulting mixture was applied directly on RP-HPLC to provide the product as TFA salt (21 mg, 49%). MS (ESI): (M+H)$^+$=405.1.

Example 219

Methyl(2S,3S,5S)-5-tert-butoxy-3-[(hydroxyamino) carbonyl]-2-[(4-phenylpiperazin-1-yl)carbonyl]piperidine-1-carboxylate Part 1. dimethyl(2S,3S,5S)-5-tert-butoxy-2-[(4-phenylpiperazin-1-yl)carbonyl]piperidine-1,3-dicarboxylate: To a mixture of methyl(2S,3S,5S)-5-tert-butoxy-2-[(4-phenylpiperazin-1-yl)carbonyl]piperidine-3-carboxylate (0.03345 g, 8.290E-5 mol) and 4-dimethylaminopyridine (0.0152 g, 0.000124 mol) in methylene chloride (1.50 mL, 0.0234 mol) was added methyl chloroformate (0.00833 mL, 0.000108 mol). The reaction was stirred at rt overnight. After quenched with aq. sodium bicaronate, the reaction was extracted with ethyl acetate. The combined organic layers were washed with brine, dried, concentrated to dry. The resulting residue was used directly in next step. MS (ESI): (M+H)$^+$=462.2.

Part 2. methyl(2S, 3S, 5S)-5-tert-butoxy-3-[(hydroxyamino)carbonyl]-2-[(4-phenylpiperazin-1-yl)carbonyl]piperidine-1-carboxylate: To a solution of dimethyl(2S, 3S,5S)-5-tert-butoxy-2-[(4-phenylpiperazin-1-yl)carbonyl]piperidine-1,3-dicarboxylate (0.038 g, 0.000082 mol) in methanol (0.30 mL, 0.0074 mol) was added 1.640 M of N-hydroxyamine in methanol (1.004 mL), freshly made from the corresponding hydroxylamine HCl salt and sodium methoxide. The mixture was stirred at rt for 1 h then acidified with 1N HCl. The resulting mixture was applied directly on RP-HPLC to give the targeted product as a TFA salt (10 mg, 45%). MS (ESI): (M+H)$^+$=463.2.

Example 220

(3R,4S)-1-[(E)-(cyanoimino)(pyrrolidin-1-yl)methyl]-N-hydroxy-4-[(3R)-3-phenylpyrrolidin-1-yl] carbonylpiperidine-3-carboxamide Part 1. methyl(3R,4S)-]-[(Z)-(cyanoimino)(phenoxy)methyl]-4-[(3R)-3-phenylpyrrolidin-1-yl]carbonylpiperidine-3-carboxylate: To a stirred solution of (3R,4S)-4-((R)-3-Phenyl-pyrrolidine-1-carbonyl)-piperidine-3-carboxylic acid methyl ester (654 mg, 0.00207 mol) in anhydrous acetonitrile (11.0 mL, 0.211 mol) at rt was added triethylamine (0.579 mL, 0.00413 mol) and diphenyl cyanocarbonimidate (762 mg, 0.00310 mol). The reaction mixture was heated to reflux (oil bath temperature: 85° C.) for 18 h. The reaction mixture was concentrated in vacuo. The residue was purified by Combiflash with 40-90% EtOAc/Hex to give the product as a colorless solid (841 mg, 88% in yield). MS (ESI): (M+H)$^+$= 461.1.

Part 2. (3R,4S)-1-[(E)-Cyanoimino]-pyrrolidin-]-yl-methyl-4-((R)-3-phenyl-pyrrolidine-1-carbonyl)-piperidine-3-carboxylic acid methyl ester: To a stirred solution of methyl (3R,4S)-1-[(Z)-(cyanoimino)(phenoxy)methyl]-4-[(3R)-3-phenylpyrrolidin-1-yl]carbonylpiperidine-3-carboxylate (112 mg, 0.000243 mol) in anhydrous isopropyl alcohol (3.00 mL, 0.0392 mol) was added pyrrolidine (61.5 uL, 0.000730 mol). The reaction mixture was heated to reflux (oil bath temperature: 85° C.) for 18 h. The reaction mixture was concentrated in vacuo. The residue was purified by Combiflash with 0-5% MeOH/CH$_2$Cl$_2$ to give the product as a colorless solid (90 mg, 85% in yield). MS (ESI): (M+H)$^+$=438.2.

Part 3. (3R, 4S)-1-[(E)-(cyanoimino)(pyrrolidin-1-yl)methyl]-N-hydroxy-4-[(3R)-3-phenylpyrrolidin-1-yl]carbonylpiperidine-3-carboxamide: Preparation of 1.50 M NH$_2$OH/NaOMe in MeOH: To a stirred suspension of hydroxylamine hydrochloride (2.106 g, 0.03000 mol) in anhydrous methanol (9.0 mL) at rt was added 4.37 M of sodium methoxide in methanol (10.3 mL). The reaction mixture was heated at 55° C. for 5 min, cooled to rt, then to 0° C. Filtration afforded a clear solution assumed to be ca. 1.50 M in methanol.

To a stirred solution of (3R,4S)-1-[(E)-cyanoimino]-pyrrolidin-1-yl-methyl-4-((R)-3-phenyl-pyrrolidine-1-carbonyl)-piperidine-3-carboxylic acid methyl ester (90.0 mg, 0.000206 mol) in anhydrous methanol (1.5 mL, 0.037 mol) at rt was added the above 1.50 M of Hydroxylamine in methanol (2.74 mL). The reaction mixture was stirred at rt for 1 h 15 min. LCMS showed the reaction was done. The reaction was quenched with saturated aqueous NH$_4$Cl (20 mL), extracted with EtOAc (2×). The combined organic layers were washed with brine, dried over sodium sulfate, filtered and concentrated in vacuo. The residue was purified by reverse phase HPLC with 5-95% MeCN/H$_2$O (0.05% NH$_4$OH) to give the pure product as a colorless solid (57.2 mg, 63% in yield). MS (ESI): (M+H)$^+$=439.2.

Example 221

(3R,4S)-1-[(E)-azetidin-1-yl(cyanoimino)methyl]-N-hydroxy-4-[(3R)-3-phenylpyrrolidin-1-yl]carbonylpiperidine-3-carboxamide The titled compound was prepared using procedures analogous to those in Example 220. MS (ESI): (M+H)$^+$=425.2.

Example 222

(3R,4S)-1-[(E)-(cyanoimino)(dimethylamino)methyl]-N-hydroxy-4-[(3R)-3-phenylpyrrolidin-1-yl]carbonylpiperidine-3-carboxamide The titled compound was prepared using procedures analogous to those in Example 220. MS (ESI): (M+H)$^+$=413.2.

Example 223

(3R,4S)-1-[(E)-(cyanoimino)(cyclopropylamino)methyl]-N-hydroxy-4-[(3R)-3-phenylpyrrolidin-1-yl]carbonylpiperidine-3-carboxamide The titled compound was prepared using procedures analogous to those in Example 220. MS (ESI): (M+H)$^+$=425.2.

Example 224

(3R,4S)-1-[(E)-(cyanoimino)(piperidin-1-yl)methyl]-N-hydroxy-4-[(3R)-3-phenylpyrrolidin-1-yl]carbonylpiperidine-3-carboxamide The titled compound was prepared using procedures analogous to those in Example 220. MS (ESI): (M+H)$^+$=453.3.

Example 225

(3R,4S)-1-[(Z)-(cyanoimino)(morpholin-4-yl)methyl]-N-hydroxy-4-[(3R)-3-phenylpyrrolidin-1-yl]carbonylpiperidine-3-carboxamide The titled compound was prepared using procedures analogous to those in Example 220. MS (ESI): (M+H)$^+$=455.3.

Example 226

(3R,4S)-1-[(Z)-(cyanoimino)(hydroxyamino)methyl]-N-hydroxy-4-[(3R)-3-phenylpyrrolidin-1-yl]carbonylpiperidine-3-carboxamide The titled compound was prepared using procedures analogous to those in Example 220. MS (ESI): (M+H)$^+$=401.2.

Example 227

(3R,4S)-1-[(E)-azepan-1-yl(cyanoimino)methyl]-N-hydroxy-4-[(3R)-3-phenylpyrrolidin-1-yl]carbonylpiperidine-3-carboxamide The titled compound was prepared using procedures analogous to those in Example 220. MS (ESI): (M+H)$^+$=467.3.

Example 228

(3R,4S)-1-[(Z)-(cyanoimino)(4-methylpiperazin-1-yl)methyl]-N-hydroxy-4-[(3R)-3-phenylpyrrolidin-1-yl]carbonylpiperidine-3-carboxamide The titled compound was prepared using procedures analogous to those in Example 220. MS (ESI): (M+H)$^+$=468.2.

Example 229

(3R,4S)-1-[(Z)-(cyanoimino)(thiomorpholin-4-yl)methyl]-N-hydroxy-4-[(3R)-3-phenylpyrrolidin-1-yl]carbonylpiperidine-3-carboxamide The titled compound was prepared using procedures analogous to those in Example 220. MS (ESI): (M+H)$^+$=471.1.

Example 230

(3R,4S)-1-[(E)-(cyanoimino)(4-methylpiperidin-1-yl)methyl]-N-hydroxy-4-[(3R)-3-phenylpyrrolidin-1-yl]carbonylpiperidine-3-carboxamide The titled compound was prepared using procedures analogous to those in Example 220. MS (ESI): (M+H)$^+$=467.2.

Example 231

(3R,4S)-1-[(Z)-(cyanoimino)(2,5-dihydro-1H-pyrrol-1-yl)methyl]-N-hydroxy-4-[(3R)-3-phenylpyrrolidin-1-yl]carbonylpiperidine-3-carboxamide The titled compound was prepared using procedures analogous to those in Example 220. MS (ESI): (M+H)$^+$=437.2.

Example 232

(3R,4S)-1-[(Z)-(cyanoimino)(1,3-dihydro-2H-isoindol-2-yl)methyl]-N-hydroxy-4-[(3R)-3-phenylpyrrolidin-1-yl]carbonylpiperidine-3-carboxamide The titled compound was prepared using procedures analogous to those in Example 220. MS (ESI): (M+H)$^+$=487.1.

Example 233

(3R,4S)-1-[(Z)-(cyanoimino)(3,4-dihydroisoquinolin-2(1H)-yl)methyl]-N-hydroxy-4-[(3R)-3-phenylpyrrolidin-1-yl]carbonylpiperidine-3-carboxamide The titled compound was prepared using procedures analogous to those in Example 220. MS (ESI): (M+H)$^+$=501.1.

Example 234

(3R,4S)-N-hydroxy-1-[(Z)-1-(hydroxyamino)-2-nitrovinyl]-4-[(3R)-3-phenylpyrrolidin-1-yl]carbonylpiperidine-3-carboxamide Part 1. methyl(3R,4S)-1-[(Z)-1-(methylthio)-2-nitrovinyl]-4-[(3R)-3-phenylpyrrolidin-1-yl]carbonylpiperidine-3-carboxylate: To a stirred solution of (3R,4S)-4-((R)-3-phenyl-pyrrolidine-1-carbonyl)-piperidine-3-carboxylic acid methyl ester (3.10E2 mg, 0.000980 mol) in anhydrous acetonitrile (9.8 mL, 0.19 mol) at rt was added triethylamine (274 uL, 0.00196 mol) and 1,1-bis(methylthio)-2-nitroethylene (248 mg, 0.00147 mol). The reaction mixture was heated to reflux (oil bath temperature: 85° C.) for 19 h. The reaction mixture was concentrated in vacuo. The residue was purified by Combiflash with 40-95% EtOAc/Hex to give the product as a yellow viscous oil (227 mg, 53% in yield). MS (ESI): (M+H)$^+$=434.1.

Part 2. methyl(3R, 4S)-1-[(E)-2-nitro-1-piperidin-1-ylvinyl]-4-[(3R)-3-phenylpyrrolidin-1-yl]carbonylpiperidine-3-carboxylate: To a stirred solution of methyl(3R,4S)-1-[(Z)-1-(methylthio)-2-nitrovinyl]-4-[(3R)-3-phenylpyrrolidin-1-yl]carbonylpiperidine-3-carboxylate (81.0 mg, 0.000187 mol) in ethanol (3.0 mL, 0.051 mol) was added piperidine (92.8 uL, 0.000934 mol). The reaction mixture was heated to reflux (oil bath temperature: 85° C.) for 17 h 45 min. The reaction mixture was concentrated in vacuo. The residue was purified by Combiflash with 0-8% MeOH/CH$_2$Cl$_2$ to give the product as a yellow solid (62 mg, 71% in yield). MS (ESI): (M+H)$^+$=471.1.

Part 3. (3R,4S)-N-hydroxy-1-[(Z)-1-(hydroxyamino)-2-nitrovinyl]-4-[(3R)-3-phenylpyrrolidin-1-yl]carbonylpiperidine-3-carboxamide: To a stirred solution of methyl (3R,4S)-1-[(E)-2-nitro-1-piperidin-1-ylvinyl]-4-[(3R)-3-phenylpyrrolidin-1-yl]carbonylpiperidine-3-carboxylate (62.0 mg, 0.000132 mol) in anhydrous methanol (1.0 mL, 0.025 mol) was added 1.50 M of hydroxylamine in Methanol (1.76 mL). The reaction mixture was stirred at rt for 2 h. The reaction was quenched with saturated aqueous NH$_4$Cl (20 mL), extracted with EtOAc (2×). The combined organic layers were washed with brine, dried over sodium sulfate, filtered and concentrated in vacuo. The residue was purified by reverse phase HPLC with 5-95% MeCN/H$_2$O to give the pure product as a colorless solid (14.3 mg, 26% in yield). MS (ESI): (M+Na)$^+$=442.2.

Example 235

(3R,4S)-1-[(E)-(cyanoimino)(piperidin-1-yl)methyl]-4-[4-(4-cyano-2-methylphenyl)piperazin-1-yl]carbonyl-N-hydroxypiperidine-3-carboxamide Part 1. 1-benzyl 3-methyl(3R,4S)-4-[4-(4-cyano-2-methylphenyl)piperazin-1-yl]carbonylpiperidine-1,3-dicarboxylate: To a stirred mixture of (3R,4S)-piperidine-1,3,4-tricarboxylic acid 1-benzyl ester 3-methyl ester (0.554 g, 0.00172 mol) in N, N-dimethylformamide (8.500 mL, 0.1098 mol) was added 3-methyl-4-piperazin-1-ylbenzonitrile dihydrochloride (0.6146 g, 0.002241 mol), (benzotriazol-1-yloxy)tripyrrolidinophosphonium hexafluorophosphate (1.017 g, 0.001896 mol), and, N, N-diisopropylethylamine (1.509 mL, 0.008620 mol). The reaction mixture was stirred overnight at room temp. Reaction quenched with KH$_2$PO4 (sat solution). Layers separated and aq layer extracted with ethyl acetate 3×. Organic layers were washed with brine and dried over magnesium sulfate. Filtered and concentrated. The residue was purified by Combiflash with 40-70% EtOAc/Hex to give the product (75% in yield). MS (ESI): (M+H)$^+$=505.

Part 2. methyl(3R,4S)-4-[4-(4-cyano-2-methylphenyl)piperazin-1-yl]carbonylpiperidine-3-carboxylate: To a solution of 1-benzyl 3-methyl(3R,4S)-4-[4-(4-cyano-2-methylphenyl)piperazin-1-yl]carbonylpiperidine-1,3-dicarboxylate (0.5265 g, 0.001043 mol) in methanol (11.00 mL, 0.2716 mol) was added 10% palladium (93.9 mg, 0.0000883 mol) on carbon at room temp. The reaction mixture was stirred under hydrogen balloon at 1 atm pressure overnight. After overnight stirring reaction mixture was filtered and concentrated to give the product in quantitative yield. MS (ESI): (M+H)$^+$=371.

Part 3. methyl(3R,4S)-1-[(Z)-(cyanoimino)(phenoxy)methyl]-4-[4-(4-cyano-2-methylphenyl)piperazin-1-yl]carbonylpiperidine-3-carboxylate: To a stirred solution of methyl (3R,4S)-4-[4-(4-cyano-2-methylphenyl)piperazin-1-yl]carbonylpiperidine-3-carboxylate (386.500 mg, 1.04334E-3 mol) in anhydrous acetonitrile (6.000 mL, 0.1149 mol) at rt was added triethylamine (0.2923 mL, 0.002087 mol) and diphenyl cyanocarbonimidate (384.4 mg, 0.001565 mol). The reaction mixture was heated to reflux (oil bath temperature: 85° C.) for 5 hrs. The reaction mixture was concentrated in vacuo. The residue was purified by Combiflash with 40-90% EtOAc/Hex to give the product (60% in yield). MS (ESI): (M+H)$^+$=515.

Part 4. methyl(3R, 4S)-1-[(E)-(cyanoimino)(piperidin-1-yl)methyl]-4-[4-(4-cyano-2-methylphenyl)piperazin-1-yl]carbonylpiperidine-3-carboxylate: To a stirred solution of methyl(3R,4S)-1-[(Z)-(cyanoimino)(phenoxy)methyl]-4-[4-(4-cyano-2-methylphenyl)piperazin-1-yl]carbonylpiperidine-3-carboxylate (52 mg, 0.00010 mol) in acetonitrile (2.006 mL, 0.03840 mol) was added piperidine (0.200 mL, 0.00202 mol). The reaction mixture refluxed (oil bath at 85 deg). Upon completion reaction mixture concentrated in vacuum. The residue was purified by combiflash using 0-5% methanol/dichloromethane to give the product (53.3 mg, 98% in yield). MS (ESI): (M+H)$^+$=506.

Part 5. (3R, 4S)-1-[(E)-(cyanoimino)(piperidin-1-yl)methyl]-4-[4-(4-cyano-2-methylphenyl)piperazin-1-yl]carbonyl-N-hydroxypiperidine-3-carboxamide: Preparation of 1.50 M NH$_2$OH/NaOMe in MeOH: To a stirred suspension of hydroxylamine hydrochloride (1.56573 g, 0.0223062 mol) in anhydrous methanol (6.0 mL) at rt was added 4.37 M of sodium methoxide in methanol (7.64 mL). The reaction mixture was heated at 55° C. for 5 min, cooled to rt, then to 0° C. Filtration afforded a clear solution assumed to be ca. 1.50 M in methanol.

To a stirred solution of methyl(3R,4S)-1-[(E)-(cyanoimino)(piperidin-1-yl)methyl]-4-[4-(4-cyano-2-methylphenyl)piperazin-1-yl]carbonylpiperidine-3-carboxylate (53.30 mg, 0.0001054 mol) in anhydrous methanol (1.110 mL, 0.02740 mol) at rt was added the above 1.50 M of hydroxylamine in methanol (1.40 mL). The reaction mixture was stirred at rt for 2 h. LCMS showed the reaction was done. The reaction was quenched with saturated aqueous NH$_4$Cl, extracted with EtOAc (2×). The combined organic layers were washed with brine, dried over sodium sulfate, filtered and concentrated in vacuo. The residue was purified by reverse phase HPLC with 5-95% MeCN/H$_2$O to give the product. MS (ESI): (M+H)$^+$=507.

Example 236

(3R,4S)-1-[(E)-(cyanoimino)(dimethylamino)methyl]-4-[4-(4-cyano-2-methylphenyl)piperazin-1-yl]carbonyl-N-hydroxypiperidine-3-carboxamide The titled compound was prepared using procedures analogous to those in Example 235. MS (ESI): (M+H)$^+$=467.

Example 237

(3R,4S)-1-[(E)-azepan-1-yl(cyanoimino)methyl]-4-[4-(4-cyano-2-methylphenyl)piperazin-1-yl]carbonyl-N-hydroxypiperidine-3-carboxamide The titled compound was prepared using procedures analogous to those in Example 235. MS (ESI): (M+H)$^+$=521.

Example 238

(3R,4S)-1-[(E)-(cyanoimino)(pyrrolidin-1-yl)methyl]-4-[4-(4-cyano-2-methylphenyl)piperazin-1-yl]carbonyl-N-hydroxypiperidine-3-carboxamide The titled compound was prepared using procedures analogous to those in Example 235. MS (ESI): (M+H)$^+$=493.

Example 239

(3R,4S)-1-[(E)-(cyanoimino)(cyclopropylamino)methyl]-4-[4-(4-cyano-2-methylphenyl)piperazin-1-yl]carbonyl-N-hydroxypiperidine-3-carboxamide The titled compound was prepared using procedures analogous to those in Example 235. MS (ESI): (M+H)$^+$=479.

Example 240

(3R,4S)-1-[(E)-azetidin-1-yl(cyanoimino)methyl]-4-[4-(4-cyano-2-methylphenyl)piperazin-1-yl]carbonyl-N-hydroxypiperidine-3-carboxamide The titled compound was prepared using procedures analogous to those in Example 235. MS (ESI): (M+H)$^+$=479.

Example 241

(1S,2S,5E)-5-benzylidene-N-hydroxy-2-[(4-phenylpiperazin-1-yl)carbonyl]cyclohexanecarboxamide trifluoroacetate (salt)

Part 1. methyl(1S, 2S)-5-oxo-2-[(4-phenylpiperazin-1-yl)carbonyl]cyclohexane-carboxylate: To a stirred solution of (1S,2S)-2-(methoxycarbonyl)-4-oxocyclohexanecarboxylic acid (1.014 g, 0.005065 mol) in anhydrous N, N-dimethylformamide (20.0 mL, 0.258 mol) at rt was added (benzotriazol-1-yloxy)tripyrrolidinophosphonium hexafluorophosphate (2.989 g, 0.005572 mol), 1-phenylpiperazine (1.17 mL, 0.00760 mol), followed by N,N-diisopropylethylamine (2.66 mL, 0.0152 mol). The reaction mixture was stirred at rt for 15 h. The reaction was quenched with water (40 mL), extracted with EtOAc (2×). The combined organic layers were washed with brine, dried over magnesium sulfate, filtered and concentrated in vacuo. The residue was purified by Combiflash with 40-70% EtOAc/Hex. to give the product as a colorless solid (1.299 g, 74% in yield). MS (ESI): (M+H)$^+$=345.1.

Part 2. methyl(1S, 2S, 5E)-5-benzylidene-2-[(4-phenylpiperazin-1-yl)carbonyl]-cyclohexanecarboxylate: To a suspension of benzyltriphenylphosphonium bromide (0.397 g, 0.000880 mol) in anhydrous THF (3.0 mL) at rt was added 1.00 M of sodium bis(trimethylsilyl)amide in tetrahydrofuran (0.880 mL) dropwise. The resulting orange suspension was stirred at rt for 1 h, a solution of methyl(1S,2S)-5-oxo-2-[(4-phenylpiperazin-1-yl)carbonyl]cyclohexanecarboxylate (202 mg, 0.000586 mol) in anhydrous THF (3.0 mL) was then added via cannula. The reaction mixture was stirred at rt for 18 h. The reaction was quenched with water (20 mL), extracted with EtOAc (2×). The combined organic layers were washed with brine, dried over sodium sulfate, filtered and concentrated in vacuo. The residue was purified by Combiflash with 20-60% EtOAc/Hex to give the product (141 mg, 57% in yield) as well as the S.M. (50 mg, 25% recovery of S.M.). MS (ESI): (M+H)$^+$=419.2.

Part 3. (1S, 2S, 5E)-5-benzylidene-N-hydroxy-2-[(4-phenylpiperazin-1-yl)carbonyl]-cyclohexanecarboxamide trifluoroacetate (salt): Preparation of 1.50 M NH$_2$OH/NaOMe in MeOH: To a stirred suspension of hydroxylamine hydrochloride (1.404 g, 0.02000 mol) in anhydrous methanol (6.0 mL) at rt was added 4.37 M of sodium methoxide in methanol (6.86 mL). The reaction mixture was heated at 55° C. for 5 min, cooled to rt, then to 0° C. Filtration afforded a clear solution assumed to be ca. 1.50 M in methanol.

To a stirred solution of methyl(1S,2S,5E)-5-benzylidene-2-[(4-phenylpiperazin-1-yl)carbonyl]cyclohexanecarboxylate (30.0 mg, 0.0000717 mol) in anhydrous tetrahydrofuran (2.0 mL, 0.025 mol) at rt was added the above 1.50 M of hydroxylamine in methanol (1.43 mL). The reaction mixture was stirred at rt for 17 h. The reaction was quenched with saturated aqueous NH4Cl (15 mL), extracted with EtOAc (2×). The combined organic layers were washed with brine, dried over sodium sulfate, filtered and concentrated in vacuo. The residue was purified by reverse phase HPLC with 5-95% MeCN/H$_2$O (with 0.05% TFA, pH=2.5) to give the pure product as a colorless solid (18.3 mg, 48% in yield). MS (ESI): (M+H)$^+$=420.1.

Example 242

(1S,2S,5E)-5-(cyclopropylmethylene)-N-hydroxy-2-[(4-phenylpiperazin-1-yl)carbonyl]cyclohexanecarboxamide trifluoroacetate (salt)

The titled compound was prepared using procedures analogous to those in Example 241. MS (ESI): (M+H)$^+$=384.1.

Example 243

(1S,2S,5S)-5-benzyl-N,5-dihydroxy-2-[(4-phenylpiperazin-1-yl)carbonyl]cyclohexanecarboxamide Part 1. (S, 2S, 5E)-5-benzylidene-2-[(4-phenylpiperazin-1-yl)carbonyl]cyclohexane-carboxylic acid: To a stirred solution of methyl(1S,2S,5E)-5-benzylidene-2-[(4-phenylpiperazin-1-yl)carbonyl]cyclohexanecarboxylate (116 mg, 0.000277 mol) in tetrahydrofuran (6.0 mL, 0.074 mol) at rt was added a solution of lithium hydroxide (102 mg, 0.00416 mol) in water (2.0 mL, 0.11 mol). The resulting cloudy solution was stirred at rt for 17 h. LCMS showed that there was only 40% conversion. The reaction mixture was cooled to 0°

C., hydrogen peroxide (0.113 mL, 0.00111 mol) was then added. The reaction mixture was stirred at 0° C. for 2 h. LCMS showed that there was little change. The reaction mixture was then stirred at rt over the weekend. LCMS showed the reaction was done. The reaction was quenched with 10% $Na_2S_2O_3$ (10 mL), acidified with 1 N HCl (5 mL) to pH=4, extracted with EtOAc (2×). The combined organic layers were washed with brine, dried over magnesium sulfate, filtered and concentrated in vacuo to give the desired product as a colorless solid. (112 mg, 100% in yield). MS (ESI): $(M+H)^+=405.1$.

Part 2. (1S, 2S, 5S)-5-[(S)-iodo(phenyl)methyl]-2-[4-(4-iodophenyl)piperazin-1-yl]carbonyl-6-oxabicyclo[3.2.1]octan-7-one: To a stirred solution of (1S,2S,5E)-5-benzylidene-2-[(4-phenylpiperazin-1-yl)carbonyl] cyclohexanecarboxylic acid (112 mg, 0.000277 mol) in methylene chloride (5.0 mL, 0.078 mol) at rt was added sodium bicarbonate (69.8 mg, 0.000831 mol) and Iodine (211 mg, 0.000831 mol). The reaction mixture was stirred at rt for 24 h. LCMS showed that the reaction was not done. Water (3.0 mL, 0.17 mol) was then added, the reaction mixture was stirred at rt for additional 18 h. The reaction was quenched with 10% $Na_2S_2O_3$ (20 mL), extracted with EtOAc (2×). The combined organic layers were washed with brine, dried over magnesium sulfate, filtered and concentrated in vacuo. The residue was purified by Combiflash with 20-60% EtOAc/Hex to give the desired product. (49.5 mg, 27% in yield). MS (ESI): $(M+H)^+=656.9$.

Part 3. (1S, 2S, 5S)-5-benzyl-2-[(4-phenylpiperazin-1-yl)carbonyl]-6-oxabicyclo[3.2.1]-octan-7-one: To a solution of (1S,2S,5S)-5-[(S)-iodo(phenyl)methyl]-2-[4-(4-iodophenyl)piperazin-1-yl]carbonyl-6-oxabicyclo[3.2.1]octan-7-one (49.0 mg, 0.0000747 mol) in ethyl acetate (5.0 mL, 0.051 mol) in a Parr bottle was added Calcium carbonate (15 mg, 0.00015 mol) and palladium (20 mg, 0.00002 mol) (as 10% Pd/C). The reaction mixture was stirred under hydrogen at 55 psi for 18 h. The reaction mixture was diluted with EtOAc, filtered through a pad of Celite and washed with EtOAc. The filtrate was concentrated in vacuo to give the crude product. (30 mg, 100% in yield). MS (ESI): $(M+H)^+=405.1$.

Part 4. (1S, 2S, 5S)-5-benzyl-N, 5-dihydroxy-2-[(4-phenylpiperazin-1-yl)carbonyl]-cyclohexanecarboxamide. Preparation of 1.50 M $NH_2OH$/NaOMe in MeOH: To a stirred suspension of hydroxylamine hydrochloride (1.404 g, 0.02000 mol) in anhydrous methanol (6.0 mL) at rt was added 4.37 M of sodium methoxide in methanol (6.86 mL). The reaction mixture was heated at 55° C. for 5 min, cooled to rt, then to 0° C. Filtration afforded a clear solution assumed to be ca. 1.50 M in methanol.

To a stirred solution of (1S,2S,5S)-5-benzyl-2-[(4-phenylpiperazin-1-yl)carbonyl]-6-oxabicyclo[3.2.1]-octan-7-one (8.0 mg, 0.020 mmol) in anhydrous methanol (1.0 mL, 0.025 mol) at rt was added 1.50 M of hydroxylamine in methanol (0.396 mL). The reaction mixture was stirred at rt for 3 h. The reaction was quenched with saturated aqueous $NH_4Cl$ (15 mL), extracted with EtOAc (2×). The combined organic layers were washed with brine, dried over sodium sulfate, filtered and concentrated in vacuo. The residue was purified by reverse phase HPLC with 5-95% MeCN/$H_2O$ (with 0.05% TFA) to give the pure product as a colorless solid (2.3 mg, 26% in yield). MS (ESI): $(M+H)^+=438.1$.

Example 244

(1S,2S,5R)-N,5-dihydroxy-5-phenyl-2-[(4-phenylpiperazin-1-yl)carbonyl]-cyclohexanecarboxamide trifluoroacetate (salt)

Part 1. methyl(1S,2S)-5-hydroxy-5-phenyl-2-[(4-phenylpiperazin-1-yl)carbonyl]-cyclohexanecarboxylate: To a stirred solution of methyl(1S,2S)-5-oxo-2-[(4-phenylpiperazin-1-yl)carbonyl]-cyclohexanecarboxylate (130.0 mg, 0.0003775 mol) in anhydrous tetrahydrofuran (4.0 mL, 0.049 mol) at −78° C. was added 1.00 M of phenylmagnesium bromide in tetrahydrofuran (0.755 mL). The reaction mixture was stirred at −78° C. for 1 h, then slowly warmed to −35° C. over 3 h. The reaction was quenched with saturated aqueous $NH_4Cl$ (20 mL), extracted with EtOAc (2×). The combined organic layers were washed with brine, dried over magnesium sulfate, filtered and concentrated in vacuo. The residue was purified by Combiflash with 30-80% EtOAc/Hex to give the product as a colorless solid. (123 mg, 62% in yield). MS (ESI): $(M+H)^+=423.1$.

Part 2. (1S, 2S, 5R)—N, 5-dihydroxy-5-phenyl-2-[(4-phenylpiperazin-1-yl)carbonyl]-cyclohexanecarboxamide trifluoroacetate (salt): Preparation of 1.50 M $NH_2OH$/NaOMe in MeOH: To a stirred suspension of hydroxylamine hydrochloride (1.404 g, 0.02000 mol) in anhydrous methanol (6.0 mL, 0.15 mol) at rt was added 4.37 M of sodium methoxide in methanol (6.86 mL). The reaction mixture was stirred at rt for 15 min. Filtration afforded a clear solution assumed to be ca. 1.50 M in methanol.

To a stirred solution of methyl(1S,2S,5R)-5-hydroxy-5-phenyl-2-[(4-phenylpiperazin-1-yl)carbonyl]cyclohexanecarboxylate (120.0 mg, 0.0002272 mol) in anhydrous tetrahydrofuran (1.0 mL, 0.012 mol) at rt was added 1.50 M of hydroxylamine in methanol (3.03 mL). The reaction mixture was stirred at rt for 3 h. The reaction was quenched with saturated aqueous NH4Cl (15 mL), extracted with EtOAc (2×). The combined organic layers were washed with brine, dried over sodium sulfate, filtered and concentrated in vacuo. The residue was purified by reverse phase HPLC with 5-95% MeCN/$H_2O$ (pH=2 with 0.05% TFA) to give the pure product as a colorless solid (69.2 mg, 56% in yield). MS (ESI): $(M+H)^+=424.1$.

Example 245

(1S,2S,5R)-5-benzyl-N,5-dihydroxy-2-[(4-phenylpiperazin-1-yl)carbonyl]-cyclohexanecarboxamide trifluoroacetate (salt)

The titled compound was prepared using procedures analogous to those in Example 244. MS (ESI): $(M+H)^+=438.1$.

Example 246

(1S,2S,5R)-N,5-dihydroxy-5-isopropyl-2-[(4-phenylpiperazin-1-yl)carbonyl]-cyclohexanecarboxamide trifluoroacetate (salt)

The titled compound was prepared using procedures analogous to those in Example 244. MS (ESI): $(M+H)^+=390.1$.

Example 247

(1S,2S,5R)-5-cyclopropyl-N,5-dihydroxy-2-[(4-phenylpiperazin-1-yl)carbonyl]-cyclohexanecarboxamide trifluoroacetate (salt)

The titled compound was prepared using procedures analogous to those in Example 244. MS (ESI): $(M+H)^+=388.1$.

Example 248

(2S,3S,5R)-2-[4-(4-cyano-2-methylphenyl)piperidin-1-yl]carbonyl-N-hydroxy-5-(2-oxo-2-pyrrolidin-1-ylethyl)piperidine-3-carboxamide The titled compound was prepared using procedures analogous to those in Example 11. MS (ESI): $(M+H)^+=482.1$.

Example 249

Isopropy(5S,6S)-5-[(hydroxyamino)carbonyl]-6-[(4-phenylpiperidin-1-yl)carbonyl]piperidin-3-ylmethylcarbamate The titled compound was prepared using procedures analogous to those in Example 11. MS (ESI): $(M+H)^+=447.1$.

Example 250

(1S,2S)-N-hydroxy-2-[(4-phenyl-3,6-dihydropyridin-1(2H)-yl)carbonyl]-5-(pyrrolidin-1-ylcarbonyl)cyclohexanecarboxamide Part 1. 1-tert-butyl 2-methyl(1S,2S,4S)-4-hydroxycyclohexane-1,2-dicarboxylate: tert-butyl (1 S,2S,5S)-7-oxo-6-oxabicyclo[3.2.1]octane-2-carboxylate (5.65 g, 25.0 mmol) was suspended in methanol (20 mL). To that suspension was added a 25 wt % solution of sodium methoxide in methanol (52 mL) and the reaction mixture was stirred at rt for 2 h. Then it was cooled into an ice-water bath and neutralized with a 4 M HCl solution to pH 6. After removing the volatiles, brine was added (50 mL) and the solution was extracted with ethyl acetate (3×40 mL). The combined organic layers were dried over MgSO$_4$, filtered and concentrated to provide the desired product (5.70 g, 88.4% yield). LCMS: m/z 281.1 (M+Na)$^+$.

Part 2. 1-tert-butyl 2-methyl(1S, 2S)-4-oxocyclohexane-1,2-dicarboxylate: The product from Part 1 (6.54 g, 25.3 mmol) was dissolved in acetone (65 mL) and cooled to 0° C. Chromium(VI)oxide (2.07 g, 20.7 mmol) was dissolved in water (6 mL) and to that was added sulfuric acid (1.74 mL) dropwise. The solution was cooled to 0° C. and added dropwise to the solution above over a period of 10 min. The reaction mixture was stirred at rt for 30 min. Then isopropanol (11 mL) was added and stirring was continued for extra 5 min. The reaction mixture was filtered thru a silica gel pad (elution with acetone). Following concentration, ether (60 mL) was added and the solution was washed successively with water (2×50 mL) and brine (50 mL). The organic phase was dried over MgSO$_4$, filtered and concentrated to provide the desired product as a white solid (5.75 g, 88.6% yield).

Part 3. 1-tert-butyl 2-methyl(1S,2S, 4E)-4-(methoxymethylene)cyclohexane-1,2-dicarboxylate: The product from Part 2 (2.00 g, 7.80 mmol) was dissolved in THF. Chloro(methoxymethyl)triphenylphosphorane (4.01 g, 11.7 mmol) was also dissolved in THF and cooled to 0° C. To that solution was added a 1.00 M solution of NaHMDS in THF (11.7 mL) and the reaction mixture was stirred for 15 min. This Witting reagent was added to the former solution at 0° C. over a period of 25 min. After stirring for 30 min, the reaction mixture was diluted with ethyl acetate (50 mL) and was washed successively with water (2×100 mL) and brine (1×100 mL). The organic phase was dried over MgSO$_4$, filtered and concentrated. The residue was flash chromatographed (silica, hexanes:EtOAc, 12:1 to 10:1 to 8:1 to 6:1) to provide the desired product as a yellow oil (1.43 g, 64.6% yield).

Part 4. 1-tert-butyl 2-methyl(1S,2S)-4-formylcyclohexane-1,2-dicarboxylate: The product from Part 3 (0.510 g, 1.79 mmol) was dissolved in acetonitrile (18.0 mL) and water (4.5 mL) and treated with mercury(II)acetate (2.29 g, 7.17 mmol). The heterogeneous reaction mixture was stirred at rt overnight. It was diluted with a saturated aqueous solution of potassium iodide and subsequently extracted with EtOAc. The organic phase was washed with brine, dried over MgSO$_4$, filtered and concentrated. The residue was flash chromatographed (silica, hexanes:EtOAc, 5:1 to 3:1 to 1:1) to provide the desired aldehyde (0.456 g, 94% yield) as a mixture of two isomers (equatorial:axial, 3.5:1, based on $^1$H NMR).

Part 5. (3S, 4S)-4-(tert-butoxycarbonyl)-3-(methoxycarbonyl)cyclohexanecarboxylic acid: The product from Part 4 (52 mg, 0.192 mmol) was dissolved in DMF (1.9 mL) and treated with oxone (118 mg, 0.192 mmol). The reaction mixture was stirred at rt for 4.5 h. It was diluted with a small volume of a 0.1 N HCl solution, followed by EtOAc and water. The layers were separated and the organic layer was dried over MgSO$_4$, filtered and concentrated to provide the desired product as yellow oil (52 mg, 94.4% yield). LCMS: m/z 309.0 (M+Na)$^+$.

Part 6. 1-tert-butyl 2-methyl(1S,2S)-4-(pyrrolidin-1-ylcarbonyl)cyclohexane-1,2-dicarboxylate: The product from Part 5 (0.265 g, 0.925 mmol) was dissolved in DMF (9.3 mL) and treated with BOP reagent (0.491 g, 1.11 mmol). After stirring for 10 min, pyrrolidine (81.1 µL, 0.971 mmol) was added followed by N, N-diisopropylethylamine (322 µL, 1.85 mmol). The reaction mixture was stirred at rt overnight. It was poured into a saturated aq. NaHCO$_3$ solution and extracted with EtOAc. The organic phase was washed with water (2×) and brine, dried over MgSO$_4$, filtered and concentrated. The residue was flash chromatographed (silica, hexanes:EtOAc, 5:1 to 4:1 to 3:1) to provide the desired product (0.265 g, 84.4% yield). LCMS: m/z 340.1 (M+H)$^+$.

Part 7. (1S,2S)-2-(methoxycarbonyl)-4-(pyrrolidin-1-ylcarbonyl)cyclohexanecarboxylic acid: The product from Part 6 (0.260 g, 0.766 mmol) was dissolved in dichloromethane (2.7 mL), cooled to 0° C. and treated with TFA (2.74 mL). The reaction mixture was stirred at rt for 2 h. Water was added followed by additional dichloromethane, and the layers were separated. The organic phase was dried over MgSO$_4$, filtered and concentrated. The residue was azeotroped with toluene (3×) and dried under high vacuum to provide the desired product (217 mg, 100% yield). LCMS: m/z 284.2 (M+H)$^+$.

Part 8. methyl(1S, 2S)-2-[(4-phenylpiperidin-1-yl)carbonyl]-5-(pyrrolidin-1-ylcarbonyl)cyclohexanecarboxylate: The product from Part 7 (0.112 g, 0.395 mmol) was dissolved in DMF (4.0 mL) and treated with BOP reagent (0.210 g, 0.474 mmol). After stirring for 10 min, the HCl salt of 4-phenyl-1,2,3,6-tetrahydropyridine (81 mg, 0.415 mmol) was added followed by N, N-diisopropylethylamine (206 µL, 1.18 mmol). The reaction mixture was stirred at rt overnight. It was poured into a saturated aq. NaHCO$_3$ solution and extracted with EtOAc. The organic phase was washed with water (2×) and brine, dried over MgSO$_4$, filtered and concentrated. The residue was flash chromatographed (silica, hexanes:EtOAc, 5:1 to 4:1 to 3:1) to provide the desired product (0.126 g, 79.7% yield). LCMS: m/z 425.2 (M+H)$^+$.

Part 9. (1S,2S)-N-hydroxy-2-[(4-phenyl-3,6-dihydropyridin-1(2H)-yl)carbonyl]-5-(pyrrolidin-1-ylcarbonyl)cyclohexanecarboxamide: The product from Part 8 (89 mg, 0.210 mmol) was dissolved in methanol (2.1 mL) and treated with a 1.5 M NH$_2$OH/NaOMe solution in methanol (2.8 mL). (Preparation of a 1.5 M NH$_2$OH/NaOMe solution in methanol: To a stirred suspension of hydroxylamine hydrochloride (1.404 g, 20.20 mmol) in anhydrous methanol (6 mL) at rt was added a 4.37 M solution of sodium methoxide in methanol (6.86 mL). The reaction mixture was heated at 55° C. for 5 min and then cooled to rt first and then to 0° C. Filtration thru a filter plug afforded a clear solution assumed to be ca. 1.50 M in methanol.) The reaction was monitored by LCMS and when complete was poured into a saturated NH$_4$Cl solution and extracted twice with EtOAc. The combined organic extracts were dried over MgSO$_4$, filtered and concentrated. The residue was purified by prep HPLC (reverse phase, 5% MeCN to 95% MeCN in 35 min, pH=2.5) to provide the desired hydroxamic acid (36 mg, 40.4% yield). LCMS: m/z 426.2 (M+H)$^+$.

Example 251

N-cyclopropyl-N-({(3S,4S)-3-[(hydroxyamino)carbonyl]-4-[(4-phenylpiperazin-1-yl)carbonyl]cyclohexyl}methyl)morpholine-4-carboxamide Part 1. 1-tert-butyl 2-methyl(1S, 2S)-4-[(cyclopropylamino)methyl]cyclohexane-1,2-dicarboxylate: The product from Example 250, Part 4 (174 mg, 0.644 mmol) and cyclopropylamine (35.6 mg, 0.611 mmol) were dissolved in methanol (6.0 mL). That solution was treated with acetic acid (0.209 mL) and sodium cyanoborohydride (38.4 mg, 0.611 mmol). The reaction mixture was stirred at rt overnight. It was concentrated, diluted with ethyl acetate and washed with a saturated NaHCO$_3$ solution. The organic layer was dried over MgSO$_4$, filtered and concentrated. The residue was flash chromatographed (silica, 5% to 6% to 10% MeOH/CH$_2$Cl$_2$) to provide the desired product as a colorless oil (131 mg, 68.8% yield). LCMS: m/z 312.2 (M+H)$^+$.

Part 2. 1-tert-butyl 2-methyl(1S,2S)-4-([cyclopropyl(morpholin-4-ylcarbonyl)amino]methyl}cyclohexane-1,2-dicarboxylate: The product from Part 1 (131 mg, 0.421 mmol) was dissolved in dichloromethane (4.2 mL) and cooled to 0° C. That solution was treated successively with N,N-diisopropylethylamine (0.146 mL, 0.841 mmol) and morpholine-4-carbonyl chloride (54 µL, 0.463 mmol). The reaction mixture was stirred at rt for 36 hrs. It was diluted with dichloromethane and poured into a 0.1 M HCl solution. The layers were separated and the organic phase was dried over MgSO$_4$, filtered and concentrated. The residue was flash chromatographed (silica, 2% MeOH/CH$_2$Cl$_2$) to provide the desired product as a colorless oil (0.148 g, 82.9% yield). LCMS: m/z 425.2 (M+H)$^+$.

Part 3. (1S,2S)-4-{([cyclopropyl(morpholin-4-ylcarbonyl)amino]methyl}-2-(methoxycarbonyl)cyclohexanecarboxylic acid: The procedure described in Example 250, Part 7 was followed to provide the desired carboxylic acid (0.124 g, 96.5% yield). LCMS: m/z 369.1 (M+H)$^+$.

Part 4. Methyl(1S, 2S)-5-{([cyclopropyl(morpholin-4-ylcarbonyl)amino]methyl}-2-[(4-phenylpiperazin-1-yl)carbonyl]cyclohexanecarboxylate: According to the procedure described in Example 250, Part 8 and using 1-phenylpiperazine, the desired product was obtained (0.140 g, 81.1% yield). LCMS: m/z 513.3 (M+H)$^+$.

Part 5. N-cyclopropyl-N-({(3S, 4S)-3-[(hydroxyamino)carbonyl]-4-[(4-phenylpiperazin-1-yl)carbonyl]cyclohexyl}methyl)morpholine-4-carboxamide: Using the procedure described in Example 250, Part 9, the desired product was obtained (56 mg, 46% yield). LCMS: m/z 514.3 (M+H)$^+$.

Example 252

(1S,2S, 5S)-N-hydroxy-2-[(4-phenylpiperazin-1-yl)carbonyl]-5-(piperidin-1-ylcarbonyl)cyclohexanecarboxamide This compound was prepared according to Example 250. LCMS: m/z 443.1 (M+H)$^+$.

Example 253

(1S,2S, 5R)-N-hydroxy-2-[(4-phenylpiperazin-1-yl)carbonyl]-5-(piperidin-1-ylcarbonyl)cyclohexanecarboxamide This compound was prepared according to Example 250. LCMS: m/z 443.1 (M+H)$^+$.

Example 254

(1S,2S, 5S)-N-hydroxy-2-[(4-phenylpiperazin-1-yl)carbonyl]-5-(pyrrolidin-1-ylcarbonyl)cyclohexanecarboxamide This compound was prepared according to Example 250. LCMS: m/z 429.1 (M+H)$^+$.

Example 255

(1S,2S, 5R)-N-hydroxy-2-[(4-phenylpiperazin-1-yl)carbonyl]-5-(pyrrolidin-1-ylcarbonyl)cyclohexanecarboxamide This compound was prepared according to Example 250. LCMS: m/z 429.1 (M+H)$^+$.

Example 256

(1S,2S)-N-hydroxy-5-(morpholin-4-ylcarbonyl)-2-[(4-phenylpiperazin-1-yl)carbonyl]cyclohexanecarboxamide It was prepared according to Example 250. LCMS: m/z 445.2 (M+H)$^+$.

Example 257

N-cyclopentyl-N-({(3S,4S, 5S)-3-[(hydroxyamino)carbonyl]-4-[(4-phenylpiperazin-1-yl)carbonyl]cyclohexyl}methyl)piperidine-1-carboxamide This compound was prepared according to Example 251. LCMS: m/z 540.2 (M+H)$^+$.

Example 258

N-cyclopentyl-N-({(3S,4S, 5R)-3-[(hydroxyamino)carbonyl]-4-[(4-phenylpiperazin-1-yl)carbonyl]cyclohexyl}methyl)piperidine-1-carboxamide This compound was prepared according to Example 251. LCMS: m/z 540.2 (M+H)$^+$.

Example 259

(1R,3S,4S)-3-[(hydroxyamino)carbonyl]-4-{[(3R)-3-phenylpyrrolidin-1-yl]carbonyl}cyclohexyl pyrrolidine-1-carboxylate This compound was prepared using procedures analogous to those for example 72. MS (ESI): (M+H)$^+$=430.1.

Example 260

(1R,3S,4S)-3-[(hydroxyamino)carbonyl]-4-[{(3R)-3-phenylpyrrolidin-1-yl]carbonyl}cyclohexyl dimethylcarbamate This compound was prepared using procedures analogous to those for example 72. MS (ESI): (M+H)$^+$=404.1.

Example 261

(1R,3S,4S)-3-[(hydroxyamino)carbonyl]-4-[(4-phenyl-3,6-dihydropyridin-1(2H)-yl)carbonyl]cyclohexyl Morpholine-4-carboxylate This compound was prepared using procedures analogous to those for example 72. MS (ESI): (M+H)$^+$=458.1.

Example 262

(1R,3S,4S)-3-[(hydroxyamino)carbonyl]-4-[(4-phenyl-3,6-dihydropyridin-1(2H)-yl)carbonyl]cyclohexyl Pyrrolidine-1-carboxylate This compound was prepared using procedures analogous to those for example 72. MS (ESI): (M+H)$^+$=442.1.

Example 263

(1R,3S,4S)-3-[(hydroxyamino)carbonyl]-4-[(4-phenyl-3,6-dihydropyridin-1(2H)-yl)carbonyl]cyclohexyl methylcarbamate This compound was prepared using procedures analogous to those for example 72. MS (ESI): (M+H)$^+$=402.1.

Example 264

(1R,3S,4S)-3-[(hydroxyamino)carbonyl]-4-[(4-phenyl-3,6-dihydropyridin-1(2H)-yl)carbonyl]cyclohexyl dimethylcarbamate This compound was prepared using procedures analogous to those for example 72. MS (ESI): (M+H)$^+$=416.1.

Example 265

(1S,2S,5R)-N,5-dihydroxy-2-{1[(3R)-3-phenylpyrrolidin-1-yl]carbonyl}cyclohexanecarboxamide This compound was prepared using procedures analogous to those for example 72. MS (ESI): (M+H)$^+$=333.1.

Example 266

(1S,3S,4S)-3-[(hydroxyamino)carbonyl]-4-[(4-phenyl-3,6-dihydropyridin-1 (2H)-yl)carbonyl]cyclohexyl dimethylcarbamate This compound was prepared using procedures analogous to those for example 72. MS (ESI): (M+H)$^+$=416.1.

Example 267

(1S,3S,4S)-3-[(hydroxyamino)carbonyl]-4-[(4-phenyl-3,6-dihydropyridin-1(2H)-yl)carbonyl]cyclohexyl pyrrolidine-1-carboxylate This compound was prepared using procedures analogous to those for example 72. MS (ESI): (M+H)$^+$=442.1.

Example 268

(1S,3S,4S)-3-[(hydroxyamino)carbonyl]-4-[(4-phenyl-3,6-dihydropyridin-1(2H)-yl)carbonyl]cyclohexyl methylcarbamate This compound was prepared using procedures analogous to those for example 72. MS (ESI): (M+H)$^+$=402.1.

Example 269

(1S,3S,4S)-3-[(hydroxyamino)carbonyl]-4-[(4-phenyl-3,6-dihydropyridin-1(2H)-yl)carbonyl]cyclohexyl morpholine-4-carboxylate This compound was prepared using procedures analogous to those for example 72. MS (ESI): (M+H)$^+$=458.1.

Example 270

(1R,3S,4S)-3-[(hydroxyamino)carbonyl]-4-{[(3R)-3-phenylpyrrolidin-1-yl]carbonyl}cyclohexyl methylcarbamate This compound was prepared using procedures analogous to those for example 72. MS (ESI): (M+H)$^+$=390.1.

Example 271

(1R,3S,4S)-3-[(hydroxyamino)carbonyl]-4-{[(3R)-3-phenylpyrrolidin-1-yl]carbonyl}cyclohexyl morpholine-4-carboxylate This compound was prepared using procedures analogous to those for example 72. MS (ESI): (M+H)$^+$=446.1.

Example 272

(1R,3S,4S)-3-[(hydroxyamino)carbonyl]-4-[(4-phenylpiperidin-1-yl)carbonyl]cyclohexyl pyrrolidine-1-carboxylate This compound was prepared using procedures analogous to those for example 72. MS (ESI): (M+H)$^+$=444.2.

Example 273

(1R,3S,4S)-3-[(hydroxyamino)carbonyl]-4-[(4-phenylpiperazin-1-yl)carbonyl]cyclohexyl piperidine-1-carboxylate This compound was prepared using procedures analogous to those for example 72. MS (ESI): (M+H)$^+$=459.2.

Example 274

(1R,3S,4S)-3-[(hydroxyamino)carbonyl]-4-[(4-phenylpiperazin-1-yl)carbonyl]cyclohexyl pyrrolidine-1-carboxylate This compound was prepared using procedures analogous to those for example 72. MS (ESI): $(M+H)^+=445.2$.

Example 275

(1R,3S,4S)-3-[(hydroxyamino)carbonyl]-4-[(4-phenylpiperazin-1-yl)carbonyl]cyclohexyl dimethylcarbamate This compound was prepared using procedures analogous to those for example 72. MS (ESI): $(M+H)^+=419.2$.

Example 276

(1R,3S,4S)-3-[(hydroxyamino)carbonyl]-4-[(4-phenylpiperazin-1-yl)carbonyl]cyclohexyl methylcarbamate This compound was prepared using procedures analogous to those for example 72. MS (ESI): $(M+H)^+=405.2$.

Example 277

(1R,3S,4S)-3-[(hydroxyamino)carbonyl]-4-[(4-phenyl-3,6-dihydropyridin-1(2H)-yl)carbonyl]cyclohexyl pyrrolidine-1-carboxylate This compound was prepared using procedures analogous to those for example 72. MS (ESI): $(M+H)^+=442.2$.

Example 278

(1R,3S,4S)-3-[(hydroxyamino)carbonyl]-4-[(4-phenyl-3,6-dihydropyridin-1(2H)-yl)carbonyl]cyclohexyl methylcarbamate This compound was prepared using procedures analogous to those for example 72. MS (ESI): $(M+H)^+=402.1$.

Example 279

(1R,3S,4S)-3-[(hydroxyamino)carbonyl]-4-[(4-phenyl-3,6-dihydropyridin-1(2H)-yl)carbonyl]cyclohexyl dimethylcarbamate This compound was prepared using procedures analogous to those for example 72. MS (ESI): $(M+H)^+=416.1$.

Example 280

(1R,3S,4S)-3-[(hydroxyamino)carbonyl]-4-[(4-phenylpiperidin-1-yl)carbonyl]cyclohexyl dimethylcarbamate This compound was prepared using procedures analogous to those for example 72. MS (ESI): $(M+H)^+=418.2$.

Example 281

(1R,3S,4S)-3-[(hydroxyamino)carbonyl]-4-[(4-phenylpiperidin-1-yl)carbonyl]cyclohexyl piperidine-1-carboxylate This compound was prepared using procedures analogous to those for example 72. MS (ESI): $(M+H)^+=458.2$.

Example 282

(1S,2S,5R)-N,5-dihydroxy-5-methyl-2-[(4-phenylpiperazin-1-yl)carbonyl]cyclohexanecarboxamide This compound was prepared using procedures analogous to those for example 243. MS (ESI): $(M+H)^+=362.1$.

Example 283

(1S,2S,5S)-N,5-dihydroxy-5-methyl-2-[(4-phenyl-3,6-dihydropyridin-1(2H)-yl)carbonyl]cyclohexanecarboxamide This compound was prepared using procedures analogous to those for example 243. MS (ESI): $(M+H)^+=359.1$.

Example 284

(1R,3R,4S)-3-[(hydroxyamino)carbonyl]-4-[(4-phenylpiperazin-1-yl)carbonyl]cyclohexyl (3R)-3-hydroxypyrrolidine-1-carboxylate This compound was prepared using procedures analogous to those for example 72. MS (ESI): $(M+H)^+=461.2$.

Example 285

N-{(1R,3S,4S)-3-[(hydroxyamino)carbonyl]-4-[(4-phenylpiperazin-1-yl)carbonyl]cyclohexyl}-azetidine-1-carboxylate This compound was prepared using procedures analogous to those for example 72. MS (ESI): $(M+H)^+=430.2$.

Example 286

(1R,3S,4S)-3-[(hydroxyamino)carbonyl]-4-[(4-phenylpiperazin-1-yl)carbonyl]cyclohexyl diethylcarbamate This compound was prepared using procedures analogous to those for example 72. MS (ESI): $(M+H)^+=447.2$.

Example 287

(1S,2S,5R)-5-allyl-N,5-dihydroxy-2-[(4-phenyl-3,6-dihydropyridin-1(2H)-yl)carbonyl]cyclohexanecarboxamide This compound was prepared using procedures analogous to those for example 243. MS (ESI): $(M+H)^+=385.2$.

Example 288

(1S,2S,5R)-5-allyl-N,5-dihydroxy-2-[(4-phenylpiperazin-1-yl)carbonyl]cyclohexanecarboxamide This compound was prepared using procedures analogous to those for example 243. MS (ESI): $(M+H)^+=388.2$.

Example 289

(1S,2S,5S)-5-allyl-N,5-dihydroxy-2-[(4-phenyl-3,6-dihydropyridin-1(2H)-yl)carbonyl]cyclohexanecarboxamide This compound was prepared using procedures analogous to those for example 243. MS (ESI): $(M+H)^+=385.2$.

Example 290

(1S,2S,5S)-5-allyl-N,5-dihydroxy-2-[(4-phenylpiperazin-1-yl)carbonyl]cyclohexanecarboxamide This compound was prepared using procedures analogous to those for example 243. MS (ESI): $(M+H)^+=388.2$.

Example 291

(1S,2S,5R)-N,5-dihydroxy-5-methyl-2-[(4-phenylpiperidin-1-yl)carbonyl]cyclohexanecarboxamide This compound was prepared using procedures analogous to those for example 243. MS (ESI): $(M+H)^+=361.2$.

Example 292

(1S,2S,5S)-N,5-dihydroxy-5-methyl-2-[(4-phenylpiperidin-1-yl)carbonyl]cyclohexanecarboxamide This compound was prepared using procedures analogous to those for example 243. MS (ESI): $(M+H)^+=361.2$.

Example 293

(1S,2S,5S)-N,5-dihydroxy-5-methyl-2-[(4-phenylpiperazin-1-yl)carbonyl]cyclohexanecarboxamide This compound was prepared using procedures analogous to those for example 243. MS (ESI): $(M+H)^+=362.2$.

Example 294

(1S,2S,5R)-N,5-dihydroxy-2-[(4-phenyl-3,6-dihydropyridin-1(2H)-yl)carbonyl]-5-propylcyclohexanecarboxamide This compound was prepared using procedures analogous to those for example 243.

Example 295

(1S,2S,5S)-N,5-dihydroxy-2-[(4-phenyl-3,6-dihydropyridin-1(2H)-yl)carbonyl]-5-propylcyclohexanecarboxamide This compound was prepared using procedures analogous to those for example 243. MS (ESI): $(M+H)^+=369.2$.

Example 296

(1S,2S,5R)-N-hydroxy-5-phenoxy-2-[(4-phenylpiperazin-1-yl)carbonyl]cyclohexanecarboxamide Part 1. (1S, 2S, 5S)-2-[(4-phenylpiperazin-1-yl)carbonyl]-6-oxabicyclo[3.2.1]octan-7-one. Benzotriazol-1-yloxytris(dimethylamino)phosphonium hexafluorophosphate (7.0 g, 0.016 mol) was added to a solution of (1S,2S,5S)-7-oxo-6-oxabicyclo[3.2.1]octane-2-carboxylic acid (14.4 mmol, 0.0144 mol) and 1-Phenylpiperazine (2.4 mL, 0.016 mol) in N,N-dimethylformamide (30 mL, 0.4 mol) at 0 Celsius. After 5 minutes, N, N-diisopropylethylamine (7.5 mL, 0.043 mol) was added at 0 Celsius. The mixture was stirred at RT for overnight. The product was purified by flash chromatography on silica gel column (ethyl acetate in hexanes: 60%).

Part 2. Methyl(1S, 2S,5R)-5-phenoxy-2-[(4-phenylpiperazin-1-yl)carbonyl]cyclohexane-carboxylate. Triphenylphosphine (150 mg, 0.00058 mol) was added to a solution of methyl (1S,2S,5S)-5-hydroxy-2-[(4-phenylpiperazin-1-yl)carbonyl]cyclohexane-carboxylate (100.0 mg, 0.00029 mol) and phenol (54 mg, 0.00058 mol) in tetrahydrofuran (2.0 mL) at RT under nitrogen. A solution of diethyl azodicarboxylate (91 uL, 0.00058 mol) in tetrahydrofuran (2.0 mL) was added. The reaction mixture was stirred at RT for overnight. The product was purified by flash chromatography on silica gel column (ethyl acetate in hexanes: 30%).

Part 3. (1S, 2S, 5R)-N-hydroxy-5-phenoxy-2-[(4-phenylpiperazin-1-yl)carbonyl]cyclohexanecarboxamide. A solution of hydroxyamine in MeOH (1.5 M, 0.75 ml) was added to methyl(1S,2S,5R)-5-phenoxy-2-[(4-phenylpiperazin-1-yl)carbonyl]cyclohexane-carboxylate (0.29 mmol, 0.00029 mol) in MeOH (0.5 mL) at RT. The resulting mixture was stirred at RT for 2 hrs, and was adjusted to PH=2.0 with TFA, and then was purified by Prep-HPLC to give the desired product. LCMS: $(M+H)^+=424.2$.

Example 297

(1S,2S,5R)-N-hydroxy-5-[(6-methylpyridin-3-yl)oxy]-2-[(4-phenylpiperazin-1-yl)carbonyl]cyclohexanecarboxamide This compound was prepared using procedures analogous to those for example 296. LCMS: $(M+H)^+=439.2$.

Example 298

(1S,2S,5R)-N-hydroxy-5-(4-methylphenoxy)-2-[(4-phenylpiperazin-1-yl)carbonyl]cyclohexanecarboxamide This compound was prepared using procedures analogous to those for example 296. LCMS: $(M+H)^+=438.1$.

Example 299

(1S,2S,5R)-5-(2,3-difluorophenoxy)-N-hydroxy-2-[(4-phenylpiperazin-1-yl)carbonyl]cyclohexanecarboxamide This compound was prepared using procedures analogous to those for example 296. LCMS: $(M+H)^+=460.2$.

Example 300

(1S,2S,5R)-N-hydroxy-5-[(6-methylpyridin-2-yl)oxy]-2-[(4-phenylpiperazin-1-yl)carbonyl]cyclohexanecarboxamide This compound was prepared using procedures analogous to those for example 296. LCMS: $(M+H)^+=439.2$.

Example 301

(1S,2S,5R)-N-hydroxy-2-[(4-phenylpiperazin-1-yl)carbonyl]-5-[(2-methylquinolin-4-yl)oxy]cyclohexanecarboxamide This compound was prepared using procedures analogous to those for example 296. LCMS: $(M+H)^+=489.2$.

Example 302

(1S,2S,5R)-5-(3,4-difluorophenoxy)-N-hydroxy-2-[(4-phenylpiperazin-1-yl)carbonyl]cyclohexanecarboxamide This compound was prepared using procedures analogous to those for example 296. LCMS: $(M+H)^+=460.2$.

Example 303

(1S,2S,5R)-5-[(5-chloropyridin-3-yl)oxy]-N-hydroxy-2-[(4-phenylpiperazin-1-yl)carbonyl]cyclohexanecarboxamide This compound was prepared using procedures analogous to those for example 296. LCMS: $(M+H)^+=459.1/461.1$.

Example 304

(1S,2S,5R)-N-hydroxy-5-[1-(methylsulfonyl)piperidin-4-yl]oxy-2-[(4-phenylpiperazin-1-yl)carbonyl]cyclohexanecarboxamide This compound was prepared using procedures analogous to those for example 317. LCMS: $(M+H)^+=509.0$.

Example 305

(1S,2S,5R)-5-(2,4-dichlorophenoxy)-N-hydroxy-2-[(4-phenylpiperazin-1-yl)carbonyl]cyclohexanecarboxamide This compound was prepared using procedures analogous to those for example 296. LCMS: $(M+H)^+=492.1/494.1$.

Example 306

Methyl 4-((1R,3S,4S)-3-[(hydroxyamino)carbonyl]-4-[(4-phenylpiperazin-1-yl)carbonyl]cyclohexyloxy)piperidine-1-carboxylate This compound was prepared using procedures analogous to those for example 317. LCMS: $(M+H)^+=489.1$.

Example 307

(1S,2S,5R)-N-hydroxy-2-[(4-phenylpiperazin-1-yl)carbonyl]-5-(pyridin-3-yloxy)cyclohexanecarboxamide This compound was prepared using procedures analogous to those for example 296. LCMS: $(M+H)^+=425.1$.

Example 308

(1S,2S,5R)-5-(4-fluorophenoxy)-N-hydroxy-2-[(4-phenylpiperazin-1-yl)carbonyl]cyclohexanecarboxamide This compound was prepared using procedures analogous to those for example 296. LCMS: $(M+H)^+=442.2$.

Example 309

(1S,2S,5R)-5-[(1-ethylpiperidin-4-yl)oxy]-N-hydroxy-2-[(4-phenylpiperazin-1-yl)carbonyl]cyclohexanecarboxamide This compound was prepared using procedures analogous to those for example 317. LCMS: $(M+H)^+=459.2$.

Example 310

(1S,2S,5R)-5-[(1-ethylpiperidin-4-yl)oxy]-N-hydroxy-2-[(3-phenyl-2,5-dihydro-1H-pyrrol-1-yl)carbonyl]cyclohexanecarboxamide This compound was prepared using procedures analogous to those for example 317. LCMS: $(M+H)^+=442.2$.

Example 311

(1S,2S,5R)-N-hydroxy-2-[(4-phenylpiperazin-1-yl)carbonyl]-5-(quinolin-6-yloxy)cyclohexanecarboxamide This compound was prepared using procedures analogous to those for example 296. LCMS: $(M+H)^+=475.2$.

Example 312

(1S,2S,5R)-5-(2,3-dichlorophenoxy)-N-hydroxy-2-[(4-phenylpiperazin-1-yl)carbonyl]cyclohexanecarboxamide This compound was prepared using procedures analogous to those for example 296. LCMS: $(M+H)^+=492.0/494.0$.

Example 313

(1S,2S,5R)-5-(benzyloxy)-N-hydroxy-2-[(4-phenylpiperazin-1-yl)carbonyl]cyclohexanecarboxamide This compound was prepared using procedures analogous to those for example 296. LCMS: $(M+H)^+=438.2$.

Example 314

(1S,2S,5R)-N-hydroxy-5-[(4-methylpyridin-2-yl)oxy]-2-[(4-phenylpiperazin-1-yl)carbonyl]cyclohexanecarboxamide This compound was prepared using procedures analogous to those for example 296. LCMS: $(M+H)^+=439.2$.

Example 315

(1S,2S,5R)-5-(3-fluorophenoxy)-N-hydroxy-2-[(4-phenylpiperazin-1-yl)carbonyl]cyclohexanecarboxamide This compound was prepared using procedures analogous to those for example 296. LCMS: $(M+H)^+=442.2$.

Example 316

(1S,2S,5R)-N-hydroxy-2-[(4-phenylpiperazin-1-yl)carbonyl]-5-(pyridin-4-yloxy)cyclohexanecarboxamide This compound was prepared using procedures analogous to those for example 296. LCMS: $(M+H)^+=425.2$.

Example 317

(1S,2S,5R)-5-[(1-acetylpiperidin-4-yl)oxy]-N-hydroxy-2-[(4-phenylpiperazin-1-yl)carbonyl]cyclohexanecarboxamide Triphenylphosphine (2.0E3 mg, 0.0077 mol) was added to a solution of 1-tert-butyl 2-methyl (1S,2S,4S)-4-hydroxycyclohexane-1,2-dicarboxylate (1.0 g, 0.0039 mol) and 4-pyridinol (730 mg, 0.0076 mol) in tetrahydrofuran (10.0 mL, 0.123 mol) at rt. A solution of diethyl azodicarboxylate (1200 uL, 0.0077 mol) in tetrahydrofuran (10.0 mL, 0.123 mol) was added. The reaction mixture was stirred at rt overnight. The reaction was chromatographed by combiflash (ethyl acetate in hexanes: 80%) to give 1-tert-butyl 2-methyl(1S,2S,4R)-4-(pyridin-4-yloxy)cyclohexane-1,2-dicarboxylate, contaminated with a little Ph₃PO, which was used in next step.

20 mg of Pd black and 1 ml of 1 M HCl in ether was added a solution of 1-tert-butyl 2-methyl (1S,2S,4R)-4-(pyridin-4-yloxy)cyclohexane-1,2-dicarboxylate (0.1 g, 0.0003 mol) in methanol (50 mL, 1 mol). The reaction was shaken under an atmosphere of hydrogen (60 Psi) overnight. LCMS showed the reaction was complete.

A solution of acetyl chloride (24 uL, 0.00033. mol) in 0.5 ml of ACN was added to a solution of 1-tert-butyl 2-methyl (1S,2S,4R)-4-(piperidin-4-yloxy)cyclohexane-1,2-dicarboxylate hydrochloride made above (50 mg, 0.0001 mol) and 4-methylmorpholine (44 uL, 0.00040 mol) in acetonitrile (1.5 mL, 0.029 mol) at 22 Celsius. It was stirred at rt for 30 min, then quenched with Water, extracted with EA, and concentrated to give 1-tert-butyl 2-methyl (1S,2S,4R)-4-[(1-acetylpiperidin-4-yl)oxy]cyclohexane-1,2-dicarboxylate.

2 ml of TFA was added in 1-tert-butyl 2-methyl(1S,2S,4R)-4-[(1-acetylpiperidin-4-yl)oxy]cyclohexane-1,2-dicarboxylate (0.1 mmol, 0.0001 mol) in dichloromethane (2 ml). It was stirred at rt overnight and concentrated to give the corresponding TFA salt for next step. Benzotriazol-1-yloxytris(dimethylamino)-phosphonium hexafluorophosphate (49 mg, 0.00011 mol) was added to a solution of (1S,2S,4R)-4-[(1-acetylpiperidin-4-yl)oxy]-2-(methoxycarbonyl)cyclohexanecarboxylic acid made above (0.1 mmol, 0.0001 mol) and 1-phenylpiperazine (17 uL, 0.00011 mol) in N, N-dimethylformamide (0.5 mL, 0.006 mol) at rt. After 5 min, N, N-diisopropylethylamine (52 uL, 0.00030 mol) was added at 0 Celsius. It was stirred at rt overnight. The reaction was chromatographed by combiflash (ethyl acetate in hexanes: 100%).

1.5 M of H₂NOH in MeOH (0.75 ml) was added into a solution of methyl(1S,2S,5R)-5-[(1-acetylpiperidin-4-yl)oxy]-2-[(4-phenylpiperazin-1-yl)carbonyl]cyclohexane-carboxylate (0.1 mmol, 0.0001 mol) in 0.5 ml of MeOH. It was stirred at rt for 2 hrs. It was purified by Prep-HPLC. LCMS: $(M+H)^+=473.1$.

Example 318

(1S,2S,5R)-N-hydroxy-5-[(2-methylpyridin-3-yl)oxy]-2-[(4-phenylpiperazin-1-yl)carbonyl]cyclohexanecarboxamide This compound was prepared using procedures analogous to those for example 296. LCMS: $(M+H)^+=439.2$.

Example 319

(1S,2S,5R)-5-[3,5-bis(trifluoromethyl)phenoxy]-N-hydroxy-2-[(4-phenylpiperazin-1-yl)carbonyl]cyclohexanecarboxamide This compound was prepared using procedures analogous to those for example 296. LCMS: $(M+H)^+=560.2$.

Example 320

(1S,2S,5R)-5-(2-chlorophenoxy)-N-hydroxy-2-[(4-phenylpiperazin-1-yl)carbonyl]cyclohexanecarboxamide This compound was prepared using procedures analogous to those for example 296. LCMS: $(M+H)^+=458.1/460.1$.

Example 321

(1S,2S,5R)-5-(4-chlorophenoxy)-N-hydroxy-2-[(4-phenylpiperazin-1-yl)carbonyl]cyclohexanecarboxamide This compound was prepared using procedures analogous to those for example 296. LCMS: $(M+H)^+=458.2/460.1$.

Example 322

(1S,2S,5R)-5-(3-bromophenoxy)-N-hydroxy-2-[(4-phenylpiperazin-1-yl)carbonyl]cyclohexanecarboxamide This compound was prepared using procedures analogous to those for example 296. LCMS: $(M+H)^+=502.1/504.1$.

Example 323

(1S,2S,5R)-5-(1,3-benzothiazol-2-yloxy)-N-hydroxy-2-[(4-phenylpiperazin-1-yl)carbonyl]cyclohexanecarboxamide This compound was prepared using procedures analogous to those for example 296. LCMS: $(M+H)^+=481.1$.

Example 324

(1S,2S,5R)-5-(3-chlorophenoxy)-N-hydroxy-2-[(4-phenylpiperazin-1-yl)carbonyl]cyclohexanecarboxamide This compound was prepared using procedures analogous to those for example 296.

Example 325

(1S,2S,5R)-N-hydroxy-2-[(4-phenylpiperazin-1-yl)carbonyl]-5-(pyrimidin-2-yloxy)cyclohexanecarboxamide This compound was prepared using procedures analogous to those for example 296. LCMS: $(M+H)^+=426.2$.

Example 326

(1S,2S,5R)-N-hydroxy-2-[(4-phenylpiperazin-1-yl)carbonyl]-5-[3-(trifluoromethyl)phenoxy]cyclohexanecarboxamide This compound was prepared using procedures analogous to those for example 296. LCMS: (M+H)$^+$=492.1.

Example 327

(1S,2S,5R)-N-hydroxy-2-[(4-phenylpiperazin-1-yl)carbonyl]-5-(quinolin-4-yloxy)cyclohexanecarboxamide This compound was prepared using procedures analogous to those for example 296. LCMS: (M+H)$^+$=475.2.

Example 328

(1S,2S,5R)-N-hydroxy-2-[(4-phenylpiperazin-1-yl)carbonyl]-5-(thieno[3,2-b]pyridin-7-yloxy)cyclohexanecarboxamide This compound was prepared using procedures analogous to those for example 296. LCMS: (M+H)$^+$=481.2.

Example 329

(1S,2S,5R)-N-hydroxy-5-[isobutyryl(methyl)amino]-2-[(4-phenylpiperazin-1-yl)carbonyl]cyclohexanecarboxamide This compound was prepared using procedures analogous to those for example 72. LCMS: (M+H)$^+$=431.3.

Example 330

(1R,3S,4S)-3-[(hydroxyamino)carbonyl]-4-[(4-phenylpiperidin-1-yl)carbonyl]cyclohexyl cyclopropylcarbamate This compound was prepared using procedures analogous to those for example 72. LCMS: (M+H)$^+$=430.2.

Example 331

(1R,3S,4S)-3-[(hydroxyamino)carbonyl]-4-[(4-phenylpiperidin-1-yl)carbonyl]cyclohexyl ethylcarbamate This compound was prepared using procedures analogous to those for example 72. LCMS: (M+H)$^+$=418.1.

Example 332

(1R,3S,4S)-3-[(hydroxyamino)carbonyl]-4-[(4-phenylpiperidin-1-yl)carbonyl]cyclohexyl methylcarbamate This compound was prepared using procedures analogous to those for example 72. LCMS: (M+H)$^+$=404.1.

Example 333

(1R,3S,4S)-3-[(hydroxyamino)carbonyl]-4-[(4-phenylpiperidin-1-yl)carbonyl]cyclohexyl isopropylcarbamate This compound was prepared using procedures analogous to those for example 72. LCMS: (M+H)$^+$=432.1.

Example 334

(1R,3S,4S)-3-[(hydroxyamino)carbonyl]-4-[(4-phenylpiperidin-1-yl)carbonyl]cyclohexyl prop-2-yn-1-ylcarbamate This compound was prepared using procedures analogous to those for example 72. LCMS: (M+H)$^+$=428.1.

Example 335

(1R,3S,4S)-3-[(hydroxyamino)carbonyl]-4-[(4-phenylpiperidin-1-yl)carbonyl]cyclohexyl piperidine-1-carboxylate This compound was prepared using procedures analogous to those for example 72.

Example 336

(1R,3S,4S)-3-[(hydroxyamino)carbonyl]-4-[(4-phenylpiperidin-1-yl)carbonyl]cyclohexyl 4-methylpiperazine-1-carboxylate This compound was prepared using procedures analogous to those for example 72. LCMS: (M+H)$^+$=473.2.

Example 337

(1R,3S,4S)-3-[(hydroxyamino)carbonyl]-4-[(4-phenylpiperidin-1-yl)carbonyl]cyclohexyl carbamate This compound was prepared using procedures analogous to those for example 72. LCMS: (M+H)$^+$=390.2.

Example 338

(1R,3S,4S)-3-[(hydroxyamino)carbonyl]-4-[(4-phenylpiperazin-1-yl)carbonyl]cyclohexyl (1-methylpiperidin-4-yl)carbamate This compound was prepared using procedures analogous to those for example 72. LCMS: (M+H)$^+$=488.3.

Example 339

(1R,3S,4S)-3-[(hydroxyamino)carbonyl]-4-[(4-phenylpiperazin-1-yl)carbonyl]cyclohexyl isobutyl(methyl)carbamate This compound was prepared using procedures analogous to those for example 72. LCMS: (M+H)$^+$=461.2.

Example 340

(1R,3S,4S)-3-[(hydroxyamino)carbonyl]-4-[(4-phenylpiperazin-1-yl)carbonyl]cyclohexyl methyl(3-phenylpropyl)carbamate This compound was prepared using procedures analogous to those for example 72. LCMS: (M+H)$^+$=523.3.

Example 341

(1R,3S,4S)-3-[(hydroxyamino)carbonyl]-4-[(4-phenylpiperazin-1-yl)carbonyl]cyclohexyl cyclohexyl (methyl)carbamate This compound was prepared using procedures analogous to those for example 72. LCMS: $(M+H)^+=487.3$.

Example 342

(1R,3S,4S)-3-[(hydroxyamino)carbonyl]-4-[(4-phenylpiperazin-1-yl)carbonyl]cyclohexyl (4-methoxyphenyl)methylcarbamate This compound was prepared using procedures analogous to those for example 72. LCMS: $(M+H)^+=511.3$.

Example 343

(1R,3S,4S)-3-[(hydroxyamino)carbonyl]-4-[(4-phenylpiperazin-1-yl)carbonyl]cyclohexyl indoline-1-carboxylate This compound was prepared using procedures analogous to those for example 72. LCMS: $(M+H)^+=493.2$.

Example 344

(1R,3S,4S)-3-[(hydroxyamino)carbonyl]-4-[(4-phenylpiperazin-1-yl)carbonyl]cyclohexyl 1,3-dihydro-2H-isoindole-2-carboxylate This compound was prepared using procedures analogous to those for example 72. LCMS: $(M+H)^+=493.2$.

Example 345

(1R,3S,4S)-3-[(hydroxyamino)carbonyl]-4-[(4-phenylpiperazin-1-yl)carbonyl]cyclohexyl (2-phenylcyclopropyl)carbamate This compound was prepared using procedures analogous to those for example 72. LCMS: $(M+H)^+=507.3$.

Example 346

(1R,3S,4S)-3-[(hydroxyamino)carbonyl]-4-[(4-phenylpiperazin-1-yl)carbonyl]cyclohexyl cyclobutylcarbamate This compound was prepared using procedures analogous to those for example 72. LCMS: $(M+H)^+=445.2$.

Example 347

Ethyl 4-{[({(1R,3S,4S)-3-[(hydroxyamino)carbonyl]-4-[(4-phenylpiperazin-1-yl)carbonyl]cyclohexyl}oxy)carbonyl]amino}piperidine-1-carboxylate This compound was prepared using procedures analogous to those for example 72. LCMS: $(M+H)^+=546.3$.

Example 348

(1R,3S,4S)-3-[(hydroxyamino)carbonyl]-4-[(4-phenylpiperazin-1-yl)carbonyl]cyclohexyl tetrahydrofuran-3-ylcarbamate This compound was prepared using procedures analogous to those for example 72. LCMS: $(M+H)^+=461.2$.

Example 349

(1R,3S,4S)-3-[(hydroxyamino)carbonyl]-4-[(4-phenylpiperazin-1-yl)carbonyl]cyclohexyl (4-hydroxycyclohexyl)carbamate This compound was prepared using procedures analogous to those for example 72. LCMS: $(M+H)^+=489.2$.

Example 350

(1R,3S,4S)-3-[(hydroxyamino)carbonyl]-4-[(4-phenylpiperazin-1-yl)carbonyl]cyclohexyl (2-methoxyethyl)carbamate This compound was prepared using procedures analogous to those for example 72. LCMS: $(M+H)^+=449.2$.

Example 351

(1R,3S,4S)-3-[(hydroxyamino)carbonyl]-4-[(4-phenylpiperazin-1-yl)carbonyl]cyclohexyl (pyridin-2-ylmethyl)carbamate This compound was prepared using procedures analogous to those for example 72. LCMS: $(M+H)^+=482.2$.

Example 352

(1R,3S,4S)-3-[(hydroxyamino)carbonyl]-4-[(4-phenylpiperazin-1-yl)carbonyl]cyclohexyl (pyridin-3-ylmethyl)carbamate This compound was prepared using procedures analogous to those for example 72. LCMS:

Example 353

(1R,3S,4S)-3-[(hydroxyamino)carbonyl]-4-[(4-phenylpiperazin-1-yl)carbonyl]cyclohexyl (pyridin-4-ylmethyl)carbamate This compound was prepared using procedures analogous to those for example 72. LCMS: $(M+H)^+=482.2$.

Example 354

(1R,3S,4S)-3-[(hydroxyamino)carbonyl]-4-[(4-phenylpiperazin-1-yl)carbonyl]cyclohexyl 2,5-dihydro-1H-pyrrole-1-carboxylate This compound was prepared using procedures analogous to those for example 72.

Example 355

(1R,3S,4S)-3-[(hydroxyamino)carbonyl]-4-[(4-phenylpiperazin-1-yl)carbonyl]cyclohexyl cyclopentylcarbamate This compound was prepared using procedures analogous to those for example 72. LCMS: $(M+H)^+=459.2$.

Example 356

(1R,3S,4S)-3-[(hydroxyamino)carbonyl]-4-[(4-phenylpiperazin-1-yl)carbonyl]cyclohexyl cyclohexylcarbamate This compound was prepared using procedures analogous to those for example 72. LCMS: $(M+H)^+=473.3$.

Example 357

Ethyl(1R,3S,4S)-3-[(hydroxyamino)carbonyl]-4-[(4-phenylpiperazin-1-yl)carbonyl]cyclohexyl piperazine-1,4-dicarboxylate This compound was prepared using procedures analogous to those for example 72. LCMS: $(M+H)^+=532.3$.

Example 358

(1R,3S,4S)-3-[(hydroxyamino)carbonyl]-4-[(4-phenylpiperazin-1-yl)carbonyl]cyclohexyl 4-{2-[methyl(phenyl)amino]-2-oxoethyl}piperazine-1-carboxylate This compound was prepared using procedures analogous to those for example 72. LCMS: $(M+H)^+=607.3$.

Example 359

(1R,3S,4S)-3-[(hydroxyamino)carbonyl]-4-[(4-phenylpiperazin-1-yl)carbonyl]cyclohexyl 4-hydroxypiperidine-1-carboxylate This compound was prepared using procedures analogous to those for example 72. LCMS: $(M+H)^+=475.2$.

Example 360

(1R,3S,4S)-3-[(hydroxyamino)carbonyl]-4-[(4-phenylpiperazin-1-yl)carbonyl]cyclohexyl (3R)-3-(acetylamino)pyrrolidine-1-carboxylate This compound was prepared using procedures analogous to those for example 72. LCMS: $(M+H)^+=502.3$.

Example 361

(1R,3S,4S)-3-[(hydroxyamino)carbonyl]-4-[(4-phenylpiperazin-1-yl)carbonyl]cyclohexyl (3S)-3-(acetylamino)pyrrolidine-1-carboxylate This compound was prepared using procedures analogous to those for example 72. LCMS: $(M+H)^+=502.2$.

Example 362

(1R,3S,4S)-3-[(hydroxyamino)carbonyl]-4-[(4-phenylpiperazin-1-yl)carbonyl]cyclohexyl (2R)-2-(hydroxymethyl)pyrrolidine-1-carboxylate This compound was prepared using procedures analogous to those for example 72. LCMS: $(M+H)^+=475.2$.

Example 363

(1R,3S,4S)-3-[(hydroxyamino)carbonyl]-4-[(4-phenylpiperazin-1-yl)carbonyl]cyclohexyl (2S)-2-(hydroxymethyl)pyrrolidine-1-carboxylate This compound was prepared using procedures analogous to those for example 72. LCMS: $(M+H)^+=475.2$.

Example 364

(1R,3S,4S)-3-[(hydroxyamino)carbonyl]-4-[(4-phenylpiperazin-1-yl)carbonyl]cyclohexyl [1-(hydroxymethyl)cyclopentyl]carbamate This compound was prepared using procedures analogous to those for example 72. LCMS: $(M+H)^+=489.3$.

Example 365

(1R,3S,4S)-3-[(hydroxyamino)carbonyl]-4-[(4-phenylpiperazin-1-yl)carbonyl]cyclohexyl [(1R,2R)-2-hydroxycyclopentyl]carbamate This compound was prepared using procedures analogous to those for example 72. LCMS: $(M+H)^+=475.2$.

Example 366

(1R,3S,4S)-3-[(hydroxyamino)carbonyl]-4-[(4-phenylpiperazin-1-yl)carbonyl]cyclohexyl [2-(hydroxymethyl)cyclohexyl]carbamate This compound was prepared using procedures analogous to those for example 72. LCMS: $(M+H)^+=503.3$.

Example 367

(1R,3S,4S)-3-[(hydroxyamino)carbonyl]-4-[(4-phenylpiperazin-1-yl)carbonyl]cyclohexyl [(2R)-2-hydroxycyclohexyl]carbamate This compound was prepared using procedures analogous to those for example 72. LCMS: $(M+H)^+=489.3$.

Example 368

(1R,3S,4S)-3-[(hydroxyamino)carbonyl]-4-[(4-phenylpiperazin-1-yl)carbonyl]cyclohexyl [(1R)-2-hydroxy-1-phenylethyl]carbamate This compound was prepared using procedures analogous to those for example 72. LCMS: $(M+H)^+=511.2$.

Example 369

(1R,3S,4S)-3-[(hydroxyamino)carbonyl]-4-[(4-phenylpiperazin-1-yl)carbonyl]cyclohexyl [(1R)-2-hydroxy-1-methylethyl]carbamate This compound was prepared using procedures analogous to those for example 72. LCMS: $(M+H)^+=449.2$.

Example 370

(1R,3S,4S)-3-[(hydroxyamino)carbonyl]-4-[(4-phenylpiperazin-1-yl)carbonyl]cyclohexyl [(1R)-1-(hydroxymethyl)propyl]carbamate This compound was prepared using procedures analogous to those for example 72. LCMS: $(M+H)^+=463.2$.

Example 371

(1R,3S,4S)-3-[(hydroxyamino)carbonyl]-4-[(4-phenylpiperazin-1-yl)carbonyl]cyclohexyl [(1R)-1-(hydroxymethyl)-2-methylpropyl]carbamate This compound was prepared using procedures analogous to those for example 72. LCMS: $(M+H)^+=477.2$.

Example 372

(1R,3S,4S)-3-[(hydroxyamino)carbonyl]-4-[(4-phenylpiperazin-1-yl)carbonyl]cyclohexyl [(2R)-2-hydroxypropyl]carbamate This compound was prepared using procedures analogous to those for example 72. LCMS: $(M+H)^+=449.2$.

Example 373

(1R,3S,4S)-3-[(hydroxyamino)carbonyl]-4-[(4-phenylpiperazin-1-yl)carbonyl]cyclohexyl(3-hydroxy-1-phenylpropyl)carbamate This compound was prepared using procedures analogous to those for example 72. LCMS: $(M+H)^+=525.3$.

Example 374

(1R,3S,4S)-3-[(hydroxyamino)carbonyl]-4-[(4-phenylpiperazin-1-yl)carbonyl]cyclohexyl [(1R)-1-(hydroxymethyl)-3-methylbutyl]carbamate This compound was prepared using procedures analogous to those for example 72. LCMS: $(M+H)^+=491.2$.

Example 375

(1R,3S,4S)-3-[(hydroxyamino)carbonyl]-4-[(4-phenylpiperazin-1-yl)carbonyl]cyclohexyl 4-formylpiperazine-1-carboxylate This compound was prepared using procedures analogous to those for example 72. LCMS: $(M+H)^+=488.2$.

Example 376

(1S,2S,5R)-N-hydroxy-2-[(4-phenylpiperazin-1-yl)carbonyl]-5-(pyridin-3-ylmethoxy)cyclohexanecarboxamide 1.00 M of Potassium tert-butoxide in tetrahydrofuran (0.212 ml) was added to a mixture of methyl (1S,2S,5R)-5-hydroxy-2-[(4-phenylpiperazin-1-yl)carbonyl]cyclohexanecarboxylate (36.8 mg, 0.000106 mol) and 3-chloromethylpyridine hydrochloride (17.4 mg, 0.106 mmol) in tetrahydrofuran (1.0 mL, 0.012 mol) at 0 Celsius. The mixture was stirred at room temperature for 1 hr then purified by HPLC.

1.5 M of hydroxyamine solution (0.7 ml) was added to a solution of methyl(1S,2S,5R)-2-[(4-phenylpiperazin-1-yl)carbonyl]-5-(pyridin-3-ylmethoxy)cyclohexanecarboxylate (0.075 mmol, 0.000075 mol) made above in methanol (0.5 mL, 0.01 mol). It was stirred at rt for 2 hrs then purified by Prep-HPLC. LCMS: $(M+H)^+=439.3$.

Example 377

(1S,2S,5R)-N-hydroxy-2-[(4-phenylpiperazin-1-yl)carbonyl]-5-(pyridin-2-yloxy)cyclohexanecarboxamide This compound was prepared using procedures analogous to those for example 296. LCMS: $(M+H)^+=425.2$.

Example 378

(1S,2S,5R)-N-hydroxy-2-[(4-phenylpiperazin-1-yl)carbonyl]-5-(quinolin-6-yloxy)cyclohexanecarboxamide This compound was prepared using procedures analogous to those for example 296. LCMS: $(M+H)^+=475.2$.

Example 379

(1S,2S,5R)-5-[(1-ethylpiperidin-4-yl)oxy]-N-hydroxy-2-[(4-phenyl-3,6-dihydropyridin-1 (2H)-yl)carbonyl]cyclohexanecarboxamide This compound was prepared using procedures analogous to those for example 317. LCMS: $(M+H)^+=459.2$.

Example 380

(1S,2S,5R)-N-hydroxy-5-(4-hydroxyphenoxy)-2-[(4-phenylpiperazin-1-yl)carbonyl]cyclohexanecarboxamide This compound was prepared using procedures analogous to those for example 296.

Example 381

(1S,2S,5R)-N-hydroxy-5-[(4-methoxycyclohexyl)oxy]-2-[(4-phenylpiperazin-1-yl)carbonyl]cyclohexanecarboxamide This compound was prepared using procedures analogous to those for example 317. LCMS: $(M+H)^+=460.2$.

Example 383

(1S,2S,5R)-N-hydroxy-5-[(4-methoxycyclohexyl)oxy]-2-[(4-phenyl-3,6-dihydropyridin-1(2H)-yl)carbonyl]cyclohexanecarboxamide This compound was prepared using procedures analogous to those for example 317. LCMS: (M+H)$^+$=457.2.

Example 384

(1S,2S,5R)-N-hydroxy-2-[(4-phenylpiperazin-1-yl)carbonyl]-5-{[2-(trifluoromethyl)quinolin-4-yl]oxy}cyclohexanecarboxamide This compound was prepared using procedures analogous to those for example 296. LCMS: (M+H)$^+$=543.2.

Example 385

(1S,2S,5R)-N-hydroxy-2-[(4-phenylpiperazin-1-yl)carbonyl]-5-(quinolin-2-yloxy)cyclohexanecarboxamide This compound was prepared using procedures analogous to those for example 296. LCMS: (M+H)$^+$=475.2.

Example 386

(1S,2S,5R)-N-hydroxy-2-[(4-phenylpiperazin-1-yl)carbonyl]-5-(quinolin-3-yloxy)cyclohexanecarboxamide This compound was prepared using procedures analogous to those for example 296. LCMS: (M+H)$^+$=475.1.

Example 387

(1S,2S,5R)-N-hydroxy-2-[(4-phenylpiperazin-1-yl)carbonyl]-5-(quinolin-5-yloxy)cyclohexanecarboxamide This compound was prepared using procedures analogous to those for example 296. LCMS: (M+H)$^+$=475.1.

Example 388

(1S,2S,5R)-N-hydroxy-2-[(4-phenylpiperazin-1-yl)carbonyl]-5-(quinolin-7-yloxy)cyclohexanecarboxamide This compound was prepared using procedures analogous to those for example 296. LCMS: (M+H)$^+$=475.2.

Example 389

(1S,2S,5R)-N-hydroxy-2-[(4-phenylpiperazin-1-yl)carbonyl]-5-(quinolin-8-yloxy)cyclohexanecarboxamide This compound was prepared using procedures analogous to those for example 296. LCMS: (M+H)$^+$=475.1.

Example 390

(1S,2S,5R)-N-hydroxy-2-[(4-phenyl-3,6-dihydropyridin-1(2H)-yl)carbonyl]-5-(pyridin-2-yloxy)cyclohexanecarboxamide This compound was prepared using procedures analogous to those for example 296. LCMS: (M+H)$^+$=422.1.

Example 391

(1S,2S,5R)-N-hydroxy-2-[(4-phenyl-3,6-dihydropyridin-1(2H)-yl)carbonyl]-5-(pyridin-4-yloxy)cyclohexanecarboxamide This compound was prepared using procedures analogous to those for example 296. LCMS: (M+H)$^+$=422.1.

Example 392

(1S,2S,5R)-N-hydroxy-2-[(4-phenyl-3,6-dihydropyridin-1(2H)-yl)carbonyl]-5-(quinolin-6-yloxy)cyclohexanecarboxamide This compound was prepared using procedures analogous to those for example 296. LCMS: (M+H)$^+$=472.1.

Example 393

(1S,2S,5R)-5-[(1-ethylpiperidin-4-yl)oxy]-N-hydroxy-2-[(4-phenylpiperidin-1-yl)carbonyl]cyclohexanecarboxamide This compound was prepared using procedures analogous to those for example 317. LCMS: (M+H)$^+$=458.3.

Example 394

(1S,2S,5R)-N-hydroxy-2-[(4-phenylpiperidin-1-yl)carbonyl]-5-(pyridin-2-yloxy)cyclohexanecarboxamide This compound was prepared using procedures analogous to those for example 296. LCMS: (M+H)$^+$=424.2.

Example 395

(1S,2S,5R)-N-hydroxy-2-[(4-phenylpiperidin-1-yl)carbonyl]-5-(pyridin-4-yloxy)cyclohexanecarboxamide This compound was prepared using procedures analogous to those for example 296. LCMS: (M+H)$^+$=424.2.

Example 396

(1S,2S,5R)-N-hydroxy-2-[(4-phenylpiperidin-1-yl)carbonyl]-5-(quinolin-6-yloxy)cyclohexanecarboxamide This compound was prepared using procedures analogous to those for example 296. LCMS: (M+H)$^+$=474.2.

Example 397

(1S,2S,5R)-5-(3-chlorophenoxy)-N-hydroxy-2-[(4-phenyl-3,6-dihydropyridin-1(2H)-yl)carbonyl]cyclohexanecarboxamide This compound was prepared using procedures analogous to those for example 296. LCMS: $(M+H)^+=455.1, 457.1$.

Example 398

(1S,2S,5R)-5-(3,4-difluorophenoxy)-N-hydroxy-2-[(4-phenyl-3,6-dihydropyridin-1(2H)-yl)carbonyl]cyclohexanecarboxamide This compound was prepared using procedures analogous to those for example 296. LCMS: $(M+H)^+=457.1$.

Example 399

(1S,2S,5R)-5-(2,3-difluorophenoxy)-N-hydroxy-2-[(4-phenyl-3,6-dihydropyridin-1 (2H)-yl)carbonyl]cyclohexanecarboxamide This compound was prepared using procedures analogous to those for example 296. LCMS: $(M+H)^+=457.1$.

Example 400

(1S,2S,5R)-N-hydroxy-5-(isoquinolin-1-yloxy)-2-[(4-phenylpiperazin-1-yl)carbonyl]cyclohexanecarboxamide This compound was prepared using procedures analogous to those for example 296. LCMS: $(M+H)^+=475.2$.

Example 401

(1S,2S,5R)-N-hydroxy-5-(isoquinolin-3-yloxy)-2-[(4-phenylpiperazin-1-yl)carbonyl]cyclohexanecarboxamide This compound was prepared using procedures analogous to those for example 296. LCMS: $(M+H)^+=475.2$.

Example 402

(1S,2S,5R)-N-hydroxy-5-(isoquinolin-5-yloxy)-2-[(4-phenylpiperazin-1-yl)carbonyl]cyclohexanecarboxamide This compound was prepared using procedures analogous to those for example 296. LCMS: $(M+H)^+=475.2$.

Example 403

(1S,2S,5R)-N-hydroxy-5-(isoquinolin-7-yloxy)-2-[(4-phenylpiperazin-1-yl)carbonyl]cyclohexanecarboxamide This compound was prepared using procedures analogous to those for example 296. LCMS: $(M+H)^+=475.2$.

Example 404

(1S,2S,5R)-N-hydroxy-5-(2-naphthyloxy)-2-[(4-phenylpiperazin-1-yl)carbonyl]cyclohexanecarboxamide This compound was prepared using procedures analogous to those for example 296. LCMS: $(M+H)^+=474.2$.

Example 405

(1S,2S,5R)-5-(2,4-difluorophenoxy)-N-hydroxy-2-[(4-phenylpiperazin-1-yl)carbonyl]cyclohexanecarboxamide This compound was prepared using procedures analogous to those for example 296. LCMS: $(M+H)^+=460.1$.

Example 406

(1S,2S,5R)-5-(3,5-difluorophenoxy)-N-hydroxy-2-[(4-phenylpiperazin-1-yl)carbonyl]cyclohexanecarboxamide This compound was prepared using procedures analogous to those for example 296. LCMS: $(M+H)^+=460.1$.

Example 407

(1S,2S,5R)-5-(3-chloro-4-fluorophenoxy)-N-hydroxy-2-[(4-phenylpiperazin-1-yl)carbonyl]cyclohexanecarboxamide This compound was prepared using procedures analogous to those for example 296. LCMS: $(M+H)^+=476.1, 478.1$.

Example 408

(1S,2S,5R)-5-(3,4-dichlorophenoxy)-N-hydroxy-2-[(4-phenylpiperazin-1-yl)carbonyl]cyclohexanecarboxamide This compound was prepared using procedures analogous to those for example 296. LCMS: $(M+H)^+=492.1, 494.1$.

Example 409

(1S,2S,5R)-5-(3,5-dichlorophenoxy)-N-hydroxy-2-[(4-phenylpiperazin-1-yl)carbonyl]cyclohexanecarboxamide This compound was prepared using procedures analogous to those for example 296. LCMS: $(M+H)^+=492.1, 494.1$.

Example 410

(1S,2S,5R)-5-(2,5-dioxopyrrolidin-1-yl)-N-hydroxy-2-[(4-phenylpiperazin-1-yl)carbonyl]cyclohexanecarboxamide This compound was prepared using procedures analogous to those for example 296. LCMS: $(M+H)^+=429.2$.

Example 411

(1S,2S,5R)-5-(5,5-dimethyl-2,4-dioxo-1,3-oxazolidin-3-yl)-N-hydroxy-2-[(4-phenylpiperazin-1-yl)carbonyl]cyclohexanecarboxamide This compound was prepared using procedures analogous to those for example 296. LCMS: (M+H)$^+$=459.2.

Example 412

(1S,2S,5R)-N-hydroxy-5-(3-methyl-2,5-dioxoimidazolidin-1-yl)-2-[(4-phenylpiperazin-1-yl)carbonyl]cyclohexanecarboxamide This compound was prepared using procedures analogous to those for example 296.

Example 413

(3S,5S,6S)-5-[(hydroxyamino)carbonyl]-1-methyl-6-[(4-phenylpiperazin-1-yl)carbonyl]piperidin-3-yl 2,5-dihydro-1H-pyrrole-1-carboxylate This compound was prepared using procedures analogous to those for example 204. MS(ESI) (M+H) 458.1.

Example 414

(3S,5S,6S)-5-[(hydroxyamino)carbonyl]-1-methyl-6-[(4-phenylpiperazin-1-yl)carbonyl]piperidin-3-yl azepane-1-carboxylate This compound was prepared using procedures analogous to those for example 204. MS(ESI) (M+H) 488.1.

Example 415

(3S,5S,6S)-5-[(hydroxyamino)carbonyl]-1-methyl-6-[(4-phenylpiperazin-1-yl)carbonyl]piperidin-3-yl dimethylcarbamate This compound was prepared using procedures analogous to those for example 204. MS(ESI) (M+H) 434.1.

Example 416

(3S,5S,6S)-5-[(hydroxyamino)carbonyl]-1-methyl-6-[(4-phenylpiperazin-1-yl)carbonyl]piperidin-3-yl azocane-1-carboxylate This compound was prepared using procedures analogous to those for example 204. MS(ESI) (M+H) 502.2.

Example 417

(2S,3S,5S)-5-(2-fluorophenoxy)-N-hydroxy-1-methyl-2-[(4-phenylpiperazin-1-yl)carbonyl]piperidine-3-carboxamide This compound was prepared using procedures analogous to those for example 152. MS (ESI): (M+H) 457.2.

Example 418

(2S,3S,5S)-N-hydroxy-1-methyl-5-[(6-methylpyridin-2-yl)oxy]-2-[(4-phenylpiperazin-1-yl)carbonyl]piperidine-3-carboxamide This compound was prepared using procedures analogous to those for example 152. MS (ESI): (M+H) 454.2.

Example 419

(2S,3S,5S)-N-hydroxy-1-methyl-2-[(4-phenylpiperazin-1-yl)carbonyl]-5-(pyridin-4-yloxy)piperidine-3-carboxamide This compound was prepared using procedures analogous to those for example 152. MS (ESI): (M+H) 440.1.

Example 420

(2S,3S,5S)-5-(3-fluorophenoxy)-N-hydroxy-1-methyl-2-[(4-phenylpiperazin-1-yl)carbonyl]piperidine-3-carboxamide This compound was prepared using procedures analogous to those for example 152. MS (ESI): (M+H) 457.2.

Example 421

(2S,3S,5S)-N-hydroxy-1-methyl-2-[(4-phenylpiperazin-1-yl)carbonyl]-5-(pyridin-2-yloxy)piperidine-3-carboxamide This compound was prepared using procedures analogous to those for example 152. MS (ESI): (M+H) 440.2.

Example 422

(2S,3S,5S)-5-(1,3-benzothiazol-2-yloxy)-N-hydroxy-1-methyl-2-[(4-phenylpiperazin-1-yl)carbonyl]piperidine-3-carboxamide This compound was prepared using procedures analogous to those for example 152.

Example 423

(2S,3S,5S)-N-hydroxy-1-methyl-5-(3-methylphenoxy)-2-[(4-phenylpiperazin-1-yl)carbonyl]piperidine-3-carboxamide This compound was prepared using procedures analogous to those for example 152. MS (ESI): (M+H) 453.2.

Example 424

(2S,3S,5S)-N-hydroxy-1-methyl-5-[(4-methylpyridin-2-yl)oxy]-2-[(4-phenylpiperazin-1-yl)carbonyl]piperidine-3-carboxamide This compound was prepared using procedures analogous to those for example 152. MS (ESI): (M+H) 454.2.

Example 425

(2S,3S,5S)-5-(3,4-difluorophenoxy)-N-hydroxy-1-methyl-2-[(4-phenylpiperazin-1-yl)carbonyl]piperidine-3-carboxamide This compound was prepared using procedures analogous to those for example 152. MS (ESI): (M+H) 475.1.

Example 426

(2S,3S,5S)-5-(2-chlorophenoxy)-N-hydroxy-1-methyl-2-[(4-phenylpiperazin-1-yl)carbonyl]piperidine-3-carboxamide This compound was prepared using procedures analogous to those for example 152. MS (ESI): (M+H) 473.2.

Example 427

(3S,5S,6S)-5-[(hydroxyamino)carbonyl]-1-methyl-6-[(4-phenylpiperazin-1-yl)carbonyl]piperidin-3-yl 3,3-difluoropyrrolidine-1-carboxylate This compound was prepared using procedures analogous to those for example 204. MS (ESI) (M+H): 496.1.

Example 428

Methyl(2S,3S,5S)-3-[(hydroxyamino)carbonyl]-2-[(4-phenylpiperazin-1-yl)carbonyl]-5-(quinolin-6-yloxy)piperidine-1-carboxylate This compound was prepared using procedures analogous to those for example 126. ESI (MS): (M+H) 534.2.

Example 429

(2S,3S,5S)-N-hydroxy-1-methyl-2-[(3-phenyl-2,5-dihydro-1H-pyrrol-1-yl)carbonyl]-5-(pyridin-3-yloxy)piperidine-3-carboxamide This compound was prepared using procedures analogous to those for example 152. MS (ESI): (M+H) 423.1.

Example 430

(2S,3S,5S)-N-hydroxy-1-methyl-2-[(3-phenyl-2,5-dihydro-1H-pyrrol-1-yl)carbonyl]-5-(pyridin-4-yloxy)piperidine-3-carboxamide This compound was prepared using procedures analogous to those for example 152. MS (ESI): (M+H) 423.0.

Example 431

(2S,3S,5S)-5-(3-fluorophenoxy)-N-hydroxy-1-methyl-2-[(3-phenyl-2,5-dihydro-1H-pyrrol-1-yl)carbonyl]piperidine-3-carboxamide This compound was prepared using procedures analogous to those for example 152. MS (ESI): (M+H) 440.1.

Example 432

(2S,3S,5S)-N-hydroxy-1-methyl-5-phenoxy-2-[(3-phenyl-2,5-dihydro-1H-pyrrol-1-yl)carbonyl]piperidine-3-carboxamide This compound was prepared using procedures analogous to those for example 152. LCMS (ESI): (M+H) 422.1.

Example 433

(2S,3S,5S)-N-hydroxy-1-methyl-2-[(3-phenyl-2,5-dihydro-1H-pyrrol-1-yl)carbonyl]-5-(pyridin-2-yloxy)piperidine-3-carboxamide This compound was prepared using procedures analogous to those for example 152. LCMS (ESI): (M+H) 423.1.

Example 434

(2S,3S,5S)-N-hydroxy-1-methyl-5-[(4-methylpyridin-2-yl)oxy]-2-[(3-phenyl-2,5-dihydro-1H-pyrrol-1-yl)carbonyl]piperidine-3-carboxamide This compound was prepared using procedures analogous to those for example 152. MS (ESI): (M+H) 437.1.

Example 435

(2S,3S,5S)-N-hydroxy-1-methyl-5-[(6-methylpyridin-2-yl)oxy]-2-[(3-phenyl-2,5-dihydro-1H-pyrrol-1-yl)carbonyl]piperidine-3-carboxamide This compound was prepared using procedures analogous to those for example 152. MS (ESI): (M+H) 437.1.

Example 436

(2S,3S,5S)-N-hydroxy-1-methyl-2-[(4-phenylpiperazin-1-yl)carbonyl]-5-(pyridin-2-yloxy)piperidine-3-carboxamide This compound was prepared using procedures analogous to those for example 152. MS (ESI): (M+H) 440.2.

Example 437

(2S,3S,5S)-N-hydroxy-1-methyl-2-[(4-phenylpiperazin-1-yl)carbonyl]-5-(pyridin-3-yloxy)piperidine-3-carboxamide This compound was prepared using procedures analogous to those for example 152. MS (ESI): (M+H) 440.1.

Example 438

(2S,3S,5S)-N-hydroxy-1-methyl-5-[(2-methylquinolin-4-yl)oxy]-2-[(4-phenylpiperazin-1-yl)carbonyl]piperidine-3-carboxamide This compound was prepared using procedures analogous to those for example 152. MS (ESI): (M+H) 504.2.

Example 439

(2S,3S,5S)-N-hydroxy-1-methyl-5-[(2-methylquinolin-4-yl)oxy]-2-[(3-phenyl-2,5-dihydro-1H-pyrrol-1-yl)carbonyl]piperidine-3-carboxamide This compound was prepared using procedures analogous to those for example 152. MS (ESI): (M+H) 487.2.

Example 440

(2S,3S,5S)-N-hydroxy-1-methyl-2-[(4-phenylpiperazin-1-yl)carbonyl]-5-(quinolin-4-yloxy)piperidine-3-carboxamide This compound was prepared using procedures analogous to those for example 152. MS (ESI): (M+H) 490.3.

Example 441

(2S,3S,5S)-N-hydroxy-1-methyl-2-[(3-phenyl-2,5-dihydro-1H-pyrrol-1-yl)carbonyl]-5-(quinolin-6-yloxy)piperidine-3-carboxamide This compound was prepared using procedures analogous to those for example 152. MS (ESI): (M+H) 473.1.

Example 442

(2S,3S,5S)-N-hydroxy-1-methyl-2-[(3-phenyl-2,5-dihydro-1H-pyrrol-1-yl)carbonyl]-5-(quinolin-4-yloxy)piperidine-3-carboxamide This compound was prepared using procedures analogous to those for example 152. MS (ESI): (M+H) 473.1.

Example 443

(2S,3S,5S)-N-hydroxy-2-[(4-phenylpiperazin-1-yl)carbonyl]-5-(pyridin-2-yloxy)piperidine-3-carboxamide This compound was prepared using procedures analogous to those for example 152. MS (ESI): (M+H) 426.1.

Example 444

(2S,3S,5S)-N-hydroxy-1-methyl-5-[(4-methylpyridin-2-yl)oxy]-2-[(4-phenylpiperazin-1-yl)carbonyl]piperidine-3-carboxamide This compound was prepared using procedures analogous to those for example 152. MS (ESI): (M+H) 454.2.

Example 445

(2S,3S,5S)-5-[(5-chloropyridin-3-yl)oxy]-2-[4-(4-cyano-3,5-dimethylphenyl)-3,6-dihydropyridin-1(2H)-yl]carbonyl-N-hydroxypiperidine-3-carboxamide Part 1. tert-butyl 4-[(trifluoromethyl)sulfonyl]oxy-3,6-dihydropyridine-1(2H)-carboxylate To a solution of tert-butyl 4-oxo-1-piperidinecarboxylate (10.50 g, 0.05270 mol) in tetrahydrofuran (200.0 mL) at −78 Celsius, under nitrogen, was added 1.00 M of lithium hexamethyldisilazide in tetrahydrofuran (55.96 mL). After stirred at −78 Celsius for 1 h, to the resultant mixture was added solid N-phenylbis(trifluoromethanesulphonimide) (20.00 g, 0.05598 mol). The reaction mixture was stirred at −78 Celsius for 2 h, then allowed to warm to rt gradually and stirred at rt overnight. After evaporation of THF under reduced pressure, the residue was diluted with ether. The mixture was washed with 1N HCl, 1N NaOH, and brine, successively. The organic layers were then dried and evaporated to dry. The residue was applied on silica gel column, eluting 0 to 20% ethyl acetate in hexane, to provide the enol triflate (14.60 g, 83.6%). MS (ESI): (M+2−Boc) 232.0.

Part 2. Tert-butyl 4-(4-hydroxy-3,5-dimethylphenyl)-3,6-dihydropyridine-1(2H)-carboxylate Nitrogen was bubbled through a mixture of tert-butyl 4-[(trifluoromethyl)sulfonyl]oxy-3,6-dihydropyridine-1 (2H)-carboxylate (5.80 g, 0.0175 mol), 2,6-dimethyl-4-(4,4,5,5-tetramethyl-1,3,2-dioxaborolan-2-yl)phenol (4.82 g, 0.0194 mol) and potassium carbonate (7.26 g, 0.0525 mol) in N, N-dimethylformamide (50.0 mL, 0.646 mol) for 10 min. To the reaction mixture was then added [1,1'-Bis(diphenylphosphino)ferrocene]-dichloropalladium(II), complex with dichloromethane (1:1) (0.8 g, 0.001 mol). The resultant mixture was heated at at 80 Celsius overnight. After quenched with water, the mixture was neutralized with 1N HCl, extracted with ethyl acetate. The combined organic layers were washed with water, brine, dried and evaporated to dry. The residue was applied on coloumn, eluting with 0 to 50% EtOAc in hexane, to yield the desired product (4.36 g, 82.09%). MS (ESI): (M−Boc+2) 204.0.

Part 3. Tert-butyl 4-(3,5-dimethyl-4-[(trifluoromethyl)sulfonyl]oxyphenyl)-3,6-dihydropyridine-1(2H)-carboxylate To a solution of tert-butyl 4-(4-hydroxy-3,5-dimethylphenyl)-3,6-dihydropyridine-1 (2H)-carboxylate (2.30 g, 0.00758 mol) in methylene chloride (50.0 mL, 0.780 mol) at −78 Celsius was added triethylamine (3.17 mL, 0.0227 mol), followed by trifluoromethane-sulfonic anhydride (1.40 mL, 0.00834 mol). The reaction mixture was allowed to slowly warm to rt over a period of 1.5 h. The reaction was quenched with satd aqueous ammonium chloride and extracted with ethyl acetate. The combined organic layers were washed with brine, then dried (sodium sulfate) and were concentrated. The resulting residue was purified by flash chromatography (eluting with 0 to 10% EtOAc/Hexane) to provide the triflate as a yellow oil (3.10 g, 93.91%). MS (ESI): (M-Bu+1): 380.0.

Part 4. tert-butyl 4-(4-cyano-3,5-dimethylphenyl)-3,6-dihydropyridine-1(2H)-carboxylate A mixture of tert-butyl 4-(3,5-dimethyl-4-[(trifluoromethyl)sulfonyl]oxyphenyl)-3,6-dihydropyridine-1(2H)-carboxylate (2.80 g, 0.00643 mol) and zinc cyanide (1.51 g, 0.0128 mol) in N,N-dimethylformamide (15.0 mL, 0.194 mol) was degassed with nitrogen for 15 min. To the mixture was added tetrakis(triphenylphosphine)palladium(0) (0.74 g, 0.00064 mol). The reaction mixture was heated at 100 Celsius for 4 h. The mixture was diluted with ether, washed with aq. sodium bicarbonate, brine, dried over magnesium sulfate and evaporated in vacuo. The residue was purified on silica gel, eluting with 0 to 10% EtOAc in hexane, to generate the titled compound (1.08 g, 53.66%). LCMS (M+H) 313.1.

Part 5. 1-tert-butyl 3-methyl(2S,3S,5R)-2-[4-(4-cyano-3,5-dimethylphenyl)-3,6-dihydropyridin-1(2H)-yl]carbonyl-5-hydroxypiperidine-1,3-dicarboxylate (1) tert-butyl 4-(4-cyano-3,5-dimethylphenyl)-3,6-dihydropyridine-1 (2H)-carboxylate (0.88 g, 0.0028 mol) was treated with 5 mL of TFA at rt for 1 h. After evaporated to dry, the resultant TFA salt was used directly in next step.

(2) To a mixture of (2S,3S,5R)-5-hydroxy-3-(methoxycarbonyl)piperidine-2-carboxylic acid (0.477 g, 0.00235 mol) and the TFA salt made above in N, N-dimethylformamide (2.38 mL, 0.0308 mol) was added benzotriazol-1-yloxytris(dimethylamino)phosphonium hexafluorophosphate (1.24 g, 0.00282 mol), followed by N, N-diisopropylethylamine (0.981 mL, 0.00563 mol) at 0 Celsius. The resultant mixture was stirred at rt for 3 h. After quenched with aq. sodium bicarbonate, the mixture was extracted with methylene chloride. The combined organic layers were dried and evaporated under reduced pressure.

(3) The residue was then diluted with methylene chloride (4.77 mL, 0.0744 mol) and treated with N,N-diisopropylethylamine (0.818 mL, 0.00469 mol) followed by di-tert-butyldicarbonate (1.02 g, 0.00469 mol) at rt overnight. The reaction was diluted with aq. sodium bicarbonate, extracted with ethyl acetate. The combined organic layers were dried washed with brine, dried and evaporated to dry in vacuo. The residue was applied on silica gel, eluting with 0 to 100% EtOAc in hexane, to provide the desired product (790 mg, 67.64%). MS (ESI): (M−Boc+2H) 398.1.

Part 6. 1-tert-butyl 3-methyl(2S,3S,5S)-5-[(5-chloropyridin-3-yl)oxy]-2-[4-(4-cyano-3,5-dimethylphenyl)-3,6-dihydropyridin-1(2H)-yl]carbonylpiperidine-1,3-dicarboxylate To a solution of 1-tert-butyl 3-methyl(2S,3S,5R)-2-[4-(4-cyano-3,5-dimethylphenyl)-3,6-dihydropyridin-1 (2H)-yl]carbonyl-5-hydroxypiperidine-1,3-dicarboxylate (100 mg, 0.0002 mol) in tetrahydrofuran (0.912 mL, 0.0112 mol) was added 5-chloropyridin-3-ol (35.0 mg, 0.000270 mol), triphenylphosphine (70.8 mg, 0.000270 mol), followed by diisopropyl azodicarboxylate (0.0532 mL, 0.000270 mol). The mixture was heated at 70 Celsius overnight. After concentrated to dry, the mixture was purified on silica gel, elutin with 0 to 40% EtOAc in hexane, to yield the desired product (45 mg, 32.84%). MS (ESI) (M+H) 609.1.

Part 7. 1-tert-butyl 3-methyl(2S,3S,5S)-5-[(5-chloropyridin-3-yl)oxy]-2-[4-(4-cyano-3,5-dimethylphenyl)-3,6-dihydropyridin-1 (2H)-yl]carbonylpiperidine-1,3-dicarboxylate was treated with hydroxylamine solution in methanol, using procedures analogous to those for example 152, to provide the titled product. ESI MS: (M+H) 510.1.

Example 446

(2S,3S,5S)-2-[4-(4-cyano-3,5-dimethylphenyl)-3,6-dihydropyridin-1(2H)-yl]carbonyl-N-hydroxy-5-[(6-methylpyridin-2-yl)oxy]piperidine-3-carboxamide This compound was prepared using procedures analogous to those for example 445. ESI MS: (M+H) 490.1.

Example 447

(2S,3S,5S)-2-[4-(4-cyano-3,5-dimethylphenyl)-3,6-dihydropyridin-1(2H)-yl]carbonyl-N-hydroxy-5-[(4-methylpyridin-2-yl)oxy]piperidine-3-carboxamide This compound was prepared using procedures analogous to those for example 445. ESI MS: (M+H) 490.2.

Example 448

(2S,3S,5S)-2-[4-(4-cyano-3,5-dimethylphenyl)-3,6-dihydropyridin-1(2H)-yl]carbonyl-N-hydroxy-5-(pyridin-2-yloxy)piperidine-3-carboxamide This compound was prepared using procedures analogous to those for example 445. ESI MS: (M+H) 476.2.

Example 449

(2S,3S,5S)-2-[4-(4-cyano-3,5-dimethylphenyl)-3,6-dihydropyridin-1(2H)-yl]carbonyl-N-hydroxy-5-phenoxypiperidine-3-carboxamide This compound was prepared using procedures analogous to those for example 445. ESI MS: (M+H) 475.2.

Example 450

(2S,3S,5S)-N-hydroxy-2-[(4-phenyl-3,6-dihydropyridin-1(2H)-yl)carbonyl]-5-(pyridin-2-yloxy)piperidine-3-carboxamide This compound was prepared using procedures analogous to those for example 152. ESI MS: (M+H) 423.1.

Example 451

(2S,3S,5S)-2-[4-(4-cyano-3,5-dimethylphenyl)-3,6-dihydropyridin-1(2H)-yl]carbonyl-N-hydroxy-5-[(3-methyl-1H-pyrazol-5-yl)oxy]piperidine-3-carboxamide This compound was prepared using procedures analogous to those for example 445.

Example 452

(2S,3S,5S)-N-hydroxy-5-[(5-methylisoxazol-3-yl)oxy]-2-[(3R)-3-phenylpyrrolidin-1-yl]carbonylpiperidine-3-carboxamide This compound was prepared using procedures analogous to those for example 152. ESI MS: (M+H) 415.1.

Example 453

(2S,3S,5S)-N-hydroxy-5-[(3-methyl-1H-pyrazol-5-yl)oxy]-2-[(3R)-3-phenylpyrrolidin-1-yl]carbonylpiperidine-3-carboxamide This compound was prepared using procedures analogous to those for example 152. ESI MS: (M+H) 414.1.

Example 454

(2S,3S,5S)-5-[(5-chloropyridin-3-yl)oxy]-N-hydroxy-2-[(3R)-3-phenylpyrrolidin-1-yl]carbonylpiperidine-3-carboxamide This compound was prepared using procedures analogous to those for example 152. ESI MS: (M+H) 445.1.

Example 455

(2S,3S,5S)-N-hydroxy-5-[(4-methylpyridin-2-yl)oxy]-2-[(3R)-3-phenylpyrrolidin-1-yl]carbonylpiperidine-3-carboxamide This compound was prepared using procedures analogous to those for example 152. ESI MS: (M+H) 425.0.

Example 456

(2S,3S,5S)-N-hydroxy-2-[(3R)-3-phenylpyrrolidin-1-yl]carbonyl-5-(pyridin-2-yloxy)piperidine-3-carboxamide This compound was prepared using procedures analogous to those for example 152. ESI MS: (M+H) 411.1.

Example 457

(2S,3S,5S)-2-[4-(4-cyano-3,5-dimethylphenyl)-3,6-dihydropyridin-1(2H)-yl]carbonyl-5-(3,4-difluorophenoxy)-N-hydroxypiperidine-3-carboxamide This compound was prepared using procedures analogous to those for example 152. ESI MS: (M+H) 511.1.

Example 458

(2S,3S,5S)-2-[4-(4-cyano-3,5-dimethylphenyl)-3,6-dihydropyridin-1(2H)-yl]carbonyl-N-hydroxy-5-[(5-methylisoxazol-3-yl)oxy]piperidine-3-carboxamide This compound was prepared using procedures analogous to those for example 152. ESI MS: (M+H) 480.1.

Example 459

(2S,3S,5S)-2-[4-(4-cyano-3,5-dimethylphenyl)-3,6-dihydropyridin-1 (2H)-yl]carbonyl-N-hydroxy-5-[(2-methylquinolin-4-yl)oxy]piperidine-3-carboxamide This compound was prepared using procedures analogous to those for example 152. ESI MS: (M+H) 540.1.

Example 460

(2S,3S,5S)-N-hydroxy-5-[(2-methylquinolin-4-yl)oxy]-2-[(3R)-3-phenylpyrrolidin-1-yl]carbonylpiperidine-3-carboxamide This compound was prepared using procedures analogous to those for example 296. ESI MS: (M+H) 475.1.

Example 461

(2S,3S)-2-[4-(4-cyano-3,5-dimethylphenyl)-3,6-dihydropyridin-1(2H)-yl]carbonyl-5,5-difluoro-N-hydroxy-1-methylpiperidine-3-carboxamide Part 1. 1,2-dibenzyl 3-tert-butyl(2S,3S)-5,5-difluoropiperidine-1,2,3-tricarboxylate A solution of 1,2-dibenzyl 3-tert-butyl(2S,3S)-5-oxopiperidine-1,2,3-tricarboxylate (1.87 g, 0.00400 mol) in methylene chloride (3.00 mL, 0.0468 mol), contained in a teflon bottle equipped with a nitrogen inlet tube and stirring bar, was treated with 2-methoxy-N-(2-methoxyethyl)-N-(trifluoro-<lambda>(4)-sulfanyl)ethanamine (1.25 mL, 0.00680 mol) at rt. Ethanol (0.047 mL, 0.00080 mol) was added, and the mixture was stirred at rt overnight. On completion, the solution was poured into saturated sodium bicarbonate, extracted with methylene chloride, dried and evaporated in vacuo. Flash chromatography on silica gel in 0 to 10% EtOAc/hexane afforded the pure product (370 mg, 18.9%). MS (ESI): (M+Na) 512.1. The product was contaminated with small amount (inseperable) of corresponding vinyl floride (M+Na) 493.1.

Part 2. (2S,3S)-3-(tert-butoxycarbonyl)-5,5-difluoropiperidine-2-carboxylic acid A solution of 1,2-dibenzyl 3-tert-butyl(2S,3S)-5,5-difluoropiperidine-1,2,3-tricarboxylate (0.370 g, 0.000756 mol) in EtOH (7.0 mL) was hydrogenated in the presence of 10% Pd/C, under a ballon pressure of hydrogen, for 2 h. After filtered off the catalyst, the filtration was evaporated to dry. The residue was used directly in next step (190 mg, 94.77%). LC MS (M-Bu+1) 210.0.

Part 3. Tert-butyl(2S,3S)-2-[4-(4-cyano-3,5-dimethylphenyl)-3,6-dihydropyridin-1(2H)-yl]carbonyl-5,5-difluoropiperidine-3-carboxylate To a mixture of (2S,3S)-3-(tert-butoxycarbonyl)-5,5-difluoropiperidine-2-carboxylic acid (48 mg, 0.00018 mol) and 2,6-dimethyl-4-(1,2,3,6-tetrahydropyridin-4-yl)benzonitrile hydrochloride (84.7 mg, 0.000217 mol) TFA salt in N,N-dimethylformamide (0.406 mL, 0.00524 mol) was added benzotriazol-1-yloxytris(dimethylamino)phosphonium hexafluorophosphate (96.0 mg, 0.000217 mol), followed by N, N-diisopropylethylamine (0.0756 mL, 0.000434 mol). The mixture was stirred at rt overnight, then quenched with aq. sodium bicarbonate. The mixture was extracted with EtOAc. The combined organic layers were washed with water, brine, dried, and evaporated to dry. The residue was used directly in next step without further purification. LCMS (M+H) 460.2.

Part 4 Tert-butyl(2S,3S)-2-[4-(4-cyano-3,5-dimethylphenyl)-3,6-dihydropyridin-1(2H)-yl]carbonyl-5,5-difluoro-1-methylpiperidine-3-carboxylate The crude reaction mixture from 3256-82 was diluted with acetonitrile (0.64 mL, 0.012 mol) and tetrahydrofuran (0.64 mL, 0.0078 mol). To the mixture was added 12.32 M of formaldehyde in water (0.035 mL) followed by sodium triacetoxyborohydride (92 mg, 0.00044 mol). After stirred at rt overnight, the mixture was evaporated to dry, diluted with aq. sodium bicarbonate, and extracted with EtOAc. The combined organic layers were washed with water, brine and dried. After evaporated to dry, the residue was used directly in next step. LCMS (M+H) 474.2.

Part 5. (2S,3S)-2-[4-(4-cyano-3,5-dimethylphenyl)-3,6-dihydropyridin-1(2H)-yl]carbonyl-5,5-difluoro-N-hydroxy-1-methylpiperidine-3-carboxamide (1) tert-Butyl(2S,3S)-5,5-difluoro-2-[(4-[(2-methylquinolin-4-yl)methoxy]phenylamino)-carbonyl]piperidine-3-carboxylate was treated with 0.5 mL of TFA at rt for 30 min. After evaporation of the TFA, the residue was exposed on high vaccum and then used directly in next step.

(2) To a mixture of the crude TFA salt made above in N, N-dimethylformamide (0.20 mL, 0.0025 mol) was added N-hydroxyamine hydrochloride (7.44 mg, 0.000107 mol), and benzotriazol-1-yloxytris(dimethylamino)phosphonium hexafluorophosphate (47.4 mg, 0.000107 mol). After stirred for 10 min, to the mixture was added N, N-diisopropylethylamine (0.0373 mL, 0.000214 mol). The resulting mixture was stirred at rt overnight. The crude mixture was applied directly on RP-HPLC to generate the desired product as a TFA salt. LC MS (M+H) 433.1.

Example 462

(2S,3S)-2-[4-(4-cyano-3,5-dimethylphenyl)-3,6-dihydropyridin-1(2H)-yl]carbonyl-5,5-difluoro-N-hydroxypiperidine-3-carboxamide This compound was prepared using procedures analogous to those for example 461. LC MS (M+H) 419.1.

Example 463

(2S,3S)-5,5-difluoro-N-hydroxy-2-[4-(3-isopropylphenyl)-3,6-dihydropyridin-1(2H)-yl]carbonyl-1-methylpiperidine-3-carboxamide This compound was prepared using procedures analogous to those for example 461. LC MS (M+H) 422.2.

Example 464

(2S,3S)-5,5-difluoro-N-hydroxy-2-[4-(3-isopropylphenyl)-3,6-dihydropyridin-1(2H)-yl]carbonylpiperidine-3-carboxamide This compound was prepared using procedures analogous to those for example 461. LC MS (M+H) 408.15.

Example 465

(2S,3S)-5,5-difluoro-N(3)-hydroxy-1-methyl-N(2)-4-[(2-methylquinolin-4-yl)methoxy]phenylpiperidine-2,3-dicarboxamide This compound was prepared using procedures analogous to those for example 461. LC MS (M+H) 485.1.

Example 466

(2S,3S)-5,5-difluoro-N(3)-hydroxy-N(2)-4-[(2-methylquinolin-4-yl)methoxy]phenylpiperidine-2,3-dicarboxamide This compound was prepared using procedures analogous to those for example 461. LC MS (M+H) 471.1.

Example 467

(3S,5S,6S)-5-[(hydroxyamino)carbonyl]-6-[(4-[(2-methylquinolin-4-yl)methoxy]phenylamino)carbonyl]piperidin-3-yl azepane-1-carboxylate This compound was prepared using procedures analogous to those for example 204. LC MS (M+H) 576.2.

Example 468

(2S,3S,5R)-5-fluoro-N(3)-hydroxy-N(2)-4-[(2-methylquinolin-4-yl)methoxy]phenylpiperidine-2,3-dicarboxamide Step 1: 2-benzyl 3-methyl(2S,3S,5S)-1-benzyl-5-hydroxypiperidine-2,3-dicarboxylate (1.89 g, 0.00493 mol) was dissolved in methylene chloride (2.7 mL, 0.042 mol), cooled to −78 Celsius, and then treated with diethylaminosulfur trifluoride (0.650 mL, 0.00492 mol) (DAST). The resulting reaction mixture was warmed to rt and stirred at rt for 18 h. The reaction mixture was poured into ice-water containing NaHCO$_3$, extracted with CH$_2$Cl$_2$ (3×). The organic layers were dried over Na$_2$SO$_4$, concentrated and purified on silica gel (eluting with 0~5% MeOH in CH$_2$Cl$_2$). Yield: 1.73 g, 91.24%. LCMS (M+H) 386.1.

Step 2: To a soln. of the product made above (1.73 g, 0.00449 mol) in methanol (20 mL, 0.5 mol) was added 0.34 g of Pd/C (10% wt. on activated carbon, wet), then hydrogenated on par shaker at 43 psi for 3 h. After filtration, the filtrate was concentrated under reduced pressure and dried under high vacuum to give (2S,3S,5R)-5-fluoro-3-(methoxycarbonyl)piperidine-2-carboxylic acid as a white solid. LC-MS (M+H) 206.1.

Step 3: To a mixture of (2S,3S,5R)-5-fluoro-3-(methoxycarbonyl)piperidine-2-carboxylic acid (75.0 mg, 0.000366 mol) and 4-[(2-methylquinolin-4-yl)methoxy]aniline dihydrochloride (148 mg, 0.000439 mol) in N,N-dimethylformamide (0.56 mL, 0.0073 mol) was added benzotriazol-1-yloxytris(dimethylamino)phosphonium hexafluorophosphate (194 mg, 0.000439 mol) followed by N,N-diisopropylethylamine (0.229 mL, 0.00132 mol). After stirred at rt for 2 h, the reaction was quenched with aq. sodium bicarbonate, extracted with EtOAc. The combined organic layers were washed with brine, dired and evaporated to dry under reduced pressure. The residue was used directly in next step. LCMS (M+H) 452.1.

Step 4: methyl(2S,3S,5R)-5-fluoro-2-[(4-[(2-methylquinolin-4-yl)methoxy]-phenylamino)carbonyl]piperidine-3-carboxylate (80.0 mg, 0.000177 mol) was treated with 1.640 M of N-hydroxyamine in methanol (2.161 mL) (made from hydroxylamine HCl salt and sodium methoxide) at rt for 2 h. After acidified with 1:1 TFA/water, the mixture was applied directly on RP-HPLC to give the product as TFA salt. LC MS (M+H) 453.0.

Example 469

(3S,5S,6S)-5-[(hydroxyamino)carbonyl]-1-methyl-6-[(4-[(2-methylquinolin-4-yl)methoxy]phenylamino)carbonyl]piperidin-3-yl azepane-1-carboxylate This compound was prepared using procedures analogous to those for example 204. LCMS (M+H)=590.2.

Example 470

(3S,5S,6S)-6-[4-(4-cyano-3,5-dimethylphenyl)-3,6-dihydropyridin-1(2H)-yl]carbonyl-5-[(hydroxyamino)carbonyl]piperidin-3-yl azepane-1-carboxylate This compound was prepared using procedures analogous to those for example 204. LCMS (M+H) 524.2.

Example 471

(2S,3S,5R)-5-fluoro-N-hydroxy-1-methyl-2-[(3R)-3-phenylpyrrolidin-1-yl]carbonylpiperidine-3-carboxamide This compound was prepared using procedures analogous to those for example 468. LCMS (M+H) 350.1.

Example 472

(2S,3S,5R)-5-fluoro-N-hydroxy-2-[(3R)-3-phenylpyrrolidin-1-yl]carbonylpiperidine-3-carboxamide This compound was prepared using procedures analogous to those for example 468. LCMS (M+H) 336.1.

Example 473

(2S,3S,5S)-N-hydroxy-5-phenoxy-2-[(3-phenyl-2,5-dihydro-1H-pyrrol-1-yl)carbonyl]piperidine-3-carboxamide This compound was prepared using procedures analogous to those for example 152. LCMS (M+H) 408.2.

Example 474

(2S,3S,5S)-N-hydroxy-2-[(3-phenyl-2,5-dihydro-1H-pyrrol-1-yl)carbonyl]-5-(pyridin-2-yloxy)piperidine-3-carboxamide This compound was prepared using procedures analogous to those for example 152. LCMS (M+H) 409.2, (M+Na) 431.2.

Example 475

(2S,3S,5S)-N-hydroxy-2-[(3-phenyl-2,5-dihydro-1H-pyrrol-1-yl)carbonyl]-5-(pyridin-4-yloxy)piperidine-3-carboxamide This compound was prepared using procedures analogous to those for example 152. LCMS (M+H) 409.2, (M+Na) 431.2.

Example 476

(2S,3S,5S)-N-hydroxy-2-[(3-phenyl-2,5-dihydro-1H-pyrrol-1-yl)carbonyl]-5-(pyridin-3-yloxy)piperidine-3-carboxamide This compound was prepared using procedures analogous to those for example 152. LCMS (M+H) 409.2, (M+Na) 431.2.

Example 477

(2S,3S,5S)-N-hydroxy-5-[(6-methylpyridin-2-yl)oxy]-2-[(3-phenyl-2,5-dihydro-1H-pyrrol-1-yl)carbonyl]piperidine-3-carboxamide This compound was prepared using procedures analogous to those for example 152. LCMS (M+H) 423.2.

Example 478

(2S,3S,5S)-N-hydroxy-5-[(4-methylpyridin-2-yl)oxy]-2-[(3-phenyl-2,5-dihydro-1H-pyrrol-1-yl)carbonyl]piperidine-3-carboxamide This compound was prepared using procedures analogous to those for example 152. LCMS (M+H) 423.2.

Example 479

(2S,3S,5S)-5-(3-fluorophenoxy)-N-hydroxy-2-[(3-phenyl-2,5-dihydro-1H-pyrrol-1-yl)carbonyl]piperidine-3-carboxamide This compound was prepared using procedures analogous to those for example 152. LCMS (M+H) 426.2.

Example 480

(2S,3S,5S)-N-hydroxy-2-[(3-phenyl-2,5-dihydro-1H-pyrrol-1-yl)carbonyl]-5-(quinolin-6-yloxy)piperidine-3-carboxamide This compound was prepared using procedures analogous to those for example 152. LCMS (M+H) 459.2.

Example 481

(2S,3S,5S)-N-hydroxy-2-[(3-phenyl-2,5-dihydro-1H-pyrrol-1-yl)carbonyl]-5-(quinolin-7-yloxy)piperidine-3-carboxamide This compound was prepared using procedures analogous to those for example 152. LCMS (M+H) 459.2.

Example 482

(2S,3S,5S)-N-hydroxy-2-[(3-phenyl-2,5-dihydro-1H-pyrrol-1-yl)carbonyl]-5-(quinolin-4-yloxy)piperidine-3-carboxamide This compound was prepared using procedures analogous to those for example 152. LCMS (M+H) 459.2.

Example 483

(2S,3S,5S)-N-hydroxy-5-[(2-methylquinolin-4-yl)oxy]-2-[(3-phenyl-2,5-dihydro-1H-pyrrol-1-yl)carbonyl]piperidine-3-carboxamide This compound was prepared using procedures analogous to those for example 152. LCMS (M#H) 473.2.

Example 484

(2S,3S,5R)-2-[4-(4-cyano-3,5-dimethylphenyl)-3,6-dihydropyridin-1(2H)-yl]carbonyl-5-fluoro-N-hydroxypiperidine-3-carboxamide This compound was prepared using procedures analogous to those for example 468. (M+H) 401.2.

Example 485

(2S,3S,5R)-5-fluoro-N-hydroxy-2-[4-(3-isopropylphenyl)-3,6-dihydropyridin-1(2H)-yl]carbonylpiperidine-3-carboxamide This compound was prepared using procedures analogous to those for example 468. (M+H) 390.2.

Example 486

(2S,3S,5R)-2-[4-(4-cyano-3,5-dimethylphenyl)-3,6-dihydropyridin-1(2H)-yl]carbonyl-5-fluoro-N-hydroxy-1-methylpiperidine-3-carboxamide This compound was prepared using procedures analogous to those for example 468. (M+H) 415.2.

Example 487

(2S,3S,5R)-5-fluoro-N-hydroxy-2-[4-(3-isopropylphenyl)-3,6-dihydropyridin-1(2H)-yl]carbonyl-1-methylpiperidine-3-carboxamide This compound was prepared using procedures analogous to those for example 468. LCMS (M+H) 404.2 (base)

Example 488

(1S,2S,5E)-5-benzylidene-2-[4-(4-cyano-2-methylphenyl)piperazin-1-yl]carbonyl-N-hydroxycyclohexanecarboxamide trifluoroacetate (salt)

This compound was prepared using procedures analogous to those for example 241. The crude products were purified by reverse phase HPLC with 5-95% MeCN/H$_2$O (with 0.05% TFA, pH=2.5) to give the trans product [Peak 1, 3.6 mg, 14% in yield, (M+H)=459.2] as a colorless solid as well as the cis product as a colorless solid [peak 2, 1.9 mg, 7% in yield, (M+H)=459.2].

Example 489

(1S,2S,5E)-2-[4-(4-cyano-2-methylphenyl)piperazin-1-yl]carbonyl-5-(cyclopropylmethylene)-N-hydroxycyclohexanecarboxamide trifluoroacetate (salt)

This compound was prepared using procedures analogous to those for example 241. The crude material was purified by reverse phase HPLC with 5-95% MeCN/H$_2$O (with 0.05% TFA) to give the trans product [peak 1, 12.0 mg, 20% in yield, (M+H)=423.2]as a colorless solid as well as the cis product as a colorless solid [peak 2, 6.4 mg, 11% in yield, (M+H)=423.2].

Example 490

(1S,2S,5E)-5-benzylidene-N-hydroxy-2-[(3R)-3-phenylpyrrolidin-1-yl]carbonylcyclohexanecarboxamide This compound was prepared using procedures analogous to those for example 241. The crude material was purified by reverse phase HPLC with 5-95% MeCN/H$_2$O (with 0.05% TFA, pH=2) to give the trans product as a colorless solid [peak 1, 20.5 mg, 48% in yield, (M+H)=405.1] as well as cis product as a colorless solid [peak 2, 9.4 mg, 22% in yield, (M+H)=405.2].

Example 491

(1S,2S,5S)-N,5-dihydroxy-5-isobutyl-2-[(4-phenyl-3,6-dihydropyridin-1 (2H)-yl)carbonyl]cyclohexanecarboxamide This compound was prepared using procedures analogous to those for example 244. LCMS (M+Na)=423.2.

Example 492

(1S,2S,5S)-5-butyl-N,5-dihydroxy-2-[(4-phenyl-3,6-dihydropyridin-1(2H)-yl)carbonyl]cyclohexanecarboxamide This compound was prepared using procedures analogous to those for example 243. LCMS (M+H)=401.2.

Example 493

(1R,3S,4S)-3-[(hydroxyamino)carbonyl]-1-methyl-4-[(4-phenylpiperazin-1-yl)carbonyl]cyclohexyl azetidine-1-carboxylate trifluoroacetate (salt)

This compound was prepared using procedures analogous to those for example 204. LCMS (M+H)=445.2.

Example 494

(1S,3S,4S)-3-[(hydroxyamino)carbonyl]-1-methyl-4-[(4-phenylpiperazin-1-yl)carbonyl]cyclohexyl pyrrolidine-1-carboxylate trifluoroacetate (salt)

This compound was prepared using procedures analogous to those for example 204. LCMS (M+Na)=481.2.

Example 495

(1S,2S,5S)-N,5-dihydroxy-5-isobutyl-2-[(4-phenylpiperazin-1-yl)carbonyl]cyclohexanecarboxamide trifluoroacetate (salt)

This compound was prepared using procedures analogous to those for example 244. LCMS (M+H)=404.0.

Example 496

(1S,2S,5R)-5-(cyclopropylmethyl)-N,5-dihydroxy-2-[(4-phenylpiperazin-1-yl)carbonyl]cyclohexanecarboxamide trifluoroacetate (salt)

This compound was prepared using procedures analogous to those for example 243. LC MS (M+H)=402.1.

Example 497

(1S,2S,5R)-5-butyl-N,5-dihydroxy-2-[(4-phenylpiperazin-1-yl)carbonyl]cyclohexanecarboxamide trifluoroacetate (salt)

This compound was prepared using procedures analogous to those for example 244. The crude material was purified by reverse phase HPLC with 5-95% MeCN/H$_2$O (with 0.05% TFA) to give the ax-OH product [peak2, 9.1 mg, 5% in yield for two steps, (M+H)=404.2]as a colorless solid as well as the eq-OH product [peak1, 1.5 mg, 1% in yield for two steps, (M+H)=404.2]as a colorless solid.

Example 498

(1R,3S,4S)-3-[(hydroxyamino)carbonyl]-1-methyl-4-[(4-phenylpiperazin-1-yl)carbonyl]cyclohexyl pyrrolidine-1-carboxylate trifluoroacetate (salt)

This compound was prepared using procedures analogous to those for example 204. LCMS (M+H)=459.2.

Example 499

(1S,2S,5E)-5-(cyclopropylmethylene)-N-hydroxy-2-[(3R)-3-phenylpyrrolidin-1-yl]carbonylcyclohexanecarboxamide This compound was prepared using procedures analogous to those for example 241. The crude material was purified by reverse phase HPLC with 5-95% MeCN/H$_2$O (with 0.05% TFA) to give the peak1 [9.8 mg, 33% in yield, (M+H)=369.2] as a colorless solid as well as the peak2 [7.6 mg, 25% in yield, (M+H)=369.2] as a colorless solid.

Example 500

(1S,2S,5R)-5-ethyl-N,5-dihydroxy-2-[(4-phenylpiperazin-1-yl)carbonyl]cyclohexanecarboxamide trifluoroacetate (salt)

This compound was prepared using procedures analogous to those for example 244. The crude material was purified by reverse phase HPLC with 5-95% MeCN/H$_2$O (with 0.05% TFA) to give the ax-OH product [peak2, 39.1 mg, 22% in yield for two steps, (M+H)=376.2]as a colorless solid as well as the eq-OH product [peak 1, 25.0 mg, 14% in yield for two steps, (M+H)=376.2]as a colorless solid.

Example 501

(3R,4S)-1-[(E)-(cyanoimino)(cyclopropylamino)methyl]-4-[4-(4-cyano-2-methylphenyl)-3,6-dihydropyridin-1(2H)-yl]carbonyl-N-hydroxypiperidine-3-carboxamide This compound was prepared using procedures analogous to those for example 220. LCMS (M+H)=476.2.

Example 502

(3R,4S)-1-[(E)-(cyanoimino)(dimethylamino)methyl]-4-[4-(4-cyano-2-methylphenyl)-3,6-dihydropyridin-1(2H)-yl]carbonyl-N-hydroxypiperidine-3-carboxamide This compound was prepared using procedures analogous to those for example 220. LCMS (M+H)=464.2.

Example 503

(3R,4S)-1-[(E)-(cyanoimino)(piperidin-1-yl)methyl]-4-[4-(4-cyano-2-methylphenyl)piperazin-1-yl]carbonyl-N-hydroxypiperidine-3-carboxamide This compound was prepared using procedures analogous to those for example 220. LCMS (M+H) 507.2.

Example 504

(3R,4S)-1-[(E)-azetidin-1-yl(cyanoimino)methyl]-4-[4-(4-cyano-2-methylphenyl)-3,6-dihydropyridin-1(2H)-yl]carbonyl-N-hydroxypiperidine-3-carboxamide This compound was prepared using procedures analogous to those for example 220. LCMS (M+H) 476.1.

Example 505

(3R,4S)-1-[(E)-azetidin-1-yl(cyanoimino)methyl]-4-[4-(4-cyano-2-methylphenyl)piperidin-1-yl]carbonyl-N-hydroxypiperidine-3-carboxamide This compound was prepared using procedures analogous to those for example 220. LCMS (M+H) 478.1.

Example 506

(3R,4S)-1-[(E)-(cyanoimino)(pyrrolidin-1-yl)methyl]-4-[4-(4-cyano-2-methylphenyl)-3,6-dihydropyridin-1(2H)-yl]carbonyl-N-hydroxypiperidine-3-carboxamide This compound was prepared using procedures analogous to those for example 220. LCMS (M+H)=490.2.

Example 507

(3R,4S)-1-[(E)-(cyanoimino)(piperidin-1-yl)methyl]-4-[4-(4-cyano-2-methylphenyl)-3,6-dihydropyridin-1(2H)-yl]carbonyl-N-hydroxypiperidine-3-carboxamide This compound was prepared using procedures analogous to those for example 220. LCMS (M+H) 504.2.

Example 508

(3R,4S)-1-[(E)-(cyanoimino)(piperidin-1-yl)methyl]-4-[4-(4-cyano-2-methylphenyl)piperidin-1-yl]carbonyl-N-hydroxypiperidine-3-carboxamide This compound was prepared using procedures analogous to those for example 220. LCMS (M+H)=506.2.

The structural aspects of the novel compounds exemplified above are summarized in Table 1 through Table 7.

TABLE 1

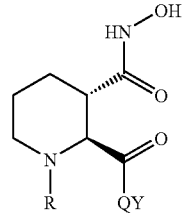

| Ex. | R | QY | MS |
|---|---|---|---|
| 42 | tetrahydrofuran-(3S)-yl oxo-carbonyl | 4-(3-isopropyl-phenyl)-piperidinyl | 488.2 |
| 43 | tetrahydrofuran-(3R)-yl oxo-carbonyl | 4-(3-isopropyl-phenyl)-piperidinyl | 488.2 |

TABLE 1-continued

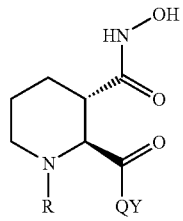

| Ex. | R | QY | MS |
|---|---|---|---|
| 44 | tetrahydro-2H-pyran-4-yl oxo-carbonyl | 4-(3-isopropyl-phenyl)-piperidinyl | 502.2 |
| 45 | tetrahydrofuran-(3R)-yl oxo-carbonyl | 4-phenyl-piperazinyl | 447.2 |
| 46 | tetrahydrofuran-(3S)-yl oxo-carbonyl | 4-phenyl-piperazine | 447.2 |

TABLE 1-continued

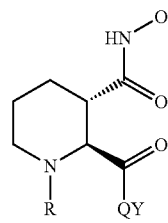

| Ex. | R | QY | MS |
|---|---|---|---|
| 47 | tetrahydropyran-2H-4-yl oxo-carbonyl | 4-phenyl-piperazine | 461.2 |
| 71 | tetrahydrofuran-(3S)-yl oxo-carbonyl | 4-(4-tert-Butyl-phenyl)-piperazinyl | 503.3 |

TABLE 2

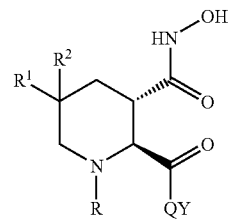

| Ex. | R | R$^1$/R$^2$ | QY | MS |
|---|---|---|---|---|
| 1 | H | (R)-[(3R)-hydroxy-pyrrolin-1-yl] | 4-(4-Cyano-2-methyl-phenyl)-3,6-dihydro-2H-pyridinyl | 454.1 |
| 2 | H | (RS)-[(2-dimethylamino-ethylcarbamoyl)-methyl] | 4-(4-Cyano-2-methyl-phenyl)-3,6-dihydro-2H-pyridinyl | 497 |
| 3 | H | (R)-{[2-(3R)-hydroxy-pyrrolidin-1-yl]-2-oxo-ethyl} | 4-(4-Cyano-2-methyl-phenyl)-3,6-dihydro-2H-pyridinyl | 496.2 |
| 3 | H | (S)-{[2-(3R)-hydroxy-pyrrolidin-1-yl]-2-oxo-ethyl} | 4-(4-Cyano-2-methyl-phenyl)-3,6-dihydro-2H-pyridinyl | 496.2 |
| 4 | H | (S)-(2-morpholin-4-yl-2-oxo-ethyl) | 4-(4-Cyano-2-methyl-phenyl)-3,6-dihydro-2H-pyridinyl | 496.2 |
| 4 | H | (R)-(2-morpholin-4-yl-2-oxo-ethyl) | 4-(4-Cyano-2-methyl-phenyl)-3,6-dihydro-2H-pyridinyl | 496.2 |
| 5 | H | (R)-[2-(4-hydroxy-piperidin-1-yl)-2-oxo-ethyl] | 4-(4-Cyano-2-methyl-phenyl)-3,6-dihydro-2H-pyridinyl | 510.3 |
| 5 | H | (S)-[2-(4-hydroxy-piperidin-1-yl)-2-oxo-ethyl] | 4-(4-Cyano-2-methyl-phenyl)-3,6-dihydro-2H-pyridinyl | 510.3 |
| 6 | H | (R)-[(2-methoxy-acetyl)-methyl-amino] | 4-(4-Cyano-2-methyl-phenyl)-piperazin-1yl | 473.2 |
| 6 | H | (S)-[(2-methoxy-acetyl)-methyl-amino] | 4-(4-Cyano-2-methyl-phenyl)-piperazin-1yl | 473.2 |
| 7 | H | (S)-[(2-methoxy-ethylcarbamoyl)-methyl] | 4-(4-Cyano-2-methyl-phenyl)-3,6-dihydro-2H-pyridinyl | 484.2 |
| 7 | H | (R)-[(2-methoxy-ethylcarbamoyl)-methyl] | 4-(4-Cyano-2-methyl-phenyl)-3,6-dihydro-2H-pyridinyl | 484.2 |
| 8 | H | (S)-[(tetrahydro-furan-(3R)-ylcarbamoyl)-methyl] | 4-(4-Cyano-2-methyl-phenyl)-3,6-dihydro-2H-pyridinyl | 496.2 |
| 8 | H | (R)-[(tetrahydro-furan-(3R)-ylcarbamoyl)-methyl] | 4-(4-Cyano-2-methyl-phenyl)-3,6-dihydro-2H-pyridinyl | 496.2 |
| 9 | H | (R)-[methoxy-carbonyloxy] | (3R)-phenyl-pyrrolidinyl | 392.2 |
| 9 | H | (S)-[methoxy-carbonyloxy] | (3R)-phenyl-pyrrolidinyl | 392.2 |
| 10 | H | (RS)-Hydroxy | (3R)-phenyl-pyrrolidinyl | 334.2 |
| 11 | H | (RS)-[Methylamino-carbonyloxy] | (3R)-phenyl-pyrrolidinyl | 391.2 |
| 48 | H | (RS)-{2-[(5-Cbz-aminopentyl)amino]-2-oxoethyl} | (3RS)-phenyl-pyrrolidinyl | 594 |
| 49 | H | (RS)-{2-[(5-aminopentyl)amino]-2-oxoethyl} | (3RS)-phenyl-pyrrolidinyl | 460 |
| 54 | H | (R)-Hydroxy | 4-(3-isopropyl-phenyl)-3,6-dihydro-2H-pyridinyl | 388.3 |

TABLE 2-continued

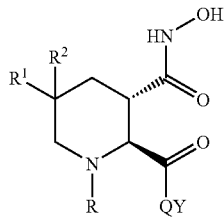

| Ex. | R | R¹/R² | QY | MS |
|---|---|---|---|---|
| 54 | H | (S)-Hydroxy | 4-(3-isopropyl-phenyl)-3,6-dihydro-2H-pyridinyl | 388.3 |
| 55 | H | (R)-Hydroxy | 4-phenyl-piperazinyl | 349.3 |
| 55 | H | (S)-Hydroxy | 4-phenyl-piperazinyl | 349.3 |
| 56 | H | (R)-(2-Morpholin-4-yl-2-oxo-ethyl) | 4-phenyl-piperazinyl | 460.3 |
| 56 | H | (S)-(2-Morpholin-4-yl-2-oxo-ethyl) | 4-phenyl-piperazinyl | 460.3 |
| 57 | H | (R)-Hydroxy | 4-(3-isopropyl-phenyl)-piperidinyl | 390.2 |
| 57 | H | (S)-Hydroxy | 4-(3-isopropyl-phenyl)-piperidinyl | 390.2 |
| 58 | H | (S)-(2-Morpholin-4-yl-2-oxo-ethyl) | 4-(3-isopropyl-phenyl)-piperidinyl | 501.3 |
| 58 | H | (S)-(2-Morpholin-4-yl-2-oxo-ethyl) | 4-(3-isopropyl-phenyl)-piperidinyl | 501.3 |
| 70 | Me | (R)-[Pyrrolidin-1-yl)-carbonyloxy] | (3R)-phenyl-pyrrolidinyl | 445.2 |
| 70 | Me | (S)-[(Pyrrolidin-1-yl)-carbonyloxy] | (3R)-phenyl-pyrrolidinyl | 445.2 |
| 81 | H | [(Pyrrolidin-1-yl)-carbonyloxy] | 4-phenyl-3,6-dihydro-2H-pyridinyl | 443.2 |
| 82 | H | [(Pyrrolidin-1-yl)-carbonyloxy] | 4-phenyl-piperidinyl | 445.5 |
| 84 | H | (2-Oxo-2-piperidin-1-yl-ethyl) | (3R)-phenyl-pyrrolidinyl | 443.3 |
| 85 | H | (R)-(2-Oxo-2-pyrrolidin-1-yl-ethyl) | (3R)-phenyl-pyrrolidinyl | 429.3 |
| 85 | H | (S)-(2-Oxo-2-pyrrolidin-1-yl-ethyl) | (3R)-phenyl-pyrrolidinyl | 429.3 |
| 86 | H | (RS)-(2-Oxo-2-pyrrolidin-1-yl-ethyl) | 4-phenyl-piperazinyl | 444.0 |
| 87 | H | (RS)-(2-Oxo-2-piperidin-1-yl-ethyl) | 4-phenyl-piperazinyl | 458.2 |
| 88 | Me | (RS)-(2-Oxo-2-piperidin-1-yl-ethyl) | 4-phenyl-piperazinyl | 472.1 |
| 89 | Me | (RS)-(2-Oxo-2-pyrrolidin-1-yl-ethyl) | 4-phenyl-piperazinyl | 458.2 |
| 90 | Me | (RS)-(2-Oxo-2-piperidin-1-yl-ethyl) | (3R)-phenyl-pyrrolidinyl | 457.1 |
| 91 | Me | (RS)-(2-Oxo-2-pyrrolidin-1-yl-ethyl) | (3R)-phenyl-pyrrolidinyl | 443.0 |
| 93 | H | (RS)-(Isobutyryl-methyl-amino) | (3R)-phenyl-pyrrolidinyl | 417.2 |
| 94 | H | (RS)-(Isobutyryl-methyl-amino) | 3-phenyl-2,5-dihydro-pyrrolyl | 415.2 |
| 95 | H | (RS)-(Isobutyryl-methyl-amino) | 4-phenyl-3,6-dihydro-2H-pyridinyl | 429.2 |
| 96 | H | (RS)-(Isobutyryl-methyl-amino) | 4-phenyl-piperidinyl | 431.3 |
| 97 | H | (RS)-(Isobutyryl-methyl-amino) | 4-phenyl-piperazinyl | 432.3 |
| 103 | H | (RS)-[(Pyrrolidin-1-yl)-carbonyloxy] | (3R)-phenyl-pyrrolidinyl | 431.2 |
| 104 | H | (RS)-[(Pyrrolidin-1-yl)-carbonyloxy] | 4-phenyl-piperazinyl | 446.2 |
| 105 | H | (RS)-[(Pyrrolidin-1-yl)-carbonyloxy] | 3-phenyl-2,5-dihydro-pyrrolyl | 429.2 |
| 106 | CO₂Me | (RS)-[(Pyrrolidin-1-yl)-carbonyloxy] | 3-phenyl-2,5-dihydro-pyrrolyl | 487.2 |
| 107 | CO₂Me | (RS)-[(Pyrrolidin-1-yl)-carbonyloxy] | (3R)-phenyl-pyrrolidinyl | 489.2 |
| 108 | CO₂Me | (RS)-[(Pyrrolidin-1-yl)-carbonyloxy] | 4-phenyl-piperidinyl | 503.3 |
| 109 | CO₂Me | (RS)-[(Pyrrolidin-1-yl)-carbonyloxy] | 4-phenyl-3,6-dihydro-2H-pyridinyl | 501.2 |

TABLE 2-continued

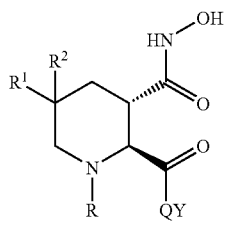

| Ex. | R | R¹/R² | QY | MS |
|---|---|---|---|---|
| 110 | CO₂Me | (RS)-[(Pyrrolidin-1-yl)-carbonyloxy] | 4-phenyl-piperazinyl | 504.3 |
| 111 | H | (RS)-(Benzoyl-methyl-amino) | 4-phenyl-3,6-dihydro-2H-pyridinyl | 463.2 |
| 112 | H | (RS)-(Benzoyl-methyl-amino) | 4-phenyl-piperazinyl | 466.2 |
| 113 | H | (RS)-[Isopropyl-oxocarbonyl-(methyl)amino] | 4-phenyl-piperazinyl | 448.3 |
| 461 | Me | 5,5-difluoro | 4-(4-cyano-3,5-dimethylphenyl)-3,6-dihydropyridin-1(2H)-yl | 433.1 |
| 462 | H | 5,5-difluoro | 4-(4-cyano-3,5-dimethylphenyl)-3,6-dihydropyridin-1(2H)-yl | 419.1 |
| 463 | Me | 5,5-difluoro | 4-(3-isopropylphenyl-3,6-dihydropyridin-1(2H)-yl | 422.2 |
| 464 | H | 5,5-difluoro | 4-(3-isopropylphenyl-3,6-dihydropyridin-1(2H)-yl | 408.2 |
| 465 | Me | 5,5-difluoro | 4-[(2-methylquinolin-4-yl)methoxy]phenylamino | 485.1 |
| 466 | H | 5,5-difluoro | 4-[(2-methylquinolin-4-yl)methoxy]phenylamino | 471.1 |
| 468 | H | (5R)-F | 4-[(2-methylquinolin-4-yl)methoxy]phenylamino | 453.0 |
| 471 | Me | (5R)-F | (3R)-phenylpyrrolidin-1-yl | 350.1 |
| 472 | H | (5R)-F | (3R)-phenylpyrrolidin-1-yl | 336.1 |
| 484 | H | (5R)-F | 4-(4-cyano-3,5-dimethylphenyl)-3,6-dihydropyridin-1(2H)-yl | 401.2 |
| 485 | H | (5R)-F | 4-(3-isopropylphenyl-3,6-dihydropyridin-1(2H)-yl | 390.2 |
| 486 | Me | (5R)-F | 4-(4-cyano-3,5-dimethylphenyl)-3,6-dihydropyridin-1(2H)-yl | 415.2 |
| 487 | Me | (5R)-F | 4-(3-isopropylphenyl-3,6-dihydropyridin-1(2H)-yl | 404.2 |

TABLE 3

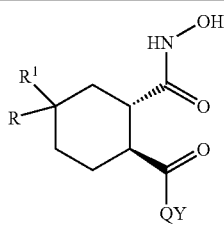

| Ex. | R | R¹ | QY | MS |
|---|---|---|---|---|
| 25 | H | (S)-Hydroxy | 4-phenyl-3,6-dihydro-2H-pyridinyl | 345.1 |
| 26 | H | (S)-Hydroxy | 4-phenyl-piperidinyl | 347.1 |
| 27 | H | (S)-Hydroxy | 4-phenyl-piperazinyl | 348.1 |
| 28 | H | (S)-Hydroxy | 3-phenyl-2,5-dihydro-pyrrolyl | 331.1 |
| 29 | H | (RS)-pyrrolidin1-yl | (3R)-phenyl-pyrrolidinyl | 386.2 |
| 30 | H | (R)-[Morpholin-4-yl] | (3R)-phenyl-pyrrolidinyl | 402.2 |
| 31 | H | (S)-[Morpholin-4-yl] | (3R)-phenyl-pyrrolidinyl | 402.2 |
| 32 | H | (RS)-[(3R)-Hydroxy-pyrrolidin-1-yl] | (3R)-phenyl-pyrrolidinyl | 402.2 |
| 33 | H | (S)-Hydroxy | [4-(4-tert-Butyl-phenyl)-piperazinyl | 404.2 |
| 34 | H | (RS)-[tetrahydro-furan-(3S)-yl-oxocarbonyl (methyl)amino] | (3R)-phenyl-pyrrolidinyl | 460.2 |
| 35 | H | (RS)-[tetrahydro-furan-(3R)-yl-oxocarbonyl (methyl)amino] | (3R)-phenyl-pyrrolidinyl | 460.2 |

TABLE 3-continued

| Ex. | R | R¹ | QY | MS |
|---|---|---|---|---|
| 36 | H | (RS)-[tetrahydro-2H-pyran-4-yl oxocarbonyl (methyl)amino] | (3R)-phenyl-pyrrolidinyl | 474.2 |
| 37 | H | (S)-[Pyrrolidin-1-yl carbonyloxy] | (3R)-phenyl-pyrrolidinyl | 430.3 |
| 38 | H | (S)-[Methylamino-carbonyloxy] | (3R)-phenyl-pyrrolidinyl | 390.2 |
| 39 | H | (S)-[Dimethylamino-carbonyloxy] | (3R)-phenyl-pyrrolidinyl | 404.3 |
| 40 | H | (S)-[(Morpholin-4-yl)-carbonyloxy] | (3R)-phenyl-pyrrolidinyl | 446.2 |
| 41 | H | (S)-[(3R)-Hydroxy-pyrrolidin-1-yl]-carbonyloxy | (3R)-phenyl-pyrrolidinyl | 446.3 |
| 50 | H | (RS)-(2-Oxo-2-piperidin-1-yl-ethyl) | 4-phenyl-piperazinyl | 457 |
| 51 | H | (RS)-(2-Oxo-2-pyrrolidin-1-yl-ethyl) | 4-phenyl-piperazinyl | 443 |
| 52 | H | (RS)-{2-Oxo-2-[(3R)-hydroxypyrrolidin-1-yl]-ethyl} | 4-phenyl-piperazinyl | 459 |
| 53 | H | (RS)-(2-Oxo-2-piperidin-1-yl-ethyl) | [4-(2-methyl-quinolin-4-ylmethoxy)-phenyl]-amino | 559 |
| 59 | H | (RS)-[2-(4-Methyl-piperazin-1-yl)-2-oxo-ethyl] | 4-phenyl-piperazinyl | 472.2 |
| 60 | H | (RS)-(2-Morpholin-4-yl-2-oxo-ethyl) | 4-phenyl-piperazinyl | 459.2 |
| 61 | H | (RS)-[(2-Methoxy-ethylcarbamoyl)-methyl] | 4-phenyl-piperazinyl | 447.2 |
| 62 | H | (S)-[Methylamino-carbonyloxy] | 4-phenyl-piperazinyl | 405.1 |
| 63 | H | (S)-[Dimethylamino-carbonyloxy] | 4-phenyl-piperazinyl | 419.1 |
| 64 | H | (S)-[(Pyrrolidin-1-yl)-carbonyloxyl | 4-phenyl-piperazinyl | 445.1 |
| 65 | H | (S)-[(Piperidin-1-yl)-carbonyloxy] | 4-phenyl-piperazinyl | 459.2 |
| 66 | H | (S)-[(Morpholin-4-yl)-carbonyloxy] | 4-phenyl-piperazinyl | 461.1 |
| 67 | H | (S)-{[(3R)-Hydroxy-pyrrolidin-1-yl]-carbonyloxy} | 4-phenyl-piperazinyl | 461.1 |
| 68 | H | (S)-[Cyclopropylamino-carbonyloxy] | 4-phenyl-piperazinyl | 431.1 |
| 72 | H | (R)-[(Pyrroiidin-1-yl)-carbonyloxy] | (3R)-phenyl-pyrrolidinyl | 430.2 |
| 73 | H | (R)-[(Morpholin-4-yl)-carbonyloxy] | (3R)-phenyl-pyrrolidinyl | 446.2 |
| 74 | H | (R)-[Dimethylamino-carbonyloxy] | (3R)-phenyl-pyrrolidinyl | 404.2 |
| 75 | H | (R)-[Methylamino-carbonyloxy] | (3R)-phenyl-pyrrolidinyl | 390.2 |
| 76 | H | (S)-[Methyoxy-carbonylamino] | (3R)-phenyl-pyrrolidinyl | 390.1 |
| 77 | H | (R)-Methanesulfonylamino | (3R)-phenyl-pyrrolidinyl | 410.1 |
| 78 | H | (R)-Acetylamino | (3R)-phenyl-pyrrolidinyl | 374.2 |
| 83 | H | (S)-(2-oxo-2-piperidin-1-yl-ethyl) | 4-(3-Isopropyl-phenyl)-piperidinyl | 498.3 |
| 83 | H | (R)-(2-oxo-2-piperidin-1-yl-ethyl) | 4-(3-Isopropyl-phenyl)-piperidinyl | 498.3 |
| 92 | H | (RS)-(2-Oxo-2-piperidin-1-yl-ethyl) | 4-phenyl-piperazinyl | 457 |
| 115 | n-Pr | (S)-Hydroxy | (3R)-phenyl-pyrrolidinyl | 375.2 |
| 115 | n-Pr | (R)-Hydroxy | (3R)-phenyl-pyrrolidinyl | 375.2 |
| 116 | H | (S)-Methylamino-carbonyloxy | 4-(4-tert-butyl-phenyl)-piperazinyl | 461.3 |
| 117 | H | (S)-Dimethylamino-carbonyloxy | 4-(4-tert-butyl-phenyl)-piperazinyl | 475.3 |
| 118 | H | (S)-Cyclopropylamino-carbonyloxy | 4-(4-tert-butyl-phenyl)-piperazinyl | 487.3 |
| 119 | H | (S)-(Pyrrolidin-1-yl carbonyloxy) | 4-(4-tert-butyl-phenyl)-piperazinyl | 501.3 |
| 120 | H | (S)-[(3R)-Hydroxypyrrolidin-1-yl carbonyloxy] | 4-(4-tert-butyl-phenyl)-piperazinyl | 517.3 |
| 121 | H | (S)-(Morpholin-4-yl carbonyloxy) | 4-(4-tert-butyl-phenyl)-piperazinyl | 517.3 |
| 122 | H | (S)-(Piperidin-1-yl carbonyloxy) | 4-(4-tert-butyl-phenyl)-piperazinyl | 515.3 |

TABLE 3-continued

| Ex. | R | R¹ | QY | MS |
|---|---|---|---|---|
| 123 | H | (R)-Methylamino-carbonyloxy | 4-phenyl-3,6-dihydro-2H-pyridinyl | 402.1 |
| 124 | H | (R)-Dimethylamino-carbonyloxy | 4-phenyl-3,6-dihydro-2H-pyridinyl | 416.1 |
| 125 | H | (R)-(Pyrrolidin-1-yl carbonyloxy) | 4-phenyl-3,6-dihydro-2H-pyridinyl | 442.1 |

TABLE 4

| Ex. | R | QY | MS |
|---|---|---|---|
| 12 | [Tetrahydro-pyran-4-yl]-oxo-carbonyl | (3R)-phenyl-pyrrolidinyl | 446.1 |
| 13 | [(3R)-tetrahydro-furan-3-yl]-oxy-carbonyl | (3R)-phenyl-pyrrolidinyl | 432.1 |
| 14 | [(3S)-tetrahydro-furan-3-yl]-oxy-carbonyl | (3R)-phenyl-pyrrolidinyl | 432.1 |
| 15 | 2-methoxy-ethyloxy-carbonyl | (3R)-phenyl-pyrrolidinyl | 420.1 |
| 16 | [tetrahydro-pyran-4-yl]-oxo-carbonyl | 4-phenyl-piperazinyl | 461.2 |
| 17 | [(3R)-tetrahydro-furan-3-yl]-oxo-carbonyl | 4-phenyl-piperazinyl | 447.1 |
| 18 | [(3S)-tetrahydro-furan-3-yl]-oxo-carbonyl | 4-phenyl-piperazinyl | 447.2 |
| 19 | 2-methoxy-ethyloxy-carbonyl | 4-phenyl-piperazinyl | 435.1 |
| 20 | [tetrahydro-pyran-4-yl]-oxo-carbonyl | 4-phenyl-piperidinyl | 460.2 |
| 21 | [(3R)-tetrahydro-furan-3-yl]-oxo-carbonyl | 4-phenyl-piperidinyl | 446.2 |
| 22 | [(3S)-tetrahydro-furan-3-yl]-oxo-carbonyl | 4-phenyl-piperidinyl | 446.2 |
| 23 | 2-methoxy-ethyloxy-carbonyl | 4-phenyl-piperidinyl | 444.2 |
| 69 | Morpholine-4-carbonyl | 4-phenyl-piperidinyl | 445.2 |
| 79 | piperidine-1-carbonyl | 4-phenyl-piperidinyl | 443.2 |
| 80 | pyrrolidine-1-carbonyl | 4-phenyl-piperidinyl | 429.2 |
| 98 | 4-trifluoromethoxy-benzoyl | (3R)-phenyl-pyrrolidinyl | 506.2 |
| 99 | 4-trifluoromethoxy-benzenesulfonyl | (3R)-phenyl-pyrrolidinyl | 542.0 |
| 100 | 3-trifluoromethoxy-benzoyl | (3R)-phenyl-pyrrolidinyl | 506.2 |
| 101 | 2-trifluoromethoxy-benzoyl | (3R)-phenyl-pyrrolidinyl | 506.0 |
| 102 | 4-Difluoromethoxy-benzoyl | (3R)-phenyl-pyrrolidinyl | 488.2 |

TABLE 5

| Ex. | R | R¹ | QY | MS |
|---|---|---|---|---|
| 126 | $CO_2Me$ | 3-fluorophenoxy | 4-phenylpiperazin-1-yl | 501.2 |
| 127 | $CO_2Me$ | 3-(trifluoromethyl)-phenoxy | 4-phenylpiperazin-1-yl | 551.1 |
| 128 | $CO_2Me$ | 2,4-difluorophenoxy | 4-phenylpiperazin-1-yl | 519.0 |

TABLE 5-continued

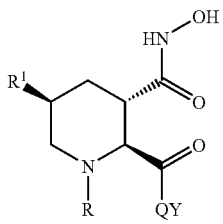

| Ex. | R | R$^1$ | QY | MS |
|---|---|---|---|---|
| 129 | CO$_2$Me | 3-chloro-4-fluorophenoxy | 4-phenylpiperazin-1-yl | 535.0 |
| 130 | CO$_2$Me | 5-chloropyridin-3-yl)oxy | 4-phenylpiperazin-1-yl | 518.1 |
| 131 | CO$_2$Me | 3-bromophenoxy | 4-phenylpiperazin-1-yl | 561.0 |
| 132 | CO$_2$Me | Pyridin-3-yloxy | 4-phenylpiperazin-1-yl | 484.1 |
| 133 | CO$_2$Me | Quinolin-6-yloxy | 4-phenylpiperazin-1-yl | 534.1 |
| 134 | CO$_2$Me | 3-methylphenoxy | 4-phenylpiperazin-1-yl | 497.1 |
| 135 | CO$_2$Me | 3-methoxyphenoxy | 4-phenylpiperazin-1-yl | 513.1 |
| 136 | CO$_2$Me | (6-methylpyridin-2-yl)oxy | 4-phenylpiperazin-1-yl | 498.1 |
| 137 | CO$_2$Me | (2-methylquinolin-4-yl)oxy | 4-phenylpiperazin-1-yl | 548.15 |
| 138 | CO$_2$Me | phenoxy | 4-phenylpiperazin-1-yl | 483.2 |
| 139 | CO$_2$Me | 3-chlorophenoxy | 4-phenylpiperazin-1-yl | 517.0 |
| 140 | CO$_2$Me | 2,3-difluorophenoxy | 4-phenylpiperazin-1-yl | 519.1 |
| 141 | CO$_2$Me | Pyridin-2-yloxy | 4-phenylpiperazin-1-yl | 484.1 |
| 142 | CO$_2$Me | Quinolin-4-yloxy | 4-phenylpiperazin-1-y1 | 534.1 |
| 143 | CO$_2$Me | Pyridin-4-yloxy | 4-phenylpiperazin-1-yl | 484.05 |
| 144 | CO$_2$Me | (4-methylpyridin-2-yl)oxy | 4-phenylpiperazin-1-yl | 498.2 |
| 145 | CO$_2$Me | 2-fluorophenoxy | 4-phenylpiperazin-1-yl | 501.1 |
| 146 | CO$_2$Me | 2-methylphenoxy | 4-phenylpiperazin-1-yl | 497.1 |
| 147 | CO$_2$Me | 4-fluorophenoxy | 4-phenylpiperazin-1-yl | 501.1 |
| 148 | CO$_2$Me | 3,5-difluorophenoxy | 4-phenylpiperazin-1-yl | 519.0 |
| 150 | CO$_2$Me | 1,3-benzothiazol-2-yl | 4-phenylpiperazin-1-yl | 540.1 |
| 151 | CO$_2$Me | 3,4-difluorophenoxy | 4-phenylpiperazin-1-yl | 519.0 |
| 152 | Me | Pyridin-4-yloxy | 4-phenyl-3,6-dihydropyridin-1(2H)-yl | 437.1 |
| 153 | Me | (4-methylpyridin-2-yl)oxy | 4-phenyl-3,6-dihydropyridin-1(2H)-yl | 451.1 |
| 154 | Me | Phenoxy | 4-phenyl-3,6-dihydropyridin-1(2H)-yl | 436.0 |
| 155 | Me | 3-fluorophenoxy | 4-phenyl-3,6-dihydropyridin-1(2H)-yl | 454.1 |
| 156 | Me | Quinolin-6-yloxy | 4-phenyl-3,6-dihydropyridin-1(2H)-yl | 487.0 |
| 157 | Me | (2-methylquinolin-4-yl)oxy | 4-phenyl-3,6-dihydropyridin-1(2H)-yl | 501.1 |
| 158 | Me | Pyridin-2-yloxy | 4-phenyl-3,6-dihydropyridin-1(2H)-yl | 437.0 |
| 159 | Me | 3,5-difluorophenoxy | 4-phenyl-3,6-dihydropyridin-1(2H)-yl | 472.1 |
| 160 | Me | Quinolin-4-yloxy | 4-phenyl-3,6-dihydropyridin-1(2H)-yl | 486.9 |
| 161 | Me | Pyridin-4-yloxy | 4-phenylpiperidin-1-yl | 439.2 |
| 162 | Me | (2-methyl-1,2,3,4-tetrahydroquinolin-4-yl)oxy | 4-phenylpiperidin-1-yl | 507.2 |
| 163 | Me | (4-methylpyridin-2-yl)oxy | 4-phenylpiperidin-1-yl | 453.0 |
| 164 | Me | Pyridin-2-yloxy | 4-phenylpiperidin-1-yl | 439.1 |
| 165 | MeSO$_2$ | phenoxy | 4-phenylpiperazin-1-yl | 503.2 |
| 166 | 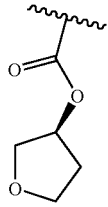 | phenoxy | 4-phenylpiperazin-1-yl | 539.2 |
| 167 | CO$_2$Me | 2-bromophenoxy | 4-phenylpiperazin-1-yl | |
| 168 | CO$_2$Me | 2-chlorophenoxy | 4-phenylpiperazin-1-yl | 517.2 |

TABLE 5-continued

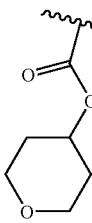

| Ex. | R | R$^1$ | QY | MS |
|---|---|---|---|---|
| 169 | (tetrahydropyran-4-yl ester group) | phenoxy | 4-phenylpiperazin-1-yl | 553.2 |
| 170 | CO$_2$Et | phenoxy | 4-phenylpiperazin-1-yl | 497.2 |
| 171 | H | 3-methylphenoxy | 4-phenylpiperazin-1-yl | 439.1 |
| 172 | H | 3-(trifluoromethyl)-pheoxy | 4-phenylpiperazin-1-yl | 493.2 |
| 173 | H | 3-chlorophenoxy | 4-phenylpiperazin-1-yl | 459.2 |
| 174 | H | 3-methoxyphenoxy | 4-phenylpiperazin-1-yl | 455.0 |
| 175 | H | 3-fluorophenoxy | 4-phenylpiperazin-1-yl | 443.2 |
| 176 | Me | (piperidin-1-ylcarbonyl)oxy | 4-phenyl-3,6-dihydropyridin-1(2H)-yl | 471.1 |
| 177 | Me | [(2S)-2-(hydroxymethyl)pyrrolidin-1-yl]-carbonyloxy | 4-phenyl-3,6-dihydropyridin-1(2H)-yl | 487.15 |
| 178 | Me | Azepan-1-yl-carbonyloxy | 4-phenyl-3,6-dihydropyridin-1(2H)-yl | 485.2 |
| 179 | Me | Azetidin-1-yl-carbonyloxy | 4-phenyl-3,6-dihydropyridin-1(2H)-yl | 443.2 |
| 180 | Me | [(dimethylamino)-carbonyl]oxy | 4-phenyl-3,6-dihydropyridin-1(2H)-yl | 431.1 |
| 181 | Me | 2,5-dihydro-1H-pyrrol-1-yl-carbonyloxy | 4-phenyl-3,6-dihydropyridin-1(2H)-yl | 455.1 |
| 182 | Me | (pyrrolidin-1-ylcarbonyl)oxy | 4-phenyl-3,6-dihydropyridin-1(2H)-yl | 457.1 |
| 183 | Me | Azetidin-1-yl-carbonyloxy | 4-phenylpiperazin-1-yl | 446.2 |
| 184 | Me | Azetidin-1-yl-carbonyloxy | 3-phenyl-2,5-dihydro-1H-pyrrol-1-yl | 429.2 |
| 185 | Me | Azetidin-1-yl-carbonyloxy | 1,3-dihydro-2H-benzo[e]isoindol-2-yl | 453.2 |
| 186 | Me | (pyrrolidin-1-ylcarbonyl)oxy | 4-phenylpiperazin-1-yl | 460.2 |
| 187 | Me | Azetidin-1-yl-carbonyloxy | (3R)-3-phenylpyrrolidin-1-yl | 431.2 |
| 188 | Me | (piperidin-1-ylcarbonyl)oxy | 4-phenylpiperazin-1-yl | 474.2 |
| 189 | Me | Azetidin-1-yl-carbonyloxy | 1,3-dihydro-2H-isoindol-2-yl | 403.2 |
| 190 | Me | (pyrrolidin-1-ylcarbonyl)oxy | 3-phenyl-2,5-dihydro-1H-pyrrol-1-yl | 443.05 |
| 191 | Me | (pyrrolidin-1-ylcarbonyl)oxy | 4-phenylpiperidin-1-yl | 459.15 |
| 192 | Me | Azepan-1-yl-carbonyloxy | 4-phenylpiperidin-1-yl | 487.2 |
| 193 | Me | [(2S)-2-(hydroxymethyl)pyrrolidin-1-yl]-carbonyloxy | 4-phenylpiperidin-1-yl | 489.2 |
| 194 | Me | (piperidin-1-ylcarbonyl)oxy | 4-phenylpiperidin-1-yl | 473.2 |
| 195 | Me | [(dimethylamino)-carbonyl]oxy | 4-phenylpiperidin-1-yl | 433.1 |
| 196 | CO$_2$Me | [(2S)-2-(hydroxymethyl)pyrrolidin-1-yl]-carbonyloxy | 4-phenylpiperazin-1-yl | 534.2 |

TABLE 5-continued

![structure](chemical structure with R, R¹, QY substituents on piperidine)

| Ex. | R | R¹ | QY | MS |
|---|---|---|---|---|
| 197 | CO$_2$Me | (pyrrolidin-1-ylcarbonyl)oxy | 1,3-dihydro-2H-isoindol-2-yl | 461.2 |
| 198 | CO$_2$Me | (piperidin-1-ylcarbonyl)oxy | 4-phenylpiperazin-1-yl | 518.15 |
| 199 | CO$_2$Me | (pyrrolidin-1-ylcarbonyl)oxy | 4-phenylpiperazin-1-yl | 504.2 |
| 200 | CO$_2$Me | (pyrrolidin-1-ylcarbonyl)oxy | (3R)-3-phenylpyrrolidin-1-yl | 489.2 |
| 201 | CO$_2$Me | [(dimethylamino)-carbonyl]oxy | 4-phenylpiperazin-1-yl | 478.1 |
| 202 | CO$_2$Me | (pyrrolidin-1-ylcarbonyl)oxy | 4-phenyl-3,6-dihydropyridin-1(2H)-yl | 501.2 |
| 203 | CO$_2$Me | (pyrrolidin-1-ylcarbonyl)oxy | 4-phenylpiperidin-1-yl | 503.2 |
| 204 | H | (pyrrolidin-1-ylcarbonyl)oxy | 4-phenyl-3,6-dihydropyridin-1(2H)-yl | 443.2 |
| 205 | H | Azetidin-1-yl-carbonyloxy | 1,3-dihydro-2H-benzo[e]isoindol-2-yl | 439.2 |
| 206 | H | Azetidin-1-yl-carbonyloxy | 1,3-dihydro-2H-isoindol-2-yl | 389.2 |
| 207 | H | Azetidin-1-yl-carbonyloxy | 4-phenyl-3,6-dihydropyridin-1(2H)-yl | 429.2 |
| 208 | H | Azetidin-1-yl-carbonyloxy | (3R)-3-phenylpyrrolidin-1-yl | 417.2 |
| 209 | H | Azetidin-1-yl-carbonyloxy | 4-phenylpiperazin-1-yl | 432.2 |
| 210 | H | Azetidin-1-yl-carbonyloxy | 3-phenyl-2,5-dihydro-1H-pyrrol-1-yl | 415.2 |
| 211 | H | Azetidin-1-yl-carbonyloxy | 4-phenylpiperidin-1-yl | 431.3 |
| 212 | H | (pyrrolidin-1-ylcarbonyl)oxy | 4-phenylpiperidin-1-yl | 445.2 |
| 213 | CO$_2$Me | 2-oxo-2-pyrrolidin-1-ylethoxy | 4-phenylpiperazin-1-yl | 518.2 |
| 214 | CO$_2$Me | phenylthio | 4-phenylpiperazin-1-yl | 499.1 |
| 215 | CO$_2$Me | Allyloxy | 4-phenylpiperazin-1-yl | 447.1 |
| 216 | CO$_2$Me | propoxy | 4-phenylpiperazin-1-yl | 449.2 |
| 217 | CO$_2$Me | methoxy | 4-phenylpiperazin-1-yl | 421.2 |
| 218 | H | tert-butoxy | 4-phenylpiperazin-1-yl | 405.1 |
| 219 | CO$_2$Me | tert-butoxy | 4-phenylpiperazin-1-yl | 463.2 |
| 248 | H | 2-oxo-2-pyrrolidin-1-ylethyl | 4-(4-cyano-2-methylphenyl)piperidin-1-yl | 482.1 |
| 249 | H | Methyl-carbamic acid isopropyl ester | 4-phenylpiperidin-1-yl | 447.1 |
| 413 | Me | 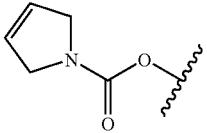 | 4-phenylpiperazin-1-yl | 458.1 |
| 414 | Me | 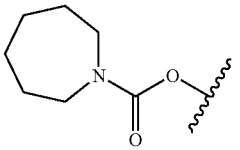 | 4-phenylpiperazin-1-yl | 488.1 |

TABLE 5-continued

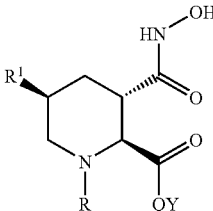

| Ex. | R | R¹ | QY | MS |
|---|---|---|---|---|
| 415 | Me | 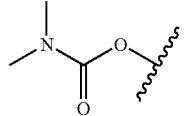 | 4-phenylpiperazin-1-yl | 434.1 |
| 416 | Me | 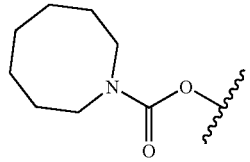 | 4-phenylpiperazin-1-yl | 502.2 |
| 417 | Me | 2-fluorophenoxy | 4-phenylpiperazin-1-yl | 457.2 |
| 418 | Me | (6-methylpyridin-2-yl)oxy | 4-phenylpiperazin-1-yl | 454.2 |
| 419 | Me | Pyridin-4-yloxy | 4-phenylpiperazin-1-yl | 440.1 |
| 420 | Me | 3-fluorophenoxy | 4-phenylpiperazin-1-yl | 457.2 |
| 421 | Me | Pyridine-2-yloxy | 4-phenylpiperazin-1-yl | 440.2 |
| 422 | Me | 1,3-benzothiazol-2-yloxy | 4-phenylpiperazin-1-yl | |
| 423 | Me | 3-methylphenoxy | 4-phenylpiperazin-1-yl | 453.2 |
| 424 | Me | (4-methylpyridin-2-yl)oxy | 4-phenylpiperazin-1-yl | 454.2 |
| 425 | Me | 3,4-difluorophenoxy | 4-phenylpiperazin-1-yl | 475.1 |
| 426 | Me | 2-chlorophenoxy | 4-phenylpiperazin-1-yl | 473.2 |
| 427 | Me | 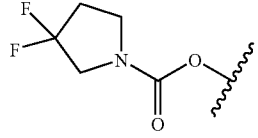 | 4-phenylpiperazin-1-yl | 496.1 |
| 428 | CO₂Me | Quinolin-6-yloxy | 4-phenylpiperazin-1-yl | 534.2 |
| 429 | Me | Pyridine-3-yloxy | 3-phenyl-2,5-dihydro-1H-pyrrol-1-yl | 423.1 |
| 430 | Me | Pyridine-4-yl | 3-phenyl-2,5-dihydro-1H-pyrrol-1-yl | 423.0 |
| 431 | Me | 3-fluorophenoxy | 3-phenyl-2,5-dihydro-1H-pyrrol-1-yl | 440.1 |
| 432 | Me | phenoxy | 3-phenyl-2,5-dihydro-1H-pyrrol-1-yl | 422.1 |
| 433 | Me | Pyridine-2-yloxy | 3-phenyl-2,5-dihydro-1H-pyrrol-1-yl | 423.1 |
| 434 | Me | (4-methylpyridin-2-yl)oxy | 3-phenyl-2,5-dihydro-1H-pyrrol-1-yl | 437.1 |
| 435 | Me | (6-methylpyridin-2-yl)oxy | 3-phenyl-2,5-dihydro-1H-pyrrol-1-yl | 437.1 |
| 436 | Me | Pyridine-2-yloxy | 4-phenylpiperazin-1-yl | 440.2 |
| 437 | Me | Pyridine-3-yloxy | 4-phenylpiperazin-1-yl | 440.1 |
| 438 | Me | (2-methylquinolin-4-yl)oxy | 4-phenylpiperazin-1-yl | 504.2 |
| 439 | Me | (2-methylquinolin-4-yl)oxy | 3-phenyl-2,5-dihydro-1H-pyrrol-1-yl | 487.2 |
| 440 | Me | quinolin-4-yloxy | 4-phenylpiperazin-1-yl | 490.3 |
| 441 | Me | quinolin-6-yloxy | 3-phenyl-2,5-dihydro-1H-pyrrol-1-yl | 473.1 |
| 442 | Me | quinolin-4-yloxy | 3-phenyl-2,5-dihydro-1H-pyrrol-1-yl | 473.1 |
| 443 | H | Pyridine-2-yloxy | 4-phenylpiperazin-1-yl | 426.1 |
| 444 | Me | (4-methylpyridin-2-yl)oxy | 4-phenylpiperazin-1-yl | 454.2 |
| 445 | H | (5-chloropyridin-3-yl)oxy | 4-(4-cyano-3,5-dimethylphenyl)-3,6-dihydropyridin-1(2H)-yl | 510.1 |
| 446 | H | (6-methylpyridin-2-yl)oxy | 4-(4-cyano-3,5-dimethylphenyl)-3,6-dihydropyridin-1(2H)-yl | 490.1 |
| 447 | H | (4-methylpyridin-2-yl)oxy | 4-(4-cyano-3,5-dimethylphenyl)-3,6-dihydropyridin-1(2H)-yl | 490.2 |

TABLE 5-continued

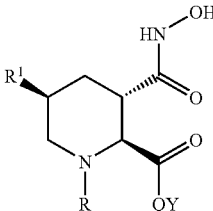

| Ex. | R | R¹ | QY | MS |
|---|---|---|---|---|
| 448 | H | Pyridin-2-yloxy | 4-(4-cyano-3,5-dimethylphenyl)-3,6-dihydropyridin-1(2H)-yl | 476.2 |
| 449 | H | phenoxy | 4-(4-cyano-3,5-dimethylphenyl)-3,6-dihydropyridin-1(2H)-yl | 475.2 |
| 450 | H | Pyridin-2-yloxy | 4-phenyl-3,6-dihydropyridin-1(2H)-yl | 423.1 |
| 451 | H | (3-methyl-1H-pyrazol-5-yl)oxy | 4-(4-cyano-3,5-dimethylphenyl)-3,6-dihydropyridin-1(2H)-yl | |
| 452 | H | (5-methylisoxazol-3-yl)oxy | (3R)-phenylpyrrolidin-1-yl | 415.1 |
| 453 | H | (3-methyl-1H-pyrazol-5-yl)oxy | (3R)-phenylpyrrolidin-1-yl | 414.1 |
| 454 | H | (5-chloropyridin-3-yl)oxy | (3R)-phenylpyrrolidin-1-yl | 445.1 |
| 455 | H | (4-methylpyridin-2-yl)oxy | (3R)-phenylpyrrolidin-1-yl | 425.0 |
| 456 | H | Pyridin-2-yloxy | (3R)-phenylpyrrolidin-1-yl | 411.1 |
| 457 | H | 3,4-difluorophenoxy | 4-(4-cyano-3,5-dimethylphenyl)-3,6-dihydropyridin-1(2H)-yl | 511.1 |
| 458 | H | (5-methylisoxazol-3-yl)oxy | 4-(4-cyano-3,5-dimethylphenyl)-3,6-dihydropyridin-1(2H)-yl | 480.1 |
| 459 | H | (2-methylquinolin-4-yl)oxy | 4-(4-cyano-3,5-dimethylphenyl)-3,6-dihydropyridin-1(2H)-yl | 540.1 |
| 460 | H | (2-methylquinolin-4-yl)oxy | (3R)-phenylpyrrolidin-1-yl | 475.1 |
| 467 | H | 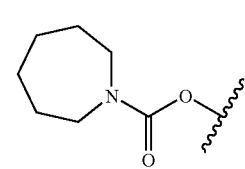 | (4-[(2-methylquinolin-4-yl)methoxy]phenylamino) | 576.2 |
| 469 | Me | 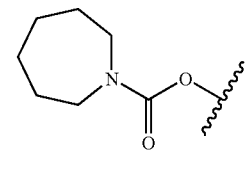 | (4-[(2-methylquinolin-4-yl)methoxy]phenylamino) | 590.2 |
| 470 | H | 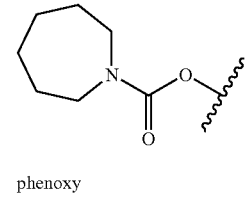 | 4-(4-cyano-3,5-dimethylphenyl)-3,6-dihydropyridin-1(2H)-yl | 524.2 |
| 473 | H | phenoxy | 3-phenyl-2,5-dihydro-1H-pyrrol-1-yl | 408.2 |
| 474 | H | Pyridin-2-yloxy | 3-phenyl-2,5-dihydro-1H-pyrrol-1-yl | 409.2 |
| 475 | H | Pyridin-4-yloxy | 3-phenyl-2,5-dihydro-1H-pyrrol-1-yl | 409.2 |
| 476 | H | Pyridin-3-yloxy | 3-phenyl-2,5-dihydro-1H-pyrrol-1-yl | 409.2 |
| 477 | H | (6-methylpyridin-2-yl)oxy | 3-phenyl-2,5-dihydro-1H-pyrrol-1-yl | 423.2 |
| 478 | H | (4-methylpyridin-2-yl)oxy | 3-phenyl-2,5-dihydro-1H-pyrrol-1-yl | 423.2 |
| 479 | H | 3-fluorophenoxy | 3-phenyl-2,5-dihydro-1H-pyrrol-1-yl | 426.2 |
| 480 | H | Quinolin-6-yloxy | 3-phenyl-2,5-dihydro-1H-pyrrol-1-yl | 459.2 |
| 481 | H | Quinolin-7-yloxy | 3-phenyl-2,5-dihydro-1H-pyrrol-1-yl | 459.2 |
| 482 | H | Quinolin-4-yloxy | 3-phenyl-2,5-dihydro-1H-pyrrol-1-yl | 459.2 |
| 483 | H | (2-methylquinolin-4-yl)oxy | 3-phenyl-2,5-dihydro-1H-pyrrol-1-yl | 473.2 |

TABLE 6

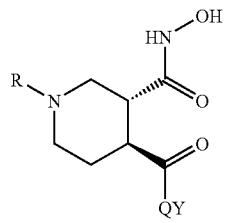

| Ex. | R | QY | MS |
|---|---|---|---|
| 220 | (E)-(cyanoimino)pyrrolidin-1-yl)methyl | (3R)-phenylpyrrolidin-1-yl | 439.2 |
| 221 | (E)-azetidin-1-yl(cyanoimino)methyl | (3R)-phenylpyrrolidin-1-yl | 425.2 |
| 222 | (E)-(cyanoimino)(dimethylamino)methyl | (3R)-phenylpyrrolidin-1-yl | 413.2 |
| 223 | (E)-(cyanoimino)(cyclopropylamino)methyl | (3R)-phenylpyrrolidin-1-yl | 425.2 |
| 224 | (E)-(cyanoimino)(piperidin-1-yl)methyl | (3R)-phenylpyrrolidin-1-yl | 453.3 |
| 225 | (Z)-(cyanoimino)(morpholin-4-yl)methyl | (3R)-phenylpyrrolidin-1-yl | 455.3 |
| 226 | (Z)-(cyanoimino)(hydroxyamino)methyl | (3R)-phenylpyrrolidin-1-yl | 401.1 |
| 227 | (E)-azepan-1-yl(cyanoimino)methyl | (3R)-phenylpyrrolidin-1-yl | 467.3 |
| 228 | (Z)-(cyanoimino)(4-methylpiperazin-1-yl)methyl | (3R)-phenylpyrrolidin-1-yl | 468.2 |
| 229 | (Z)-cyanoimino)(thiomorpholin-4-yl)methyl | (3R)-phenylpyrrolidin-1-yl | 471.1 |
| 230 | (E)-(cyanoimino)(4-methylpiperidin-1yl)methyl | (3R)-phenylpyrrolidin-1-yl | 467.2 |
| 231 | (Z)-(cyanoimino)(2,5-dihydro-1H-pyrrol-1-yl)methyl | (3R)-phenylpyrrolidin-1-yl | 437.2 |
| 232 | (Z)-(cyanoimino)(1,3-dihydro-2H-isoindol-2-yl)methyl | (3R)-phenylpyrrolidin-1-yl | 487.1 |
| 233 | (Z)-(cyanoimino)(3,4-dihydroisoquinolin-2(1H)-yl)methyl | (3R)-phenylpyrrolidin-1-yl | 487.1 |
| 234 | (Z)-1-(hydroxyamino)-2-nitrovinyl | (3R)-phenylpyrrolidin-1-yl | 442.2 |
| 235 | (E)-(cyanoimino)(piperidin-1-yl)methyl | 4-(4-cyano-2-methylphenyl)piperazin-1-yl) | 507 |
| 236 | (E)-(cyanoimino)(dimethylamino)methyl | 4-(4-cyano-2-methylphenyl)piperazin-1-yl) | 467 |
| 237 | (E)-azepan-1-yl(cyanoimino)methyl | 4-(4-cyano-2-methylphenyl)piperazin-1-yl) | 521 |
| 238 | (E)-(cyanoimino)pyrrolidin-1-yl)methyl | 4-(4-cyano-2-methylphenyl)piperazin-1-yl) | 493 |
| 239 | (E)-(cyanoimino)(cyclopropylamino)methyl | 4-(4-cyano-2-methylphenyl)piperazin-1-yl) | 479 |
| 240 | (E)-azetidin-1-yl(cyanoimino)methyl | 4-(4-cyano-2-methylphenyl)piperazin-1-yl) | 479 |
| 501 | (E)-(Cyanoimino)(cyclopropylamino)methyl | 4-(4-cyano-2-methylphenyl)-3,6-dihydropyridin-1(2H)-yl | 476.2 |
| 502 | (E)-(Cyanoimino)(dimethylamino)methyl | 4-(4-cyano-2-methylphenyl)-3,6-dihydropyridin-1(2H)-yl | 464.2 |
| 503 | (E)-(Cyanoimino)(piperidin-1-yl)methyl | 4-(4-cyano-2-methylphenyl)piperazin-1-yl) | 507.2 |
| 504 | (E)-azetidin-1-yl(cyanoimino)methyl | 4-(4-cyano-2-methylphenyl)-3,6-dihydropyridin-1(2H)-yl | 476.1 |
| 505 | (E)-azetidin-1-yl(cyanoimino)methyl | 4-(4-cyano-2-methylphenyl)piperidin-1-yl | 478.1 |
| 506 | (E)-(Cyanoimino)(pyrrolidin-1-yl)methyl | 4-(4-cyano-2-methylphenyl)-3,6-dihydropyridin-1(2H)-yl | 490.2 |
| 507 | (E)-(Cyanoimino)(piperidin-1-yl)methyl | 4-(4-cyano-2-methylphenyl)-3,6-dihydropyridin-1(2H)-yl | 504.2 |
| 508 | (E)-(Cyanoimino)(piperidin-1-yl)methyl | 4-(4-cyano-2-methylphenyl)piperidin-1-yl | 506.2 |

TABLE 7
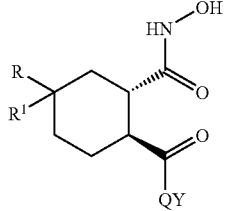
| Ex. | R | R¹ | QY | MS |
|-----|---|----|----|----|
| 241 | 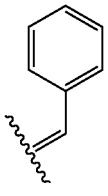 | | 4-phenylpiperazin-1-yl | 420.1 |
| 242 | 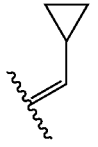 | | 4-phenylpiperazin-1-yl | 384.1 |
| 243 | (5S) CH₂Ph | OH | 4-phenylpiperazin-1-yl | 438.1 |
| 244 | (5R) Ph | OH | 4-phenylpiperazin-1-yl | 424.1 |
| 245 | (5R) CH₂Ph | OH | 4-phenylpiperazin-1-yl | 438.1 |
| 246 | (5R) iPr | OH | 4-phenylpiperazin-1-yl | 390.1 |
| 247 | (5R)  | OH | 4-phenylpiperazin-1-yl | 388.1 |
| 250 | 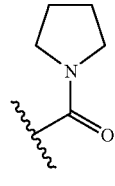 | H | 4-phenyl-3,6-dihydropyridin-1(2H)-yl | 426.2 |
| 251 | 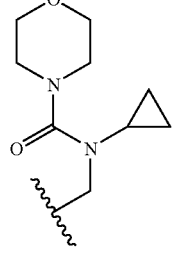 | H | 4-phenylpiperazin-1-yl | 514.3 |
| 252 | (5S) 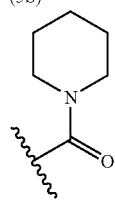 | H | 4-phenylpiperazin-1-yl | 443.1 |

TABLE 7-continued
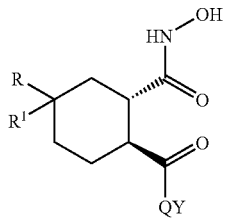
| Ex. | R | R¹ | QY | MS |
|---|---|---|---|---|
| 253 | (5R) piperidine-carbonyl | H | 4-phenylpiperazin-1-yl | 443.1 |
| 254 | (5S) pyrrolidine-carbonyl | H | 4-phenylpiperazin-1-yl | 429.1 |
| 255 | (5R) pyrrolidine-carbonyl | H | 4-phenylpiperazin-1-yl | 429.1 |
| 256 | morpholine-carbonyl | H | 4-phenylpiperazin-1-yl | 445.2 |
| 257 | (5S) piperidine-N-cyclopentyl-carboxamide | H | 4-phenylpiperazin-1-yl | 540.2 |

TABLE 7-continued
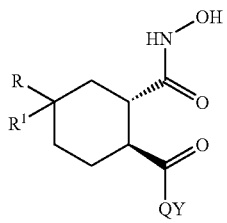
| Ex. | R | R¹ | QY | MS |
|---|---|---|---|---|
| 258 | (5R) [piperidine-N-C(O)-N(cyclopentyl)-CH2- group] | H | 4-phenylpiperazin-1-yl | 540.2 |
| 259 | (1R) [pyrrolidine-N-C(O)-O- group] | H | (3R)-phenylpyrrolidin-1-yl | 430.1 |
| 260 | (1R) [(CH3)2N-C(O)-O- group] | H | (3R)-phenylpyrrolidin-1-yl | 404.1 |
| 261 | (1R) [morpholine-N-C(O)-O- group] | H | 4-phenyl-3,6-dihydropyridin-1(2H)-yl | 458.1 |
| 262 | (1R) [pyrrolidine-N-C(O)-O- group] | H | 4-phenyl-3,6-dihydropyridin-1(2H)-yl | 442.1 |
| 263 | (1R) [CH3-NH-C(O)-O- group] | H | 4-phenyl-3,6-dihydropyridin-1(2H)-yl | 402.1 |

TABLE 7-continued

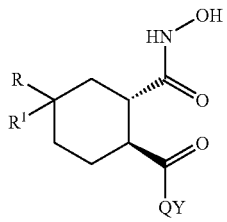

| Ex. | R | R¹ | QY | MS |
|---|---|---|---|---|
| 264 | (1R) [N,N-dimethylcarbamate] | H | 4-phenyl-3,6-dihydropyridin-1(2H)-yl | 416.1 |
| 265 | (5R)-hydroxy | H | (3R)-phenylpyrrolidin-1-yl | 333.1 |
| 266 | (1S) [N,N-dimethylcarbamate] | H | 4-phenyl-3,6-dihydropyridin-1(2H)-yl | 416.1 |
| 267 | (1S) [pyrrolidine carbamate] | H | 4-phenyl-3,6-dihydropyridin-1(2H)-yl | 442.1 |
| 268 | (1S) [N-methylcarbamate] | H | 4-phenyl-3,6-dihydropyridin-1(2H)-yl | 402.1 |
| 269 | (1S) [morpholine carbamate] | H | 4-phenyl-3,6-dihydropyridin-1(2H)-yl | 458.1 |
| 270 | (1R) [N-methylcarbamate] | H | (3R)-phenylpyrrolidin-1-yl | 390.1 |

TABLE 7-continued

[Structure: cyclohexane with R, R¹ substituents at one position, and two adjacent substituents: C(=O)NHOH and C(=O)QY]

| Ex. | R | R¹ | QY | MS |
|---|---|---|---|---|
| 271 | (1R) morpholin-4-yl-carbonyloxy | H | (3R)-phenylpyrrolidin-1-yl | 446.1 |
| 272 | (1R) pyrrolidin-1-yl-carbonyloxy | H | 4-phenylpiperidin-1-yl | 444.2 |
| 273 | (1R) piperidin-1-yl-carbonyloxy | H | 4-phenylpiperazin-1-yl | 459.2 |
| 274 | (1R) pyrrolidin-1-yl-carbonyloxy | H | 4-phenylpiperazin-1-yl | 445.2 |
| 275 | (1R) dimethylaminocarbonyloxy | H | 4-phenylpiperazin-1-yl | 419.2 |
| 276 | (1R) methylaminocarbonyloxy | H | 4-phenylpiperazin-1-yl | 405.2 |

TABLE 7-continued

| Ex. | R | R¹ | QY | MS |
|---|---|---|---|---|
| 277 | (1R) pyrrolidine-N-carbonyloxy | H | 4-phenyl-3,6-dihydropyridin-1(2H)-yl | 442.1 |
| 278 | (1R) methylcarbamoyloxy | H | 4-phenyl-3,6-dihydropyridin-1(2H)-yl | 402.1 |
| 279 | (1R) dimethylcarbamoyloxy | H | 4-phenyl-3,6-dihydropyridin-1(2H)-yl | 416.1 |
| 280 | (1R) dimethylcarbamoyloxy | H | 4-phenylpiperidin-1-yl | 418.2 |
| 281 | (1R) piperidine-N-carbonyloxy | H | 4-phenylpiperidin-1-yl | 458.2 |
| 282 | (5R)-CH₃ | OH | 4-phenylpiperazin-1-yl | 362.1 |
| 283 | (5S)-CH₃ | OH | 4-phenyl-3,6-dihydropyridin-1(2H)-yl | 359.1 |
| 284 | (1R)- (3-hydroxypyrrolidine-N-carbonyloxy) | H | 4-phenylpiperazin-1-yl | 461.2 |

TABLE 7-continued

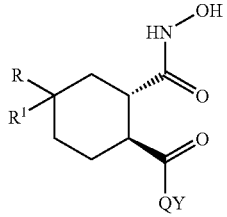

| Ex. | R | R¹ | QY | MS |
|---|---|---|---|---|
| 285 | (1R) 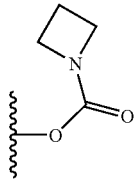 | H | 4-phenylpiperazin-1-yl | |
| 286 | (1R) 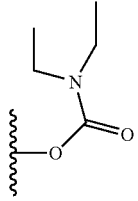 | H | 4-phenylpiperazin-1-yl | 447.2 |
| 287 | (5R)-CH$_2$CH═CH$_2$ | OH | 4-phenyl-3,6-dihydropyridin-1(2H)-yl | 385.2 |
| 288 | (5R)-CH$_2$CH═CH$_2$ | OH | 4-phenylpiperazin-1-yl | 388.2 |
| 289 | (5S)-CH$_2$CH═CH$_2$ | OH | 4-phenyl-3,6-dihydropyridin-1(2H)-yl | 385.2 |
| 290 | (5S)-CH$_2$CH═CH$_2$ | OH | 4-phenylpiperazin-1-yl | 388.2 |
| 291 | (5R)-CH$_3$ | OH | 4-phenylpiperidin-1-yl | 361.2 |
| 292 | (5S)-CH$_3$ | OH | 4-phenylpiperidin-1-yl | 361.2 |
| 293 | (5S)-CH$_3$ | OH | 4-phenylpiperazin-1-yl | 362.2 |
| 294 | (5R)-CH$_2$CH$_2$CH$_3$ | OH | 4-phenyl-3,6-dihydropyridin-1(2H)-yl | |
| 295 | (5S)-CH$_2$CH$_2$CH$_3$ | OH | 4-phenyl-3,6-dihydropyridin-1(2H)-yl | |
| 296 | (5R)-OPh | H | 4-phenylpiperazin-1-yl | 424.2 |
| 297 | (5R)- 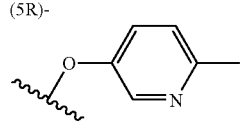 | H | 4-phenylpiperazin-1-yl | 439.2 |
| 298 | (5R)-(4-methylphenoxy) | H | 4-phenylpiperazin-1-yl | 438.1 |
| 299 | (5R)-(2,3-difluorophenoxy) | H | 4-phenylpiperazin-1-yl | 460.1 |
| 300 | (5R)- 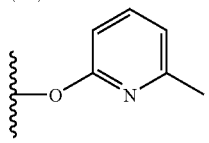 | H | 4-phenylpiperazin-1-yl | 439.2 |
| 301 | (5R)- 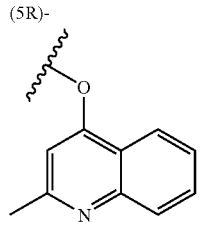 | H | 4-phenylpiperazin-1-yl | 489.2 |

TABLE 7-continued

| Ex. | R | R¹ | QY | MS |
|---|---|---|---|---|
| 302 | (5R)-(3,4-difluorophenoxy) | H | 4-phenylpiperazin-1-yl | 460.2 |
| 303 | (5R)- [5-chloropyridin-3-yloxy] | H | 4-phenylpiperazin-1-yl | 459.1 |
| 304 | (5R)- [4-(methylsulfonyl)piperidin-4-yloxy] | H | 4-phenylpiperazin-1-yl | 509.0 |
| 305 | (5R)-(2,4-dichlorophenoxy) | H | 4-phenylpiperazin-1-yl | 492.1 |
| 306 | (5R)- [1-(methoxycarbonyl)piperidin-4-yloxy] | H | 4-phenylpiperazin-1-yl | 489.1 |
| 307 | (5R)- [pyridin-3-yloxy] | H | 4-phenylpiperazin-1-yl | 425.1 |
| 308 | (5R)-(4-fluorophenoxy) | H | 4-phenylpiperazin-1-yl | 442.2 |
| 309 | (5R)- [1-ethylpiperidin-4-yloxy] | H | 4-phenylpiperazin-1-yl | 459.2 |
| 310 | (5R)- [1-ethylpiperidin-4-yloxy] | H | 3-phenyl-2,5-dihydro-1-H-pyrrol-1-yl | 442.2 |
| 311 | (5R)- [quinolin-4-yloxy] | H | 4-phenylpiperazin-1-yl | 475.2 |

TABLE 7-continued

| Ex. | R | R¹ | QY | MS |
|---|---|---|---|---|
| 312 | (5R)-(2,3-dichlorophenoxy) | H | 4-phenylpiperazin-1-yl | 492.0 |
| 313 | (5R)-benzyloxy | H | 4-phenylpiperazin-1-yl | 438.2 |
| 314 | (5R)- [4-methylpyridin-2-yloxy] | H | 4-phenylpiperazin-1-yl | 439.2 |
| 315 | (5R)-(3-fluorophenoxy) | H | 4-phenylpiperazin-1-yl | 442.2 |
| 316 | (5R)- [pyridin-4-yloxy] | H | 4-phenylpiperazin-1-yl | 425.2 |
| 317 | (5R)- [1-acetylpiperidin-4-yloxy] | H | 4-phenylpiperazin-1-yl | 473.1 |
| 318 | (5R)- [2-methylpyridin-3-yl] | H | 4-phenylpiperazin-1-yl | 439.2 |
| 319 | (5R)-[3,5-bis(trifluoromethyl)phenoxy] | H | 4-phenylpiperazin-1-yl | 560.2 |
| 320 | (5R)-(2-chlorophenoxy) | H | 4-phenylpiperazin-1-yl | 458.1 |
| 321 | (5R)-(4-chlorophenoxy) | H | 4-phenylpiperazin-1-yl | 458.2 |
| 322 | (5R)-(3-bromophenoxy) | H | 4-phenylpiperazin-1-yl | 502.1 |
| 323 | (5R)- [benzothiazol-2-yloxy] | H | 4-phenylpiperazin-1-yl | 481.1 |
| 324 | (5R)-(3-chlorophenoxy) | H | 4-phenylpiperazin-1-yl | 458.2 |
| 325 | (5R)- [pyrimidin-2-yloxy] | H | 4-phenylpiperazin-1-yl | 426.2 |
| 326 | (5R)-]3-(trifluoromethyl)phenoxy] | H | 4-phenylpiperazin-1-yl | 492.1 |

TABLE 7-continued

| Ex. | R | R¹ | QY | MS |
|---|---|---|---|---|
| 327 | (5R)- 6-quinolinyloxy | H | 4-phenylpiperazin-1-yl | 475.2 |
| 328 | (5R)- thieno[3,2-b]pyridin-7-yloxy | H | 4-phenylpiperazin-1-yl | 481.2 |
| 329 | (5R)-[isobutyryl(methyl)amino] | H | 4-phenylpiperazin-1-yl | 431.3 |
| 330 | (1R)- cyclopropylcarbamoyloxy | H | 4-phenylpiperidin-1-yl | 430.2 |
| 331 | (1R)- ethylcarbamoyloxy | H | 4-phenylpiperidin-1-yl | 418.1 |
| 332 | (1R)- methylcarbamoyloxy | H | 4-phenylpiperidin-1-yl | 404.1 |
| 333 | (1R)- isopropylcarbamoyloxy | H | 4-phenylpiperidin-1-yl | 432.1 |
| 334 | (1R)- propargylcarbamoyloxy | H | 4-phenylpiperidin-1-yl | 428.1 |
| 335 | (1R)- piperidin-1-ylcarbonyloxy | H | 4-phenylpiperidin-1-yl | |

TABLE 7-continued

| Ex. | R | R¹ | QY | MS |
|---|---|---|---|---|
| 336 | (1R)- 4-methylpiperazine-1-carboxylate | H | 4-phenylpiperidin-1-yl | 473.2 |
| 337 | (1R)- carbamate (H₂N-C(O)O-) | H | 4-phenylpiperidin-1-yl | 390.2 |
| 338 | (1R)- (1-methylpiperidin-4-yl)carbamate | H | 4-phenylpiperazin-1-yl | 488.3 |
| 339 | (1R)- isobutyl(methyl)carbamate | H | 4-phenylpiperazin-1-yl | 461.2 |
| 340 | (1R)- methyl(3-phenylpropyl)carbamate | H | 4-phenylpiperazin-1-yl | 523.3 |
| 341 | (1R)- cyclohexyl(methyl)carbamate | H | 4-phenylpiperazin-1-yl | 487.3 |
| 342 | (1R)- (4-methoxyphenyl)(methyl)carbamate | H | 4-phenylpiperazin-1-yl | 511.3 |
| 343 | (1R)- indoline-1-carboxylate | H | 4-phenylpiperazin-1-yl | 493.2 |

TABLE 7-continued
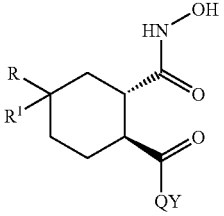
| Ex. | R | R¹ | QY | MS |
|---|---|---|---|---|
| 344 | (1R)- 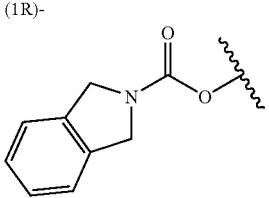 | H | 4-phenylpiperazin-1-yl | 493.2 |
| 345 | (1R)- 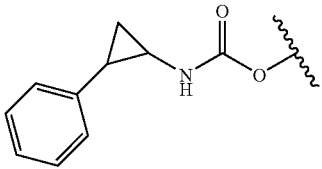 | H | 4-phenylpiperazin-1-yl | 507.3 |
| 346 | (1R)- 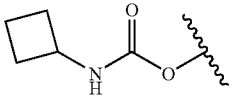 | H | 4-phenylpiperazin-1-yl | 445.2 |
| 347 | (1R)- 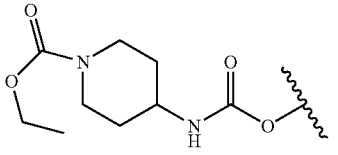 | H | 4-phenylpiperazin-1-yl | 546.3 |
| 348 | (1R)- 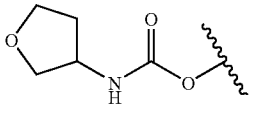 | H | 4-phenylpiperazin-1-yl | 461.2 |
| 349 | (1R)- 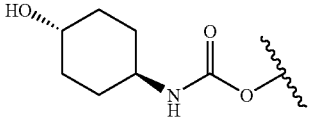 | H | 4-phenylpiperazin-1-yl | 489.2 |
| 350 | (1R)- 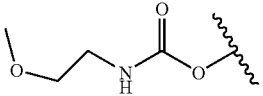 | H | 4-phenylpiperazin-1-yl | 449.2 |

TABLE 7-continued
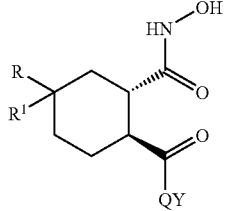
| Ex. | R | R¹ | QY | MS |
|---|---|---|---|---|
| 351 | (1R)- 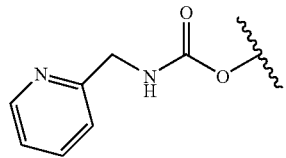 | H | 4-phenylpiperazin-1-yl | 482.2 |
| 352 | (1R)- 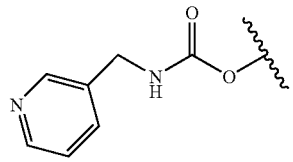 | H | 4-phenylpiperazin-1-yl | 482.2 |
| 353 | (1R)- 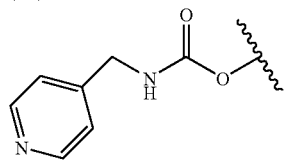 | H | 4-phenylpiperazin-1-yl | 482.2 |
| 354 | (1R)- 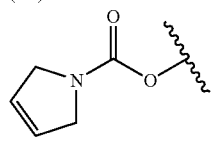 | H | 4-phenylpiperazin-1-yl | |
| 355 | (1R)- 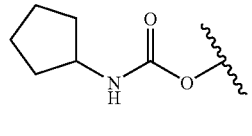 | H | 4-phenylpiperazin-1-yl | 459.2 |
| 356 | (1R)- 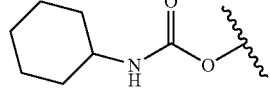 | H | 4-phenylpiperazin-1-yl | 473.3 |
| 357 | (1R)- 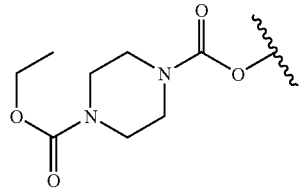 | H | 4-phenylpiperazin-1-yl | 532.3 |

TABLE 7-continued

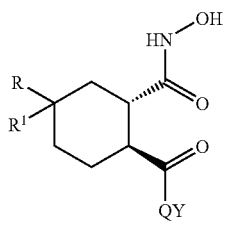

| Ex. | R | R¹ | QY | MS |
|---|---|---|---|---|
| 358 | (1R)- [piperazine carbamate with N-methyl-N-phenyl acetamide] | H | 4-phenylpiperazin-1-yl | 607.3 |
| 359 | (1R)- [4-hydroxypiperidine carbamate] | H | 4-phenylpiperazin-1-yl | 475.2 |
| 360 | (1R)- [(3S)-3-acetamidopyrrolidine carbamate] | H | 4-phenylpiperazin-1-yl | 502.3 |
| 361 | (1R)- [(3R)-3-acetamidopyrrolidine carbamate] | H | 4-phenylpiperazin-1-yl | 502.2 |
| 362 | (1R)- [(2S)-2-(hydroxymethyl)pyrrolidine carbamate] | H | 4-phenylpiperazin-1-yl | 475.2 |
| 363 | (1R)- [(2R)-2-(hydroxymethyl)pyrrolidine carbamate] | H | 4-phenylpiperazin-1-yl | 475.2 |
| 364 | (1R)- [1-(hydroxymethyl)cyclopentyl carbamate] | H | 4-phenylpiperazin-1-yl | 489.3 |

TABLE 7-continued
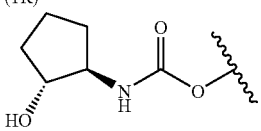
| Ex. | R | R¹ | QY | MS |
|---|---|---|---|---|
| 365 | (1R)- 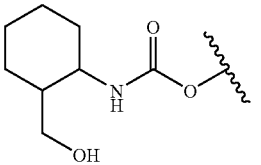 | H | 4-phenylpiperazin-1-yl | 475.2 |
| 366 | (1R)- 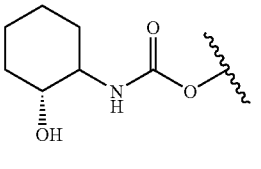 | H | 4-phenylpiperazin-1-yl | 503.3 |
| 367 | (1R)- 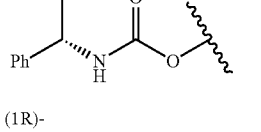 | H | 4-phenylpiperazin-1-yl | 489.3 |
| 368 | (1R)- 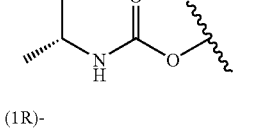 | H | 4-phenylpiperazin-1-yl | 511.2 |
| 369 | (1R)- 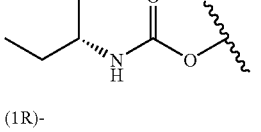 | H | 4-phenylpiperazin-1-yl | 449.2 |
| 370 | (1R)- 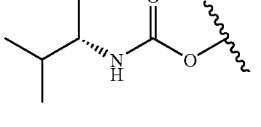 | H | 4-phenylpiperazin-1-yl | 463.2 |
| 371 | (1R)- 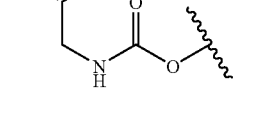 | H | 4-phenylpiperazin-1-yl | 477.2 |
| 372 | (1R)- HO,,, <br> (structure) | H | 4-phenylpiperazin-1-yl | 449.2 |

TABLE 7-continued

| Ex. | R | R¹ | QY | MS |
|---|---|---|---|---|
| 373 | (1R)- [structure: HO-CH2CH2-CH(Ph)-NH-C(=O)-O-] | H | 4-phenylpiperazin-1-yl | 525.3 |
| 374 | (1R)- [structure: HO-CH2-CH(iBu)-NH-C(=O)-O-] | H | 4-phenylpiperazin-1-yl | 491.2 |
| 375 | (1R)- [structure: 4-formylpiperazine-1-carboxylate] | H | 4-phenylpiperazin-1-yl | 488.2 |
| 376 | (5R)-pyridin-3-ylmethoxy | H | 4-phenylpiperazin-1-yl | 439.3 |
| 377 | (5R)-pyridin-2-yloxy | H | 4-phenylpiperazin-1-yl | 425.2 |
| 378 | (5R)-quinolin-6-yloxy | H | 4-phenylpiperazin-1-yl | 475.2 |
| 379 | (5R)-[(1-ethylpiperidin-4-yl)oxy] | H | 4-phenyl-3,6-dihydropyridin-1(2H)-yl | |
| 380 | (5R)-(4-hydroxyphenoxy) | H | 4-phenylpiperazin-1-yl | 440.1 |
| 381 | (5R)-[(4-methoxycyclohexyl)oxy] | H | 4-phenylpiperazin-1-yl | 460.2 |
| 383 | (5R)-[(4-methoxycyclohexyl)oxy] | H | 4-phenyl-3,6-dihydropyridin-1(2H)-yl | 457.2 |
| 384 | (5R)-{[2-(trifluoromethyl)quinolin-4-yl]oxy} | H | 4-phenylpiperazin-1-yl | 543.2 |
| 385 | (5R)-(quinolin-2-yloxy) | H | 4-phenylpiperazin-1-yl | 475.2 |
| 386 | (5R)-(quinolin-3-yloxy) | H | 4-phenylpiperazin-1-yl | 475.1 |
| 387 | (5R)-(quinolin-5-yloxy) | H | 4-phenylpiperazin-1-yl | 475.1 |
| 388 | (5R)-(quinolin-7-yloxy) | H | 4-phenylpiperazin-1-yl | 475.2 |
| 389 | (5R)-(quinolin-8-yloxy) | H | 4-phenylpiperazin-1-yl | 475.1 |
| 390 | (5R)-(pyridine-2-yloxy) | H | 4-phenyl-3,6-dihydropyridin-1(2H)-yl | 422.1 |
| 391 | (5R)-(pyridine-4-yloxy) | H | 4-phenyl-3,6-dihydropyridin-1(2H)-yl | 422.1 |
| 392 | (5R)-(quinolin-6-yloxy) | H | 4-phenyl-3,6-dihydropyridin-1(2H)-yl | 472.1 |
| 393 | (5R)-[(1-ethylpiperidin-4-yl)oxy] | H | 4-phenylpiperidin-1-yl | 458.3 |
| 394 | (5R)-(pyridine-2-yloxy) | H | 4-phenylpiperidin-1-yl | 424.2 |
| 395 | (5R)-(pyridine-4-yloxy) | H | 4-phenylpiperidin-1-yl | 424.2 |
| 396 | (5R)-(quinolin-6-yloxy) | H | 4-phenylpiperidin-1-yl | 474.2 |
| 397 | (5R)-(3-chlorophenoxy) | H | 4-phenyl-3,6-dihydropyridin-1(2H)-yl | 455.1 |
| 398 | (5R)-(3,4-difluorophenoxy) | H | 4-phenyl-3,6-dihydropyridin-1(2H)-yl | 457.1 |
| 399 | (5R)-(2,3-difluorophenoxy) | H | 4-phenyl-3,6-dihydropyridin-1(2H)-yl | 457.1 |
| 400 | (5R)-(isoquinolin-1-yloxy) | H | 4-phenylpiperazin-1-yl | 475.2 |
| 401 | (5R)-(isoquinolin-3-yloxy) | H | 4-phenylpiperazin-1-yl | 475.2 |
| 402 | (5R)-(isoquinolin-5-yloxy) | H | 4-phenylpiperazin-1-yl | 475.2 |
| 403 | (5R)-(isoquinolin-7-yloxy) | H | 4-phenylpiperazin-1-yl | 475.2 |
| 404 | (5R)-(2-naphthyloxy) | H | 4-phenylpiperazin-1-yl | 474.2 |
| 405 | (5R)-(2,4-difluorophenoxy) | H | 4-phenylpiperazin-1-yl | 460.1 |
| 406 | (5R)-(3,5-difluorophenoxy) | H | 4-phenylpiperazin-1-yl | 460.1 |
| 407 | (5R)-(3-chloro-4-fluorophenoxy) | H | 4-phenylpiperazin-1-yl | 476.1 |
| 408 | (5R)-(3,4-dichlorophenoxy) | H | 4-phenylpiperazin-1-yl | 492.1 |
| 409 | (5R)-(3,5-dichlorophenoxy) | H | 4-phenylpiperazin-1-yl | 492.1 |
| 410 | (5R)-(2,5-dioxopyrrolidin-1-yl) | H | 4-phenylpiperazin-1-yl | 429.2 |
| 411 | (5R)-(5,5-dimethyl-2,4-dioxo-1,3-oxazolidin-3-yl) | H | 4-phenylpiperazin-1-yl | 459.2 |
| 412 | (5R)-(3,methyl-2,5-dioxoimidazolidin-1-yl) | H | 4-phenylpiperazin-1-yl | |

TABLE 7-continued

[Structure: cyclohexane with R, R¹ substituents on one carbon, and adjacent carbons bearing C(=O)NHOH and C(=O)QY groups]

| Ex. | R | R¹ | QY | MS |
|---|---|---|---|---|
| 488 | (styryl group) | | 4-(4-cyano-2-methylphenyl)piperazin-1-yl | 459.2 |
| 489 | (2-cyclopropylvinyl group) | | 4-(4-cyano-2-methylphenyl)piperazin-1-yl | 423.2 |
| 490 | (styryl group) | | (3R)-phenylpyrrolidin-1-yl | 405.2 |
| 491 | (5S)-isobutyl | | OH | 4-phenyl-3,6-dihydropyridin-1(2H)-yl | 423.2 (M + Na) |
| 492 | (5S)-butyl | | OH | 4-phenyl-3,6-dihydropyridin-1(2H)-yl | 401.2 |
| 493 | (1R)- (azetidin-1-ylcarbonyloxy) | | Me | 4-phenylpiperazin-1-yl | 445.2 |
| 494 | (1S)- (pyrrolidin-1-ylcarbonyloxy) | | Me | 4-phenylpiperazin-1-yl | 481.2 (M + Na) |
| 495 | (5S)-isobutyl | | OH | 4-phenylpiperazin-1-yl | 404.0 |
| 496 | (5R)-cyclopropylmethyl | | OH | 4-phenylpiperazin-1-yl | 402.1 |
| 497 | butyl | | OH | 4-phenylpiperazin-1-yl | 404.2 |
| 498 | (1R)- (pyrrolidin-1-ylcarbonyloxy) | | Me | 4-phenylpiperazin-1-yl | 459.2 |

TABLE 7-continued

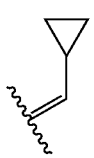

| Ex. | R | R¹ | QY | MS |
|---|---|---|---|---|
| 499 | (cyclopropylmethylene) | | (3R)-phenylpyrrolidin-1-yl | 369.2 |
| 500 | ethyl | | OH 4-phenylpiperazin-1-yl | 376.2 |

Biological Experimental Procedures

The capacity of the novel compounds of the invention to inhibit TNFα, or inhibit MMP function i.e., sheddase inhibition can be determined using a suitable screen (e.g., high through-put assay). For example, an agent can be tested in an extracellular acidification assay, calcium flux assay, ligand binding assay or chemotaxis assay. For example, the capacity of the compounds of general formula (I) to act as inhibitors of the production of TNFα may be determined using the following procedure. A 100 μM solution of the inhibitor being tested or dilutions thereof is incubated at 37° C. in an atmosphere of 5% $CO_2$ with THP-1 cells (human monocytes) suspended in RPMI 1640 medium and 20 μM β-mercaptoethanol at a cell density of $1\times10^6$/ml and stimulated with LPS. After 18 hours the supernatant is assayed for the levels of TNFα using a commercially available ELISA kit. The activity in the presence of 0.1 mM inhibitor or dilutions thereof is compared to activity in a control devoid of inhibitor and results reported as that inhibitor concentration effecting 50% inhibition of the production of TNFα.

Example 509

PBMC Assay Measuring TNFα Activity

A leukophoresis (Biological Specialties, Comlmar Pa.) was obtained from normal drug-free (no aspirin, ibuprofen, NSAIDs, etc.) donors. In a 50 ml conical tube (VWR, NJ), there was added 20 mls of blood and 20 mls of sterile 0.9% saline (Baxter Healthcare, Dearfield, Ill.) and mixed well. Underlay 10 mls of endotoxin free ficoll paque (Pharmacia, Uppsala, Sweden) and spinned at 3000 RPM for 30 minutes. The layer of white blood cells was removed and washed with 50 mls 0.9% saline. Cells are then counted and there is added 0.250 ml to 96 well plate (Costar/Corning VWR, NJ) at 2×10 6 c/ml, in RPMI 1640 medium (Gibco BRL). Compounds were added and preincubated with cells for 10 min before they were added LPS (Calbiochem, CA) at 1ug/ml for 5 hours. Supernatent was collected and assayed for TNFα production by standard sandwich ELISA (R&D Systems, Minneapolis, Minn.). Compound inhibition was determined relative to cells cultured with LPS alone.

Example 510

Assay for Her-2 Sheddase Activity

A human breast cell cancer line BT474 (ATCC, Manassas, Va.), was seeded at $2\times10^4$ cells/well in 100 ul in a 96 well plate (Costar/Corning VWR, NJ) in RPMI 1640 media (In Vitrogen, Carlsbad, Calif.) containing 10% fetal bovine serum (Hyclone, Lenexa, Kans.), and incubated overnight at 37° C., 5% $CO_2$. The following morning media was removed and fresh media was added back at 100 ul/well. Compounds were added at appropriate concentrations and the cells were incubated for 72 hour at 37° C., 5% $CO_2$. Supernatants were removed and either tested immediately or stored at −20° C. until testing can be performed. Supernatants were tested at a 1/20 dilution for inhibition of Her-2 sheddase by commercial ELISA (Oncogene Research, San Diego, Calif.)). Compound inhibition was determined relative to cells cultured alone.

Example 512

MMP2 Assay 5 mM compound stock was prepared in DMSO. Compound plate was prepared by 2-fold dilution for 11-point curve, with highest concentration of 500 uM. 1 uL of compound in DMSO was transferred from compound plate to the assay plate. Enzyme solution was prepared in assay buffer with a concentration of 10 ng/50 ul. Substrate solution was prepared in assay buffer with a concentration of 20 uM. 50 uL of enzyme solution was added to the assay plate. The assay plate was incubated for 5 minutes. 50 uL of substrate solution was then added to the assay plate. Protect the plate from the light and incubate the reaction at room temperature for 1 hour. The reaction was stopped by adding 10 uL of 500 mM EDTA solution. Read the plate on a plate reader with excitation of 320 nm and emission of 405 nm.

Example 513

MMP3 Assay 5 mM compound stock was prepared in DMSO. Compound plate was prepared by 2-fold dilution for 11-point curve, with highest concentration of 500 uM. 1 uL of compound in DMSO was transferred from compound plate to the assay plate. Enzyme solution was prepared in assay buffer with a concentration of 50 ng/50 ul. Substrate solution was prepared in assay buffer with a concentration of 20 uM. 50 uL of enzyme solution was added to the assay plate. The assay plate was incubated for 5 minutes. Add 10 ul of 500 mM EDTA to Background wells. 50 uL of substrate solution was then added to the assay plate. Protect the plate from the light and incubate the reaction at room temperature for 1 hour. The reaction was stopped by adding 10 uL of 500 mM EDTA solution. Read the plate on a plate reader with excitation of 320 nm and emission of 405 nm.

Example 514

MMP12 Assay 5 mM compound stock was prepared in DMSO. Compound plate was prepared by 2-fold dilution for 11-point curve, with highest concentration of 500 uM. 1 uL of compound in DMSO was transferred from compound plate to the assay plate. Enzyme solution was prepared in assay buffer with a concentration of 10 ng/50 ul. Substrate ((7-methoxy-coumarin-4-yl)acetyl-Pro-Leu-Gly-Leu-(3-[2,4-dinitrophenyl]-L-2,3-diaminopropionyl)-Ala-Arg-NH2) solution was prepared in assay buffer with a concentration of 20 uM. 50 uL of enzyme solution was added to the assay plate. The assay plate was incubated for 5 minutes. Add 10 ul of 500 mM EDTA in the Background well. 50 uL of substrate solution was then added to the assay plate. Protect the plate from the light and incubate the reaction at Rt. for 1 hours. The reaction was stopped by adding 10 uL of 500 mM EDTA solution. Read the plate on a plate reader with excitation of 320 nm and emission of 405 nm.

Example 515

ADAM10 Assay 5 mM compound stock was prepared in DMSO. Compound plate was prepared by 2-fold dilution for 11-point curve, with highest concentration of 500 uM. 1 uL of compound in DMSO was transferred from compound plate to the assay plate. Enzyme solution was prepared in assay buffer with a concentration of 100 ng/50 ul. Substrate ((7-methoxy-courmarin-4-yl)-acetyl-Pro-Leu-Ala-Gln-Ala-Val-(3-[2,4-dinitrophenyl]-L-2,3-diaminopropionyl)-Arg-Ser-Ser-Ser-Arg-NH2) solution was prepared in assay buffer with a concentration of 20 uM. 50 uL of enzyme solution was added to the assay plate. The assay plate was incubated for 5 minutes. 50 uL of substrate solution was then added to the assay plate. Protect the plate from the light and incubate the reaction at 37° C. for 4 hours. The reaction was stopped by adding 10 uL of 500 mM EDTA solution. Read the plate on a plate reader with excitation of 320 nm and emission.

When the above assay protocols are used, the compounds of the present invention have $IC_{50}$ in the range of about 10 nM to about 10 µM for Her2 sheddase inhibition, TNF-α inhibition as well as MMP2, MMP12 and MMP3 inhibition.

Pharmaceutical Compositions and Uses of the Invention

The compounds of the invention are administered to a mammal, such as a human, but can also be administered therapeutically to other mammals such as an animal in need of veterinary treatment, e.g., domestic animals (e.g., dogs, cats, and the like), livestock animals (e.g., cows, sheep, pigs, horses, and the like) and laboratory animals (e.g., rats, mice, guinea pigs, and the like). The mammal treated in the methods of the invention is a subject, male or female, in whom modulation of matrix metalloprotease activity is desired. The term modulation is intended to encompass antagonism, agonism, partial antagonism and/or partial agonism.

In the present specification, the term therapeutically effective amount means the amount of the subject compound that will elicit the biological or medical response of a tissue, system, non-human animal or human that is being sought by the researcher, veterinarian, medical doctor or other clinician.

The compounds of the invention are administered in therapeutic effective amounts to treat a disease for example such as rheumatoid arthritis. A therapeutically effective amount of a compound is that amount which results in the inhibition of one or more of the processes mediated by matrix metalloproteases in a subject with a disease associated with aberrant MMPs activity. Alternatively, a therapeutically effective amount of a compound is the quantity required to achieve a desired therapeutic and/or prophylactic effect, such as an amount which results in the prevention of, or a decrease in, the symptoms associated with a disease associated with aberrant MMP activity.

Diseases or conditions of human or other species which can be treated with the inhibitors or modulators of MMP function according to the invention, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; neoplastic diseases, cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

The compounds represented by Formulae I, II, and III of the invention can be administered in such oral dosage forms as tablets, capsules (each of which includes sustained-release or timed-release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but will generally be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the metabolic stability, rate of excretion, drug combination, and length of action of that compound the species, age, sex, health, medical condition, and weight of the recipient; the nature and extent of the symptoms; the kind of concurrent treatment; the frequency of treatment; the specific route of administration, the renal and hepatic function of the patient, and the desired effect. A physician or veterinarian can determine and prescribe the effective amount of the drug required to prevent, counter, or arrest the progress of the specific disorder for which treatment is necessary.

Generally, the daily oral dosage of each active ingredient, when used for the indicated effects, will range between about 0.0001 to 1000 mg/kg of body weight, preferably between about 0.001 to 100 mg/kg of body weight per day, and most preferably between about 0.1 to 20 mg/kg/day. For intravenous use, the most preferred doses will range from about 0.1 to about 10 mg/kg/minute during a constant rate infusion. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

The compounds of the instant invention can also be administered in intranasal form via topical use of suitable intranasal vehicles, or via transdermal routes, using transdermal skin patches. When administered in the form of a transdermal delivery system, the dosage administration will of course be continuous rather than intermittent throughout the dosage regimen.

The compounds of the invention are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component, can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. For oral administration in liquid form, the oral drug components can be combined with any oral, non-toxic, pharmaceutically acceptable inert carrier such as ethanol, glycerol, water, and the like. Additionally, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be provided to a patient in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or poly-ethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, and crosslinked or amphipathic block copolymers of hydrogels.

Dosage forms for the compounds of the invention suitable for administration may contain from about 0.1 milligram to about 100 milligrams of active ingredient per dosage unit. In these pharmaceutical compositions the active ingredient will ordinarily be present in an amount of about 0.5-95% by weight based on the total weight of the composition.

Gelatin capsules can also be used as dosage forms and may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

When using liquid dosage forms for oral administration the formulation can contain coloring and flavoring agents to increase patient acceptance.

Generally, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in the field of pharmacology.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. As used herein, topical application is also meant to include the use of mouth washes and gargles.

The pharmaceutical compositions and methods of the present invention, in addition to a compound of Formulae I, II, or III, may further comprise other therapeutically active compounds which are customarily administered in the treatment of the aforedescribed pathological conditions, provided that such combination(s) does not cause adverse reaction in the subject being treated or diminish the activity of the presently described metalloprotease inhibitors.

Representative useful pharmaceutical dosage-forms for administration of the compounds of this invention can be illustrated as follows:

Capsules

A large number of unit capsules can be prepared by filling standard two-piece hard gelatin capsules each with 50 milligrams of powdered active ingredient, 100 milligrams of lactose, 25 milligrams of cellulose, and 3 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 75 milligrams of the active ingredient. The capsules should be washed and dried.

Tablets

Tablets may be prepared by conventional procedures so that the dosage unit is 75 milligrams of active ingredient, 0.15 milligrams of colloidal silicon dioxide, 4 milligrams of magnesium stearate, 250 milligrams of microcrystalline cellulose, 9 milligrams of starch and 75 milligrams of lactose. Appropriate coatings well known to one skilled in the art may be applied to increase palatability or delay absorption.

Injectable

A parenteral composition suitable for administration by injection may be prepared by stirring 1.0% by weight of active ingredient in 8% by volume propylene glycol and water. The solution should be made isotonic with sodium chloride and sterilized.

Suspension

An aqueous suspension can be prepared for oral administration so that each 5 mL contain 75 mg of finely divided active ingredient, 150 mg of sodium carboxymethyl cellulose, 3.75 mg of sodium benzoate, 0.75 g of sorbitol solution, U.S.P., and 0.015 mL of vanillin.

All patents, patent applications and publications cited in this application are hereby incorporated by reference in their entirety for all purposes to the same extent as if each individual patent, patent application or publication were so individually denoted.

While the many embodiments of the invention have been disclosed above and include presently preferred embodiments, many other embodiments and variations are possible within the scope of the present disclosure and in the appended claims that follow. Accordingly, the details of the preferred embodiments and examples provided are not to be construed as limiting. It is to be understood that the terms used herein are merely descriptive rather than limiting and that various changes, numerous equivalents may be made without departing from the spirit or scope of the claimed invention.

What is claimed is:

1. A compound according to the following formula:

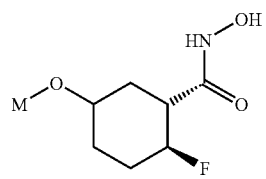

or pharmaceutically acceptable salt thereof, wherein

P is —D-E-G-Q-L-T-X-Y;

D is C(O);

E is absent or is selected from the group consisting of $C_{1-10}$alkylene, $C_{2-10}$alkenylene, and $C_{2-10}$ alkynylene;

G is absent or is selected from the group consisting of O, $NR^{a-1}$, $S(O)_p$, and C(O);

Q is absent or is selected from the group consisting of a $C_{3-13}$ carbocycle substituted with 0-5 $R^b$, and a heterocycle wherein said heterocycle is piperazine substituted with 0-5 $R^b$;

L is absent or is selected from the group consisting of O, $NR^{a1}$, C(O), C(O)O, OC(O), C(O)$NR^{a1}$, $NR^{a1}$, OC(O)$NR^{a1}$, $NR^{a1}$C(O)O, $S(O)_p$, $S(O)_pNR^{a1}$, and $NR^{a1}S(O)_p$;

T is absent or is selected from the group consisting of $C_{1-10}$ alkylene, $C_{2-10}$ alkenylene, and $C_{2-10}$ alkynylene;

X is absent or is selected from the group consisting of O, $NR^{a1}$, $S(O)_p$, and C(O);

Y is selected from the group consisting of H and a $C_{3-10}$ carbocycle substituted with 0-5 $R^c$, provided that E, G, Q, L, T, X and Y do not combine to form a N—N, N—O, O—N, O—O, $S(O)_p$—O, O—$S(O)_p$ or $S(O)_p$—$S(O)_p$ group;

M is an aromatic heterocycle selected from the group consisting of pyridyl, quinolyl, and isoquinolyl and substituted with 0-5 $R^d$;

$R^b$ at each occurrence is independently selected from the group consisting of $C_{1-6}$ alkyl optionally substituted with $R^{c1}$, O(primary, secondary, or tertiary)$C_1$-$C_8$ alkyl, OH, Cl, F, —CN, $NO_2$, $NR^aR^{a1}$, $C(O)R^a$, $C(O)OR^a$, $C(O)NR^aR^{a1}$, $R^aNC(O)NR^aR^a$, $OC(O)NR^aR^{a1}$, $R^aNC(O)O\ R^{a1}$, $S(O)_2NR^aR^{a1}NR^aS(O)_2R^{a2}$, $NR^aS(O)_2NR^aR^{a1}$, $OS(O)_2NR^aR^{a1}$, $S(O)_pR^{a2}$, $CF_3$, $CH_2F$, $CHF_2$, $CF_2CH_3$, $C(CH_3)_2F$, $OCF_3$, $OCHF_2CF_3$, a $C_{3-10}$ carbocyclic residue and $C_3$-$C_{10}$ carbocyclyl($C_{1-8}$)alkyl, wherein said $C_{3-10}$ carbocyclic residue, and $C_3$-$C_{10}$ carbocyclyl($C_{1-8}$)alky are optionally substituted with $R^{c1}$;

$R^a$, $R^{a1}$, and $R^{a2}$ at each occurrence are independently selected from the group consisting of H, $C_1$-$C_8$ alkyl, $C_2$-$C_8$ alkenyl, $C_2$-$C_8$ alkynyl, wherein said alkyl, alkenyl and alkynyl groups are optionally substituted with 0(primary, secondary, or tertiary)$C_1$-$C_8$, OH, Cl, F, —CN, alkylamino, dialkylamino, alkarylamino, arylamino, alkylcarbonyl, aralkylcarbonyl, arylcarbonyl, carboxyl, alkylcarboxylate, alkylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamidoalkyl, N-alkylsufonamidodialkyl, alkylamidosulfonate, dialkylamidosulfonate, alkylsulfinyl, alkylsulfonyl, $CF_3$, $CF_2CF_3$, $CH_2F$, $CHF_2$, $CF_2CH_3$, $C(CH_3)_2F$, $OCF_3$, and $OCH_2CF_3$; $C_3$-$C_{10}$, carbocycle, $C_3$-$C_{10}$ carbocyclylalkyl, and wherein said $C_3$-$C_{10}$ carbocycle and $C_3$-$C_{10}$ carbocyclylalkyl, may be optionally substituted with one or more substituents selected from the group consisting of $C_1$-$C_8$ alkyl, O(primary, secondary, or tertiary)$C_1$-$C_8$ alkyl, OH, Cl, F, Br, =O, —CN, $NO_2$, alkylamino, dialkylamino, alkarylamino, arylamino, alkylcarbonyl, aralkylcarbonyl, arylcarbonyl, carboxyl, alkylcarboxylate, ailcylamido, dialkylamido, alkylureidoalkyl, alkylureidodialkyl, carbamoylalkyl, carbamoyldialkyl, alkylcarbamoyl, sulfonamidoalkyl, sulfonamidodialkyl, N-alkylsulfonamidoalkyl, N-alkylsulfonamido alkyl, N-alkylsufonamidodialkyl, alkylamidosulfonate, dialkylamidosulfonate, alkylsulfinyl, alkylsulfonyl, $CF_3$, $CH_2F$, $CHF_2$, $CF_2CH_3$, $C(CH_3)_2F$, $OCF_3$, and $OCH_2CF_3$;

$R^c$ at each occurrence is independently selected from the group consisting of $C_{1-6}$ alkyl optionally substituted with $R^{c1}$, $OR^a$, Cl, F, —CN, $NO_2$, $NR^aR^{a1}$, $C(O)R^a$, $C(O)OR^a$, $C(O)NR^aR^{a1}$, $R^aNC(O)NR^a$, $R^a$, $OC(O)NR^aR^{a1}R^aNC(O)OR^{a1}$, $S(O)_2NR^aR^{a1}$, $NR^a\ S(O)_2R^{a2}$, $NR^aS(O)_2NR^aR^{a1}$, $S(O)_pR^{a2}$, $CF_3$, $CH_2F$, $CHF_2$, $CF_2CH_3$, $C(CH_3)_2F$, $OCF_3$, $OCHF_2$, $OCH_2CF_3$, a $C_{3-10}$ carbocyclic residue and $C_3$-$C_{10}$ carbocyclyl($C_{1-8}$)alkyl, wherein said $C_{3-10}$ carbocyclic residue and $C_3$-$C_{10}$ carbocyclyl($C_{1-8}$)alkyl are optionally substituted with $R^{c1}$;

$R^{c1}$ at each occurrence is independently selected from the group consisting of $C_{1-6}$ alkyl, $OR^a$, Cl, F, Br, =O, —CN, $NO_2$, $NR^aR^{a1}$, $C(O)R^a$, $C(O)OR^a$, $C(O)NR^aR^{a1}$, $OC(O)NR^aR^{a1}$, $R^aNC(O)OR^a$, $S(O)_2NR^aR^{a1}$, $NR^aS(O)_2R^{a2}$, $S(O)_pR^{a2}CF_3$, and $CH_2F$, and $CHF_2$;

$R^d$ at each occurrence is independently selected from the group consisting of H, $C_{1-6}$ alkyl optionally substituted with $R^{c1}$, $OR^a$, Cl, F, Br, =O, —CN, $NO_2$, $NR^aR^{a1}$, $C(O)R^a$, $C(O)OR^a$, $C(O)NR^aR^{a1}$, $R^aNC(O)NR^aR^a$, $OC(O)NR^aR^a$, $R^aNC(O)OR^{a1}$, $S(O)_2\ NR^a\ R^{a1}$, $NR^aS(O)_2\ R^{a2}$, $OS(O)_2\ NR^aR^{a1}$, $S(O)_p\ R^{a2}$, $CF_3$, $CF_2CF_3$, $CH_2F$, $CHF_2$, $CF_2CH_3$, $C(CH_3)_2F$, $OCF_3$, $OCHF_2$, $OCH_2CF_3$, a $C_{3-10}$ carbocyclic residue and $C_3$-$C_{10}$ carbocyclyl($C_{1-8}$)alkyl wherein said $C_{3-10}$ carbocyclic residue and $C_3$-$C_{10}$ carbocyclyl($C_{1-8}$)alkyl, are optionally substituted with $R^{c1}$;

and p at each occurrence is 0, 1, and 2.

2. A compound according to claim 1, or pharmaceutically acceptable salt thereof, wherein the compound is according to the formula:

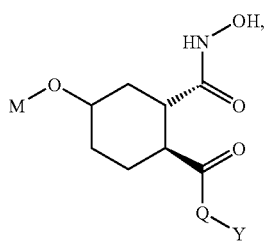

wherein:

Q is absent or is selected from the group consisting of a $C_{3-13}$ carbocycle substituted with 0-5 $R^b$, and a heterocycle wherein said heterocycle is piperazine substituted with 0-5 $R^b$; and Y is $C_{3-13}$ carbocycle substituted with 0-5 $R^c$.

3. The compound according to claim 1, or pharmaceutically acceptable salt thereot wherein the compound exists in the form of a single enantiomer or diastereomer.

4. A phannaceutical composition, comprising a compound of claim 1, or phannaceutically acceptable salt thereof, and a pharmaceutically-acceptable diluent or carrier.

5. A compound according to claim 1, selected from the group consisting of:
(1S,2S,5R)-N-hydroxy-5-[(6-methylpyridin-3-yl)oxy]-2-[(4-phenylpiperazin-1-yl)carbonyl]cyclohexanecarboxamide;
(1S,2S,5R)-N-hydroxy-5-[(6-methylpyridin-2-yl)oxy]-2-[(4-phenylpiperazin-1-yl)carbonyl]cyclohexanecarboxamide;
(1S,2S,5R)-N-hydroxy-2-[(4-phenylpiperazin-1-yl)carbonyl]-5-[(2-metbylquinolin-4-yl)oxy]cyclohexanecarboxamide;
(1S,2S,5R)-5-[(5-chloropyridin-3-yl)oxy]-N-hydroxy-2-[(4-phenylpiperazin-1-yl)carbonyl]cyclohexanecarboxamide;
(1S,2S,5R)-N-hydroxy-2-[(4-phenylpiperazin-1-yl)carbonyl]-5-(pyridin-3-yloxy)cyclohexanecarboxainide;
(1S,2S,5R)-N-hydroxy-2-[(4-phenylpiperazin-1-yl)carbonyl]-5-(quinolin-6-yloxy)cyclohexanecarboxamide;
(1S,2S, SR)-N-hydroxy-5-[(4-methylpyridin-2-yl)oxy]-2-[(4-phenylpiperazin-1-yl)carbonyl]cyclohexanecarboxainide;
(1S,2S,5R)-N-hydroxy-2-[(4-phenylpiperazin-1-yl)carbonyl]-5-(pyridin-4-yloxy)cyclohexanecarboxamide;
(1S,2S,5R)-N-hydroxy-5-[(2-methylpyridin-3-yl)oxy]-2-[(4-phenylpiperazin-1-yl)carbonyl]cyclohexanecarboxamide; and
(1S,2S,5R)-N-hydroxy-2-[(4-phenylpiperazin-1-yl)carbonyl]-5-(quinolin-4-yloxy)cyclohexaoecarboxamide; or a pharmaceutically acceptable salt thereof.

6. A compound according to claim 1, selected from the group consisting of:
(1S,2S,5R)-N-hydroxy-2-[(4-phenylpiperazin-1-yl)carbonyl]-5-(quinolin-6-yloxy)cyclohexanecarboxamide,
(1S,2S,5R)-N-hydroxy-2-[(4-phenylpiperazin-1-yl)carbonyl]-5-{[2-(trifluoromethyl)quinolin-4-yl]oxy}cyclohexanecarboxamide,
(1S,2S,5R)-N-hydroxy-2-[(4-phenylpiperazin-1-yl)carbonyl]-5-(quinolin-2-yloxy)cyclohexanecarboxamide, (1S,2S,5R)-N-hydroxy-2-[(4-phenylpiperazin-1-yl)carbonyl]-5-(quinolin-3-yloxy)cyclohexanecarboxamide, (1S,2S,5R)-N-hydroxy-2-[(4-phenylpiperazin-1-yl)carbonyl]-5-(quinolin-5-yloxy)cyclohexanecarboxamide, (1S,2S,5R)-N-hydroxy-2-[(4-phenylpiperazin-1-yl)carbonyl]-5-(quinolin-7-yloxy)cyclohexanecarboxamide, (1S,2S,5R)-N-hydroxy-2-[(4-phenylpiperazin-1-yl)carbonyl]-5-(quinolin-8-yloxy)cyclohexanecarboxamide, (1S,2S,5R)-N-hydroxy-5-(isoquinolin-1-yloxy)-2-[(4-phenylpiperazin-1-yl)carbonyl]cyclohexanecarboxamide, (1S,2S,5R)-N-hydroxy-5-(isoquinolin-3-yloxy)-2-[(4-phenylpiperazin-1-yl)carbonyl]cyclohexanecarboxamide, (1S,2S,5R)-N-hydroxy-5-(isoquinolin-5-yloxy)-2-[(4-phenylpiperazin-1-yl)carbonyl]cyclohexanecarboxamide, and (1S,2S,5R)-N-hydroxy-5-(isoquinolin-7-yloxy)-2-[(4-phenylpiperazin-1-yl)carbonyl]cyclohexanecarboxamide, or a pharmaceutically acceptable salt thereof.

7. A compound according to claim 1 wherein the compound is (1S,2S,5R)-N-hydroxy-2-[(4-phenylpiperazin-1-yl)carbonyl]-5-(quinolin-6-yloxy)cyclohexanecarboxamide, or a pharmaceutically acceptable salt thereof.

8. A compound according to claim 2 wherein Q is:

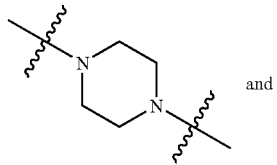

and

Y is phenyl substituted with 0-5 $R^c$.

9. A compound according to claim 2 wherein -Q-Y is 4-phenylpiperazinyl.

10. A compound selected from the group consisting of:
(1S,2S,5R)-N-hydroxy-2-[(4-phenyl-3,6-dihydropyridin-1(2H)-yl)carbonyl]-5-(pyridin-2-yloxy)cyclohexanecarboxamide, (1S,2S,5R)-N-hydroxy-2-[(4-phenyl-3,6-dihydropyridin-1(2H)-yl)carbonyl]-5-(pyridin-4-yloxy)cyclohexanecarboxamide, and (1S,2S,5R)-N-hydroxy-2-[(4(4-phenyl-3,6-dihydropyridin-1(2H)-yl)carbonyl]-5-(quinolin-6-yloxy)cyclohexanecarboxamide, or a pharmaceutically acceptable salt thereof.

* * * * *

UNITED STATES PATENT AND TRADEMARK OFFICE
CERTIFICATE OF CORRECTION

PATENT NO. : 7,491,724 B2  Page 1 of 1
APPLICATION NO. : 10/965215
DATED : February 17, 2009
INVENTOR(S) : Li et al.

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 337 days Delete the phrase "by 337 days" and insert -- by 540 days --

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,491,724 B2 | |
| APPLICATION NO. | : 10/965215 | |
| DATED | : February 17, 2009 | |
| INVENTOR(S) | : Yun-Long Li et al. | |

It is certified that error appears in the above-identified patent and that said Letters Patent is hereby corrected as shown below:

On the Title Page

First page, col. 2 (Other Publications), line 1, delete "CAS:" and insert -- CAS: 132: --.

First page, col. 2 (Other Publications), line 16, delete "Yardem" and insert -- Yarden --.

Page 2, col. 1 (Other Publications), line 18, delete "Indentification" and insert -- Identification --.

Page 2, col. 1 (Other Publications), line 18, delete "ADAM 10" and insert -- ADAM10 --.

Page 2, col. 2 (Other Publications), line 26, delete "to" and insert -- of --.

In the Specification

Col. 3, line 9, delete "R A;" and insert -- R A, --.

Col. 3, line 26, delete "ADAM 15" and insert -- ADAM15 --.

Col. 3, line 63, delete "N H," and insert -- M H, --.

Col. 4, line 21, delete "Danros" and insert -- Danlos --.

Col. 4, line 22, delete "ADAMTS-11," and insert -- ADAMTS-11 --.

Col. 5, line 18, delete "formuale" and insert -- formulae --.

Col. 5, line 23, delete "formuale" and insert -- formulae --.

Signed and Sealed this
Eleventh Day of August, 2015

Michelle K. Lee
*Director of the United States Patent and Trademark Office*

CERTIFICATE OF CORRECTION (continued)

U.S. Pat. No. 7,491,724 B2

Col. 5, line 44 (approx.), delete "methodolgies" and insert -- methodologies --.

Col. 5, line 51, delete "ADAM 10," and insert -- ADAM10, --.

Col. 6, line 50, delete "consisiting" and insert -- consisting --.

Col. 7, line 26, after "$(CR^dR^{d1})_rP(O)(OR^a)_2$" insert -- , --.

Col. 7, lines 31-32, delete "carbocyclesubstituted" and insert -- carbocycle substituted --.

Col. 7, lines 43-44 (approx.), delete "$S(O)R_1$," and insert -- $S(O)_pR^{a2}$, --.

Col. 7, line 65, delete "$OC(O)NR^aR$ a," and insert -- $OC(O)NR^aR^{a1}$, --.

Col. 8, line 39, delete "N-alkylsufonamidodialkyl," and insert -- N-alkylsulfonamidodialkyl, --.

Col. 8, lines 55-56, delete "N-alkylsufonamidodialkyl," and insert -- N-alkylsulfonamidodialkyl, --.

Col. 9, line 2, delete "$NR^aS(O)_2R^{a2}NR^aS(O)_2 NR^aR^{a1}$," and insert -- $NR^aS(O)_2R^{a2}$, $NR^aS(O)_2NR^aR^{a1}$, --.

Col. 9, line 3, delete "$OS(O)_2 NR^aR^{a1}S(O)_p R^{a2}$," and insert -- $OS(O)_2NR^aR^{a1}$, $S(O)_pR^{a2}$, --.

Col. 9, line 35, delete "$S(O)_pR^a$," and insert -- $S(O)_pR^{a2}$, --.

Col. 9, lines 41-42 (approx.), delete "$NR^aS(O)_2R^a$," and insert -- $NR^aS(O)_2R^{a2}$, --.

Col. 10, line 19, delete "N-alkylsufonamidodialkyl," and insert -- N-alkylsulfonamidodialkyl, --.

Col. 10, line 32, delete "N-alkylsufonamidodialkyl," and insert -- N-alkylsulfonamidodialkyl, --.

Col. 10, line 48, delete "N-alkylsufonamidodialkyl," and insert -- N-alkylsulfonamidodialkyl, --.

Col. 10, line 54, delete "$S(O)_pR^a$," and insert -- $S(O)_pR^a$; --.

Col. 10, line 56, delete "$S(O)_pR^a$," and insert -- $S(O)_pR^a$; --.

Col. 11, line 11 (approx.), delete "$C_{10}$" and insert -- $C_{1-10}$ --.

Col. 14, line 43, delete "ADAM 10" and insert -- ADAM10 --.

Col. 16, line 19 (approx.), delete "consisiting" and insert -- consisting --.

Col. 16, line 24 (approx.), delete "$NR^{a1}$, C(O)O," and insert -- $NR^{a1}C(O)O$, --.

Col. 16, line 27 (approx.), delete "$C_{2\text{-}10}$" and insert -- $C_{2\text{-}10}$ --.

Col. 16, line 56, delete "$O(CR^dR^{d1})_rM$," and insert -- $O(CR^dR^{d1})_r\text{-}M$, --.

Col. 17, line 6, delete "$C_A=CR^dR^d$," and insert -- $C_A=CR^dR^{d1}$, --.

Col. 17, line 8, delete "$C_{2\text{-}0}$" and insert -- $C_{2\text{-}10}$ --.

Col. 17, line 50, delete "benezene" and insert -- benzene --.

Col. 17, line 57, delete "benezene" and insert -- benzene --.

Col. 17, line 61, delete "O— S(O)p," and insert -- O—S(O)p, --.

Col. 18, line 7, delete "N-alkylsufonamidodialkyl," and insert -- N-alkylsulfonamidodialkyl, --.

Col. 18, lines 23-24, delete "N-alkylsufonamidodialkyl," and insert -- N-alkylsulfonamidodialkyl, --.

Col. 18, line 49, delete "$S(O)_pR^a$," and insert -- $S(O)_pR^a$; --.

Col. 18, line 61, delete "$C_{3\text{-}}10$" and insert -- $C_{3\text{-}10}$ --.

Col. 19, line 52, delete "N-alkylsufonamidodialkyl," and insert -- N-alkylsulfonamidodialkyl, --.

Col. 19, line 65, delete "N-alkylsufonamidodialkyl," and insert -- N-alkylsulfonamidodialkyl, --.

Col. 20, line 15, delete "N-alkylsufonamidodialkyl," and insert -- N-alkylsulfonamidodialkyl, --.

Col. 20, line 21, delete "$S(O)_pR^a$," and insert -- $S(O)_pR^a$; --.

Col. 20, line 23, delete "$S(O)_pR^a$," and insert -- $S(O)_pR^a$; --.

Col. 20, line 27, delete "$R^b$;" and insert -- $R^e$; --.

Col. 21, line 50, delete "$(C_{10}$" and insert -- $(C_{1\text{-}10}$ --.

CERTIFICATE OF CORRECTION (continued)
U.S. Pat. No. 7,491,724 B2

Col. 22, line 4, delete "C(O)NR$^a$R$^a$," and insert -- C(O)NR$^a$R$^{a1}$, --.

Col. 22, line 4, delete "OC(O)NR$^a$R$^a$," and insert -- OC(O)NR$^a$R$^{a1}$, --.

Col. 22, line 17, delete "(CR$^d$R$^{d1}$)$_r$C(O)NR$^a$(CR$^d$R$^{d1}$)$_r$-M$^1$" and insert -- (CR$^d$R$^{d1}$)$_r$C(O)NR$^a$(CR$^d$R$^{d1}$)$_r$-M$^1$, --.

Col. 22, line 24, delete "C(O)NR$^8$R$^{a1}$," and insert -- C(O)NR$^a$R$^{a1}$, --.

Col. 22, line 66, delete "N-alkylsufonamidodialkyl," and insert -- N-alkylsulfonamidodialkyl, --.

Col. 23, line 15, delete "N-alkylsufonamidodialkyl," and insert -- N-alkylsulfonamidodialkyl, --.

Col. 23, line 40, delete "S(O)$_p$R$^a$," and insert -- S(O)$_p$R$^a$; --.

Col. 23, line 47, delete "C$_{3-0}$" and insert -- C$_{3-10}$ --.

Col. 24, line 8, delete "R$^c$," and insert -- R$^{c1}$, --.

Col. 24, line 27, delete "NR$^a$S(O)$_p$R$_1$, C$_1$," and insert -- NR$^a$S(O)$_p$R$^j$, C$_{1-6}$ --.

Col. 24, line 37, delete "N-alkylsufonamidodialkyl," and insert -- N-alkylsulfonamidodialkyl, --.

Col. 24, line 48, delete "N-alkylsufonamidodialkyl," and insert -- N-alkylsulfonamidodialkyl, --.

Col. 24, line 63, delete "N-alkylsufonamidodialkyl," and insert -- N-alkylsulfonamidodialkyl, --.

Col. 25, line 55, delete "NR$^a$," and insert -- NR$^{a1}$, --.

Col. 25, line 64, delete "S(O)$_n$," and insert -- S(O)$_p$ --.

Col. 26, lines 7-8, delete "C(=C(H)(NO$_2$))NR$^a$R$^{a2}$;" and insert -- C(=C(H)(NO$_2$))NR$^{a1}$R$^{a2}$; --.

Col. 26, line 20, delete "S(O)$_2$NR$^a$R" and insert -- S(O)$_2$NR$^a$R$^{a1}$, --.

Col. 26, line 28, before "alkylene" delete "to".

Col. 26, lines 29-30, delete "(CR$^d$R$^{d1}$)$_r$NR$^a$(CR$^d$R$^{d1}$)$_{r-M}$$^1$" and insert -- (CR$^d$R$^{d1}$)$_r$NR$^a$(CR$^d$R$^{d1}$)$_r$-M$^1$, --.

CERTIFICATE OF CORRECTION (continued)  
U.S. Pat. No. 7,491,724 B2  
Page 5 of 15

Col. 26, lines 32-33, delete "$(CR^dR^1)_rNR^aC(O)(CR^dR^{d1})_r$-M$^1$," and insert -- $(CR^dR^{d1})_rNR^aC(O)(CR^dR^{d1})_r$-M$^1$, --.

Col. 26, lines 35-36, delete "$(CR^dR^{d1})_rNR^aC(O)NR^{a1}(CR^dR^{d1})_{r-M}{}^1$," and insert -- $(CR^dR^{d1})_rNR^aC(O)NR^{a1}(CR^dR^{d1})_r$-M$^1$, --.

Col. 27, line 3, delete "$R^aNC(O)OR^a$," and insert -- $R^aNC(O)OR^{a1}$, --.

Col. 27, line 15, delete "$S(O)_pR^a$," and insert -- $S(O)_pR^a$; --.

Col. 27, line 51 (approx.), delete "$C(O)NR^aR^a$," and insert -- $C(O)NR^aR^{a1}$, --.

Col. 27, line 51 (approx.), delete "$R^aNC(O)NR^aR^{a1}$," and insert -- $R^aNC(O)NR^aR^a$, --.

Col. 27, lines 51-52 (approx.), delete "$R^aNC(O)OR^{a1}$" and insert -- $R^aNC(O)OR^{a1}$, --.

Col. 27, line 52 (approx.), delete "$S(O)_pR_2$," and insert -- $S(O)_pR^{a2}$, --.

Col. 27, line 57 (approx.), delete "$C_{3\ 10}$" and insert -- $C_{3-10}$ --.

Col. 28, line 13 (approx.), delete "N-alkylsufonamidodialkyl," and insert -- N-alkylsulfonamidodialkyl, --.

Col. 28, line 24, delete "N-alkylsufonamidodialkyl," and insert -- N-alkylsulfonamidodialkyl, --.

Col. 28, line 39, delete "N-alkylsufonamidodialkyl," and insert -- N-alkylsulfonamidodialkyl, --.

Col. 29, line 2, delete "0," and insert -- O, --.

Col. 29, line 36, delete "$C_A=CR^dR^d$," and insert -- $C_A=CR^dR^{d1}$, --.

Col. 29, line 40, delete "$NR^aR^a$," and insert -- $NR^aR^{a1}$, --.

Col. 29, lines 50-51, delete "$(CR^dR^{d1})_rNR(CR^dR^{d1})_r$-M$^1$," and insert -- $(CR^dR^{d1})_rNR^a(CR^dR^{d1})_r$-M$^1$, --.

Col. 29, line 51, delete "$(CR\ R^{d1})_rC(O)(CR^dR^{d1})_r$-M$^1$," and insert -- $(CR^dR^{d1})_rC(O)(CR^dR^{d1})_r$-M$^1$, --.

Col. 29, lines 51-52, Delete "$(CR^dR^{d1})_rC(O)O(CR^dR^{d1})_r$-M," and insert -- $(CR^dR^{d1})_rC(O)O(CR^dR^{d1})_r$-M$^1$, --.

Col. 30, line 42, delete "$NR^aR^{a1}$;" and insert -- $NR^aR^{a1}$, --.

Col. 30, line 49, delete "NR$^a$S(O)$_2$R$^a$," and insert -- NR$^a$S(O)$_2$R$^{a2}$, --.

Col. 31, line 20, delete "N-alkylsufonamidodialkyl," and insert -- N-alkylsulfonamidodialkyl, --.

Col. 31, line 29, delete "N-alkylsufonamidodialkyl," and insert -- N-alkylsulfonamidodialkyl, --.

Col. 31, line 41, delete "N-alkylsufonamidodialkyl," and insert -- N-alkylsulfonamidodialkyl, --.

Col. 32, line 58, delete "appropiate" and insert -- appropriate --.

Col. 34, line 38 (approx.), delete "galactunoric" and insert -- galacturonic --.

Col. 35, line 42, delete "anhdride" and insert -- anhydride --.

Col. 36, lines 44-45 (approx.), delete "substiutents" and insert -- substituents --.

Col. 36, line 46 (approx.), delete "funtionalizing" and insert -- functionalizing --.

Col. 36, line 54, delete "Funtional" and insert -- Functional --.

Col. 36, line 57, delete "Mitsnobu" and insert -- Mitsunobu --.

Col. 37, line 32, delete "formular" and insert -- formula --.

Col. 39, line 17, delete "Funtional" and insert -- Functional --.

Col. 39, line 55, delete "mecury" and insert -- mercury --.

Col. 39-40, Line 21 (approx.), delete " $\xrightarrow{[H]}$ " and insert -- $\longrightarrow$ --.

Col. 41-42, line 40 (approx.), delete " 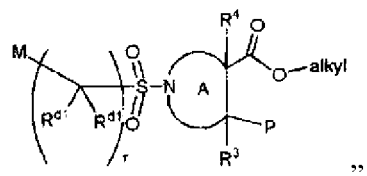 "

and insert -- 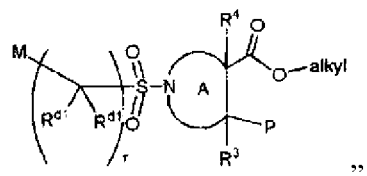 --.

CERTIFICATE OF CORRECTION (continued)
U.S. Pat. No. 7,491,724 B2

Col. 41-42, line 40 (approx.), delete " 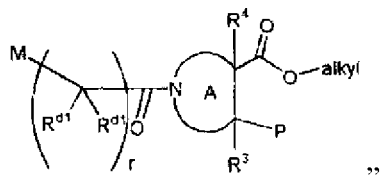 "

and insert -- 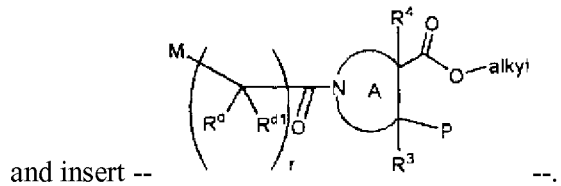 --.

Col 41-42, line 41 (approx.), delete " 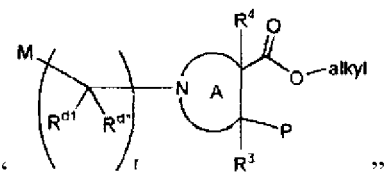 "

and insert -- 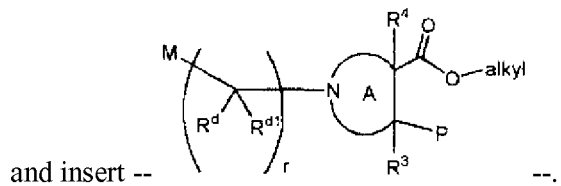 --.

Col. 43, line 27, delete "1'-chloro" and insert -- 1-chloro --.

Col. 45, line 4, delete "oxidazided" and insert -- oxidized --.

Col. 48, line 66, delete "111" and insert -- 11 --.

Col. 50, line 41 (approx.), delete " 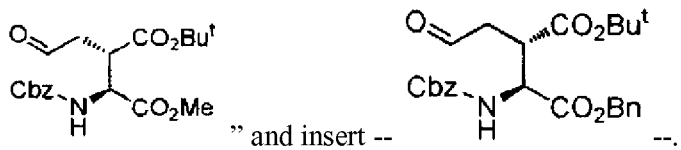 " and insert -- 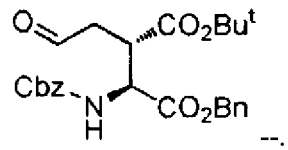 --.

Col. 53, line 5, delete "pretection" and insert -- protection --.

Col. 53, line 17 (approx.), delete "Boc)₂O" and insert -- (Boc)₂O --.

Col. 54, line 34 (approx.), delete "camphonic" and insert -- camphanic --.

Col. 54, line 51, delete "boronhydride" and insert -- borohydride --.

Col. 55, line 60, delete "arylpiprazine" and insert -- arylpiperazine --.

Col. 56, line 65, delete "nucleaphilic" and insert -- nucleophilic --.

CERTIFICATE OF CORRECTION (continued)

Col. 58, line 63, delete "nucleaphilic" and insert -- nucleophilic --.

Col. 59, line 43, delete "methylquilonine)." and insert -- methylquinoline). --.

Col. 59, line 44, delete "methylquilonine" and insert -- methylquinoline --.

Col. 62, line 58, delete "heterogeous" and insert -- heterogeneous --.

Col. 63, line 47, delete "heterogeous" and insert -- heterogeneous --.

Col. 65, line 38 (approx.), delete "(M+1+)." and insert -- $(M+1^+)$. --.

Col. 66, line 52, delete "diasteoisomer" and insert -- diastereoisomer --.

Col. 69, line 52, delete "inseperable" and insert -- inseparable --.

Col. 70, line 6, delete "cabonyl" and insert -- carbonyl --.

Col. 70, line 8-9, delete "cabonyl" and insert -- carbonyl --.

Col. 70, line 58, delete "cabonyl" and insert -- carbonyl --.

Col. 70, line 64, delete "cabonyl" and insert -- carbonyl --.

Col. 71, line 8, delete "cabonyl" and insert -- carbonyl --.

Col. 71, line 12, delete "cabonyl" and insert -- carbonyl --.

Col. 71, line 22, delete "cabonyl" and insert -- carbonyl --.

Col. 71, line 25, delete "cabonyl" and insert -- carbonyl --.

Col. 71, line 35, delete "cabonyl" and insert -- carbonyl --.

Col. 71, line 39, delete "cabonyl" and insert -- carbonyl --.

Col. 74, line 42, delete "3a, 4, 7, 7a" and insert -- 3a,4,7,7a --.

Col. 74, line 50, delete "residure" and insert -- residue --.

Col. 76, line 28 (approx.), delete "5 minDIEA" and insert -- 5 min DIEA --.

Col. 78, line 26 (approx.), after "solution" insert -- . --.

Col. 79, line 36, delete "stiiring" and insert -- stirring --.

Col. 82, line 21 (approx.), delete "exposued" and insert -- exposed --.

Col. 82, line 52 (approx.), delete "presure." and insert -- pressure. --.

Col. 83, line 8, delete "prepative HPLC" and insert -- preparative HPLC --.

Col. 84, line 48, delete "(M-t-Bu+H+)," and insert -- (M-t-Bu+H$^+$), --.

Col. 85, line 67, delete "hydroxycarbomyl" and insert -- hydroxycarbonyl --.

Col. 86, line 10, delete "hydroxycarbomyl" and insert -- hydroxycarbonyl --.

Col. 86, line 30, delete "ester]-(S)" and insert -- ester 1-(S) --.

Col. 86, line 40, delete "methylene" and insert -- methylidene --.

Col. 87, line 4, delete "(Na$_2$SO4)," and insert -- (Na$_2$SO$_4$), --.

Col. 87, line 24, delete "Benyloxycarbamoyl" and insert -- Benzyloxycarbamoyl --.

Col. 87, line 41-42, delete "benyloxycarbamoyl" and insert -- benzyloxycarbamoyl --.

Col. 87, line 45, delete "Benyloxycarbamoyl" and insert -- Benzyloxycarbamoyl --.

Col. 87, line 47, delete "benyloxycarbamoyl" and insert -- benzyloxycarbamoyl --.

Col. 87, line 56, delete "benyloxycarbamoyl" and insert -- benzyloxycarbamoyl --.

Col. 87, line 64, delete "benyloxycarbamoyl" and insert -- benzyloxycarbamoyl --.

Col. 89, line 36, delete "titureted" and insert -- titurated --.

Col. 89, line 54, delete "CS$_2$CO$_3$" and insert -- Cs$_2$CO$_3$ --.

Col. 90, line 7, delete "acid]-(S)" and insert -- acid 1-(S) --.

Col. 90, line 67, delete "(NaSO4)," and insert -- (Na$_2$SO$_4$), --.

Col. 91, line 41, delete "hydroxomic" and insert -- hydroxamic --.

Col. 92, line 62 (approx.), delete "5-(2-" and insert -- 5-{2- --.

Col. 94, line 36, delete "cycloheane" and insert -- cyclohexane --.

Col. 94, line 42, delete "residure" and insert -- residue --.

CERTIFICATE OF CORRECTION (continued)

U.S. Pat. No. 7,491,724 B2

Col. 96, line 17 (approx.), delete "titlted" and insert -- titled --.

Col. 96, line 32 (approx.), delete "2-[([(3R)" and insert -- 2-{([(3R) --.

Col. 97, line 62, delete "Hydrooxy" and insert -- Hydroxy --.

Col. 98, line 61, delete "hetereogeneous" and insert -- heterogeneous --.

Col. 99, line 1, delete "actetate" and insert -- acetate --.

Col. 99, line 63 (approx.), delete "1-4-" and insert -- 1-[4- --.

Col. 102, line 28 (approx.), delete "cycloheane" and insert -- cyclohexane --.

Col. 104, line 45, before "celite" delete "of".

Col. 104, line 45, delete "cloumn" and insert -- column --.

Col. 104, line 59, delete "silical" and insert -- silica --.

Col. 105, line 1, before "added" delete "was".

Col. 105, line 17, delete "fro" and insert -- for --.

Col. 105, line 19, delete "residure" and insert -- residue --.

Col. 105, line 20, delete "silical," and insert -- silica, --.

Col. 105, line 23, delete "(2S,3S, R)" and insert -- (2S,3S,5R) --.

Col. 109, line 58, delete "orgnica" and insert -- organic --.

Col. 110, line 10, delete "5S—methyl" and insert -- 5S-1-methyl --.

Col. 110, line 25, before "aq." delete "with".

Col. 110, line 28, delete "exposured" and insert -- exposed --.

Col. 114, line 10, before "celite" delete "of".

Col. 114, line 11, delete "cloumn" and insert -- column --.

Col. 114, line 25, delete "residure" and insert -- residue --.

Col. 114, line 26, delete "silical" and insert -- silica --.

Col. 114, line 40, delete "orgnic" and insert -- organic --.

Col. 114, line 43, delete "columnn," and insert -- column, --.

Col. 114, line 53, delete "residure" and insert -- residue --.

Col. 114, line 54, delete "cloumn" and insert -- column --.

Col. 114, line 63, delete "conetrated" and insert -- concentrated --.

Col. 115, line 26, delete "tirred" and insert -- stirred --.

Col. 115, line 26-27, delete "cocnentrated" and insert -- concentrated --.

Col. 117, line 37 (approx.), delete "carbonyl]1" and insert -- carbonyl]-1 --.

Col. 120, line 36, delete "hydrgen," and insert -- hydrogen, --.

Col. 120, line 50, delete "seperation" and insert -- separation --.

Col. 122, line 45, delete "dired." and insert -- dried. --.

Col. 123, line 10, delete "rsidue" and insert -- residue --.

Col. 124, line 54, delete "lyers" and insert -- layers --.

Col. 124, line 66, delete "bicaronate," and insert -- bicarbonate, --.

Col. 126, line 18, delete "bicaronate," and insert -- bicarbonate, --.

Col. 126, line 43, delete "-]-" and insert -- -1- --.

Col. 132, line 59, delete "(S," and insert -- (1S, --.

Col. 135, line 21, delete "Isopropy" and insert -- Isopropyl --.

Col. 135, line 35, delete "(1 S," and insert -- (1S, --.

Col. 137, line 43 (approx.), delete "-4-([" and insert -- -4-{[ --.

Col. 142, line 42 (approx.), after "example 72." delete "MS (ESI): (M+H)+=430.2.".

Col. 143, line 58 (approx.), after "example 243." delete "MS (ESI): (M+H)+=369.2.".

Col. 147, line 36, delete "0.00033. mol)" and insert -- 0.00033 mol) --.

Col. 152, line 48 (approx.), delete "LCMS:" and insert -- LCMS: (M+H)+=482.2. --.

Col. 156, line 48 (approx.), after "example 317." delete "LCMS:(M+H)+=459.2.".

Col. 156, line 58 (approx.), after "example 296." insert -- LCMS: (M+H)+=440.1. --.

Col. 166, line 1, before "-78" delete "at".

Col. 166, line 23 (approx.), before "80" delete "at".

Col. 166, line 27 (approx.), delete "coloumn," and insert -- column, --.

Col. 166, line 40, delete "satd" and insert -- satd. --.

Col. 167, line 38 (approx.), delete "elutin" and insert -- eluting --.

Col. 170, line 2, delete "inseperable" and insert -- inseparable --.

Col. 170, line 2, delete "floride" and insert -- fluoride --.

Col. 170, line 10, delete "ballon" and insert -- balloon --.

Col. 170, line 55 (approx.), delete "exposured" and insert -- exposed --.

Col. 170, line 56 (approx.), delete "vaccum" and insert -- vacuum --.

Col. 172, line 25 (approx.), delete "dired" and insert -- dried --.

Col. 174, line 48 (approx.), delete "(M#H)" and insert -- (M+H) --.

Col. 183-184, line 8 (Table 3), delete "30" and insert -- 31 --.

Col. 183-184, line 9 (Table 3), delete "31" and insert -- 30 --.

Col. 185-186, at 64 (Table 3 – continued), delete "carbonyloxyl" and insert -- carbonyloxy] --.

Col. 185-186, at 76 (Table 3 – continued), delete "Methyoxy" and insert -- Methoxy --.

Col. 191-192, at 172 (Table 5 – continued), delete "pheoxy" and insert -- phenoxy --.

Col. 215-216, (Table 7 – continued), delete " 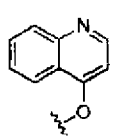 " and insert -- 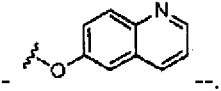 --.

CERTIFICATE OF CORRECTION (continued)

Col. 219-220, (Table 7 – continued), delete "  " and insert -- 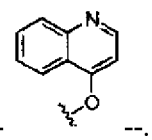 --.

Col. 231-232, at 381 (approx.) (Table 7 – continued), delete "methyoxycyclohexyl" and insert -- methoxycyclohexyl --.

Col. 235, line 53, delete "Comlmar" and insert -- Colmar --.

Col. 235, line 57, delete "Dearfield," and insert -- Deerfield, --.

Col. 235, line 67, delete "Supernatent" and insert -- Supernatant --.

Col. 236, line 35-36, delete "In Vitrogen," and insert -- Invitrogen, --.

Col. 237, line 33 (approx.), delete "NH2)" and insert -- $NH_2$) --.

Col. 237, line 57, delete "NH2)" and insert -- $NH_2$) --.

Col. 239, line 61, delete "component," and insert -- component --.

In the Claims

Col. 242, line 30-35 (approx.), in claim 1, delete " 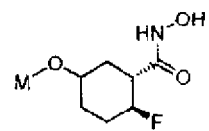 " and insert  --.

Col. 242, line 45, in claim 1, delete "$NR^{a-1}$," and insert -- $NR^{a1}$, --.

Col. 242, line 51, in claim 1, delete "$NR^{a1}$," and insert -- $NR^{a1}C(O)$, --.

Col. 243, line 3, in claim 1, delete "$S(O)_2NR^aR^{a1}NR^aS(O)_2R^{a2}$," and insert -- $S(O)_2NR^aR^{a1}$, $NR^aS(O)_2R^{a2}$, --.

Col. 243, line 5, in claim 1, delete "$OCHF_2CF_3$," and insert -- $OCHF_2$, $OCH_2CF_3$, --.

Col. 243, line 8, in claim 1, delete "alky" and insert -- alkyl --.

Col. 243, line 13 (approx.), in claim 1, delete "0(primary," and insert -- O(primary, --.

Col. 243, line 21, in claim 1, delete "N-alkylsufonamidodialkyl," and insert -- N-alkylsulfonamidodialkyl, --.

Col. 243, line 24, in claim 1, delete "$C_3$-$C_{10}$," and insert -- $C_3$-$C_{10}$ --.

Col. 243, line 26, in claim 1, delete "carbocyclylalkyl," and insert -- carbocyclylalkyl --.

Col. 243, line 32, in claim 1, delete "ailcylamido," and insert -- alkylamido, --.

Col. 243, lines 35-36, in claim 1, delete "N-alkylsulfonamidoalkyl," and insert -- N-alkylsulfonamidoalkyl, --.

Col. 243, line 36, in claim 1, delete "N-alkylsufonamidodialkyl," and insert -- N-alkylsulfonamidodialkyl, --.

Col. 243, line 43 (approx.), in claim 1, delete "$R^aNC(O)NR^a$, $R^a$," and insert -- $R^aNC(O)NR^aR^a$, --.

Col. 243, line 43-44 (approx.), in claim 1, delete "$OC(O)NR^aR^{a1}R^aNC(O)OR^{a1}$," and insert -- $OC(O)NR^aR^{a1}$, $R^aNC(O)OR^{a1}$, --.

Col. 243, line 55, in claim 1, delete "$S(O)_pR^{a2}CF_3$," and insert -- $S(O)_pR^{a2}$, $CF_3$, --.

Col. 243, line 60, in claim 1, delete "$OC(O)NR^aR$," and insert -- $OC(O)NR^aR^{a1}$, --.

Col. 243, line 65, in claim 1, delete "alkyl," and insert -- alkyl --.

Col. 244, line 23, in claim 3, delete "thereof" and insert -- thereof, --.

Col. 244, line 25 (approx.), in claim 4, delete "phannaceutical" and insert -- pharmaceutical --.

Col. 244, line 25 (approx.), in claim 4, delete "composition," and insert -- composition --.

Col. 244, line 26 (approx.), in claim 4, delete "phannaceutically" and insert -- pharmaceutically --.

Col. 244, line 38, in claim 5, delete "metbylquinolin" and insert -- methylquinolin --.

Col. 244, line 44, in claim 5, delete "cyclohexanecarboxainide;" and insert -- cyclohexanecarboxamide; --.

Col. 244, line 47, in claim 5, delete "(1S,2S, SR)" and insert -- (1S,2S,5R) --.

CERTIFICATE OF CORRECTION (continued)
U.S. Pat. No. 7,491,724 B2

Col. 244, line 48-49, in claim 5, delete "cyclohexanecarboxainide;" and insert -- cyclohexanecarboxamide; --.

Col. 244, line 56 (approx.), in claim 5, delete "cyclohexaoecarboxamide;" and insert -- cyclohexanecarboxamide; --.

Col. 245, line 7 (approx.), in claim 6, delete "cyclohexanccarboxamide," and insert -- cyclohexanecarboxamide, --.

Col. 246, line 22 (approx.), in claim 10, delete "[(4(4" and insert -- [(4 --.